US009579361B2

(12) United States Patent
Satyal et al.

(10) Patent No.: US 9,579,361 B2
(45) Date of Patent: Feb. 28, 2017

(54) WNT ANTAGONIST AND METHODS OF TREATMENT AND SCREENING

(71) Applicant: OncoMed Pharmaceuticals, Inc., Redwood City, CA (US)

(72) Inventors: Sanjeev H. Satyal, San Carlos, CA (US); Satyajit Sujit Kumar Mitra, South Pasadena, CA (US); Austin L. Gurney, San Francisco, CA (US)

(73) Assignee: ONCOMED PHARMACEUTICALS, INC., Redwood City, CA (US)

( * ) Notice: Subject to any disclaimer, the term of this patent is extended or adjusted under 35 U.S.C. 154(b) by 0 days.

(21) Appl. No.: 14/842,398

(22) Filed: Sep. 1, 2015

(65) Prior Publication Data

US 2016/0082079 A1    Mar. 24, 2016

Related U.S. Application Data

(62) Division of application No. 13/005,214, filed on Jan. 12, 2011, now Pat. No. 9,157,904.

(60) Provisional application No. 61/294,270, filed on Jan. 12, 2010, provisional application No. 61/393,675, filed on Oct. 15, 2010, provisional application No. 61/424,408, filed on Dec. 17, 2010.

(51) Int. Cl.

| A61K 6/00 | (2006.01) |
|---|---|
| A61K 31/00 | (2006.01) |
| A61K 31/28 | (2006.01) |
| A61K 31/282 | (2006.01) |
| A61K 31/33 | (2006.01) |
| A61K 31/335 | (2006.01) |
| A61K 31/337 | (2006.01) |
| A61K 39/00 | (2006.01) |
| A61K 39/395 | (2006.01) |
| A61K 45/00 | (2006.01) |
| A61K 38/17 | (2006.01) |
| C07K 14/705 | (2006.01) |
| G01N 33/50 | (2006.01) |
| A61K 31/4745 | (2006.01) |
| A61K 31/7068 | (2006.01) |
| A61K 38/00 | (2006.01) |

(52) U.S. Cl.
CPC .......... *A61K 38/177* (2013.01); *A61K 31/282* (2013.01); *A61K 31/337* (2013.01); *A61K 31/4745* (2013.01); *A61K 31/7068* (2013.01); *A61K 39/39591* (2013.01); *C07K 14/705* (2013.01); *G01N 33/5011* (2013.01); *A61K 38/00* (2013.01); *C07K 2319/02* (2013.01); *C07K 2319/30* (2013.01); *C07K 2319/70* (2013.01)

(58) Field of Classification Search
None
See application file for complete search history.

(56) References Cited

U.S. PATENT DOCUMENTS

| 3,687,808 | A | 8/1972 | Merigan, Jr. et al. |
|---|---|---|---|
| 4,109,496 | A | 8/1978 | Allemann et al. |
| 4,323,546 | A | 4/1982 | Crockford et al. |
| 4,411,990 | A | 10/1983 | Salmon et al. |
| 4,612,282 | A | 9/1986 | Schlom et al. |
| 4,670,393 | A | 6/1987 | Seeburg |
| 4,873,191 | A | 10/1989 | Wagner et al. |
| 4,968,103 | A | 11/1990 | McNab et al. |
| 4,981,785 | A | 1/1991 | Nayak |
| 5,019,497 | A | 5/1991 | Olsson |
| 5,034,506 | A | 7/1991 | Summerton et al. |
| 5,061,620 | A | 10/1991 | Tsukamoto et al. |
| 5,087,570 | A | 2/1992 | Weissman et al. |
| 5,223,409 | A | 6/1993 | Ladner et al. |
| 5,225,539 | A | 7/1993 | Winter |
| 5,283,317 | A | 2/1994 | Saifer et al. |
| 5,358,691 | A | 10/1994 | Clark et al. |
| 5,489,677 | A | 2/1996 | Sanghvi et al. |
| 5,534,617 | A | 7/1996 | Cunningham et al. |
| 5,538,848 | A | 7/1996 | Livak et al. |
| 5,539,082 | A | 7/1996 | Nielsen et al. |
| 5,565,332 | A | 10/1996 | Hoogenboom et al. |
| 5,585,089 | A | 12/1996 | Queen et al. |
| 5,589,376 | A | 12/1996 | Anderson et al. |
| 5,599,677 | A | 2/1997 | Dowell et al. |
| 5,602,240 | A | 2/1997 | De Mesmaeker et al. |
| 5,614,396 | A | 3/1997 | Bradley et al. |
| 5,631,169 | A | 5/1997 | Lakowicz et al. |
| 5,639,606 | A | 6/1997 | Willey |

(Continued)

FOREIGN PATENT DOCUMENTS

| CA | 2642665 A1 | 8/2007 |
|---|---|---|
| EP | 0861894 A1 | 9/1998 |

(Continued)

OTHER PUBLICATIONS

US 5,962,233, 10/1999, Livak et al. (withdrawn) Weinberg et al. The Biology of Cancer, Chapter 2, The Nature of Cancer, pp. 25-56, May 2013.*
National Cancer Institute, Cancer Treatment, Apr. 29, 2015.*
Gong, Y., et al., "Wnt isoform-specific interactions with coreceptor specify inhibition or potentiation of signaling by LRP6 antibodies," PLoS One 5(9):e12682:1-17, Public Library of Science, United States (2010).
Hoppler, S., et al., "Expression of a Dominant-Negative Wnt Blocks Induction of MyoD in Xenopus Embryos," Genes and Development 10(21):2805-2817, Cold Spring Harbor Laboratory Press, United States (1996).
Kahn, M., "Can we safely target the WNT pathway?" Nature Reviews Drug Discovery 13(7):513-532, Macmillan Publishers Limited, England (2014).
Papadopoulos, K.P., et al., "A Phase I Study in patients with advanced solid tumors for the human monoclonal antibody vantictumab (OMP-18R5; anti-Frizzled) targeting the WNT pathway," European Journal of Cancer 49(Suppl 2):S188, Abstract 890, European Cancer Congress 2013, 17th ECCO, 38th ESMO, 32nd ESTRO, Netherlands (2013).

(Continued)

*Primary Examiner* — Alana Harris Dent
(74) *Attorney, Agent, or Firm* — Sterne, Kessler, Goldstein and Fox P.L.L.C.

(57) ABSTRACT

The present invention relates to compositions comprising Wnt antagonists and methods of treating Wnt-associated diseases and disorders, such as cancer, inducing differentiation, and reducing the frequency of cancer stem cells, as well as novel methods of screening for such Wnt antagonists. In particular, the invention discloses soluble FZD, SFRP and Ror receptors and their use.

35 Claims, 21 Drawing Sheets

(56) References Cited

U.S. PATENT DOCUMENTS

Figure 1:
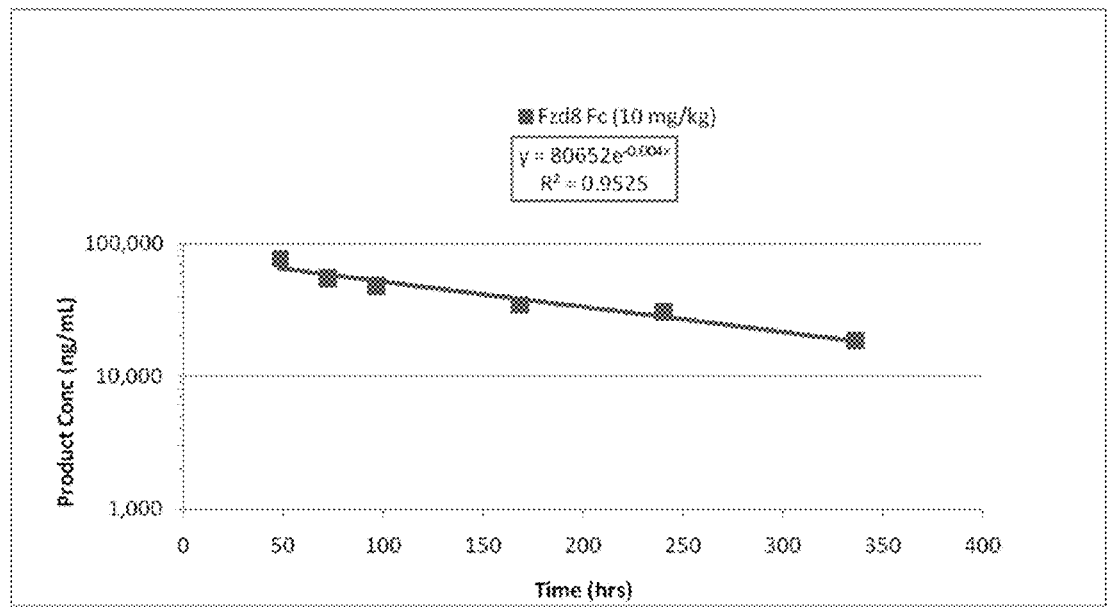

| | | |
|---|---|---|
| 5,643,741 A | 7/1997 | Tsukamoto et al. |
| 5,643,765 A | 7/1997 | Willey |
| 5,648,464 A | 7/1997 | Artavanis-Tsakonas et al. |
| 5,650,317 A | 7/1997 | Chang et al. |
| 5,654,183 A | 8/1997 | Anderson et al. |
| 5,672,499 A | 9/1997 | Anderson et al. |
| 5,674,739 A | 10/1997 | Shyjan |
| 5,688,666 A | 11/1997 | Bass et al. |
| 5,693,482 A | 12/1997 | Anderson et al. |
| 5,705,188 A | 1/1998 | Junichi et al. |
| 5,714,331 A | 2/1998 | Buchardt et al. |
| 5,719,262 A | 2/1998 | Buchardt et al. |
| 5,739,277 A | 4/1998 | Presta et al. |
| 5,750,373 A | 5/1998 | Garrard et al. |
| 5,750,376 A | 5/1998 | Weiss et al. |
| 5,753,229 A | 5/1998 | Mordoh et al. |
| 5,753,506 A | 5/1998 | Johe |
| 5,780,300 A | 7/1998 | Artavanis-Tsakonas et al. |
| 5,786,158 A | 7/1998 | Artavanis-Tsakonas et al. |
| 5,789,195 A | 8/1998 | Artavanis-Tsakonas et al. |
| 5,814,511 A | 9/1998 | Chang et al. |
| 5,821,108 A | 10/1998 | Akashi et al. |
| 5,824,489 A | 10/1998 | Anderson et al. |
| 5,824,544 A | 10/1998 | Armentano et al. |
| 5,830,730 A | 11/1998 | German et al. |
| 5,834,598 A | 11/1998 | Lowman et al. |
| 5,849,535 A | 12/1998 | Cunningham et al. |
| 5,849,553 A | 12/1998 | Anderson et al. |
| 5,849,869 A | 12/1998 | Artavanis-Tsakonas et al. |
| 5,854,026 A | 12/1998 | Cunningham et al. |
| 5,856,441 A | 1/1999 | Artavanis-Tsakonas et al. |
| 5,859,535 A | 1/1999 | Liu |
| 5,861,832 A | 1/1999 | Nagaraj |
| 5,869,282 A | 2/1999 | Ish-Horowicz et al. |
| 5,872,154 A | 2/1999 | Wilson et al. |
| 5,876,978 A | 3/1999 | Willey et al. |
| 5,885,530 A | 3/1999 | Babson et al. |
| 5,885,808 A | 3/1999 | Spooner et al. |
| 5,914,108 A | 6/1999 | Tsukamoto et al. |
| 5,935,792 A | 8/1999 | Rubin et al. |
| 5,942,225 A | 8/1999 | Bruder et al. |
| 5,981,225 A | 11/1999 | Kochanek et al. |
| 5,986,170 A | 11/1999 | Subjeck |
| 5,994,106 A | 11/1999 | Kovesdi et al. |
| 5,994,128 A | 11/1999 | Fallaux et al. |
| 5,994,132 A | 11/1999 | Chamberlain et al. |
| 5,994,617 A | 11/1999 | Dick et al. |
| 6,001,557 A | 12/1999 | Wilson et al. |
| 6,004,528 A | 12/1999 | Bergstein |
| 6,004,924 A | 12/1999 | Ish-Horowicz et al. |
| 6,019,978 A | 2/2000 | Ertl et al. |
| 6,022,711 A | 2/2000 | Cunningham et al. |
| 6,033,908 A | 3/2000 | Bout et al. |
| 6,054,297 A | 4/2000 | Carter et al. |
| 6,080,912 A | 6/2000 | Bremel et al. |
| 6,083,904 A | 7/2000 | Artavanis-Tsakonas |
| 6,090,922 A | 7/2000 | Artavanis-Tsakonas et al. |
| 6,117,985 A | 9/2000 | Thomas et al. |
| 6,121,045 A | 9/2000 | McCarthy et al. |
| 6,127,526 A | 10/2000 | Blank |
| 6,135,653 A | 10/2000 | Aichi |
| 6,136,952 A | 10/2000 | Li et al. |
| 6,143,523 A | 11/2000 | Cunningham et al. |
| 6,149,902 A | 11/2000 | Artavanis-Tsakonas et al. |
| 6,156,305 A | 12/2000 | Brauker et al. |
| 6,159,750 A | 12/2000 | Edmonds |
| 6,180,370 B1 | 1/2001 | Queen et al. |
| 6,190,876 B1 | 2/2001 | Rubin et al. |
| 6,197,523 B1 | 3/2001 | Rimm et al. |
| 6,198,107 B1 | 3/2001 | Seville |
| 6,207,147 B1 | 3/2001 | Hiserodt et al. |
| 6,218,166 B1 | 4/2001 | Ravindranath et al. |
| 6,252,050 B1 | 6/2001 | Ashkenazi et al. |
| 6,262,025 B1 | 7/2001 | Ish-Horowicz et al. |
| 6,353,150 B1 | 3/2002 | Dick et al. |
| 6,379,925 B1 | 4/2002 | Kitajewski et al. |
| 6,380,362 B1 | 4/2002 | Watson et al. |
| 6,429,186 B1 | 8/2002 | Fuh et al. |
| 6,433,138 B1 | 8/2002 | Zimrin et al. |
| 6,433,155 B1 | 8/2002 | Umansky et al. |
| 6,448,229 B2 | 9/2002 | Teall |
| 6,506,559 B1 | 1/2003 | Fire et al. |
| 6,537,775 B1 | 3/2003 | Tournier-Lasserve et al. |
| 6,551,795 B1 | 4/2003 | Rubenfield et al. |
| 6,583,115 B1 | 6/2003 | Kopchick et al. |
| 6,632,620 B1 | 10/2003 | Makarovskiy |
| 6,660,843 B1 | 12/2003 | Feige et al. |
| 6,664,098 B1 | 12/2003 | Sakano |
| 6,683,091 B2 | 1/2004 | Asberom et al. |
| 6,689,744 B2 | 2/2004 | Gao et al. |
| 6,703,221 B1 | 3/2004 | Chan et al. |
| 6,703,489 B1 | 3/2004 | Ish-Horowicz et al. |
| 6,713,206 B2 | 3/2004 | Markoski et al. |
| 6,716,974 B1 | 4/2004 | Maciag et al. |
| 6,756,511 B2 | 6/2004 | Castro Pineiro et al. |
| 6,894,522 B2 | 5/2005 | Averill et al. |
| 6,984,522 B2 | 1/2006 | Clarke et al. |
| 7,091,321 B2 | 8/2006 | Gillies et al. |
| 7,091,323 B2 | 8/2006 | Pan et al. |
| 7,115,360 B2 | 10/2006 | Clarke et al. |
| 7,115,653 B2 | 10/2006 | Baxter et al. |
| 7,118,853 B2 | 10/2006 | Botstein et al. |
| 7,138,370 B2 | 11/2006 | Oliner et al. |
| 7,183,377 B2 | 2/2007 | Rubin et al. |
| 7,211,404 B2 | 5/2007 | Lagasse et al. |
| 7,361,336 B1 | 4/2008 | Bergstein |
| 7,381,408 B2 | 6/2008 | Mezo et al. |
| 7,404,956 B2 | 7/2008 | Peters et al. |
| 7,413,873 B2 | 8/2008 | Waterman et al. |
| 7,442,778 B2 | 10/2008 | Gegg et al. |
| 7,507,406 B2 | 3/2009 | Gillies et al. |
| 7,608,453 B2 | 10/2009 | Cattaneo et al. |
| 7,635,530 B2 | 12/2009 | Kenis et al. |
| 7,659,116 B2 | 2/2010 | Buehring et al. |
| 7,662,931 B2 | 2/2010 | Gegg et al. |
| 7,682,607 B2 | 3/2010 | Rhee et al. |
| 7,713,526 B2 | 5/2010 | Rhee et al. |
| 7,723,477 B2 | 5/2010 | Gurney et al. |
| 7,803,370 B2 | 9/2010 | Nakamura et al. |
| 7,803,783 B2 | 9/2010 | Lee et al. |
| 7,803,913 B2 | 9/2010 | Dimitrov et al. |
| 7,867,705 B2 | 1/2011 | Wands et al. |
| 7,879,322 B2 | 2/2011 | Kneissel et al. |
| 7,947,277 B2 | 5/2011 | Ernst et al. |
| 7,982,013 B2 | 7/2011 | Gurney et al. |
| 8,017,559 B2 | 9/2011 | Etzerodt et al. |
| 8,158,761 B2 | 4/2012 | Wands et al. |
| 8,410,061 B2 | 4/2013 | Williams et al. |
| 8,431,532 B2 | 4/2013 | Brennan et al. |
| 8,507,442 B2 | 8/2013 | Gurney et al. |
| 8,551,789 B2 | 10/2013 | Gurney |
| 8,809,287 B2 | 8/2014 | Bafico et al. |
| 9,157,904 B2 | 10/2015 | Satyal et al. |
| 9,266,959 B2 | 2/2016 | Stagg et al. |
| 9,273,139 B2 | 3/2016 | Gurney et al. |
| 2002/0119565 A1 | 8/2002 | Clarke et al. |
| 2002/0137129 A1 | 9/2002 | Barnes et al. |
| 2002/0151487 A1 | 10/2002 | Nickoloff et al. |
| 2002/0169300 A1 | 11/2002 | Waterman et al. |
| 2002/0187502 A1 | 12/2002 | Waterman et al. |
| 2003/0032184 A1 | 2/2003 | Lagasse et al. |
| 2003/0044409 A1 | 3/2003 | Carson et al. |
| 2003/0064384 A1 | 4/2003 | Hung et al. |
| 2003/0086934 A1 | 5/2003 | Botstein et al. |
| 2003/0114387 A1 | 6/2003 | Castro Pineiro et al. |
| 2003/0119029 A1 | 6/2003 | Glick et al. |
| 2003/0135044 A1 | 7/2003 | Asberom et al. |
| 2003/0139457 A1 | 7/2003 | Baxter et al. |
| 2003/0162709 A1 | 8/2003 | Rossi et al. |
| 2003/0165500 A1 | 9/2003 | Rhee et al. |
| 2003/0166543 A1 | 9/2003 | Williams et al. |
| 2003/0175877 A1 | 9/2003 | Baker et al. |
| 2003/0180784 A1 | 9/2003 | McCarthy et al. |
| 2003/0185829 A1 | 10/2003 | Koller et al. |

(56) References Cited

U.S. PATENT DOCUMENTS

| | | |
|---|---|---|
| 2003/0229023 A1 | 12/2003 | Oliner et al. |
| 2004/0023244 A1 | 2/2004 | Griffin et al. |
| 2004/0037815 A1 | 2/2004 | Clarke et al. |
| 2004/0038876 A1 | 2/2004 | Pepinsky et al. |
| 2004/0048249 A1 | 3/2004 | Tang et al. |
| 2004/0058217 A1 | 3/2004 | Ohlsen et al. |
| 2004/0058443 A1 | 3/2004 | Artavanis-Tsakonas et al. |
| 2004/0105862 A1 | 6/2004 | Pan et al. |
| 2004/0127474 A1 | 7/2004 | Dudek et al. |
| 2004/0171559 A1 | 9/2004 | Weissman et al. |
| 2004/0203003 A1 | 10/2004 | Rhee et al. |
| 2004/0214186 A1 | 10/2004 | Engelberg et al. |
| 2004/0219579 A1 | 11/2004 | Aziz et al. |
| 2004/0247593 A1 | 12/2004 | He et al. |
| 2005/0123900 A1 | 6/2005 | Dimitrov et al. |
| 2005/0130199 A1 | 6/2005 | Carson et al. |
| 2005/0272063 A1 | 12/2005 | Nakamura et al. |
| 2005/0288864 A1 | 12/2005 | Cattaneo et al. |
| 2006/0019256 A1 | 1/2006 | Clarke et al. |
| 2006/0019320 A1 | 1/2006 | Civenni et al. |
| 2006/0040883 A1 | 2/2006 | You et al. |
| 2006/0210867 A1 | 9/2006 | Kenis et al. |
| 2007/0014776 A1 | 1/2007 | Gimeno et al. |
| 2007/0072238 A1 | 3/2007 | Bhat |
| 2007/0116701 A1 | 5/2007 | Gurney et al. |
| 2007/0117751 A1 | 5/2007 | Gurney et al. |
| 2007/0237770 A1 | 10/2007 | Lai et al. |
| 2007/0238658 A1 | 10/2007 | Levin et al. |
| 2008/0038272 A1 | 2/2008 | Buehring et al. |
| 2008/0044423 A1 | 2/2008 | Cochrane et al. |
| 2008/0075714 A1 | 3/2008 | Lee et al. |
| 2008/0118432 A1 | 5/2008 | Bergstein et al. |
| 2008/0160060 A1 | 7/2008 | Ellies |
| 2008/0171319 A1 | 7/2008 | Urdea et al. |
| 2008/0194457 A1 | 8/2008 | Wands et al. |
| 2008/0299136 A1 | 12/2008 | Ernst et al. |
| 2009/0023905 A1 | 1/2009 | Askew et al. |
| 2009/0074777 A1 | 3/2009 | Wands et al. |
| 2009/0130113 A1 | 5/2009 | Kneissel et al. |
| 2009/0163407 A1 | 6/2009 | Bafico et al. |
| 2009/0186010 A1 | 7/2009 | Li et al. |
| 2009/0234104 A1 | 9/2009 | Gegg et al. |
| 2009/0263400 A1 | 10/2009 | Urdea et al. |
| 2009/0304695 A1 | 12/2009 | He et al. |
| 2010/0104574 A1 | 4/2010 | Gurney et al. |
| 2010/0169025 A1 | 7/2010 | Arthur et al. |
| 2011/0020368 A1 | 1/2011 | Hynes |
| 2011/0224243 A1 | 9/2011 | Rethore |
| 2011/0237514 A1 | 9/2011 | Kakitani et al. |
| 2011/0318341 A1 | 12/2011 | Gurney et al. |
| 2012/0003222 A1 | 1/2012 | Brennan et al. |
| 2012/0023600 A1 | 1/2012 | Shulok et al. |
| 2012/0027778 A1 | 2/2012 | Gurney |
| 2012/0141481 A1 | 6/2012 | Ernst et al. |
| 2013/0209475 A1 | 8/2013 | Richards et al. |
| 2013/0252326 A1 | 9/2013 | Gurney et al. |
| 2013/0295105 A1 | 11/2013 | Gurney et al. |
| 2013/0295106 A1 | 11/2013 | Gurney et al. |
| 2014/0105917 A1 | 4/2014 | Gurney |
| 2014/0134159 A1 | 5/2014 | Stagg et al. |
| 2014/0242078 A1 | 8/2014 | Dupont et al. |

FOREIGN PATENT DOCUMENTS

| | | |
|---|---|---|
| EP | 1004669 A1 | 5/2000 |
| EP | 0662827 B1 | 4/2002 |
| EP | 1576119 A2 | 9/2005 |
| EP | 1805221 A1 | 7/2007 |
| EP | 1805519 A2 | 7/2007 |
| WO | WO-9008832 A1 | 8/1990 |
| WO | WO-9219734 A1 | 11/1992 |
| WO | WO-9407474 A1 | 4/1994 |
| WO | WO-9410300 A1 | 5/1994 |
| WO | WO-9701571 A1 | 1/1997 |
| WO | WO-9730731 A2 | 8/1997 |
| WO | WO-9737004 A1 | 10/1997 |
| WO | WO-9805775 A1 | 2/1998 |
| WO | WO-9845434 A1 | 10/1998 |
| WO | WO-9851799 A1 | 11/1998 |
| WO | WO-9857621 A1 | 12/1998 |
| WO | WO-9902685 A1 | 1/1999 |
| WO | WO-0006726 A2 | 2/2000 |
| WO | WO-0009675 A1 | 2/2000 |
| WO | WO-0012738 A1 | 3/2000 |
| WO | WO-0052143 A2 | 9/2000 |
| WO | WO-0102568 A2 | 1/2001 |
| WO | WO-0122920 A2 | 4/2001 |
| WO | WO-0126643 A1 | 4/2001 |
| WO | WO-0198354 A2 | 12/2001 |
| WO | WO-0198537 A2 | 12/2001 |
| WO | WO-0200576 A1 | 1/2002 |
| WO | WO-0212447 A2 | 2/2002 |
| WO | WO-0218544 A2 | 3/2002 |
| WO | WO-02078703 A1 | 10/2002 |
| WO | WO-02088081 A2 | 11/2002 |
| WO | WO-02092635 A2 | 11/2002 |
| WO | WO-02102978 A2 | 12/2002 |
| WO | WO-03000893 A2 | 1/2003 |
| WO | WO-03004045 A2 | 1/2003 |
| WO | WO-03042246 A2 | 5/2003 |
| WO | WO-03047316 A1 | 6/2003 |
| WO | WO-03050502 A2 | 6/2003 |
| WO | WO-03053921 A2 | 7/2003 |
| WO | WO-03062273 A2 | 7/2003 |
| WO | WO-03080672 A1 | 10/2003 |
| WO | WO-03088964 A1 | 10/2003 |
| WO | WO-04001004 A2 | 12/2003 |
| WO | WO-2004020668 A2 | 3/2004 |
| WO | WO-2004032838 A2 | 4/2004 |
| WO | WO-2004042028 A2 | 5/2004 |
| WO | WO-2004053069 A2 | 6/2004 |
| WO | WO-2004065545 A2 | 8/2004 |
| WO | WO-2004073657 A2 | 9/2004 |
| WO | WO-2004101739 A2 | 11/2004 |
| WO | WO-2005001025 A2 | 1/2005 |
| WO | WO-2005004912 A1 | 1/2005 |
| WO | WO-2005005601 A2 | 1/2005 |
| WO | WO-2006034328 A2 | 3/2006 |
| WO | WO-2006036173 A2 | 4/2006 |
| WO | WO-2006036175 A2 | 4/2006 |
| WO | WO-2006040163 A1 | 4/2006 |
| WO | WO-2006055635 A2 | 5/2006 |
| WO | WO-2006056340 A2 | 6/2006 |
| WO | WO-2006130076 A1 | 12/2006 |
| WO | WO-2007053577 A2 | 5/2007 |
| WO | WO-2007070538 A2 | 6/2007 |
| WO | WO-2007096149 A1 | 8/2007 |
| WO | WO-2007133250 A2 | 11/2007 |
| WO | WO-2007134876 A2 | 11/2007 |
| WO | WO-2007142711 A2 | 12/2007 |
| WO | WO-2007148417 A1 | 12/2007 |
| WO | WO-2008031009 A2 | 3/2008 |
| WO | WO-2008039071 A2 | 4/2008 |
| WO | WO-2008057459 A2 | 5/2008 |
| WO | WO-2008061020 A2 | 5/2008 |
| WO | WO-2008082730 A2 | 7/2008 |
| WO | WO-2008115890 A2 | 9/2008 |
| WO | WO-2008138639 A1 | 11/2008 |
| WO | WO-2008157179 A2 | 12/2008 |
| WO | WO-2009010530 A1 | 1/2009 |
| WO | WO-2009018233 A1 | 2/2009 |
| WO | WO-2009018238 A1 | 2/2009 |
| WO | WO-2009042971 A2 | 4/2009 |
| WO | WO-2009056634 A2 | 5/2009 |
| WO | WO-2009059994 A2 | 5/2009 |
| WO | WO-2009064675 A1 | 5/2009 |
| WO | WO-2009118300 A1 | 10/2009 |
| WO | WO-2009124535 A1 | 10/2009 |
| WO | WO-2010031979 A1 | 3/2010 |
| WO | WO-2010037041 A2 | 4/2010 |
| WO | WO-2010038756 A1 | 4/2010 |
| WO | WO-2010105110 A1 | 9/2010 |
| WO | WO-2011088123 A2 | 7/2011 |
| WO | WO-2011101409 A1 | 8/2011 |

(56) References Cited

FOREIGN PATENT DOCUMENTS

| WO | WO-2011112678 A1 | 9/2011 |
|---|---|---|
| WO | WO-2011123785 A2 | 10/2011 |
| WO | WO-2011123785 A3 | 12/2011 |
| WO | WO-2012003189 A1 | 1/2012 |
| WO | WO-2012006027 A1 | 1/2012 |
| WO | WO-2012058393 A2 | 5/2012 |
| WO | WO-2014121196 A1 | 8/2014 |

OTHER PUBLICATIONS

Pode-Shakked, N., et al., "Resistance or Sensitivity of Wilms' Tumor to Anti-FZD7 Antibody Highlights the Wnt Pathway as a Possible Therapeutic Target," Oncogene 30(14):1664-1680, Nature Publishing Group, England (2011).
Yamamoto, H. and Kikuchi, A., "Selective activation of multiple Wnt signaling pathways," Igaku no Ayumi, Journal of Clinical and Experimental Medicine 233(10):948-954, Japan (2010).
Pu, P., et al., "Downregulation of Wnt2 and β-catenin by siRNA suppresses malignant glioma cell growth," Cancer Gene Therapy 16:351-361, Nature Publishing Group, England (2009).
Accession No. GSP: ARJ99386, EBI database, First entry on May 15, 2008, accessed on Jul. 18, 2013, 1 page.
Accession No. GSP: AVA85292, EBI database, First entry on Apr. 2, 2009, accessed on Jul. 18, 2013, 1 page.
Accession No. UNITPROT: A6CA06, EBI database (Jul. 24, 2007), accessed on Jul. 8, 2013, 2 pages.
Albers, J., et al., "Control of Bone Formation by the Serpentine Receptor Frizzled-9," The Journal of Cellular Biology 192(6):1057-1072, Rockefeller University Press, United States (2011).
Al-Hajj, M., et al., "Prospective Identification of Tumorigenic Breast Cancer Cells," Proceedings of the National Academy of Sciences 10(7):3983-3988, The National Academy of Sciences, United States (2003).
Aruffo, A., et al., "CD44 is the Principal Cell Surface Receptor for Hyaluronate," Cell 61(7):1303-1313, Cell Press, United States (1990).
Austin, T.W., et al., "A role for the Wnt gene family in hematopoiesis: expansion of multilineage progenitor cells," Blood 89(10):3624-3635, The American Society of Hematology, United States (1997).
Ayyanan, A., et al., "Increased Wnt signaling triggers oncogenic conversion of human breast epithelial cells by a Notch-dependent mechanism," Proceedings of the National Academy of Sciences 103(10):3799-3804, National Academy of Sciences, United States (2006).
Bafico A., et al., "An Autocrine mechanism for constitutive Wnt pathway activation in human cancer cells," Cancer Cell 6(5):497-506, Cell Press, Elsevier (2004).
Bafico, A., et al., "Interaction of Frizzled Related Protein (FRP) with Wnt Ligands and the Frizzled Receptor Suggests Alternative Mechanisms for FRP Inhibition of Wnt Signaling," The Journal of Biological Chemistry, 274(23):16180-16187, The American Society for Biochemistry and Molecular Biology, Inc., United States (1999).
Barker, N. and Clevers, H., "Mining the Wnt pathway for cancer therapeutics," Nature Reviews/Drug Discovery 5(12):997-1014, Nature Publishing Group, United States (2006).
Battula, V.L., et al., "Prospective isolation and characterization of mesenchymal stem cells from human placenta using a frizzled-9-specific monoclonal antibody," Differentiation 76(4):326-336, International Society of Differentiation, United States (2008).
Benhamouche, S., et al., "Apc Tumor Suppressor Gene Is the "Zonation-Keeper" of Mouse Liver," Developmental Cell 10(6):759-770, Elsevier Inc., Netherlands (2006).
Bhanot, P., et al., "A new member of the frizzled family from Drosophila functions as a Wingless receptor," Nature 382(6588):225-230, Nature Publishing Group, United States (1996).
Bienz, M., "β-Catenin: A Pivot between Cell Adhesion and Wnt Signalling," Current Biology 15(2):R64-R67, Cell Press, United States (2004).
Bodey, B., et al., "Failure of cancer vaccines: the significant limitations of this approach to immunotherapy," Anticancer Research 20(4):2665-2676, International Institute of Anticancer Research, Greece (2000).
Booy, E.P., et al., "Monoclonal and bispecific antibodies as novel therapeutics," Archivum Immunologiae et Therapia Experimentalis 54(2):85-101, Birkhauser publications, Switzerland (2006).
Bourhis, E., et al., "Reconstitution of a Frizzled8.Wnt3a.LRP6 Signaling Complex Reveals Multiple Wnt andDkk1 Binding Sites on LRP6," The Journal of Biological Chemistry 285(12):9172-9179, American Society for Biochemistry and Molecular Biology, United States (2010).
Brabletz T., et al., "Variable β-catenin expression in colorectal cancers indicates tumor progression driven by the tumor environment," Proceedings of the National Academy of Sciences of the United States of America 98(18):10356-10361, National Academy of Sciences, United States (2001).
Brennan, K.R., and Brown, A.M.C., "Wnt Proteins in Mammary Development and Cancer," Journal of Mammary Gland Biology and Neoplasia 9(2):119-131, Kluwer Academic/Plenum Publishers, United States (2004).
Burgess, W.H., et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology 111(5Pt1):2129-2138, The Rockefeller University Press, United States (1990).
Cadigan, K.M. and Nusse, R., "Wnt signaling: a common theme in animal development," Genes & Development 11(24):3286-3305, Cold Spring Harbor Laboratory Press, United States (1997).
Caldwell, G.M., et al., "The Wnt Antagonist sFRP1 in Colorectal Tumorigenesis," Cancer Research 64(3):883-888, The American Association for Cancer Research, United States (2004).
Cao, Y., et al., "Nuclear-Cytoplasmic Shuttling of Menin Regulates Nuclear Translocation of {beta}-Catenin," Moleuclar and Cellular Biology 29(20):5477-5487, American Society for Microbiology, Unites states (2009).
Caricasole, A., et al., "Functional Characterization of WNT7A Signaling in PC12 Cells," The Journal of Biological Chemistry 278(39):37024-37031, The American Society for Biochemistry and Molecular Biology, United States (2003).
Casset, F., et al., "A Peptide Mimetic of an Anti-CD4 Monoclonal Antibody by Rational Design," Biochemical and Biophysical Research Communications 307(1):198-205, Academic Press, United States (2003).
Chan, E. F., et al., "A common human skin tumour is caused by activating mutations in β-catenin," Nature Genetics 21(4):410-413, Nature Publishing Company, United States (1999).
Chatterjee, M.B., et al., "Idiotypic antibody immunotherapy of cancer," Cancer Immunology, Immunotherapy 38(2):75-82, Springer International, Germany (1994).
Chen, Y., et al., "Selection and Analysis of an Optimized Anti-VEGF Antibody: Crystal Structure of an Affinity-matured Fab in Complex with Antigen," Journal of Molecular Biology 293(4):865-881, Academic Press, England (1999).
Clevers, H., "Axin and hepatocellular carcinomas," Nature Genetics 24(3):206-208, Nature Publishing Group, United States (2000).
Cong, F., et al., "Wnt Signals across the Plasma Membrane to Activate the Beta-catenin Pathway by Forming Oligomers Containing its Receptors, Frizzled and LRP," Development 131(20):5103-5115, Company of Biologists, England (2004).
Daniel, C., et al., "Mapping of Linear Antigenic Sites on the S Glycoprotein of a Neurotropic Murine Coronavirus with Synthetic Peptides: A Combination of Nine Prediction Algorithms Fails to Identify Relevant Episodes and Peptides Immunogenicity Is Drastically Influenced by the Nature of the Protein Carrier," Virology 202:540-549, Elsevier Inc., Netherlands (1994).
Dann, C.E., et al., "Insights into Wnt biding and signaling from the structures of two Frizzled cysteine-rich domains," Nature 412(6842):86-90, Nature Publishing Group, United States (2001).
Datta, D.V., "Viral Hepatitis," Jr Association of Physicians of India 25:325-330, Association of Physicians of India, India (1977).

(56) References Cited

OTHER PUBLICATIONS

Davidson, G., et al., "Casein kinase 1γ couples Wnt receptor activation to cytoplasmic signal transduction," Nature 438(7069):867-872, Nature Publishing Group, United States (2005).
De Gruijl, T. and Curiel, D.T., "Cancer vaccine strategies get bigger and better," Nature Medicine 5(10):1124-1125, Nature Publishing Company, United States (1999).
De Lau, W. and Clevers, H., "LEF1 turns over a new leaf," Nature Genetics 28(1):pp. 3-4, Nature Publishing Group, United States (2001).
De Pascalis, R., et al., "Grafting of 'Abbreviated' Complementarity-Determining Regions Containing Specificity-Determining Residues Essential for Ligand Contact to Engineer a Less Immunogenic Humanized Monoclonal Antibody," Journal of Immunology 169(6):3076-3084, The American Association of Immunologists, United States (2002).
Dealmeida, V.I., et al., "The Soluble Wnt Receptor Frizzled8CRD-hFc Inhibits the Growth of Teratocarcinomas In vivo," Cancer Research 67(11):5371-5379, American Association for Cancer Research, United States (2007).
Decypher ClustalW Multiple Alignment, Stanford University (online, Sep. 2006), accessed at http://web.archive.org/web/20060912071608/http://www2.stanford.edu/~musse/genealigns/mhfzalign.html>, accessed on Sep. 30, 2010.
Donnelly, J., "Cancer vaccine targets leukemia," Nature Medicine 9(11):1354-1356, Nature Publishing Company, United States (2003).
Dorvillius, M., et al., "Targeting of Human Brest Cancer by a Bispecific Antibody Directed against Two Tumour-Associated Antigens: ErbB-2 and Carcinoembryonic Antigen," Tumor Biology 23(6):337-347, Springer, Netherlands (2002).
English language Abstract of World Patent Publicaiton No. WO0200576A1, European Patent Office, espacenet database—Worldwide, (2002).
Ezzel, C., "Cancer 'Vaccines': An Idea Whose Time Has Come?," Journal of NIH Research 7:46-49, National Institutes of Health, United States (1995).
Fillmore, C.M., and Kuperwasser, C., et al., "Human breast cancer cell lines contain stem-like cells that self-renew, give rise to phenotypically diverse progeny and survive chemotherapy," Breast Cancer Research 10(2):R25, (2008).
Finch, P.W., et al., "Purification and molecular cloning of secreted, Frizzled-related antagonist of Wnt action," Proceedings of the National Academy of Sciences 94(13):6770-6775, The National Academy of Sciences, United States (1997).
Fogel, M. et al., "L1 expression as a predictor of progression and survival in patients with uterine and ovarian carcinomas," The Lancet 362(9387):869-875, Elsevier Inc., Netherlands (2003).
Forni, G., et al., "Immunoprevention of Cancer: Is the Time Ripe?," Cancer Research 60(10):2571-2575, American Association for Cancer Research, United States (2000).
Fredriksson, R., et al., "The G-Protein-Coupled Receptors in the Human Genome Form Five Main Families, Phylogenetic Analysis, Paralogon Groups, and Fingerprints," Molecular Pharmacology 63(6):1256-1272. The American Society for Pharmacology and Experimental Therapeutics, United States (2003).
"Frizzled 4 precursor (Frizled-4) (Fz-4) (hFz4) (FzE4)." [online], Sep. 2005, Accession Q9ULV1, Retrieved on Feb. 1, 2013 from http://www.ncbi.nlm.nih.gov/protein/62298045?sat=34&satkey=4861841.
"Frizzled 8 precursor (Frizled 8) (Fz-8) (hFz8)." [online], Sep. 2005, Accession Q9H461, Retrieved on Feb. 1, 2013 from http://www.ncbi.nlm.nih.gov/protein/17433053?sat=34 & satkey=5096022.
"Frizzled Antibody (H-300): sc-9169" accessed at http://scbt.com/datasheet-9169-frizzled-h-300-antibody.html, accessed on Mar. 20, 2015, 6 pages.

Fukukawa, C., et al., "Radioimmunotherapy of human synovial sarcoma using a monoclonal antibody against FZD10," Cancer Science 99(2):432-440, Wiley-Blackwell, United States (2008).
Gaudio, A., et al., "Increased Sclerostin Serum Levels Associated with Bone Formation and Resorption Markers in Patients with Immobilization-Induced Bone Loss," The Journal of Clinical Endocrinology and Metabolism 95(5):2248-2253, The Endocrine Society, United States (2010).
Gavert, N., et al., "L1, a novel target of β-catenin signaling, transforms cells and is expressed at the invasive front of colon cancers," Journal of Cell Biology 168(4):633-642, The Rockefeller University Press, United States (2005).
Gazit A., et al., "Human Frizzled 1 Interacts with Transforming Wnts to Transduce a TCF Dependent Transcriptional Response," Ocogene 18(44):5959-5966, Nature Publishing Group, England (1999).
GenBank, "Alkaline phosphatase [Pseudotermotoga lettingae TMO]," Accession No. ABV34137, Accessed at http://www.ncbi.nlm.nih.gov/protein/ABV34137, Accessed on May 13, 2015, 2 pages.
GenBank, "Hypothetical protein BarnMEX5DRAFT_6767 [Burkholderia ambifaria MEX-5]," Accession No. EDT37460, Accessed at http://www.ncbi.nlm.nih.gov/protein/EDT37460, Accessed on May 13, 2015, 1 page.
GenBank, "Hypothetical protein, conserved, partial [Trypanosoma cruzl]," Accession No. EAN81721, Accessed at http://www.ncbi.nlm.nih/gov/protein/EAN81721, Accessed on May 13, 2015, 2 pages.
Goan, T., et al., "The Human Frizzled 6 (HFz6) Acts as a Negative Regulator of the Canonical Wnt. β-Catenin Signaling Cascade,", The Journal of Biological Chemistry, 279(15):14879-14888, American Society for Biochemistry and Molecular Biology, United States (2004).
Gore, L., et al., "Safety, pharmacokinetics, and pharmacodynamics results from a phase I trial of BAY 86-9766 (RDEA119), a MEK inhibitor, in patients with advanced cancer," J Clin Oncol 29:2 pages, presented at the 2011 ASCO Annual Meeting, American Society of Clinical Oncology, United States (2011) (Abstract 3007).
Greenspan, N.S. and Di Cera, E., "Defining Epitopes: It's not as Easy as it Seems," Nature Biotechnology 17(10):936-937, Nature Publising Group, United States (1999).
Gregorieff, A., et al., "Expression Pattern of Wnt Signaling Components in the Adult Intestine," Gastroenterology 129(2):626-638, American Gastroenterological Association, United States (2005).
Greiner, D.L., et al., "SCID Mouse Models of Human Stem Cell Engraftment," Stem Cells 16(3):166-177, AlphaMed Press, United States (1998).
Guo, H.H., et al., "Protein tolerance to random amino acid change," Proceedings of the National Academy of Sciences, 101(25):9205-9210, The National Academy of Sciences, United States (2004).
Gurney, A., et al., "Wnt pathway inhibition via the targeting of Frizzled receptors results in decreased growth and tumorigenicity of human tumors," Proceedings of the National Academy of Sciences of the United States of America 109(29):11717-11722, National Academy of Sciences, United States (2012).
Guyre, PM et al., "Increased potency of Fc-receptor-targeted antigens," Cancer Immunology, Immunotherapy 45(3-4):146-148, Springer International, Germany (1997).
Harada, N., et al., "Intestinal Polyposis in Mice with a Dominant Stable Mutation of the β-catenin Gene," European Molecular Biology Organization Journal 18(21):5931-5942, Wiley-Blackwell, Inc., England (1999).
He, X. and Axelrod, J.D., "A WNTer wonderland in Snowbird," Develpment 133(14):2597-2603, The Company of Biologists, United States (2006).
He, X., et al., "LDL Receptor-related Proteins 5 and 6 in WNT/beta-catenin Signaling: Arrows Point the Way," Development 131(8):1663-1677, Company of Biologists Limited, England (2004).
Hering, H., et al., "Direct interaction of Frizzled-1, -2, -4 and -7 with PDZ domains of PSD-95," FEBS Letters 521:185-189, Elsevier, Netherlands (2002).

(56) References Cited

OTHER PUBLICATIONS

Hicks, et al., "Fringe differentially modulates Jagged1 and Delta1 signalling through Notch1 and Notch2," Nature Cell Biology 2(8):515-520, Macmillan Magazines Ltd, England (2000).
Hill, R.P., "Identifying cancer stem cells in solid tumors: case not proven," Cancer Research 66:1891-1896, American Association for Cancer Research, United States (2006).
Holcombe, R.F., et al., "Expression of Wnt ligands and Frizzled receptors in colonic mucosa and in colon carcinoma," Journal of Clinical Pathology—Molecular Pathology 55(4):220-226, BMJ Publishing Group, England (2002).
Holm, P., et al., "Functional Mapping and Single Chain Construction of the Anti-Cytokeratin 8 Monoclonal Antibody TS1," Molecular Immunology 44(6):1075-1084, Pergamon Press, England (2007).
Holmes, E.H., "PSMA specific antibodies and their diagnostic and therapeutic use," Expert Opinion on Investigational Drugs 10(3):511-519, Informa Pharmaceutical Science, United Kingdom (2001).
Hsieh. A.C., et al., "Targeting HER proteins in cancer therapy and the role of the non-target HER3," British Journal of Cancer 97(4):453-457, Cancer Research, United Kingdom (2007).
Hsieh, Jen-Chih, et al., "Biochemical characterization of Wnt-Frizzled interactions using a soluble, biologically active vertebrate Wnt protein," Proceedings of the National Academy of Sciences of the United States of America 96(7):3546-3551, National Academy of Sciences, United States (1999).
Hu, T. and Li, C., "Convergence between Wnt-beta-catenin and EGFR signaling in cancer," Molecular Cancer 9:236-242, BioMed Central Ltd., United States (2010).
Huang, H-C., and Klein, P.S., "The Frizzled family: receptors for multiple signal trasduction pathways," Genome Biology 5(7):234. 1-234.7, BioMed Central Ltd. (Jun. 2004).
Ilyas, M., "Wnt signalling and the mechanistic basis of tumour development," Journal of Pathology 205(2):130-144, Wiley Online Library, Ireland (2005).
International Search Report for International Application No. PCT/US09/58635, ISA/US, Alexandria, VA, mailed on Nov. 19, 2010.
International Search Report for International Application No. PCT/US14/68097, United States Patent and Trademark Office, United States, mailed on Apr. 30, 2015, 10 pages.
International Search Report for International Application No. PCT/US2012/068351, US Patent Office, Virginia, mailed on May 24, 2013, 7 pages.
International Search Report for International Application No. PCT/US2014/014443, United States Patent and Trademark Office, United States, mailed on Apr. 15, 2014, 4 pages.
International Search Report for International Patent Application No. PCT/US11/30950, ISA/US, Alexandria, Virginia 22313-1450, mailed on Oct. 18, 2011.
International Search Report of the International Searching Authority for International Application No. PCT/US07/005443, mailed on Oct. 30, 2008, United States Patent and Trademark Office, United States, 4 pages.
International Search Report of the International Searching Authority for International Application No. PCT/US11/20994, mailed on Aug. 15, 2011, United States Patent and Trademark Office, United States, 4 pages.
International Search Report of the International Searching Authority for International Application No. PCT/US13/66087 mailed on Jan. 16, 2014, United States Patent and Trademark Office, United States, 5 pages.
Ishikawa, T., et al., "Mouse Wnt receptor gene Fzd5 is essential for yolk sac and placental angiogenesis," Development 128(1):25-33, Company of Biologists Limited, England (2001).
Ishitani, T., et al., "The TAK1-NLK Mitogen-Activated Protein Kinase Cascade Functions in the Wnt-5a/Ca2+ Pathway to Antagonize Wnt/β-Catenin Signaling," Molecular and Cellular Biology 23(1):131-139, American Society for Microbiology, United States (2003).
Iverson, C., et al., "RDEA119/BAY 869766: A Potent, Selective, Allosteric Inhibitor of MEK1/2 for the Treatment of Cancer," Cancer Research 69:6839-6847, American Association for Cancer Research, United States (2009).
Jamieson, C.H.M., et al., "Granulocyte-Macrophage Progenitors as Candidate Leukemic Stem Cells in Blast-Crisis CML," The New England Journal of Medicine 351(7):657-667, Massachusetts Medical Society, United States (2004).
Janssens, N., et al., "Alteration of Frizzled Expression in Renal Cell Carcinoma," Tumor Biology 25(4):161-171, Springer, Netherlands (2004).
Jiang, B., et al, "A Novel Peptide Isolated from a Phage Display Peptide Library with Trastuzumab Can Mimic Antigen Epitope of HER-2," The Journal of Biological Chemistry 280(6):4656-4662, The American Society for Biochemistry and Molecular Biology (2005).
Jimeno, A., et al., "A first-in-human phase 1 study of anticancer stem cell agent OMP-54F28 (FZD-Fc), decoy receptor for WNT ligands, in patient with advanced solid tumors," 2014 ASCO Annual Meeting, Abstract 2505, 2 pages (2014).
Joesting, M.S., et al., "Identification of SFRP1 as Candidate Mediator of Stromal-to-Epithelial Signaling in Prostate Cancer," Cancer Research 65(22):10423-10430, The American Association for Cancer Research, United States (2005).
Johnson, M.L., et al., "LRP5 and Wnt Signaling: A Union Made for Bone," Journal of Bone Mineral Research 19(11):1749-1757, The American Society for Bone and Mineral Research, United States (2004).
Jones, D.T., "Critically assessing the state-of-the-art in protein structure prediction," Pharmacogenomics Journal 1(2):126-134, Nature Publishing Group, United States (2001).
Jonsson, M., et al., "Involvement of adenomatous polyposis coli (APC)/β-catenin signalling in human breast cancer," European Journal of Cancer 36(2):242-248, Pergamon Press, England (2000).
Kabacik, S., et al., "Gene Expression Following Ionising Radiation: Identification of Biomarkers for Dose Estimation and Prediction of Individual Response," International Journal of Radiation Biology 67(2):115-129, Informa Healthcare, England (2011).
Katoh, M. and Katoh, M., "STAT3-Induced WNT5A Signaling Loop in Embryonic Stem Cells, Adult Normal Tissues, Chronic Persistent Inflammation, Rheumatoid Arthritis and Cancer (Review)," International Journal of Molecular Medicine 19(2):273-278, Spandidos Publications (2007).
Katoh, M. and Katoh, M., "WNT Signaling Pathway and Stem Cell Signaling Network," Clinical Cancer Research 13(14):4042-4045, The American Association for Cancer Research, United States (2007).
Katoh, M., "Molecular Cloning and Characterization of MFRP, a Novel Gene Encoding a Membrane-Type Frizzled-Related Protein," Biochemical and Biophysical Research Comunications 282(1):116-123, Academic Press, United States (2001).
Katoh, Y. and Katoh, M., "Comparative genomics on Fzd8 orthologs," Oncology Reports 13(15):993-997, D.A. Spandidos, Greece (2005).
Kawakami, Y., et al., "Involvement of Frizzled-10 in Wnt-7a signaling during chick limb development," Development Growth & Differentiation 42(6):561-569, Blackwell Publishing on behalf of the Japanese Society of Developmental Biologists, Japan (2000).
Kawano, Y. and Kypta, R., "Secreted antagonists of the Wnt signaling pathway," Journal of Cell Science 116(Pt13):2627-2634, The Company of Biologists Ltd, United Kingdom (2003).
Khan, N.I., et al., "Activation of Wnt/beta-Catenin Pathway Mediates Growth and Survival in B-cell Progenitor Acute Lymphoblastic Leukaemia," British Journal of Haematology 138(3):338-348, Wiley-Blackwell, England (2007).
Kim, D., et al., "A Hidden Oncogenic Positive Feedback Loop Caused by Crosstalk between Wnt and ERK Pathways," Oncogene 26:4571-4579, Nature Publishing Group, England (2007).
Kirikoshi, H., et al., "Expression profiles of 10 members of Frizzled gene family in human gastric cancer," International Journal of Oncology 19(4):767-771, D.A. Spandidos, Greece (2001).

(56) References Cited

OTHER PUBLICATIONS

Kirikoshi, H., et al., "Molecular Cloning and Characterization of Human Frizzled-4 on Chromosome 11q14-q21," Biochemical and Biophysical Research Communications 264(3):955-961, Academic Press, United States (1999).

Kirikoshi, H., et al., "Molecular Cloning and Genomic Stricture of Human Frizzled-3 at Chromosome 8p21," Biochemical and Biophysical Research Communications 271(1):pp. 8-14, Academic Press, United States (2000).

Kirikoshi, H., et al., "Up-regulation of Frizzled-7 (FZD7) in human gastric cancer," International Journal of Oncology 19(1):111-115, D.A. Spandidos, Greece (2001).

Kirikoshi K., et al., "Expression of WNT10A in human cancer," International Journal of Oncology, 19(5):997-1001, Spandidos Publications, Greece (2001).

Kirkin A.F., et al., "Melanoma-associated antigens recognized by cytotoxic T lymphocytes," Acta Pathologica, Microbiologica et Immunologica Scandinavica 106(7):665-679, Munksgaard, Denmark (1998).

Klaus, A. and Birchmeier, W., "Wnt signaling and its impact on development and cancer," Nature Reviews/Cancer 8(5):387-398, Nature Publishing Group, United States (2008).

Kobielak A. and Fuchs E., "α-Catenin: at the junction of intercelullar adhesion and actin dynamics," Nature Reviews Molecular Cell Biology 5(8):614-625, Nature Publishing Group, England (2004).

Koike, J., et al., "Molecular Cloning of Frizzled-10, a Novel Member of the Frizzled Gene Family," Biochemical and Biophysical Research Communications 262(1):39-43, Academic Press, United States (1999).

Korinek, V. et al., "Two Members of the Tcf Family Implicated in Wnt/β-catenin Signaling during Embryogenesis in the Mouse," Molecular and Cellular Biology 18(3):1248-1256, American Society for Microbiology, United States (1998).

Krishnan, V., et al., "Regulation of Bone Mass by Wnt Signaling," The Journal of Clinical Investigation 116(5):1202-1209, American Society for Clinical Investigation, United States (2006).

Kuhnert, F., et al., "Essential Requirement for Wnt Signaling in Proliferation of Adult Small Intestine and Colon Revealed by Adenoviral Expression of Dickkopf-1," Proceedings of the National Academy of Sciences 101(1):266-271, The National Academy of Sciences, United States (2004).

Lazar, E., et al., "Transforming Growth Factor α: Mutation of Aspartic Acid 47 and Leucine 48 Results in Different Biological Activities," Molecular and Cellular Biology 8(3):1247-1252, American Society for Microbiology, United States (1988).

Le, P.N., et al., "Targeting the Wnt pathway in human cancers: Therapeutic targeting with a focus on OMP-54F28," Pharmacology & Therapeutics 146:1-11, Elsevier Inc., United States (2015).

Lee, H.X., et al., "Embryonic Dorsal-Ventral Signaling: Secreted Frizzled-related Proteins as Inhibitors of Tolloid Proteinases," Cell 124(1):147-159, Elsevier Inc., Netherlands (2006).

Lee, K.H., et al., "Increased Vaccine Specific T cell Frequency after Peptide Based Vaccination Correlates with Increased Susceptibility to in Vitro Stimulation but Does Not Lead to Tumor Regression," The Journal of Immunology 163(11):6292-6300, The American Association of Immunologists, United States (1999).

Lepourcelet, M., et al., "Small-molecule antagonists of the oncogenic Tcf/β-catenin protein complex," Cancer Cell 5(1):91-102, Cell Press, United States (2004).

Li, Y., et al., "Evidence That Transgenes Encoding Components of the Wnt Signaling Pathway Preferentially Induce Mammary Cancers from Progenitor Cells," Proceedings of the National Academy of Sciences 100(26):15853-15858, National Academy of Sciences, United States (2003).

Li, Y., et al., "LRP6 Expression Promotes Cancer Cell Proliferation and Tumorigenesis by Altering Beta-Catenin Subcellular Distribution," Oncogene 23(56):9129-9135, Nature Publishing Group, England (2004).

Li, Y., et al., "The Gene for Autosomal Dominant Familial Exudative Vitreoretinopathy (Criswick-Schepens) on the Long Arm of Chromosome 11," American Journal of Ophthalmology 113(6):712-713, Elsevier Inc., Netherlands (1992).

Lin, S.Y. et al., "β-catenin, a novel prognostic marker for breast cancer: its roles in cyclin D1 expression and cancer progression," Proceedings of the National Academy of Sciences of the United States of America 97(8):4262-4266, National Academy of Sciences, United States (2000).

Liu, S., et al., "Interaction of Hedgehog and Notch Pathways, and Bmi-1 in the Regulation of Human Breast Stem Cell Self-Renewal," Proceedings of the American Association for Cancer Research 46: Abstract #2043, The Regents of the University of Michigan, United States (2005).

Lo, P.K., et al., "Epigenetic Suppression of Secreted Frizzled Related Protein 1 (SFRP1) Expression in Human Breast Cancer," Cancer Biology & Therapy 5(3):e1-e6, Landes Bioscience, Austin, United States (2006).

Lo, P.K., et al., "Epigenetic Suppression of Secreted Frizzled Related Protein 1 (SFRP1) Expression in Human Breast Cancer" Cancer Biology & Therapy 5(3):281-286, Landes Bioscience, United States (2006).

Lodygin, D., et al., "Functional Epigenomics Identifies Genes Frequently Silenced in Prostate Cancer," Cancer Research 65(10):4218-4227, The American Association for Cancer Research, United States (2005).

Lu, C., et al., "The Binding Sites for Competitive Antagonistic, Allosteric Antagonistic, and Agonistic Antibodies to the I Domain of Integrin LFA-1," The Journal of Immunology 173(6):3972-3978, American Society of Immunologists, Inc., United States (2004).

Lu, D., et al., "Repression of β-catenin function in malignant cells by nonsteroidal antiinflammatory drugs," Proceedings of the National Academy of Sciences of the United States of America 102(51):18567-18571, The National Academy of Sciences, United States (2005).

Luu, H.H., et al., "Wnt/beta-Catenin Signaling Pathway as Novel Cancer Drug Targets," Current Cancer Drug Targets 4:653-671, Bentham Science Publishers, Netherlands (2004).

Lyons, J.P., et al., "Wnt-4 activates the canonical β-catenin-mediated Wnt pathway and binds Frizzled-6 CRD: functional implications of Wnt/β-catenin activity in kidney epithelial cells," Experimental Cell Research 298(2):369-387, Elsevier Inc., United States (2004).

Maccallum, R.M., et al., "Antibody-Antigen Interactions: Contact Analysis and Binding Site Topography," Journal of Molecular Biology 262(5):732-745, Elsevier, England (1996).

Macleod, R.J., et al., "Wnt5a Secretion Stimulated by Extracellular Calcium-Sensing Receptor Inhibits Defective Wnt Signaling in Colon Cancer Cells," American Journal of Physiology: Gastrointestinal and Liver Physiology 293(1):G403-G411, American Physiological Society, United States (2007).

Mazieres, J., et al., "Wnt signaling in lung cancer," Cancer Letters 22(1);pp. 1-10,Elsevier Science Ireland, Ireland (2005).

Merle, P., at el., "Functional consequences of frizzled-7 receptor overexpression in human hepatocellular carcinoma," Gastroenterology 127(4):1110-1122, The American Gastroenterological Assocation, Elsevier, United States (2004).

Miele, L. and Osborne, B., "Arbiter of Differentiation and Death: Notch Signaling Meets Apoptosis," Journal of Cellular Physiology 181(3):393-409, Wiley-Liss, Inc., United States (1999).

Miller, J.R., et al., "Mechanism and Function of Signal Transduction by the Wnt/β-catenin and Wnt/Ca2+ Pathways," Oncogene 18(55):7860-7872, Nature Publishing Group, England (1999).

Milovanovic, T., et al., "Expression of Wnt Genes and Frizzled 1 and 2 Receptors in Normal Breast Epithelium and Infiltrating Breast Carcinoma," International Journal of Oncology 25(5):1337-1342, D.A. Spandidos, Greece (2004).

Moon, R.T., "Wnt/β-Catenin Pathway," Signal Transduction Knowledge Environment 271, pp. 1-3, The American Association for the Advancement of Science, United States (2005).

Morrell, N.T., et al., "Liposomal Packaging Generates Wnt protein with In Vivo Biological Activity," PLoS ONE 3(8):e2930, Public Library of Science (PLoS), United States (2008).

(56) References Cited

OTHER PUBLICATIONS

Murdoch, B., et al., "Wnt-5A augments repopulating capacity and primitive hemaropoietic development of human blood stem cells in vivo," Proceedings of the National Academy of Sciences of the United States of America 100(6):3422-3427, The National Academy of Sciences, United States (2003).
Nagayama, S., et al., "Therapeutic potential of antibodies against FZD10, a cell-surface protein, for synovial sarcomas," Oncogene 24(41):6201-6212, Nature Publishing Group, England (2005).
Nunnally, A.P., and Parr, B.A., "Analysis of Fz10 expression in mouse embryos," Development Genes and Evolution 214(3):144-148, Springer-Verlag, Germany (2004).
Nusse, R. et al., "A New Nomenclature for Int-1 and Related Genes: The Wnt Gene Family," Cell 64(2):231-232, Cell Press, United States (1991).
Nusse, R., "The Wnt gene family in tumorigenesis and in normal development," Journal of Steriod Biochemistry & Molecular Biology 43(1-3):pp. 9-12, Elsevier Ltd, England (1992).
O'Connell, M.P. and Weeraratna, A.T., "Hear the Wnt Ror: how melanoma cells adjust to changes in Wnt," Pigment Cell & Melanoma Research 22:724-739, Blackwell Munksgaard, England (2009).
Olson, D.J. and Gibo, D.M., "Antisense wnt-5a Mimics wnt-1-Mediated C57MG Mammary Epithelial Cell Transformation," Experimental Cell Research 241(1):134-141,Academic Press, United States (1998).
OncoMed Pharmaceuticals Press Release, "OncoMed Announces Abstracts Accepted at the 2014 ASCO Annual Meeting," Apr. 23, 2014, 2 pages.
OncoMed Pharmaceuticals Press Release, "OncoMed Pharmaceuticals Announces FDA Clearance to Commence Phase 1 Testing of Anti-Cancer Stem Cell Therapeutic OMP-18R5," Apr. 28, 2011, 2 pages.
OncoMed Pharmaceuticals Press Release, "OncoMed Pharmaceuticals Commences Third Phase 1b Clinical Trial for OMP-54F28 (Fzd8-Fc) With Carboplatin and Paclitaxel in Ovarian Cancer," Feb. 20, 2014, 3 pages.
OncoMed Pharmaceuticals Press Release, "OncoMed Pharmaceuticals Initiates First Phase 1b Clinical Trial of First-in-Class WNT-Pathway-Targeting Antibody Vantictumab (OMP-18R5) With Paclitaxel in Breast Cancer," Oct. 29, 2013, 3 pages.
OncoMed Pharmaceuticals Press Release, "OncoMed Pharmaceuticals Initiates First Phase 1b Clinical Trial of OMP-54F28 (Fzd8-Fc) With Nab-Paclitaxel (Abraxane(R)) and Gemcitabine in Pancreatic Cancer," Jan. 13, 2014, 3 pages.
OncoMed Pharmaceuticals Press Release, "OncoMed Pharmaceuticals Initiates Phase I Clinical Trial of Anti-Cancer Stem Cell Therapeutic OMP-54F28 (Fzd8-Fc)," Jul. 12, 2012, 2 pages.
OncoMed Pharmaceuticals Press Release, "OncoMed Pharmaceuticals Initiates Second Phase 1b Clinical Trial for OMP-54F28 (Fzd8-Fc) With Sorafenib (Nexavar(R)) in Hepatocellular Cancer," Feb. 18, 2014, 3 pages.
OncoMed Pharmaceuticals Press Release, "OncoMed Pharmaceuticals Initiates Second Phase 1b Clinical Trial of First-in-Class WNTPathway-Targeting Antibody Vantictumab (OMP-18R5) With Docetaxel in Non-Small Cell Lung Cancer (NSCLC)," Nov. 15, 2013, 3 pages.
OncoMed Pharmaceuticals Press Release, "OncoMed Pharmaceuticals Initiates Third Phase 1b Clinical Trial of First-in-Class WNTPathway-Targeting Antibody Vantictumab (OMP-18R5) With Nab-Paclitaxel (Abraxane®) and Gemcitabine in Stage IV Pancreatic Cancer," Dec. 4, 2013, 3 pages.
OncoMed Pharmaceuticals Press Release, "OncoMed Pharmaceuticals Presents Data From Clinical Trials of Four Novel Anti-Cancer Stem Cell (Anti-CSC) Therapeutics at the AACR-NCI-EORTC International Conference on Molecular Targets and Cancer Therapeutics in Boston, Oct. 19-23, 2013," Oct. 21, 2013, 4 pages.
OncoMed Pharmaceuticals Press Release, "OncoMed Pharmaceuticals Presents Phase 1 Data in Solid Tumor Patients for the First-in-Class Wnt Pathway Targeting Antibody Vantictumab (OMP-18R5) at ASCO," Jun. 3, 2013, 2 pages.
OncoMed Pharmaceuticals Press Release, "OncoMed Pharmaceuticals Presents Updated Phase 1 Data in Advanced Solid Tumor Patients for the First-in-Class WNT-Pathway-Targeting Antibody Vantictumab (OMP-18R5) at the European Cancer Congress 2013," Sep. 29, 2013, 3 pages.
OncoMed Pharmaceuticals Press Release, "OncoMed Pharmaceuticals Recaps New Data Presented at AACR," Apr. 3, 2012, 2 pages.
OncoMed Pharmaceuticals Press Release, "OncoMed Pharmaceuticals to Present Data From Clinical Trials of Four Novel Anti-Cancer Stem Cell (Anti-CSC) Therapeutics in Five Posters at the AACR-NCI-EORTC International Conference on Molecular Targets and Cancer Therapeutics in Boston, Oct. 19-23, 2013," Oct. 14, 2013, 4 pages.
OncoMed Pharmaceuticals Press Release, "OncoMed Pharmaceuticals Presents Phase 1a Data in Advanced Solid Tumor Patients for the First-in-Class WNT-Pathway-Targeting Antibody Vantictumab (OMP-18R5) at European Cancer Congress 2013 (ECC 2013)," Sep. 23, 2013, 2 pages.
OncoMed Pharmaceuticals Press Release, "OncoMed Pharmaceuticals Presents Data on Clinical and Preclinical Anti-Cancer Stem Cell Programs at American Association for Cancer Research Annual Meeting," Apr. 21, 2015, 3 pages.
OncoMed Pharmaceuticals, Press Release, "OncoMed Presents Data on Multiple Anti-Cancer Stem Cell Programs at American Association for Cancer Research Annual Meeting," Apr. 8, 2014, 4 pages.
OncoMed Pharmaceuticals Press Release, "OncoMed Presents New Data in Six Anti-Cancer Stem Cell Programs at AACR," Apr. 9, 2013, 3 pages.
OncoMed Pharmaceuticals Press Release, "OncoMed Provides Update on FZD8-Fc (OMP-54F28) Phase I Clinical Trials," Jun. 18, 2014, 2 pages.
OncoMed Pharmaceuticals Press Release, "OncoMed to Present Data From Three Clinical Studies at the 2014 ASCO Annual Meeting," May 14, 2014, 4 pages.
OncoMed Pharmaceuticals Press Release, "OncoMed to Present Data on Multiple Anti-Cancer Stem Cell Candidates at the American Association of Cancer Research Meeting," Mar. 19, 2015, 2 pages.
OncoMed Pharmaceuticals Press Release, "OncoMed to Present New Data in Six Anti-Cancer Stem Cell Programs at AACR," Apr. 2, 2013, 2 pages.
OncoMed Pharmaceuticals Press Release, "PNAS Publishes OncoMed Data Demonstrating Potent Anti-Cancer Activity for Novel Wnt Pathway Antibody OMP-18R5," Jul. 3, 2012, 2 pages.
Oshima, H., et al., "Morphological and Molecular Processes of Polyp Formation in ApcΔ716 Knockout Mice," Cancer Research 57(9):1644-1649, The American Association for Cancer Research, United States (1997).
Patel, S., et al., "Glycogen synthase kinase-3 in insulin and Wnt signalling: a double-edged sword?," Biochemical Society Transactions 32(pt5):803-808, Portland Press Ltd., United Kingdom (2004).
Pinto, D. and Clevers, H., "Wnt control of stem cells and differentiation in the intestinal epithelium," Experimental Cell Research 306(2):357-363,Academic Press, United States (2005).
Polakis, P., "Evidence for Wnt Signaling in Cancers lacking Genetic Defects," PowerPoint NYAS Presentation and transcript, presented on Oct. 25, 2005, 71 pages.
Polakis, P., "Wnt signaling and cancer," Genes & Development 14:1837-1851, Cold Spring Harbor Laboratory Press, United States (2000).
Radtke, F. and Clevers, H., "Self-Renewal and Cancer of the Gut: Two sides of a Coin," Science 307(5717):1904-1909, The Company of Biologists Ltd, United Kingdom (2005).
Reya, T. and Clevers, H., "Wnt signalling in stem cells and cancer," Nature 434(7035):843-850, Nature Publishing Group, United States (2005).
Reya, T., et al., "A role for Wnt signalling in self-renewal of haematopoietic stem cells," Nature 423(6938):409-414, Nature Publishing Group,England (2003).

(56) References Cited

OTHER PUBLICATIONS

Reya, T., et al., "Stem Cells, Cancer, and Cancer Stem Cells," Nature 414(6859):105-111, Nature Publishing Group, England (2001).
Reya T., et al., "Wnt Signaling Regulates B Lymphocyte Proliferation through a LEF-1 Dependent Mechanism," Immunity 13(1):15-24, Cell Press, United States (2000).
Rhee, C.S., et al., "Wnt and frizzled receptors as potential targets for immunotherapy in head and neck squamous cell carcinomas," Oncogene 21(43):6598-6605, Nature Publishing Group, England (2002).
Rudikoff, S., et al., "Single Amino Acid Substitution Altering Antigen-Binding Specificity," Proceedings of the National Academy of Sciences 79(6):1979-1983, The National Academy of Sciences, United States (1982).
Sagara, N., et al., "FZD4S, a Splicing Variant of Frizzled-4, Encodes a Soluble-Type Positive Regulator of the WNT Signaling Pathway," Biochemical and Biophysical Research Communications 282(3):750-756, Academic Press, United States (2001).
Sagara, N., et al., "Molecular Cloning, Differential Expression, and Chromosomal Localization of Human Frizzled-1, Frizzled-2, and Frizzled-7," Biochemical and Biophysical Research Communications 252(1):117-122, Academic Press, United States (1998).
Saitoh, T. et al., "Frequent up-regulation of WNT5A mRNA in primary gastric cancer," Journal of Molecular Medicine 9(5):515-519, Spandidos Publications, Greece (2002).
Saitoh, T., et al., "Molecular cloning and characterization of human Frizzled-8 gene on chromosome 10p11.2," International Journal of Oncology 18(5);991-996, D.A. Spandidos, Greece (2001).
Saitoh, T., et al., "Up-regulation of Frizzled-10 (FZD10) by β-estradiol in MCF-7 cells and by retinoic acid in NT2 cells," International Journal of Oncology 20(1):117-120, D.A. Spandidos, Greece (2002).
Sala, C.F., et al., "Identification, Gene Structure, and Expression of Human Frizzled-3 (FZD3)," Biochemical and Biophysical Research Communications 273(1):27-34, Academic Press, United States (2000).
Saldanha, J., et al., "Identification of a Frizzled-like cysteine rich domain in the extracellular region of developmental receptor tyrosine kinases," Protein Science 798):1632-1635, The Protein Society, United States (1998).
Saneyoshi, T., et al., "The Wnt/calcium pathway activates NF-AT and promotes ventral cell fate in Xenopus embryos," Nature 417(6886):295-299, Nature Publishing Group, United States (2002).
Schulte, G. and Bryja, V., "The Frizzled family of unconventional G-protein-coupled receptors," Trends Pharmacol Science 28(10):518-525, Elsevier in Association With the International Union of Pharmacology, England (2007).
Schulte, G., "Frizzleds and WNT/beta-catenin Signaling—The Black Box of Ligand-receptor Selectivity, Complex Stoichiometry and Activation Kinetics," European Journal of Pharmacology, epub:1-5, Elsevier B.V., Netherlands (2015).
Schweizer, L. and Varmus, H., "Wnt/Wingless signaling through β-catenin requires the function of both LRP/Arrow and frizzled classes of receptors," BMC Cell Biology 4:4, BioMed Central Ltd., United Kingdom (2003).
Semba, S., et al., "Nuclear Accumulation of B-Catenin in Human Endocrine Tumors: Association with Ki-67 (MIB-1) Proliferative Activity," Endocrine Pathology 11(3):243-250, Humana Press, United States (2000).
Semenov, M., et al., "SOST Is a Ligand for LRP5/LRP6 and a Wnt Signaling Inhibitor," The Journal of Biological Chemistry 280(29):26770-26775, American Society for Biochemistry and Molecular Biology, United States (2005).
Sen, M., et al., "Blockade of Wnt-5A/Frizzled 5 Signaling Inhibits Rheumatoid Synoviocyte Activation," Arthritis Rheumatology 44(4):772-781, Arthritis Foundation, United States (2001).
Shalaby, M.R., et al., "Bispecific HER X CD3 Antibodies Enhance T-Cell Cytotoxicity in Vitro and Localize to HER2-Overexpressing Xenografts in Nude Mice," Journal of Clinical Immunology and Immunopathology 74(2):185-192, Elsevier Inc., Netherlands (1995).
Skolnick, "From Genes to Protein Structure and Function: Novel Applications of Computational Approaches in the Genomic Era," Trends in Biotechnology 18:34-39, Elsevier Science Publishers, London (2000).
Smith, D.C., et al., "A first-in-human Phase 1 study of anti-cancer stem cell (CSC) agent OMP-54F28 (FZD8-Fc) targeting the WNT pathway in patients with advanced solid tumors," AACR-NCI-EORTC International Conference on Molecular Targets and Cancer Therapeutics, Oct. 19-23, 2013, Abstract B79, 1 page (2013).
Smith, D.C., et al., "Biomarker analysis in the first-in-human Phase 1a study for vanticumab (OMP-18R5; anti-Frizzled) demonstrates pharmacodynamics (PD) modulation of the Wnt pathway in patients with advanced solid tumors," AACR-NCI-EORTC International Conference on Molecular Targets and Cancer Therapeutics in Boston, Oct. 19-23, 2013, Poster 823, 1 page (2013).
Sperger, J.M., et al., "Gene expression patterns in human ebryonic stem cells and human pluripotent germ cell tumors," Proceedings of the National Academy of Sciences of the United States of America 100(23):13350-13355, The National Academy of Sciences, United States (2003).
Supplementary European Search Report for Application No. 07752161, European Patent Office, Netherlands, mailed on Oct. 15, 2009.
Suresh M.R. et al., "Advantages of bispecific hybridomas in one-step immunocytochemistry and immunoassays," Neurobiology, Proceedings of the National Academy of Sciences of the United States of America 83(20):7989-7993, The National Academy of Science, United States (1986).
Suzuki, H., et al., "A genomic screen for genes unregulated by demethylation and histone deacetylase inhibition in human colorectal cancer," Nature Genetics 31(2):141-149, Nature Publishing Group, United States (2002).
Suzuki, H., et al., "Epigentic inactivation of SFRP genes allows constitutive WNT signaling in colorectal cancer," Nature Genetics 36(4):417-422, Nature Publishing Group, United States (2004).
Suzuki, H., et al., "Frequent Epigenetics Inactivation of Wnt Antagonist Genes in Breast Cancer," British Journal of Cancer 98(6):1147-1156, Nature Publishing Group, United States (2008).
Tamura, M., et al., "Structural Correlates of an Anticarcinoma Antibody: Identification of Specificity-Determing Residues (SDRs) and Development of a Minimally Immunogenic Antibody Variant by Retention of SDRs Only," The Journal of Immunology 164(3):1432-1441, American Association of Immunologists, United States (2000).
Tanaka, S., et al., "A novel frizzled gene identified in human esophageal carcinoma mediates APC/β-catenin signals," Proceedings of the National Academy of Sciences of the United States of America 95(17):10164-10169, National Academy of Sciences, United States (1998).
Terasaki, H., et al., "Frizzled-10, up-regulated in primary colorectal cancer, is a positive regulator of the WNT-β-catenin-TCF signaling pathway," International Journal of Molecular Medicine 9(2):107-112, D.A. Spandidos, Greece (2002).
Tokuhara, M., et al., "Molecular Cloning of Human Frizzled-6," Biochemical and Biophysical Research Communications 243(2):622-627, Academic Press, United States (1998).
Topol, L., et al., "Wnt-5a inhibits the canonical Wnt pathway by promoting GSK-3-independent β-catenin degradation," The Journal of Cell Biology 162(5):899-908, The Rockefeller University Press, United States (2003).
Tosatto, S.C.E. and Toppo, S., "Large-Scale Prediction of Protein Structure and Function from Sequence," Current Pharmaceutical Design 12(17):2067-2086, Bentham Science Publishers,Netherlands (2006).
Townsend, A. and Trowsdale, J., "The transporters associates with antigen presentation," Seminars in Cell Biology 4:53-61, Academic Press Limited, United States (1993).
Toyofuku, T., et al., "Wnt/frizzled-2 Signaling Induces Aggregation and Adhesion among Cardiac Myocytes by Increased Cadherin-β-

(56) References Cited

OTHER PUBLICATIONS

Catenin Complex," The Journal of Cell Biology 150(1):225-241, Rockefeller University Press, United States (2000).
Ueno, K., et al., "Frizzled homolog proteins, microRNAs and Wnt Signaling cancer," International Journal of Cancer 132(8):1731-1740, Wiley-Liss, United States (2013).
Umbhauer, M., et al., "The C-terminal cytoplasmic Lys-thr-X-X-X-trp motif in frizzled receptors mediates Wnt/β-catenin signaling," The EMBO Journal 19(18):4944-4954,Wiley Blackwell, England (2000).
UniProtKB Database, "Submitted name: Putative uncharacterized protein," Accession No. B7AJZ5, Accessed on May 13, 2015, 5 pages.
UniProtKB Database, "Submitted name: Helix-turn-helix protein," Accession No. A2W361, Accessed on May 13, 2015, 5 pages.
Unkeless, J.C., "Characterization of a Monoclonal Antibody Directed Against Mouse Macrophage and Lymphocyte Fc Receptors," The Journal of Experimental Medicine 150(3):580-596, The Rockefeller University Press, United States (1979).
Unknown Author, "Biotinylated Anti-mouse Fzd-2 Antibody,", 1 page, R&D Systems, dated Feb. 11, 2004, URL:http://www.rndsystems.com/pdf/baf1307.pdf, downloaded Sep. 27, 2012.
Unknown Author, "Purified Rat Anti-Mouse CD16/CD32 (Mouse BD Fc BlockTM)", Technical Data Sheet 553142 Rev. 16, 2 pages, BD Biosciences (copyright date 2006), URL:http://www.bdbiosciences.com/external_files/pm/doc/tds/mouse/live/web_enabled/01241D_553142.pdf.
Uren, A., et al., "Secreted Frizzled-related Protein-1 Binds Directly to Wingless and Is a Biphasic Modulator of Wnt Signaling," The Journal of Biological Chemistry 275(6):4374-4382, American Society for Biochemistry and Molecular Biology, United States (2000).
Uyttendaele, H., et al., "Notch4 and Wnt-1 Proteins Function to Regulate Branching Morphogenesis of Mammary Epithelial Cells in an Opposing Fashion," Develpmental Biology 196(2):204-217, Elsevier Inc., Netherlands (1998).
Vajdos, F.F., et al., "Comprehensive Functional Maps of the Antigen-Binding Site of an Anti-ErbB2 Antibody obtained with Shotgun Scanning Mutagenesis," Journal of Molecular Biology 320(2):415-428, Elsevier Science, United States (2002).
Van De Vijver, M. et al., "A gene-expression signature as a predictor of survival in breast cancer," The New England Journal of Medicine 347(25):1999-2009, Massachusetts Medical Society, United States (2002).
Van De Wetering, M. et al., "The β-catenin/TCF-4 complex imposes a crypt progenitor phenotype on colorectal cancer cells," Cell 111(2):241-250, Cell Press, United States (2002).
Van Den Berg, D.J., et al., "Role of Members of the Wnt Gene Family in Human Hematopoiesis," Blood 92(9):3189-3202, The American Society of Hematology, United States (1998).
Van Es, J.H., and Clevers, H., "Notch and Wnt Inhibitors as Potential New Drugs for Intestinal Neoplastic Disease," Trends in Molecular Medicine 11(11):496-502, Elsevier Inc., Netherlands (2005).
Van't Veer L.J., et al., "Gene expression profiling predicts clinical outcome of breast cancer," Nature 415(6871):530-536, Nature Publishing Group, England (2002).
Veeman, M.T., et al., "A Second Canon: Functions and Mechanisms of β-Catenin-Independent Wnt Signaling," Developmental Cell 5(3):367-377,Cell Press, United States (2003).
Vincan, E., et al., "Frizzled-7 receptor ectodomain expression in a colon cancer cell line induces morphological change and attenuates tumor growth," Differentiation 73(4):142-153, Elsevier, England (2005).
Voronkov, A., et al., "Molecular Model of the Wnt Protein Binding Site on the Surface of Dimeric CRD Domain of the hFzd8 Receptor," Doklady Biochemistry and Biophysics 419(5):75-78, Pleiades Publishing Ltd., Russia (2008).
Wang, Y., et al., "A Large Family of Putative Transmembrane Receptors Homologous to the Product of the *Drosophila* Tissue Polarity Gene frizzled," The Journal of Biological Chemistry 271(8):4468-4476, American Society for Biochemistry and Molecular Biology, United States (1996).
Wang, Y-K., et al., "Characterization and Expression Pattern of the frizzled Gene Fzd9, the Mouse Homolog of FZD9 which Is Deleted in Williams-Beuren Syndrome," Genomics 57(2):235-248, Academic Press, United States (1999).
Wang, Z., et al., "Wnt7b Activates Canonical Signaling in Epithelial and Vascular Smooth Muscle Cells through Interactions with Fzd1, Fzd10, and LRP5," Molecular and Cellular Biology 25(12):5022-5030, American Society for Microbiology, United States (2005).
Webb, T., "Work on Breast Cancer Stem Cells Raises Questions About Treatment Strategies," Journal of the National Cancer Institute. 95(11):774-775, (2003).
Weeraratna, A.T., et al., "Wnt5a signaling directly affects cell motility and invasion of metastatic melanoma," Cancer Cell 1(3):279-288, Cell Press, United States (2002).
Wheater, G., et al., "The clinical utility of bone marker measurements in osteoporosis," Journal of Tranlational Medicine 11(201):11 pages, BioMed Central Ltd, England (2013).
Willert, K. and Jones, K.A., "Wnt signaling: is the party in the nucleus?," Genes & Development 20(11):1394-1404, Cold Spring Harbor Laboratory Press, United States (2006).
Willert, K., et al., "Wnt proteins are lipid-modified and can act as stem cell growth factors," Nature 423(6938):448-452, Nature Publishing Group, United States (2003).
Wnt-3a COPE, (Online 2010), accessed on Oct. 1, 2010, accessed from http://www.copewithcytokines.de/cope.cgi?key=Wnt-3a paras 2 and 5.
Wong, N.A.C.S., and Pignatelli, M., "β-catenin—A Linchpin in Colorectal Carcinogenesis?, " American Journal of Pathology 160(2):389-401, American Society for Investigative Pathology, United States (2002).
Wong, S.C.C. et al., "Expression of frizzled-related protein and Wnt-signalling molecules in invasive human breast tumours," The Journal of Pathology 196(2):145-153, John Wiley and Sons, England (2002).
Wood, V., et al., "The genome sequence of Schizosaccharomyces pombe," Nature 415(6874):871-880, Nature Publishing Group, United Kingdom (2002).
Woodward, W.A., et al., "WNT/β-catenin mediates radiation resistance of mouse mammary progenitor cells," Proceedings of the National Academy of Sciences of the United States of America 104(2):618-623, The National Academy of Science, United States (2007).
Written Opinion for International Application No. PCT/US09/58635, ISA/US, Alexandria, VA, mailed on Nov. 19, 2010, 8 pages.
Written Opinion for International Application No. PCT/US14/68097, United States Patent and Trademark Office, United States, mailed on Apr. 30, 2015, 25 pages.
Written Opinion for the International Searching Authority for International Application No. PCT/US07/05443, mailed on Oct. 30, 2008, The International Bureau of WIPO, Switzerland, 4 pages.
Written Opinion for the International Searching Authority for International Application No. PCT/US11/20994, mailed on Aug. 15, 2011, International Searching Authority, United States, 7 pages.
Written Opinion for the International Searching Authority for International Application No. PCT/US13/66087 mailed on Jan. 16, 2014 The International Bureau of WIPO, Switzerland, 5 pages.
Written Opinion for the International Searching Authority for International Application No. PCT/US2014/014443, mailed on Apr. 15, 2014, International Searching Authority, United States, 17 pages.
Wu, C-H., and Nusse, R., "Ligand Receptor Interactions in the Wnt Signaling Pathway in *Drosophila*," The Journal of Biological Chemistry 277(44):41762-41769, American Society for Biochemistry and Molecular Biology, United States (2002).
Wu, H., et al., "Humanization of a Murine Monoclonal Antibody by Simultaneous Optimization of Framework and CDR Residues," Journal of Molecular Biology 294(1):151-162, Elsevier, England (1999).

(56) References Cited

OTHER PUBLICATIONS

Yamashita, J.K., et al., "Prospective identification of cardiac progenitors by a novel single cell-based cardiomyocyte induction," The FASEB Journal 19(11):29 pages, The Federation, United States (2005).

Yang P., et al., "Study design considerations in clinical outcome research of lung cancer using microarray analysis," Lung Cancer 46(2):215-226, Elsevier, Ireland (2004).

Yang-Snyder, J., et al., "A frizzled homolog functions in a vertebrate Wnt signaling pathway," Current Biology 6(10):1302-1306, Cell Press, United States (1996).

Yen, W-C., et al., "Enhanced anti-tumor effect of WNT pathway antagonists in combination with taxanes," AACR Annual Meeting Apr. 5-9, 2014, Abstract 4547, 1 page (2014).

Yeung, P et al., "Wnt pathway antagonist OMP-54F28 (FZD8-Fc) inhibits tumor growth and reduces tumor-initiating cell frequency in patient-derived hepatocellular carcinoma and ovarian cancer xenograft models," AACR Annual Meeting Apr. 5-9, 2014, Abstract 1907, 1 page (2014).

You, L., et al., "Wnt-1 signal as a potential cancer therapeutic target," Drug News Perspect 19(1):27-31, Thomson Reuters, United States (2006).

Zeng, X., et al., "A dual-kinase mechanism for Wnt co-receptor phosphorylation and activation," Nature 438(7069):873-877, Nature Publishing Group, England (2005).

Zhang, C., et al., "Predictive biomarker identification for response to vantictumab (OMP-18R5; anti-Frizzled) by mining gene expression data of human breast cancer xenografts," AACR Annual Meeting, Apr. 5-9, Abstract 2830, 1 page (2014).

Zhao, Z., et al., "A Human Homologue of the *Drosphila* Polarity Gene frizzled Has Been Identified and Mapped to 17q21.1," Genomics 27(2):370-373, Academic Press, United States (1995).

Zhu, A.J. and Watt F.M., "β-Catenin signaling modulates proliferative potential of human epidermal keratinocytes independently of intracellular adhesion," Development 126(10):2285-2298, Company of Biologists Limited, England (1999).

Non-Final Office Action mailed Dec. 23, 2014, in U.S. Appl. No. 13/005,214, Satyal, S.H., et al., filed Jan. 12, 2011.

\* cited by examiner

PN4

CONTROL

FZD8Fc

Gem

Gem + FZD8Fc

PN8

Control mAb

Gemcitabine

FZD8-Fc

FZD8-Fc + Gemcitabine

PN13

CONTROL　　　　　　　　　FZD8Fc

PN13

CONTROL　　　　　　　　　FZD8Fc

C28

Control    FZD8-Fc

PN21

Control mAb    FZD8-Fc

PN21

Control mAb

FZD8-Fc

Gemcitabine

FZD8-Fc + Gemcitabine

SEQUENCE LISTING

<160> NUMBER OF SEQ ID NOS: 76

<210> SEQ ID NO 1
<211> LENGTH: 361
<212> TYPE: PRT
<213> ORGANISM: Artificial Sequence
<220> FEATURE:
<223> OTHER INFORMATION: FZD8-Fc amino acid sequence-variant 54F03
      (without predicted signal)
<220> FEATURE:
<221> NAME/KEY: MISC_FEATURE
<223> OTHER INFORMATION: GRA linker sequence between the FZD8 sequence
      and the Fc sequence of the fusion protein

<400> SEQUENCE: 1

Ala Ser Ala Lys Glu Leu Ala Cys Gln Glu Ile Thr Val Pro Leu Cys
1               5                   10                  15

Lys Gly Ile Gly Tyr Asn Tyr Thr Tyr Met Pro Asn Gln Phe Asn His
            20                  25                  30

Asp Thr Gln Asp Glu Ala Gly Leu Glu Val His Gln Phe Trp Pro Leu
        35                  40                  45

Val Glu Ile Gln Cys Ser Pro Asp Leu Lys Phe Phe Leu Cys Ser Met
    50                  55                  60

Tyr Thr Pro Ile Cys Leu Glu Asp Tyr Lys Lys Pro Leu Pro Pro Cys
65                  70                  75                  80

Arg Ser Val Cys Glu Arg Ala Lys Ala Gly Cys Ala Pro Leu Met Arg
                85                  90                  95

Gln Tyr Gly Phe Ala Trp Pro Asp Arg Met Arg Cys Asp Arg Leu Pro
            100                 105                 110

Glu Gln Gly Asn Pro Asp Thr Leu Cys Met Asp Tyr Asn Arg Thr Asp
        115                 120                 125

Leu Thr Thr Gly Arg Ala Asp Lys Thr His Thr Cys Pro Pro Cys Pro
130                 135                 140

Ala Pro Glu Leu Leu Gly Gly Pro Ser Val Phe Leu Phe Pro Pro Lys
145                 150                 155                 160

Pro Lys Asp Thr Leu Met Ile Ser Arg Thr Pro Glu Val Thr Cys Val
                165                 170                 175

Val Val Asp Val Ser His Glu Asp Pro Glu Val Lys Phe Asn Trp Tyr
            180                 185                 190

Val Asp Gly Val Glu Val His Asn Ala Lys Thr Lys Pro Arg Glu Glu
        195                 200                 205

Gln Tyr Asn Ser Thr Tyr Arg Val Val Ser Val Leu Thr Val Leu His
    210                 215                 220

Gln Asp Trp Leu Asn Gly Lys Glu Tyr Lys Cys Lys Val Ser Asn Lys
225                 230                 235                 240

Ala Leu Pro Ala Pro Ile Glu Lys Thr Ile Ser Lys Ala Lys Gly Gln
                245                 250                 255

```
Pro Arg Glu Pro Gln Val Tyr Thr Leu Pro Pro Ser Arg Asp Glu Leu
            260                 265                 270
Thr Lys Asn Gln Val Ser Leu Thr Cys Leu Val Lys Gly Phe Tyr Pro
        275                 280                 285
Ser Asp Ile Ala Val Glu Trp Glu Ser Asn Gly Gln Pro Glu Asn Asn
    290                 295                 300
Tyr Lys Thr Thr Pro Pro Val Leu Asp Ser Asp Gly Ser Phe Phe Leu
305                 310                 315                 320
Tyr Ser Lys Leu Thr Val Asp Lys Ser Arg Trp Gln Gln Gly Asn Val
                325                 330                 335
Phe Ser Cys Ser Val Met His Glu Ala Leu His Asn His Tyr Thr Gln
            340                 345                 350
Lys Ser Leu Ser Leu Ser Pro Gly Lys
        355                 360

<210> SEQ ID NO 2
<211> LENGTH: 1167
<212> TYPE: DNA
<213> ORGANISM: Artificial Sequence
<220> FEATURE:
<223> OTHER INFORMATION: FZD8-Fc
<220> FEATURE:
<221> NAME/KEY: misc_feature
<222> LOCATION: (1)..(474)
<223> OTHER INFORMATION: nucleotides encoding FZD8-derived sequences

<400> SEQUENCE: 2
atggagtggg gttacctgtt ggaagtgacc tcgctgctgg ccgccttggc gctgctgcag     60
cgctctagcg gcgctgcggc cgcctcggcc aaggagctgg catgccaaga gatcaccgtg    120
ccgctgtgta agggcatcgg ctacaactac acctacatgc caatcagtt caaccacgac    180 acgcaagacg aggcgggcct ggaggtgcac cagttctggc cgctggtgga gatccagtgc    240
tcgcccgatc tcaagttctt cctgtgcagc atgtacacgc ccatctgcct agaggactac    300
aagaagccgc tgccgccctg ccgctcggtg tgcgagcgcg ccaaggccgg ctgcgcgccg    360
ctcatgcgcc agtacggctt cgcctggccc gaccgcatgc gctgcgaccg gctgcccgag    420
caaggcaacc ctgacacgct gtgcatggac tacaaccgca ccgacctaac caccgggcgc    480
gccgacaaaa ctcacacatg cccaccgtgc ccagcacctg aactcctggg gggaccgtca    540
gtcttcctct tccccccaaa acccaaggac accctcatga tctcccggac ccctgaggtc    600
acatgcgtgg tggtggacgt gagccacgaa gaccctgagg tcaagttcaa ctggtacgtg    660
gacggcgtgg aggtgcataa tgccaagaca aagccgcggg aggagcagta caacagcacg    720
taccgtgtgg tcagcgtcct caccgtcctg caccaggact ggctgaatgg caaggagtac    780
aagtgcaagg tctccaacaa agccctccca gcccccatcg agaaaaccat ctccaaagcc    840
aaagggcagc cccgagaacc acaggtgtac accctgcccc catcccggga tgagctgacc    900
aagaaccagg tcagcctgac ctgcctggtc aaaggcttct atcccagcga catcgccgtg    960
gagtgggaga gcaatgggca gccggagaac aactacaaga ccacgcctcc cgtgctggac   1020
tccgacggct ccttcttcct ctacagcaag ctcaccgtgg acaagagcag gtggcagcag   1080
gggaacgtct tctcatgctc cgtgatgcat gaggctctgc acaaccacta cacacagaag   1140
agcctctccc tgtctccggg taaatga                                       1167

<210> SEQ ID NO 3
<211> LENGTH: 112
<212> TYPE: PRT
```

-continued

<213> ORGANISM: Artificial Sequence
<220> FEATURE:
<223> OTHER INFORMATION: h-FZD1 amino acids 116-227

<400> SEQUENCE: 3

Cys Gln Pro Ile Ser Ile Pro Leu Cys Thr Asp Ile Ala Tyr Asn Gln
1               5                   10                  15

Thr Ile Met Pro Asn Leu Leu Gly His Thr Asn Gln Glu Asp Ala Gly
            20                  25                  30

Leu Glu Val His Gln Phe Tyr Pro Leu Val Lys Val Gln Cys Ser Ala
        35                  40                  45

Glu Leu Lys Phe Phe Leu Cys Ser Met Tyr Ala Pro Val Cys Thr Val
    50                  55                  60

Leu Glu Gln Ala Leu Pro Pro Cys Arg Ser Leu Cys Glu Arg Ala Arg
65                  70                  75                  80

Gln Gly Cys Glu Ala Leu Met Asn Lys Phe Gly Phe Gln Trp Pro Asp
                85                  90                  95

Thr Leu Lys Cys Glu Lys Phe Pro Val His Gly Ala Gly Glu Leu Cys
            100                 105                 110

<210> SEQ ID NO 4
<211> LENGTH: 112
<212> TYPE: PRT
<213> ORGANISM: Artificial Sequence
<220> FEATURE:
<223> OTHER INFORMATION: h-FZD2 amino acids 39-150

<400> SEQUENCE: 4

Cys Gln Pro Ile Ser Ile Pro Leu Cys Thr Asp Ile Ala Tyr Asn Gln
1               5                   10                  15

Thr Ile Met Pro Asn Leu Leu Gly His Thr Asn Gln Glu Asp Ala Gly
            20                  25                  30

Leu Glu Val His Gln Phe Tyr Pro Leu Val Lys Val Gln Cys Ser Pro
        35                  40                  45

Glu Leu Arg Phe Phe Leu Cys Ser Met Tyr Ala Pro Val Cys Thr Val
    50                  55                  60

Leu Glu Gln Ala Ile Pro Pro Cys Arg Ser Ile Cys Glu Arg Ala Arg
65                  70                  75                  80

Gln Gly Cys Glu Ala Leu Met Asn Lys Phe Gly Phe Gln Trp Pro Glu
                85                  90                  95

Arg Leu Arg Cys Glu His Phe Pro Arg His Gly Ala Glu Gln Ile Cys
            100                 105                 110

<210> SEQ ID NO 5
<211> LENGTH: 106
<212> TYPE: PRT
<213> ORGANISM: Artificial Sequence
<220> FEATURE:
<223> OTHER INFORMATION: h-FZD3 amino acids 28-133

<400> SEQUENCE: 5

Cys Glu Pro Ile Thr Leu Arg Met Cys Gln Asp Leu Pro Tyr Asn Thr
1               5                   10                  15

Thr Phe Met Pro Asn Leu Leu Asn His Tyr Asp Gln Gln Thr Ala Ala
            20                  25                  30

Leu Ala Met Glu Pro Phe His Pro Met Val Asn Leu Asp Cys Ser Arg
        35                  40                  45

Asp Phe Arg Pro Phe Leu Cys Ala Leu Tyr Ala Pro Ile Cys Met Glu
    50                  55                  60

```
Tyr Gly Arg Val Thr Leu Pro Cys Arg Arg Leu Cys Gln Arg Ala Tyr
 65                  70                  75                  80

Ser Glu Cys Ser Lys Leu Met Glu Met Phe Gly Val Pro Trp Pro Glu
                 85                  90                  95

Asp Met Glu Cys Ser Arg Phe Pro Asp Cys
            100                 105
```

<210> SEQ ID NO 6
<211> LENGTH: 114
<212> TYPE: PRT
<213> ORGANISM: Artificial Sequence
<220> FEATURE:
<223> OTHER INFORMATION: h-FZD4 amino acids 48-161

<400> SEQUENCE: 6

```
Cys Asp Pro Ile Arg Ile Ser Met Cys Gln Asn Leu Gly Tyr Asn Val
  1               5                  10                  15

Thr Lys Met Pro Asn Leu Val Gly His Glu Leu Gln Thr Asp Ala Glu
                 20                  25                  30

Leu Gln Leu Thr Thr Phe Thr Pro Leu Ile Gln Tyr Gly Cys Ser Ser
             35                  40                  45

Gln Leu Gln Phe Phe Leu Cys Ser Val Tyr Val Pro Met Cys Thr Glu
         50                  55                  60

Lys Ile Asn Ile Pro Ile Gly Pro Cys Gly Gly Met Cys Leu Ser Val
 65                  70                  75                  80

Lys Arg Arg Cys Glu Pro Val Leu Lys Glu Phe Gly Phe Ala Trp Pro
                 85                  90                  95

Glu Ser Leu Asn Cys Ser Lys Phe Pro Pro Gln Asn Asp His Asn His
            100                 105                 110

Met Cys
```

<210> SEQ ID NO 7
<211> LENGTH: 115
<212> TYPE: PRT
<213> ORGANISM: Artificial Sequence
<220> FEATURE:
<223> OTHER INFORMATION: h-FZD5 amino acids 33-147

<400> SEQUENCE: 7

```
Cys Gln Glu Ile Thr Val Pro Met Cys Arg Gly Ile Gly Tyr Asn Leu
  1               5                  10                  15

Thr His Met Pro Asn Gln Phe Asn His Asp Thr Gln Asp Glu Ala Gly
                 20                  25                  30

Leu Glu Val His Gln Phe Trp Pro Leu Val Glu Ile Gln Cys Ser Pro
             35                  40                  45

Asp Leu Arg Phe Phe Leu Cys Ser Met Tyr Thr Pro Ile Cys Leu Pro
         50                  55                  60

Asp Tyr His Lys Pro Leu Pro Pro Cys Arg Ser Val Cys Glu Arg Ala
 65                  70                  75                  80

Lys Ala Gly Cys Ser Pro Leu Met Arg Gln Tyr Gly Phe Ala Trp Pro
                 85                  90                  95

Glu Arg Met Ser Cys Asp Arg Leu Pro Val Leu Gly Arg Asp Ala Glu
            100                 105                 110

Val Leu Cys
        115
```

<210> SEQ ID NO 8

-continued

<211> LENGTH: 106
<212> TYPE: PRT
<213> ORGANISM: Artificial Sequence
<220> FEATURE:
<223> OTHER INFORMATION: h-FZD6 amino acids 24-129

<400> SEQUENCE: 8

```
Cys Glu Pro Ile Thr Val Pro Arg Cys Met Lys Met Ala Tyr Asn Met
1               5                   10                  15

Thr Phe Phe Pro Asn Leu Met Gly His Tyr Asp Gln Ser Ile Ala Ala
            20                  25                  30

Val Glu Met Glu His Phe Leu Pro Leu Ala Asn Leu Glu Cys Ser Pro
        35                  40                  45

Asn Ile Glu Thr Phe Leu Cys Lys Ala Phe Val Pro Thr Cys Ile Glu
    50                  55                  60

Gln Ile His Val Val Pro Pro Cys Arg Lys Leu Cys Glu Lys Val Tyr
65                  70                  75                  80

Ser Asp Cys Lys Lys Leu Ile Asp Thr Phe Gly Ile Arg Trp Pro Glu
                85                  90                  95

Glu Leu Glu Cys Asp Arg Leu Gln Tyr Cys
            100                 105
```

<210> SEQ ID NO 9
<211> LENGTH: 112
<212> TYPE: PRT
<213> ORGANISM: Artificial Sequence
<220> FEATURE:
<223> OTHER INFORMATION: h-FZD7 amino acids 49-160

<400> SEQUENCE: 9

```
Cys Gln Pro Ile Ser Ile Pro Leu Cys Thr Asp Ile Ala Tyr Asn Gln
1               5                   10                  15

Thr Ile Leu Pro Asn Leu Leu Gly His Thr Asn Gln Glu Asp Ala Gly
            20                  25                  30

Leu Glu Val His Gln Phe Tyr Pro Leu Val Lys Val Gln Cys Ser Pro
        35                  40                  45

Glu Leu Arg Phe Phe Leu Cys Ser Met Tyr Ala Pro Val Cys Thr Val
    50                  55                  60

Leu Asp Gln Ala Ile Pro Pro Cys Arg Ser Leu Cys Glu Arg Ala Arg
65                  70                  75                  80

Gln Gly Cys Glu Ala Leu Met Asn Lys Phe Gly Phe Gln Trp Pro Glu
                85                  90                  95

Arg Leu Arg Cys Glu Asn Phe Pro Val His Gly Ala Gly Glu Ile Cys
            100                 105                 110
```

<210> SEQ ID NO 10
<211> LENGTH: 114
<212> TYPE: PRT
<213> ORGANISM: Artificial Sequence
<220> FEATURE:
<223> OTHER INFORMATION: h-FZD8 amino acids 35-148

<400> SEQUENCE: 10

```
Cys Gln Glu Ile Thr Val Pro Leu Cys Lys Gly Ile Gly Tyr Asn Tyr
1               5                   10                  15

Thr Tyr Met Pro Asn Gln Phe Asn His Asp Thr Gln Asp Glu Ala Gly
            20                  25                  30

Leu Glu Val His Gln Phe Trp Pro Leu Val Glu Ile Gln Cys Ser Pro
        35                  40                  45
```

```
Asp Leu Lys Phe Phe Leu Cys Ser Met Tyr Thr Pro Ile Cys Leu Glu
 50                  55                  60

Asp Tyr Lys Lys Pro Leu Pro Pro Cys Arg Ser Val Cys Glu Arg Ala
 65                  70                  75                  80

Lys Ala Gly Cys Ala Pro Leu Met Arg Gln Tyr Gly Phe Ala Trp Pro
                 85                  90                  95

Asp Arg Met Arg Cys Asp Arg Leu Pro Glu Gln Gly Asn Pro Asp Thr
            100                 105                 110

Leu Cys

<210> SEQ ID NO 11
<211> LENGTH: 114
<212> TYPE: PRT
<213> ORGANISM: Artificial Sequence
<220> FEATURE:
<223> OTHER INFORMATION: h-FZD9 amino acids 39-152

<400> SEQUENCE: 11

Cys Gln Ala Val Glu Ile Pro Met Cys Arg Gly Ile Gly Tyr Asn Leu
 1               5                  10                  15

Thr Arg Met Pro Asn Leu Leu Gly His Thr Ser Gln Gly Glu Ala Ala
             20                  25                  30

Ala Glu Leu Ala Glu Phe Ala Pro Leu Val Gln Tyr Gly Cys His Ser
         35                  40                  45

His Leu Arg Phe Phe Leu Cys Ser Leu Tyr Ala Pro Met Cys Thr Asp
 50                  55                  60

Gln Val Ser Thr Pro Ile Pro Ala Cys Arg Pro Met Cys Glu Gln Ala
 65                  70                  75                  80

Arg Leu Arg Cys Ala Pro Ile Met Glu Gln Phe Asn Phe Gly Trp Pro
                 85                  90                  95

Asp Ser Leu Asp Cys Ala Arg Leu Pro Thr Arg Asn Asp Pro His Ala
            100                 105                 110

Leu Cys

<210> SEQ ID NO 12
<211> LENGTH: 114
<212> TYPE: PRT
<213> ORGANISM: Artificial Sequence
<220> FEATURE:
<223> OTHER INFORMATION: h-FZD10 amino acids 34-147

<400> SEQUENCE: 12

Cys Gln Pro Ile Glu Ile Pro Met Cys Lys Asp Ile Gly Tyr Asn Met
 1               5                  10                  15

Thr Arg Met Pro Asn Leu Met Gly His Glu Asn Gln Arg Glu Ala Ala
             20                  25                  30

Ile Gln Leu His Glu Phe Ala Pro Leu Val Glu Tyr Gly Cys His Gly
         35                  40                  45

His Leu Arg Phe Phe Leu Cys Ser Leu Tyr Ala Pro Met Cys Thr Glu
 50                  55                  60

Gln Val Ser Thr Pro Ile Pro Ala Cys Arg Val Met Cys Glu Gln Ala
 65                  70                  75                  80

Arg Leu Lys Cys Ser Pro Ile Met Glu Gln Phe Asn Phe Lys Trp Pro
                 85                  90                  95

Asp Ser Leu Asp Cys Arg Lys Leu Pro Asn Lys Asn Asp Pro Asn Tyr
            100                 105                 110

Leu Cys
```

```
<210> SEQ ID NO 13
<211> LENGTH: 109
<212> TYPE: PRT
<213> ORGANISM: Artificial Sequence
<220> FEATURE:
<223> OTHER INFORMATION: h-SFRP1 amino acids 57-165

<400> SEQUENCE: 13

Cys Val Asp Ile Pro Ala Asp Leu Arg Leu Cys His Asn Val Gly Tyr
1               5                   10                  15

Lys Lys Met Val Leu Pro Asn Leu Leu Glu His Glu Thr Met Ala Glu
            20                  25                  30

Val Lys Gln Gln Ala Ser Ser Trp Val Pro Leu Leu Asn Lys Asn Cys
        35                  40                  45

His Ala Gly Thr Gln Val Phe Leu Cys Ser Leu Phe Ala Pro Val Cys
    50                  55                  60

Leu Asp Arg Pro Ile Tyr Pro Cys Arg Trp Leu Cys Glu Ala Val Arg
65                  70                  75                  80

Asp Ser Cys Glu Pro Val Met Gln Phe Phe Gly Phe Tyr Trp Pro Glu
                85                  90                  95

Met Leu Lys Cys Asp Lys Phe Pro Glu Gly Asp Val Cys
            100                 105

<210> SEQ ID NO 14
<211> LENGTH: 113
<212> TYPE: PRT
<213> ORGANISM: Artificial Sequence
<220> FEATURE:
<223> OTHER INFORMATION: h-SFRP2 amino acids 40-152

<400> SEQUENCE: 14

Cys Lys Pro Ile Pro Ala Asn Leu Gln Leu Cys His Gly Ile Glu Tyr
1               5                   10                  15

Gln Asn Met Arg Leu Pro Asn Leu Leu Gly His Glu Thr Met Lys Glu
            20                  25                  30

Val Leu Glu Gln Ala Gly Ala Trp Ile Pro Leu Val Met Lys Gln Cys
        35                  40                  45

His Pro Asp Thr Lys Lys Phe Leu Cys Ser Leu Phe Ala Pro Val Cys
    50                  55                  60

Leu Asp Asp Leu Asp Glu Thr Ile Gln Pro Cys His Ser Leu Cys Val
65                  70                  75                  80

Gln Val Lys Asp Arg Cys Ala Pro Val Met Ser Ala Phe Gly Phe Pro
                85                  90                  95

Trp Pro Asp Met Leu Glu Cys Asp Arg Phe Pro Gln Asp Asn Asp Leu
            100                 105                 110

Cys

<210> SEQ ID NO 15
<211> LENGTH: 113
<212> TYPE: PRT
<213> ORGANISM: Artificial Sequence
<220> FEATURE:
<223> OTHER INFORMATION: h-SFRP3 amino acids 35-147

<400> SEQUENCE: 15

Cys Glu Pro Val Arg Ile Pro Leu Cys Lys Ser Leu Pro Trp Asn Met
1               5                   10                  15

Thr Lys Met Pro Asn His Leu His His Ser Thr Gln Ala Asn Ala Ile
```

```
                    20                  25                  30
Leu Ala Ile Glu Gln Phe Glu Gly Leu Leu Gly Thr His Cys Ser Pro
            35                  40                  45

Asp Leu Leu Phe Phe Leu Cys Ala Met Tyr Ala Pro Ile Cys Thr Ile
        50                  55                  60

Asp Phe Gln His Glu Pro Ile Lys Pro Cys Lys Ser Val Cys Glu Arg
65                  70                  75                  80

Ala Arg Gln Gly Cys Glu Pro Ile Leu Ile Lys Tyr Arg His Ser Trp
                85                  90                  95

Pro Glu Asn Leu Ala Cys Glu Glu Leu Pro Val Tyr Asp Arg Gly Val
            100                 105                 110

Cys
```

<210> SEQ ID NO 16
<211> LENGTH: 113
<212> TYPE: PRT
<213> ORGANISM: Artificial Sequence
<220> FEATURE:
<223> OTHER INFORMATION: h-SFRP4 amino acids 24-136

<400> SEQUENCE: 16

```
Cys Glu Ala Val Arg Ile Pro Met Cys Arg His Met Pro Trp Asn Ile
1               5                   10                  15

Thr Arg Met Pro Asn His Leu His His Ser Thr Gln Glu Asn Ala Ile
            20                  25                  30

Leu Ala Ile Glu Gln Tyr Glu Glu Leu Val Asp Val Asn Cys Ser Ala
            35                  40                  45

Val Leu Arg Phe Phe Phe Cys Ala Met Tyr Ala Pro Ile Cys Thr Leu
        50                  55                  60

Glu Phe Leu His Asp Pro Ile Lys Pro Cys Lys Ser Val Cys Gln Arg
65                  70                  75                  80

Ala Arg Asp Asp Cys Glu Pro Leu Met Lys Met Tyr Asn His Ser Trp
                85                  90                  95

Pro Glu Ser Leu Ala Cys Asp Glu Leu Pro Val Tyr Asp Arg Gly Val
            100                 105                 110

Cys
```

<210> SEQ ID NO 17
<211> LENGTH: 110
<212> TYPE: PRT
<213> ORGANISM: Artificial Sequence
<220> FEATURE:
<223> OTHER INFORMATION: h-SFRP5 amino acids 53-162

<400> SEQUENCE: 17

```
Cys Leu Asp Ile Pro Ala Asp Leu Pro Leu Cys His Thr Val Gly Tyr
1               5                   10                  15

Lys Arg Met Arg Leu Pro Asn Leu Leu Glu His Glu Ser Leu Ala Glu
            20                  25                  30

Val Lys Gln Gln Ala Ser Ser Trp Leu Pro Leu Leu Ala Lys Arg Cys
            35                  40                  45

His Ser Asp Thr Gln Val Phe Leu Cys Ser Leu Phe Ala Pro Val Cys
        50                  55                  60

Leu Asp Arg Pro Ile Tyr Pro Cys Arg Ser Leu Cys Glu Ala Val Arg
65                  70                  75                  80

Ala Gly Cys Ala Pro Leu Met Glu Ala Tyr Gly Phe Pro Trp Pro Glu
                85                  90                  95
```

Met Leu His Cys His Lys Phe Pro Leu Asp Asn Asp Leu Cys
                100                 105                 110

<210> SEQ ID NO 18
<211> LENGTH: 227
<212> TYPE: PRT
<213> ORGANISM: Artificial Sequence
<220> FEATURE:
<223> OTHER INFORMATION: Human IgG1 Fc region

<400> SEQUENCE: 18

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 19
<211> LENGTH: 170
<212> TYPE: PRT
<213> ORGANISM: Artificial Sequence
<220> FEATURE:
<223> OTHER INFORMATION: Human FZD4 Fri domain
<220> FEATURE:
<221> NAME/KEY: MISC_FEATURE
<222> LOCATION: (1)..(39)
<223> OTHER INFORMATION: signal

<400> SEQUENCE: 19

Met Leu Ala Met Ala Trp Arg Gly Ala Gly Pro Ser Val Pro Gly Ala
1               5                   10                  15

Pro Gly Gly Val Gly Leu Ser Leu Gly Leu Leu Leu Gln Leu Leu
            20                  25                  30

```
Leu Leu Gly Pro Ala Arg Gly Phe Gly Asp Glu Glu Arg Arg Cys
        35                  40                  45

Asp Pro Ile Arg Ile Ser Met Cys Gln Asn Leu Gly Tyr Asn Val Thr
 50                  55                  60

Lys Met Pro Asn Leu Val Gly His Glu Leu Gln Thr Asp Ala Glu Leu
 65                  70                  75                  80

Gln Leu Thr Thr Phe Thr Pro Leu Ile Gln Tyr Gly Cys Ser Ser Gln
                     85                  90                  95

Leu Gln Phe Phe Leu Cys Ser Val Tyr Val Pro Met Cys Thr Glu Lys
                100                 105                 110

Ile Asn Ile Pro Ile Gly Pro Cys Gly Gly Met Cys Leu Ser Val Lys
                115                 120                 125

Arg Arg Cys Glu Pro Val Leu Lys Glu Phe Gly Phe Ala Trp Pro Glu
130                 135                 140

Ser Leu Asn Cys Ser Lys Phe Pro Pro Gln Asn Asp His Asn His Met
145                 150                 155                 160

Cys Met Glu Gly Pro Gly Asp Glu Glu Val
                165                 170
```

<210> SEQ ID NO 20
<211> LENGTH: 157
<212> TYPE: PRT
<213> ORGANISM: Artificial Sequence
<220> FEATURE:
<223> OTHER INFORMATION: Human FZD5 Fri domain
<220> FEATURE:
<221> NAME/KEY: MISC_FEATURE
<222> LOCATION: (1)..(26)
<223> OTHER INFORMATION: signal

<400> SEQUENCE: 20

```
Met Ala Arg Pro Asp Pro Ser Ala Pro Pro Ser Leu Leu Leu Leu Leu
 1               5                  10                  15

Leu Ala Gln Leu Val Gly Arg Ala Ala Ala Ser Lys Ala Pro Val
                 20                  25                  30

Cys Gln Glu Ile Thr Val Pro Met Cys Arg Gly Ile Gly Tyr Asn Leu
             35                  40                  45

Thr His Met Pro Asn Gln Phe Asn His Asp Thr Gln Asp Glu Ala Gly
 50                  55                  60

Leu Glu Val His Gln Phe Trp Pro Leu Val Glu Ile Gln Cys Ser Pro
 65                  70                  75                  80

Asp Leu Arg Phe Phe Leu Cys Ser Met Tyr Thr Pro Ile Cys Leu Pro
                 85                  90                  95

Asp Tyr His Lys Pro Leu Pro Pro Cys Arg Ser Val Cys Glu Arg Ala
                100                 105                 110

Lys Ala Gly Cys Ser Pro Leu Met Arg Gln Tyr Gly Phe Ala Trp Pro
                115                 120                 125

Glu Arg Met Ser Cys Asp Arg Leu Pro Val Leu Gly Arg Asp Ala Glu
                130                 135                 140

Val Leu Cys Met Asp Tyr Asn Arg Ser Glu Ala Thr Thr
145                 150                 155
```

<210> SEQ ID NO 21
<211> LENGTH: 158
<212> TYPE: PRT
<213> ORGANISM: Artificial Sequence
<220> FEATURE:
<223> OTHER INFORMATION: Human FZD8 Fri domain
<220> FEATURE:

-continued

<221> NAME/KEY: MISC_FEATURE
<222> LOCATION: (1)..(27)
<223> OTHER INFORMATION: signal

<400> SEQUENCE: 21

```
Met Glu Trp Gly Tyr Leu Leu Glu Val Thr Ser Leu Leu Ala Ala Leu
1               5                   10                  15

Ala Leu Leu Gln Arg Ser Ser Gly Ala Ala Ala Ser Ala Lys Glu
            20                  25                  30

Leu Ala Cys Gln Glu Ile Thr Val Pro Leu Cys Lys Gly Ile Gly Tyr
            35                  40                  45

Asn Tyr Thr Tyr Met Pro Asn Gln Phe Asn His Asp Thr Gln Asp Glu
50                  55                  60

Ala Gly Leu Glu Val His Gln Phe Trp Pro Leu Val Glu Ile Gln Cys
65                  70                  75                  80

Ser Pro Asp Leu Lys Phe Phe Leu Cys Ser Met Tyr Thr Pro Ile Cys
                85                  90                  95

Leu Glu Asp Tyr Lys Lys Pro Leu Pro Pro Cys Arg Ser Val Cys Glu
            100                 105                 110

Arg Ala Lys Ala Gly Cys Ala Pro Leu Met Arg Gln Tyr Gly Phe Ala
            115                 120                 125

Trp Pro Asp Arg Met Arg Cys Asp Arg Leu Pro Glu Gln Gly Asn Pro
130                 135                 140

Asp Thr Leu Cys Met Asp Tyr Asn Arg Thr Asp Leu Thr Thr
145                 150                 155
```

<210> SEQ ID NO 22
<211> LENGTH: 224
<212> TYPE: PRT
<213> ORGANISM: Artificial Sequence
<220> FEATURE:
<223> OTHER INFORMATION: Human FZD4 ECD with signal

<400> SEQUENCE: 22

```
Met Leu Ala Met Ala Trp Arg Gly Ala Gly Pro Ser Val Pro Gly Ala
1               5                   10                  15

Pro Gly Gly Val Gly Leu Ser Leu Gly Leu Leu Leu Gln Leu Leu
            20                  25                  30

Leu Leu Gly Pro Ala Arg Gly Phe Gly Asp Glu Glu Glu Arg Arg Cys
            35                  40                  45

Asp Pro Ile Arg Ile Ser Met Cys Gln Asn Leu Gly Tyr Asn Val Thr
            50                  55                  60

Lys Met Pro Asn Leu Val Gly His Glu Leu Gln Thr Asp Ala Glu Leu
65                  70                  75                  80

Gln Leu Thr Thr Phe Thr Pro Leu Ile Gln Tyr Gly Cys Ser Ser Gln
                85                  90                  95

Leu Gln Phe Phe Leu Cys Ser Val Tyr Val Pro Met Cys Thr Glu Lys
            100                 105                 110

Ile Asn Ile Pro Ile Gly Pro Cys Gly Gly Met Cys Leu Ser Val Lys
            115                 120                 125

Arg Arg Cys Glu Pro Val Leu Lys Glu Phe Gly Phe Ala Trp Pro Glu
            130                 135                 140

Ser Leu Asn Cys Ser Lys Phe Pro Pro Gln Asn Asp His Asn His Met
145                 150                 155                 160

Cys Met Glu Gly Pro Gly Asp Glu Glu Val Pro Leu Pro His Lys Thr
                165                 170                 175
```

```
Pro Ile Gln Pro Gly Glu Glu Cys His Ser Val Gly Thr Asn Ser Asp
                180                 185                 190

Gln Tyr Ile Trp Val Lys Arg Ser Leu Asn Cys Val Leu Lys Cys Gly
            195                 200                 205

Tyr Asp Ala Gly Leu Tyr Ser Arg Ser Ala Lys Glu Phe Thr Asp Ile
    210                 215                 220

<210> SEQ ID NO 23
<211> LENGTH: 233
<212> TYPE: PRT
<213> ORGANISM: Artificial Sequence
<220> FEATURE:
<223> OTHER INFORMATION: Human FZD5 ECD with signal

<400> SEQUENCE: 23

Met Ala Arg Pro Asp Pro Ser Ala Pro Ser Leu Leu Leu Leu Leu Leu
1               5                   10                  15

Leu Ala Gln Leu Val Gly Arg Ala Ala Ala Ser Lys Ala Pro Val
            20                  25                  30

Cys Gln Glu Ile Thr Val Pro Met Cys Arg Gly Ile Gly Tyr Asn Leu
        35                  40                  45

Thr His Met Pro Asn Gln Phe Asn His Asp Thr Gln Asp Glu Ala Gly
    50                  55                  60

Leu Glu Val His Gln Phe Trp Pro Leu Val Glu Ile Gln Cys Ser Pro
65                  70                  75                  80

Asp Leu Arg Phe Phe Leu Cys Ser Met Tyr Thr Pro Ile Cys Leu Pro
                85                  90                  95

Asp Tyr His Lys Pro Leu Pro Pro Cys Arg Ser Val Cys Glu Arg Ala
            100                 105                 110

Lys Ala Gly Cys Ser Pro Leu Met Arg Gln Tyr Gly Phe Ala Trp Pro
        115                 120                 125

Glu Arg Met Ser Cys Asp Arg Leu Pro Val Leu Gly Arg Asp Ala Glu
    130                 135                 140

Val Leu Cys Met Asp Tyr Asn Arg Ser Glu Ala Thr Thr Ala Pro Pro
145                 150                 155                 160

Arg Pro Phe Pro Ala Lys Pro Thr Leu Pro Gly Pro Pro Gly Ala Pro
                165                 170                 175

Ala Ser Gly Gly Glu Cys Pro Ala Gly Gly Pro Phe Val Cys Lys Cys
            180                 185                 190

Arg Glu Pro Phe Val Pro Ile Leu Lys Glu Ser His Pro Leu Tyr Asn
        195                 200                 205

Lys Val Arg Thr Gly Gln Val Pro Asn Cys Ala Val Pro Cys Tyr Gln
    210                 215                 220

Pro Ser Phe Ser Ala Asp Glu Arg Thr
225                 230

<210> SEQ ID NO 24
<211> LENGTH: 207
<212> TYPE: PRT
<213> ORGANISM: Artificial Sequence
<220> FEATURE:
<223> OTHER INFORMATION: Human FZD6 ECD with signal

<400> SEQUENCE: 24

Met Glu Met Phe Thr Phe Leu Leu Thr Cys Ile Phe Leu Pro Leu Leu
1               5                   10                  15

Arg Gly His Ser Leu Phe Thr Cys Glu Pro Ile Thr Val Pro Arg Cys
            20                  25                  30
```

Met Lys Met Ala Tyr Asn Met Thr Phe Phe Pro Asn Leu Met Gly His
            35                  40                  45

Tyr Asp Gln Ser Ile Ala Ala Val Glu Met Glu His Phe Leu Pro Leu
    50                  55                  60

Ala Asn Leu Glu Cys Ser Pro Asn Ile Glu Thr Phe Leu Cys Lys Ala
65                  70                  75                  80

Phe Val Pro Thr Cys Ile Glu Gln Ile His Val Val Pro Pro Cys Arg
                85                  90                  95

Lys Leu Cys Glu Lys Val Tyr Ser Asp Cys Lys Lys Leu Ile Asp Thr
            100                 105                 110

Phe Gly Ile Arg Trp Pro Glu Leu Glu Cys Asp Arg Leu Gln Tyr
            115                 120                 125

Cys Asp Glu Thr Val Pro Val Thr Phe Asp Pro His Thr Glu Phe Leu
130                 135                 140

Gly Pro Gln Lys Lys Thr Glu Gln Val Gln Arg Asp Ile Gly Phe Trp
145                 150                 155                 160

Cys Pro Arg His Leu Lys Thr Ser Gly Gly Gln Gly Tyr Lys Phe Leu
                165                 170                 175

Gly Ile Asp Gln Cys Ala Pro Pro Cys Pro Asn Met Tyr Phe Lys Ser
            180                 185                 190

Asp Glu Leu Glu Phe Ala Lys Ser Phe Ile Gly Thr Val Ser Ile
            195                 200                 205

<210> SEQ ID NO 25
<211> LENGTH: 255
<212> TYPE: PRT
<213> ORGANISM: Artificial Sequence
<220> FEATURE:
<223> OTHER INFORMATION: Human FZD7 ECD with signal

<400> SEQUENCE: 25

Met Arg Asp Pro Gly Ala Ala Ala Pro Leu Ser Ser Leu Gly Leu Cys
1               5                   10                  15

Ala Leu Val Leu Ala Leu Leu Gly Ala Leu Ser Ala Gly Ala Gly Ala
            20                  25                  30

Gln Pro Tyr His Gly Glu Lys Gly Ile Ser Val Pro Asp His Gly Phe
            35                  40                  45

Cys Gln Pro Ile Ser Ile Pro Leu Cys Thr Asp Ile Ala Tyr Asn Gln
            50                  55                  60

Thr Ile Leu Pro Asn Leu Leu Gly His Thr Asn Gln Glu Asp Ala Gly
65                  70                  75                  80

Leu Glu Val His Gln Phe Tyr Pro Leu Val Lys Val Gln Cys Ser Pro
                85                  90                  95

Glu Leu Arg Phe Phe Leu Cys Ser Met Tyr Ala Pro Val Cys Thr Val
            100                 105                 110

Leu Asp Gln Ala Ile Pro Pro Cys Arg Ser Leu Cys Glu Arg Ala Arg
            115                 120                 125

Gln Gly Cys Glu Ala Leu Met Asn Lys Phe Gly Phe Gln Trp Pro Glu
130                 135                 140

Arg Leu Arg Cys Glu Asn Phe Pro Val His Gly Ala Gly Glu Ile Cys
145                 150                 155                 160

Val Gly Gln Asn Thr Ser Asp Gly Ser Gly Pro Gly Gly Pro
                165                 170                 175

Thr Ala Tyr Pro Thr Ala Pro Tyr Leu Pro Asp Leu Pro Phe Thr Ala
            180                 185                 190

-continued

Leu Pro Pro Gly Ala Ser Asp Gly Arg Gly Arg Pro Ala Phe Pro Phe
        195                 200                 205

Ser Cys Pro Arg Gln Leu Lys Val Pro Pro Tyr Leu Gly Tyr Arg Phe
        210                 215                 220

Leu Gly Glu Arg Asp Cys Gly Ala Pro Cys Glu Pro Gly Arg Ala Asn
225                 230                 235                 240

Gly Leu Met Tyr Phe Lys Glu Glu Arg Arg Phe Ala Arg Leu
                245                 250                 255

<210> SEQ ID NO 26
<211> LENGTH: 227
<212> TYPE: PRT
<213> ORGANISM: Artificial Sequence
<220> FEATURE:
<223> OTHER INFORMATION: Human FZD10 ECD with signal

<400> SEQUENCE: 26

Met Gln Arg Pro Gly Pro Arg Leu Trp Leu Val Leu Gln Val Met Gly
1               5                   10                  15

Ser Cys Ala Ala Ile Ser Ser Met Asp Met Glu Arg Pro Gly Asp Gly
                20                  25                  30

Lys Cys Gln Pro Ile Glu Ile Pro Met Cys Lys Asp Ile Gly Tyr Asn
            35                  40                  45

Met Thr Arg Met Pro Asn Leu Met Gly His Glu Asn Gln Arg Glu Ala
        50                  55                  60

Ala Ile Gln Leu His Glu Phe Ala Pro Leu Val Glu Tyr Gly Cys His
65                  70                  75                  80

Gly His Leu Arg Phe Phe Leu Cys Ser Leu Tyr Ala Pro Met Cys Thr
                85                  90                  95

Glu Gln Val Ser Thr Pro Ile Pro Ala Cys Arg Val Met Cys Glu Gln
            100                 105                 110

Ala Arg Leu Lys Cys Ser Pro Ile Met Glu Gln Phe Asn Phe Lys Trp
        115                 120                 125

Pro Asp Ser Leu Asp Cys Arg Lys Leu Pro Asn Lys Asn Asp Pro Asn
    130                 135                 140

Tyr Leu Cys Met Glu Ala Pro Asn Asn Gly Ser Asp Glu Pro Thr Arg
145                 150                 155                 160

Gly Ser Gly Leu Phe Pro Pro Leu Phe Arg Pro Gln Arg Pro His Ser
                165                 170                 175

Ala Gln Glu His Pro Leu Lys Asp Gly Gly Pro Gly Arg Gly Gly Cys
            180                 185                 190

Asp Asn Pro Gly Lys Phe His His Val Glu Lys Ser Ala Ser Cys Ala
        195                 200                 205

Pro Leu Cys Thr Pro Gly Val Asp Val Tyr Trp Ser Arg Glu Asp Lys
    210                 215                 220

Arg Phe Ala
225

<210> SEQ ID NO 27
<211> LENGTH: 321
<212> TYPE: PRT
<213> ORGANISM: Artificial Sequence
<220> FEATURE:
<223> OTHER INFORMATION: Human FZD1 ECD with signal

<400> SEQUENCE: 27

Met Ala Glu Glu Glu Ala Pro Lys Lys Ser Arg Ala Ala Gly Gly Gly

```
  1               5                  10                 15
Ala Ser Trp Glu Leu Cys Ala Gly Ala Leu Ser Ala Arg Leu Ala Glu
                 20                 25                 30

Glu Gly Ser Gly Asp Ala Gly Gly Arg Arg Pro Pro Val Asp Pro
                 35                 40                 45

Arg Arg Leu Ala Arg Gln Leu Leu Leu Leu Trp Leu Leu Glu Ala
 50                 55                 60

Pro Leu Leu Leu Gly Val Arg Ala Gln Ala Gly Gln Gly Pro Gly
 65                 70                 75                 80

Gln Gly Pro Gly Pro Gly Gln Gln Pro Pro Pro Gln Gln Gln
                 85                 90                 95

Gln Ser Gly Gln Gln Tyr Asn Gly Glu Arg Gly Ile Ser Val Pro Asp
                100                105                110

His Gly Tyr Cys Gln Pro Ile Ser Ile Pro Leu Cys Thr Asp Ile Ala
                115                120                125

Tyr Asn Gln Thr Ile Met Pro Asn Leu Leu Gly His Thr Asn Gln Glu
130                135                140

Asp Ala Gly Leu Glu Val His Gln Phe Tyr Pro Leu Val Lys Val Gln
145                150                155                160

Cys Ser Ala Glu Leu Lys Phe Phe Leu Cys Ser Met Tyr Ala Pro Val
                165                170                175

Cys Thr Val Leu Glu Gln Ala Leu Pro Pro Cys Arg Ser Leu Cys Glu
                180                185                190

Arg Ala Arg Gln Gly Cys Glu Ala Leu Met Asn Lys Phe Gly Phe Gln
                195                200                205

Trp Pro Asp Thr Leu Lys Cys Glu Lys Phe Pro Val His Gly Ala Gly
210                215                220

Glu Leu Cys Val Gly Gln Asn Thr Ser Asp Lys Gly Thr Pro Thr Pro
225                230                235                240

Ser Leu Leu Pro Glu Phe Trp Thr Ser Asn Pro Gln His Gly Gly
                245                250                255

Gly His Arg Gly Gly Phe Pro Gly Gly Ala Gly Ala Ser Glu Arg Gly
                260                265                270

Lys Phe Ser Cys Pro Arg Ala Leu Lys Val Pro Ser Tyr Leu Asn Tyr
                275                280                285

His Phe Leu Gly Glu Lys Asp Cys Gly Ala Pro Cys Glu Pro Thr Lys
                290                295                300

Val Tyr Gly Leu Met Tyr Phe Gly Pro Glu Glu Leu Arg Phe Ser Arg
305                310                315                320

Thr

<210> SEQ ID NO 28
<211> LENGTH: 250
<212> TYPE: PRT
<213> ORGANISM: Artificial Sequence
<220> FEATURE:
<223> OTHER INFORMATION: Human FZD2 ECD with signal

<400> SEQUENCE: 28

Met Arg Pro Arg Ser Ala Leu Pro Arg Leu Leu Leu Pro Leu Leu Leu
 1                 5                 10                 15

Leu Pro Ala Ala Gly Pro Ala Gln Phe His Gly Glu Lys Gly Ile Ser
                 20                 25                 30

Ile Pro Asp His Gly Phe Cys Gln Pro Ile Ser Ile Pro Leu Cys Thr
                 35                 40                 45
```

```
Asp Ile Ala Tyr Asn Gln Thr Ile Met Pro Asn Leu Leu Gly His Thr
        50                  55                  60

Asn Gln Glu Asp Ala Gly Leu Glu Val His Gln Phe Tyr Pro Leu Val
 65                  70                  75                  80

Lys Val Gln Cys Ser Pro Glu Leu Arg Phe Phe Leu Cys Ser Met Tyr
                 85                  90                  95

Ala Pro Val Cys Thr Val Leu Glu Gln Ala Ile Pro Pro Cys Arg Ser
                100                 105                 110

Ile Cys Glu Arg Ala Arg Gln Gly Cys Glu Ala Leu Met Asn Lys Phe
            115                 120                 125

Gly Phe Gln Trp Pro Glu Arg Leu Arg Cys Glu His Phe Pro Arg His
130                 135                 140

Gly Ala Glu Gln Ile Cys Val Gly Gln Asn His Ser Glu Asp Gly Ala
145                 150                 155                 160

Pro Ala Leu Leu Thr Thr Ala Pro Pro Gly Leu Gln Pro Gly Ala
                165                 170                 175

Gly Gly Thr Pro Gly Gly Pro Gly Gly Gly Ala Pro Pro Arg Tyr
                180                 185                 190

Ala Thr Leu Glu His Pro Phe His Cys Pro Arg Val Leu Lys Val Pro
            195                 200                 205

Ser Tyr Leu Ser Tyr Lys Phe Leu Gly Glu Arg Asp Cys Ala Ala Pro
210                 215                 220

Cys Glu Pro Ala Arg Pro Asp Gly Ser Met Phe Phe Ser Gln Glu Glu
225                 230                 235                 240

Thr Arg Phe Ala Arg Leu Trp Ile Leu Thr
                245                 250

<210> SEQ ID NO 29
<211> LENGTH: 204
<212> TYPE: PRT
<213> ORGANISM: Artificial Sequence
<220> FEATURE:
<223> OTHER INFORMATION: Human FZD3 ECD with signal

<400> SEQUENCE: 29

Met Ala Met Thr Trp Ile Val Phe Ser Leu Trp Pro Leu Thr Val Phe
 1               5                  10                  15

Met Gly His Ile Gly Gly His Ser Leu Phe Ser Cys Glu Pro Ile Thr
                20                  25                  30

Leu Arg Met Cys Gln Asp Leu Pro Tyr Asn Thr Thr Phe Met Pro Asn
            35                  40                  45

Leu Leu Asn His Tyr Asp Gln Gln Thr Ala Ala Leu Ala Met Glu Pro
 50                  55                  60

Phe His Pro Met Val Asn Leu Asp Cys Ser Arg Asp Phe Arg Pro Phe
 65                  70                  75                  80

Leu Cys Ala Leu Tyr Ala Pro Ile Cys Met Glu Tyr Gly Arg Val Thr
                 85                  90                  95

Leu Pro Cys Arg Arg Leu Cys Gln Arg Ala Tyr Ser Glu Cys Ser Lys
                100                 105                 110

Leu Met Glu Met Phe Gly Val Pro Trp Pro Glu Asp Met Glu Cys Ser
            115                 120                 125

Arg Phe Pro Asp Cys Asp Glu Pro Tyr Pro Arg Leu Val Asp Leu Asn
130                 135                 140

Leu Ala Gly Glu Pro Thr Glu Gly Ala Pro Val Ala Val Gln Arg Asp
145                 150                 155                 160
```

Tyr Gly Phe Trp Cys Pro Arg Glu Leu Lys Ile Asp Pro Asp Leu Gly
            165                 170                 175

Tyr Ser Phe Leu His Val Arg Asp Cys Ser Pro Pro Cys Pro Asn Met
            180                 185                 190

Tyr Phe Arg Arg Glu Glu Leu Ser Phe Ala Arg Tyr
            195                 200

<210> SEQ ID NO 30
<211> LENGTH: 277
<212> TYPE: PRT
<213> ORGANISM: Artificial Sequence
<220> FEATURE:
<223> OTHER INFORMATION: Human FZD8 ECD with signal

<400> SEQUENCE: 30

Met Glu Trp Gly Tyr Leu Leu Glu Val Thr Ser Leu Leu Ala Ala Leu
1               5                   10                  15

Ala Leu Leu Gln Arg Ser Ser Gly Ala Ala Ala Ser Ala Lys Glu
            20                  25                  30

Leu Ala Cys Gln Glu Ile Thr Val Pro Leu Cys Lys Gly Ile Gly Tyr
        35                  40                  45

Asn Tyr Thr Tyr Met Pro Asn Gln Phe Asn His Asp Thr Gln Asp Glu
50                  55                  60

Ala Gly Leu Glu Val His Gln Phe Trp Pro Leu Val Glu Ile Gln Cys
65                  70                  75                  80

Ser Pro Asp Leu Lys Phe Phe Leu Cys Ser Met Tyr Thr Pro Ile Cys
                85                  90                  95

Leu Glu Asp Tyr Lys Lys Pro Leu Pro Pro Cys Arg Ser Val Cys Glu
            100                 105                 110

Arg Ala Lys Ala Gly Cys Ala Pro Leu Met Arg Gln Tyr Gly Phe Ala
        115                 120                 125

Trp Pro Asp Arg Met Arg Cys Asp Arg Leu Pro Glu Gln Gly Asn Pro
    130                 135                 140

Asp Thr Leu Cys Met Asp Tyr Asn Arg Thr Asp Leu Thr Thr Ala Ala
145                 150                 155                 160

Pro Ser Pro Pro Arg Arg Leu Pro Pro Pro Pro Gly Glu Gln Pro
                165                 170                 175

Pro Ser Gly Ser Gly His Gly Arg Pro Pro Gly Ala Arg Pro Pro His
            180                 185                 190

Arg Gly Gly Gly Arg Gly Gly Gly Gly Asp Ala Ala Pro Pro
        195                 200                 205

Ala Arg Gly Gly Gly Gly Gly Lys Ala Arg Pro Pro Gly Gly Gly
    210                 215                 220

Ala Ala Pro Cys Glu Pro Gly Cys Gln Cys Arg Ala Pro Met Val Ser
225                 230                 235                 240

Val Ser Ser Glu Arg His Pro Leu Tyr Asn Arg Val Lys Thr Gly Gln
                245                 250                 255

Ile Ala Asn Cys Ala Leu Pro Cys His Asn Pro Phe Phe Ser Gln Asp
            260                 265                 270

Glu Arg Ala Phe Thr
        275

<210> SEQ ID NO 31
<211> LENGTH: 230
<212> TYPE: PRT
<213> ORGANISM: Artificial Sequence
<220> FEATURE:
<223> OTHER INFORMATION: Human FZD9 ECD with signal

<400> SEQUENCE: 31

```
Met Ala Val Ala Pro Leu Arg Gly Ala Leu Leu Trp Gln Leu Leu
1               5                   10                  15

Ala Ala Gly Gly Ala Ala Leu Glu Ile Gly Arg Phe Asp Pro Glu Arg
            20                  25                  30

Gly Arg Gly Ala Ala Pro Cys Gln Ala Val Glu Ile Pro Met Cys Arg
        35                  40                  45

Gly Ile Gly Tyr Asn Leu Thr Arg Met Pro Asn Leu Leu Gly His Thr
    50                  55                  60

Ser Gln Gly Glu Ala Ala Glu Leu Ala Glu Phe Ala Pro Leu Val
65              70                  75                  80

Gln Tyr Gly Cys His Ser His Leu Arg Phe Phe Leu Cys Ser Leu Tyr
                85                  90                  95

Ala Pro Met Cys Thr Asp Gln Val Ser Thr Pro Ile Pro Ala Cys Arg
            100                 105                 110

Pro Met Cys Glu Gln Ala Arg Leu Arg Cys Ala Pro Ile Met Glu Gln
        115                 120                 125

Phe Asn Phe Gly Trp Pro Asp Ser Leu Asp Cys Ala Arg Leu Pro Thr
130                 135                 140

Arg Asn Asp Pro His Ala Leu Cys Met Glu Ala Pro Glu Asn Ala Thr
145                 150                 155                 160

Ala Gly Pro Ala Glu Pro His Lys Gly Leu Gly Met Leu Pro Val Ala
                165                 170                 175

Pro Arg Pro Ala Arg Pro Gly Asp Leu Gly Pro Gly Ala Gly Gly
            180                 185                 190

Ser Gly Thr Cys Glu Asn Pro Glu Lys Phe Gln Tyr Val Glu Lys Ser
        195                 200                 205

Arg Ser Cys Ala Pro Arg Cys Gly Pro Gly Val Glu Val Phe Trp Ser
    210                 215                 220

Arg Arg Asp Lys Asp Phe
225                 230
```

<210> SEQ ID NO 32
<211> LENGTH: 151
<212> TYPE: PRT
<213> ORGANISM: Artificial Sequence
<220> FEATURE:
<223> OTHER INFORMATION: Human FZD1 Fri domain amino acid sequence
      without predicted signal; amino acids 87-237 of SEQ ID NO:27

<400> SEQUENCE: 32

```
Gln Gln Pro Pro Pro Pro Gln Gln Gln Gln Ser Gly Gln Gln Tyr
1               5                   10                  15

Asn Gly Glu Arg Gly Ile Ser Val Pro Asp His Gly Tyr Cys Gln Pro
            20                  25                  30

Ile Ser Ile Pro Leu Cys Thr Asp Ile Ala Tyr Asn Gln Thr Ile Met
        35                  40                  45

Pro Asn Leu Leu Gly His Thr Asn Gln Glu Asp Ala Gly Leu Glu Val
    50                  55                  60

His Gln Phe Tyr Pro Leu Val Lys Val Gln Cys Ser Ala Glu Leu Lys
65              70                  75                  80

Phe Phe Leu Cys Ser Met Tyr Ala Pro Val Cys Thr Val Leu Glu Gln
                85                  90                  95
```

Ala Leu Pro Pro Cys Arg Ser Leu Cys Glu Arg Ala Arg Gln Gly Cys
            100                 105                 110

Glu Ala Leu Met Asn Lys Phe Gly Phe Gln Trp Pro Asp Thr Leu Lys
        115                 120                 125

Cys Glu Lys Phe Pro Val His Gly Ala Gly Glu Leu Cys Val Gly Gln
    130                 135                 140

Asn Thr Ser Asp Lys Gly Thr
145                 150

<210> SEQ ID NO 33
<211> LENGTH: 136
<212> TYPE: PRT
<213> ORGANISM: Artificial Sequence
<220> FEATURE:
<223> OTHER INFORMATION: Human FZD2 Fri domain amino acid sequence
      without predicted signal; amino acids 24-159 of SEQ ID NO:28

<400> SEQUENCE: 33

Gln Phe His Gly Glu Lys Gly Ile Ser Ile Pro Asp His Gly Phe Cys
1               5                   10                  15

Gln Pro Ile Ser Ile Pro Leu Cys Thr Asp Ile Ala Tyr Asn Gln Thr
            20                  25                  30

Ile Met Pro Asn Leu Leu Gly His Thr Asn Gln Glu Asp Ala Gly Leu
        35                  40                  45

Glu Val His Gln Phe Tyr Pro Leu Val Lys Val Gln Cys Ser Pro Glu
    50                  55                  60

Leu Arg Phe Phe Leu Cys Ser Met Tyr Ala Pro Val Cys Thr Val Leu
65                  70                  75                  80

Glu Gln Ala Ile Pro Pro Cys Arg Ser Ile Cys Glu Arg Ala Arg Gln
                85                  90                  95

Gly Cys Glu Ala Leu Met Asn Lys Phe Gly Phe Gln Trp Pro Glu Arg
            100                 105                 110

Leu Arg Cys Glu His Phe Pro Arg His Gly Ala Glu Gln Ile Cys Val
        115                 120                 125

Gly Gln Asn His Ser Glu Asp Gly
    130                 135

<210> SEQ ID NO 34
<211> LENGTH: 121
<212> TYPE: PRT
<213> ORGANISM: Artificial Sequence
<220> FEATURE:
<223> OTHER INFORMATION: Human FZD3 Fri domain amino acid sequence
      without predicted signal; amino acids 23-143 of SEQ ID NO:29

<400> SEQUENCE: 34

His Ser Leu Phe Ser Cys Glu Pro Ile Thr Leu Arg Met Cys Gln Asp
1               5                   10                  15

Leu Pro Tyr Asn Thr Thr Phe Met Pro Asn Leu Leu Asn His Tyr Asp
            20                  25                  30

Gln Gln Thr Ala Ala Leu Ala Met Glu Pro Phe His Pro Met Val Asn
        35                  40                  45

Leu Asp Cys Ser Arg Asp Phe Arg Pro Phe Leu Cys Ala Leu Tyr Ala
    50                  55                  60

Pro Ile Cys Met Glu Tyr Gly Arg Val Thr Leu Pro Cys Arg Arg Leu
65                  70                  75                  80

Cys Gln Arg Ala Tyr Ser Glu Cys Ser Lys Leu Met Glu Met Phe Gly
                85                  90                  95

```
Val Pro Trp Pro Glu Asp Met Glu Cys Ser Arg Phe Pro Asp Cys Asp
            100                 105                 110

Glu Pro Tyr Pro Arg Leu Val Asp Leu
        115                 120
```

<210> SEQ ID NO 35
<211> LENGTH: 131
<212> TYPE: PRT
<213> ORGANISM: Artificial Sequence
<220> FEATURE:
<223> OTHER INFORMATION: Human FZD4 Fri domain amino acid sequence
      without predicted signal; amino acids 40-170 of SEQ ID NO:22

<400> SEQUENCE: 35

```
Phe Gly Asp Glu Glu Arg Arg Cys Asp Pro Ile Arg Ile Ser Met
1               5                   10                  15

Cys Gln Asn Leu Gly Tyr Asn Val Thr Lys Met Pro Asn Leu Val Gly
                20                  25                  30

His Glu Leu Gln Thr Asp Ala Glu Leu Gln Leu Thr Thr Phe Thr Pro
            35                  40                  45

Leu Ile Gln Tyr Gly Cys Ser Ser Gln Leu Gln Phe Phe Leu Cys Ser
        50                  55                  60

Val Tyr Val Pro Met Cys Thr Glu Lys Ile Asn Ile Pro Ile Gly Pro
65                  70                  75                  80

Cys Gly Gly Met Cys Leu Ser Val Lys Arg Arg Cys Glu Pro Val Leu
                85                  90                  95

Lys Glu Phe Gly Phe Ala Trp Pro Glu Ser Leu Asn Cys Ser Lys Phe
            100                 105                 110

Pro Pro Gln Asn Asp His Asn His Met Cys Met Glu Gly Pro Gly Asp
        115                 120                 125

Glu Glu Val
    130
```

<210> SEQ ID NO 36
<211> LENGTH: 131
<212> TYPE: PRT
<213> ORGANISM: Artificial Sequence
<220> FEATURE:
<223> OTHER INFORMATION: Human FZD5 Fri domain amino acid sequence
      without predicted signal; amino acids 27-157 of SEQ ID NO:23

<400> SEQUENCE: 36

```
Ala Ser Lys Ala Pro Val Cys Gln Glu Ile Thr Val Pro Met Cys Arg
1               5                   10                  15

Gly Ile Gly Tyr Asn Leu Thr His Met Pro Asn Gln Phe Asn His Asp
                20                  25                  30

Thr Gln Asp Glu Ala Gly Leu Glu Val His Gln Phe Trp Pro Leu Val
            35                  40                  45

Glu Ile Gln Cys Ser Pro Asp Leu Arg Phe Phe Leu Cys Ser Met Tyr
        50                  55                  60

Thr Pro Ile Cys Leu Pro Asp Tyr His Lys Pro Leu Pro Pro Cys Arg
65                  70                  75                  80

Ser Val Cys Glu Arg Ala Lys Ala Gly Cys Ser Pro Leu Met Arg Gln
                85                  90                  95

Tyr Gly Phe Ala Trp Pro Glu Arg Met Ser Cys Asp Arg Leu Pro Val
            100                 105                 110

Leu Gly Arg Asp Ala Glu Val Leu Cys Met Asp Tyr Asn Arg Ser Glu
        115                 120                 125
```

Ala Thr Thr
    130

<210> SEQ ID NO 37
<211> LENGTH: 127
<212> TYPE: PRT
<213> ORGANISM: Artificial Sequence
<220> FEATURE:
<223> OTHER INFORMATION: Human FZD6 Fri domain amino acid sequence
      without predicted signal; amino acids 19-146 of SEQ ID NO:24

<400> SEQUENCE: 37

His Ser Leu Phe Thr Cys Glu Pro Ile Thr Val Pro Arg Cys Met Lys
1               5                   10                  15

Met Ala Tyr Asn Met Thr Phe Phe Pro Asn Leu Met Gly His Tyr Asp
            20                  25                  30

Gln Ser Ile Ala Ala Val Glu Met Glu His Phe Leu Pro Leu Ala Asn
        35                  40                  45

Leu Glu Cys Ser Pro Asn Ile Glu Thr Phe Leu Cys Lys Ala Phe Val
    50                  55                  60

Pro Thr Cys Ile Glu Gln Ile His Val Val Pro Pro Cys Arg Lys Leu
65                  70                  75                  80

Cys Glu Lys Val Tyr Ser Asp Cys Lys Lys Leu Ile Asp Thr Phe Gly
                85                  90                  95

Ile Arg Trp Pro Glu Glu Leu Glu Cys Asp Arg Leu Gln Tyr Cys Asp
            100                 105                 110

Glu Thr Val Pro Val Thr Phe Asp Pro His Thr Glu Phe Leu Gly
        115                 120                 125

<210> SEQ ID NO 38
<211> LENGTH: 138
<212> TYPE: PRT
<213> ORGANISM: Artificial Sequence
<220> FEATURE:
<223> OTHER INFORMATION: Human FZD7 Fri domain amino acid sequence
      without predicted signal; amino acids 33-170 of SEQ ID NO:25

<400> SEQUENCE: 38

Gln Pro Tyr His Gly Glu Lys Gly Ile Ser Val Pro Asp His Gly Phe
1               5                   10                  15

Cys Gln Pro Ile Ser Ile Pro Leu Cys Thr Asp Ile Ala Tyr Asn Gln
            20                  25                  30

Thr Ile Leu Pro Asn Leu Leu Gly His Thr Asn Gln Glu Asp Ala Gly
        35                  40                  45

Leu Glu Val His Gln Phe Tyr Pro Leu Val Lys Val Gln Cys Ser Pro
    50                  55                  60

Glu Leu Arg Phe Phe Leu Cys Ser Met Tyr Ala Pro Val Cys Thr Val
65                  70                  75                  80

Leu Asp Gln Ala Ile Pro Pro Cys Arg Ser Leu Cys Glu Arg Ala Arg
                85                  90                  95

Gln Gly Cys Glu Ala Leu Met Asn Lys Phe Gly Phe Gln Trp Pro Glu
            100                 105                 110

Arg Leu Arg Cys Glu Asn Phe Pro Val His Gly Ala Gly Glu Ile Cys
        115                 120                 125

Val Gly Gln Asn Thr Ser Asp Gly Ser Gly
    130                 135

<210> SEQ ID NO 39
<211> LENGTH: 131

```
<212> TYPE: PRT
<213> ORGANISM: Artificial Sequence
<220> FEATURE:
<223> OTHER INFORMATION: Human FZD8 Fri domain amino acid sequence
      without predicted signal; amino acids 28-158 of SEQ ID NO:30

<400> SEQUENCE: 39

Ala Ser Ala Lys Glu Leu Ala Cys Gln Glu Ile Thr Val Pro Leu Cys
1               5                   10                  15

Lys Gly Ile Gly Tyr Asn Tyr Thr Tyr Met Pro Asn Gln Phe Asn His
            20                  25                  30

Asp Thr Gln Asp Glu Ala Gly Leu Glu Val His Gln Phe Trp Pro Leu
        35                  40                  45

Val Glu Ile Gln Cys Ser Pro Asp Leu Lys Phe Phe Leu Cys Ser Met
    50                  55                  60

Tyr Thr Pro Ile Cys Leu Glu Asp Tyr Lys Lys Pro Leu Pro Pro Cys
65                  70                  75                  80

Arg Ser Val Cys Glu Arg Ala Lys Ala Gly Cys Ala Pro Leu Met Arg
                85                  90                  95

Gln Tyr Gly Phe Ala Trp Pro Asp Arg Met Arg Cys Asp Arg Leu Pro
            100                 105                 110

Glu Gln Gly Asn Pro Asp Thr Leu Cys Met Asp Tyr Asn Arg Thr Asp
        115                 120                 125

Leu Thr Thr
    130

<210> SEQ ID NO 40
<211> LENGTH: 137
<212> TYPE: PRT
<213> ORGANISM: Artificial Sequence
<220> FEATURE:
<223> OTHER INFORMATION: Human FZD9 Fri domain amino acid sequence
      without predicted signal; amino acids 23-159 of SEQ ID NO:31

<400> SEQUENCE: 40

Leu Glu Ile Gly Arg Phe Asp Pro Glu Arg Gly Arg Gly Ala Ala Pro
1               5                   10                  15

Cys Gln Ala Val Glu Ile Pro Met Cys Arg Gly Ile Gly Tyr Asn Leu
            20                  25                  30

Thr Arg Met Pro Asn Leu Leu Gly His Thr Ser Gln Gly Glu Ala Ala
        35                  40                  45

Ala Glu Leu Ala Glu Phe Ala Pro Leu Val Gln Tyr Gly Cys His Ser
    50                  55                  60

His Leu Arg Phe Phe Leu Cys Ser Leu Tyr Ala Pro Met Cys Thr Asp
65                  70                  75                  80

Gln Val Ser Thr Pro Ile Pro Ala Cys Arg Pro Met Cys Glu Gln Ala
                85                  90                  95

Arg Leu Arg Cys Ala Pro Ile Met Glu Gln Phe Asn Phe Gly Trp Pro
            100                 105                 110

Asp Ser Leu Asp Cys Ala Arg Leu Pro Thr Arg Asn Asp Pro His Ala
        115                 120                 125

Leu Cys Met Glu Ala Pro Glu Asn Ala
    130                 135

<210> SEQ ID NO 41
<211> LENGTH: 134
<212> TYPE: PRT
<213> ORGANISM: Artificial Sequence
<220> FEATURE:
```

-continued

```
<223> OTHER INFORMATION: Human FZD10 Fri domain amino acid sequence
      without predicted signal; amino acids 21-154 of SEQ ID NO:26

<400> SEQUENCE: 41
```

Ile Ser Ser Met Asp Met Glu Arg Pro Gly Asp Gly Lys Cys Gln Pro
1               5                   10                  15

Ile Glu Ile Pro Met Cys Lys Asp Ile Gly Tyr Asn Met Thr Arg Met
            20                  25                  30

Pro Asn Leu Met Gly His Glu Asn Gln Arg Glu Ala Ala Ile Gln Leu
        35                  40                  45

His Glu Phe Ala Pro Leu Val Glu Tyr Gly Cys His Gly His Leu Arg
    50                  55                  60

Phe Phe Leu Cys Ser Leu Tyr Ala Pro Met Cys Thr Glu Gln Val Ser
65                  70                  75                  80

Thr Pro Ile Pro Ala Cys Arg Val Met Cys Glu Gln Ala Arg Leu Lys
                85                  90                  95

Cys Ser Pro Ile Met Glu Gln Phe Asn Phe Lys Trp Pro Asp Ser Leu
            100                 105                 110

Asp Cys Arg Lys Leu Pro Asn Lys Asn Asp Pro Asn Tyr Leu Cys Met
        115                 120                 125

Glu Ala Pro Asn Asn Gly
        130

```
<210> SEQ ID NO 42
<211> LENGTH: 230
<212> TYPE: PRT
<213> ORGANISM: Artificial Sequence
<220> FEATURE:
<223> OTHER INFORMATION: Human IgG1 Fc region

<400> SEQUENCE: 42
```

Lys Ser Ser Asp Lys Thr His Thr Cys Pro Pro Cys Pro Ala Pro Glu
1               5                   10                  15

Leu Leu Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser His Glu Asp Pro Glu Val Lys Phe Asn Trp Tyr Val Asp Gly
    50                  55                  60

Val Glu Val His Asn Ala Lys Thr Lys Pro Arg Glu Glu Gln Tyr Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
        115                 120                 125

Pro Gln Val Tyr Thr Leu Pro Pro Ser Arg Asp Glu Leu Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Lys
            180                 185                 190

Leu Thr Val Asp Lys Ser Arg Trp Gln Gln Gly Asn Val Phe Ser Cys

```
            195                 200                 205
Ser Val Met His Glu Ala Leu His Asn His Tyr Thr Gln Lys Ser Leu
    210                 215                 220

Ser Leu Ser Pro Gly Lys
225                 230

<210> SEQ ID NO 43
<211> LENGTH: 232
<212> TYPE: PRT
<213> ORGANISM: Artificial Sequence
<220> FEATURE:
<223> OTHER INFORMATION: Human IgG1 Fc region

<400> SEQUENCE: 43

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 44
<211> LENGTH: 224
<212> TYPE: PRT
<213> ORGANISM: Artificial Sequence
<220> FEATURE:
<223> OTHER INFORMATION: Human IgG2 Fc region

<400> SEQUENCE: 44

Cys Val Glu Cys Pro Pro Cys Pro Ala Pro Pro Val Ala Gly Pro Ser
1               5                   10                  15

Val Phe Leu Phe Pro Pro Lys Pro Lys Asp Thr Leu Met Ile Ser Arg
            20                  25                  30
```

```
Thr Pro Glu Val Thr Cys Val Val Asp Val Ser His Glu Asp Pro
             35                  40                  45

Glu Val Gln Phe Asn Trp Tyr Val Asp Gly Val Glu Val His Asn Ala
 50                  55                  60

Lys Thr Lys Pro Arg Glu Gln Phe Asn Ser Thr Phe Arg Val Val
 65                  70                  75                  80

Ser Val Leu Thr Val Val His Gln Asp Trp Leu Asn Gly Lys Glu Tyr
                 85                  90                  95

Lys Cys Lys Val Ser Asn Lys Gly Leu Pro Ala Pro Ile Glu Lys Thr
                100                 105                 110

Ile Ser Lys Thr Lys Gly Gln Pro Arg Glu Pro Gln Val Tyr Thr Leu
                115                 120                 125

Pro Pro Ser Arg Glu Glu Met Thr Lys Asn Gln Val Ser Leu Thr Cys
130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Met Leu Asp
                165                 170                 175

Ser Asp Gly Ser Phe Phe Leu Tyr Ser Lys Leu Thr Val Asp Lys Ser
                180                 185                 190

Arg Trp Gln Gln Gly Asn Val Phe Ser Cys Ser Val Met His Glu Ala
                195                 200                 205

Leu His Asn His Tyr Thr Gln Lys Ser Leu Ser Leu Ser Pro Gly Lys
                210                 215                 220

<210> SEQ ID NO 45
<211> LENGTH: 364
<212> TYPE: PRT
<213> ORGANISM: Artificial Sequence
<220> FEATURE:
<223> OTHER INFORMATION: FZD8-Fc variant 54F03; without signal;
      alternative cleavage

<400> SEQUENCE: 45

Ala Ala Ala Ala Ser Ala Lys Glu Leu Ala Cys Gln Glu Ile Thr Val
 1               5                  10                  15

Pro Leu Cys Lys Gly Ile Gly Tyr Asn Tyr Thr Tyr Met Pro Asn Gln
                 20                  25                  30

Phe Asn His Asp Thr Gln Asp Glu Ala Gly Leu Glu Val His Gln Phe
             35                  40                  45

Trp Pro Leu Val Glu Ile Gln Cys Ser Pro Asp Leu Lys Phe Phe Leu
 50                  55                  60

Cys Ser Met Tyr Thr Pro Ile Cys Leu Glu Asp Tyr Lys Lys Pro Leu
 65                  70                  75                  80

Pro Pro Cys Arg Ser Val Cys Glu Arg Ala Lys Ala Gly Cys Ala Pro
                 85                  90                  95

Leu Met Arg Gln Tyr Gly Phe Ala Trp Pro Asp Arg Met Arg Cys Asp
                100                 105                 110

Arg Leu Pro Glu Gln Gly Asn Pro Asp Thr Leu Cys Met Asp Tyr Asn
                115                 120                 125

Arg Thr Asp Leu Thr Thr Gly Arg Ala Asp Lys Thr His Thr Cys Pro
                130                 135                 140

Pro Cys Pro Ala Pro Glu Leu Leu Gly Gly Pro Ser Val Phe Leu Phe
145                 150                 155                 160

Pro Pro Lys Pro Lys Asp Thr Leu Met Ile Ser Arg Thr Pro Glu Val
                165                 170                 175
```

```
Thr Cys Val Val Val Asp Val Ser His Glu Asp Pro Glu Val Lys Phe
            180                 185                 190

Asn Trp Tyr Val Asp Gly Val Glu Val His Asn Ala Lys Thr Lys Pro
            195                 200                 205

Arg Glu Glu Gln Tyr Asn Ser Thr Tyr Arg Val Val Ser Val Leu Thr
210                 215                 220

Val Leu His Gln Asp Trp Leu Asn Gly Lys Glu Tyr Lys Cys Lys Val
225                 230                 235                 240

Ser Asn Lys Ala Leu Pro Ala Pro Ile Glu Lys Thr Ile Ser Lys Ala
                245                 250                 255

Lys Gly Gln Pro Arg Glu Pro Gln Val Tyr Thr Leu Pro Pro Ser Arg
            260                 265                 270

Asp Glu Leu Thr Lys Asn Gln Val Ser Leu Thr Cys Leu Val Lys Gly
            275                 280                 285

Phe Tyr Pro Ser Asp Ile Ala Val Glu Trp Glu Ser Asn Gly Gln Pro
            290                 295                 300

Glu Asn Asn Tyr Lys Thr Thr Pro Pro Val Leu Asp Ser Asp Gly Ser
305                 310                 315                 320

Phe Phe Leu Tyr Ser Lys Leu Thr Val Asp Lys Ser Arg Trp Gln Gln
                325                 330                 335

Gly Asn Val Phe Ser Cys Ser Val Met His Glu Ala Leu His Asn His
            340                 345                 350

Tyr Thr Gln Lys Ser Leu Ser Leu Ser Pro Gly Lys
            355                 360

<210> SEQ ID NO 46
<211> LENGTH: 364
<212> TYPE: PRT
<213> ORGANISM: Artificial Sequence
<220> FEATURE:
<223> OTHER INFORMATION: FZD8-Fc variant 54F09

<400> SEQUENCE: 46

Ala Ser Ala Lys Glu Leu Ala Cys Gln Glu Ile Thr Val Pro Leu Cys
1               5                   10                  15

Lys Gly Ile Gly Tyr Asn Tyr Thr Tyr Met Pro Asn Gln Phe Asn His
            20                  25                  30

Asp Thr Gln Asp Glu Ala Gly Leu Glu Val His Gln Phe Trp Pro Leu
        35                  40                  45

Val Glu Ile Gln Cys Ser Pro Asp Leu Lys Phe Phe Leu Cys Ser Met
    50                  55                  60

Tyr Thr Pro Ile Cys Leu Glu Asp Tyr Lys Lys Pro Leu Pro Pro Cys
65                  70                  75                  80

Arg Ser Val Cys Glu Arg Ala Lys Ala Gly Cys Ala Pro Leu Met Arg
                85                  90                  95

Gln Tyr Gly Phe Ala Trp Pro Asp Arg Met Arg Cys Asp Arg Leu Pro
            100                 105                 110

Glu Gln Gly Asn Pro Asp Thr Leu Cys Met Asp Tyr Asn Arg Thr Asp
        115                 120                 125

Leu Thr Thr Ala Ala Pro Ser Pro Pro Asp Lys Thr His Thr Cys Pro
    130                 135                 140

Pro Cys Pro Ala Pro Glu Leu Leu Gly Gly Pro Ser Val Phe Leu Phe
145                 150                 155                 160

Pro Pro Lys Pro Lys Asp Thr Leu Met Ile Ser Arg Thr Pro Glu Val
                165                 170                 175
```

```
Thr Cys Val Val Val Asp Val Ser His Glu Asp Pro Glu Val Lys Phe
            180                 185                 190

Asn Trp Tyr Val Asp Gly Val Glu Val His Asn Ala Lys Thr Lys Pro
            195                 200                 205

Arg Glu Glu Gln Tyr Asn Ser Thr Tyr Arg Val Val Ser Val Leu Thr
    210                 215                 220

Val Leu His Gln Asp Trp Leu Asn Gly Lys Glu Tyr Lys Cys Lys Val
225                 230                 235                 240

Ser Asn Lys Ala Leu Pro Ala Pro Ile Glu Lys Thr Ile Ser Lys Ala
                245                 250                 255

Lys Gly Gln Pro Arg Glu Pro Gln Val Tyr Thr Leu Pro Pro Ser Arg
            260                 265                 270

Asp Glu Leu Thr Lys Asn Gln Val Ser Leu Thr Cys Leu Val Lys Gly
            275                 280                 285

Phe Tyr Pro Ser Asp Ile Ala Val Glu Trp Glu Ser Asn Gly Gln Pro
        290                 295                 300

Glu Asn Asn Tyr Lys Thr Thr Pro Pro Val Leu Asp Ser Asp Gly Ser
305                 310                 315                 320

Phe Phe Leu Tyr Ser Lys Leu Thr Val Asp Lys Ser Arg Trp Gln Gln
                325                 330                 335

Gly Asn Val Phe Ser Cys Ser Val Met His Glu Ala Leu His Asn His
            340                 345                 350

Tyr Thr Gln Lys Ser Leu Ser Leu Ser Pro Gly Lys
            355                 360

<210> SEQ ID NO 47
<211> LENGTH: 367
<212> TYPE: PRT
<213> ORGANISM: Artificial Sequence
<220> FEATURE:
<223> OTHER INFORMATION: FZD8-Fc variant 54F09

<400> SEQUENCE: 47

Ala Ala Ala Ala Ser Ala Lys Glu Leu Ala Cys Gln Glu Ile Thr Val
1               5                   10                  15

Pro Leu Cys Lys Gly Ile Gly Tyr Asn Tyr Thr Tyr Met Pro Asn Gln
            20                  25                  30

Phe Asn His Asp Thr Gln Asp Glu Ala Gly Leu Glu Val His Gln Phe
        35                  40                  45

Trp Pro Leu Val Glu Ile Gln Cys Ser Pro Asp Leu Lys Phe Phe Leu
    50                  55                  60

Cys Ser Met Tyr Thr Pro Ile Cys Leu Glu Asp Tyr Lys Lys Pro Leu
65                  70                  75                  80

Pro Pro Cys Arg Ser Val Cys Glu Arg Ala Lys Ala Gly Cys Ala Pro
                85                  90                  95

Leu Met Arg Gln Tyr Gly Phe Ala Trp Pro Asp Arg Met Arg Cys Asp
            100                 105                 110

Arg Leu Pro Glu Gln Gly Asn Pro Asp Thr Leu Cys Met Asp Tyr Asn
        115                 120                 125

Arg Thr Asp Leu Thr Thr Ala Ala Pro Ser Pro Asp Lys Thr His Thr
    130                 135                 140

Cys Pro Pro Cys Pro Ala Pro Glu Leu Leu Gly Gly Pro Ser Val
145                 150                 155                 160

Phe Leu Phe Pro Pro Lys Pro Lys Asp Thr Leu Met Ile Ser Arg Thr
                165                 170                 175
```

```
Pro Glu Val Thr Cys Val Val Asp Val Ser His Glu Asp Pro Glu
            180                 185                 190

Val Lys Phe Asn Trp Tyr Val Asp Gly Val Glu Val His Asn Ala Lys
        195                 200                 205

Thr Lys Pro Arg Glu Glu Gln Tyr Asn Ser Thr Tyr Arg Val Val Ser
    210                 215                 220

Val Leu Thr Val Leu His Gln Asp Trp Leu Asn Gly Lys Glu Tyr Lys
225                 230                 235                 240

Cys Lys Val Ser Asn Lys Ala Leu Pro Ala Pro Ile Glu Lys Thr Ile
                245                 250                 255

Ser Lys Ala Lys Gly Gln Pro Arg Glu Pro Gln Val Tyr Thr Leu Pro
            260                 265                 270

Pro Ser Arg Asp Glu Leu Thr Lys Asn Gln Val Ser Leu Thr Cys Leu
        275                 280                 285

Val Lys Gly Phe Tyr Pro Ser Asp Ile Ala Val Glu Trp Glu Ser Asn
    290                 295                 300

Gly Gln Pro Glu Asn Asn Tyr Lys Thr Thr Pro Pro Val Leu Asp Ser
305                 310                 315                 320

Asp Gly Ser Phe Phe Leu Tyr Ser Lys Leu Thr Val Asp Lys Ser Arg
                325                 330                 335

Trp Gln Gln Gly Asn Val Phe Ser Cys Ser Val Met His Glu Ala Leu
            340                 345                 350

His Asn His Tyr Thr Gln Lys Ser Leu Ser Leu Ser Pro Gly Lys
        355                 360                 365

<210> SEQ ID NO 48
<211> LENGTH: 361
<212> TYPE: PRT
<213> ORGANISM: Artificial Sequence
<220> FEATURE:
<223> OTHER INFORMATION: FZD8-Fc variant 54F15

<400> SEQUENCE: 48

Ala Ser Ala Lys Glu Leu Ala Cys Gln Glu Ile Thr Val Pro Leu Cys
1               5                   10                  15

Lys Gly Ile Gly Tyr Asn Tyr Thr Tyr Met Pro Asn Gln Phe Asn His
            20                  25                  30

Asp Thr Gln Asp Glu Ala Gly Leu Glu Val His Gln Phe Trp Pro Leu
        35                  40                  45

Val Glu Ile Gln Cys Ser Pro Asp Leu Lys Phe Phe Leu Cys Ser Met
    50                  55                  60

Tyr Thr Pro Ile Cys Leu Glu Asp Tyr Lys Lys Pro Leu Pro Pro Cys
65                  70                  75                  80

Arg Ser Val Cys Glu Arg Ala Lys Ala Gly Cys Ala Pro Leu Met Arg
                85                  90                  95

Gln Tyr Gly Phe Ala Trp Pro Asp Arg Met Arg Cys Asp Arg Leu Pro
            100                 105                 110

Glu Gln Gly Asn Pro Asp Thr Leu Cys Met Asp Tyr Asn Arg Thr Asp
        115                 120                 125

Leu Thr Thr Ala Ala Pro Asp Lys Thr His Thr Cys Pro Pro Cys Pro
    130                 135                 140

Ala Pro Glu Leu Leu Gly Gly Pro Ser Val Phe Leu Phe Pro Pro Lys
145                 150                 155                 160

Pro Lys Asp Thr Leu Met Ile Ser Arg Thr Pro Glu Val Thr Cys Val
                165                 170                 175
```

```
Val Val Asp Val Ser His Glu Asp Pro Glu Val Lys Phe Asn Trp Tyr
            180                 185                 190

Val Asp Gly Val Glu Val His Asn Ala Lys Thr Lys Pro Arg Glu Glu
            195                 200                 205

Gln Tyr Asn Ser Thr Tyr Arg Val Val Ser Val Leu Thr Val Leu His
    210                 215                 220

Gln Asp Trp Leu Asn Gly Lys Glu Tyr Lys Cys Lys Val Ser Asn Lys
225                 230                 235                 240

Ala Leu Pro Ala Pro Ile Glu Lys Thr Ile Ser Lys Ala Lys Gly Gln
                245                 250                 255

Pro Arg Glu Pro Gln Val Tyr Thr Leu Pro Pro Ser Arg Asp Glu Leu
            260                 265                 270

Thr Lys Asn Gln Val Ser Leu Thr Cys Leu Val Lys Gly Phe Tyr Pro
            275                 280                 285

Ser Asp Ile Ala Val Glu Trp Glu Ser Asn Gly Gln Pro Glu Asn Asn
            290                 295                 300

Tyr Lys Thr Thr Pro Pro Val Leu Asp Ser Asp Gly Ser Phe Phe Leu
305                 310                 315                 320

Tyr Ser Lys Leu Thr Val Asp Lys Ser Arg Trp Gln Gln Gly Asn Val
                325                 330                 335

Phe Ser Cys Ser Val Met His Glu Ala Leu His Asn His Tyr Thr Gln
            340                 345                 350

Lys Ser Leu Ser Leu Ser Pro Gly Lys
            355                 360

<210> SEQ ID NO 49
<211> LENGTH: 364
<212> TYPE: PRT
<213> ORGANISM: Artificial Sequence
<220> FEATURE:
<223> OTHER INFORMATION: FZD8-Fc variant 54F15

<400> SEQUENCE: 49

Ala Ala Ala Ala Ser Ala Lys Glu Leu Ala Cys Gln Glu Ile Thr Val
1               5                   10                  15

Pro Leu Cys Lys Gly Ile Gly Tyr Asn Tyr Thr Tyr Met Pro Asn Gln
            20                  25                  30

Phe Asn His Asp Thr Gln Asp Glu Ala Gly Leu Glu Val His Gln Phe
        35                  40                  45

Trp Pro Leu Val Glu Ile Gln Cys Ser Pro Asp Leu Lys Phe Phe Leu
    50                  55                  60

Cys Ser Met Tyr Thr Pro Ile Cys Leu Glu Asp Tyr Lys Lys Pro Leu
65                  70                  75                  80

Pro Pro Cys Arg Ser Val Cys Glu Arg Ala Lys Ala Gly Cys Ala Pro
                85                  90                  95

Leu Met Arg Gln Tyr Gly Phe Ala Trp Pro Asp Arg Met Arg Cys Asp
            100                 105                 110

Arg Leu Pro Glu Gln Gly Asn Pro Asp Thr Leu Cys Met Asp Tyr Asn
        115                 120                 125

Arg Thr Asp Leu Thr Thr Ala Ala Pro Asp Lys Thr His Thr Cys Pro
    130                 135                 140

Pro Cys Pro Ala Pro Glu Leu Leu Gly Gly Pro Ser Val Phe Leu Phe
145                 150                 155                 160

Pro Pro Lys Pro Lys Asp Thr Leu Met Ile Ser Arg Thr Pro Glu Val
                165                 170                 175
```

```
Thr Cys Val Val Val Asp Val Ser His Glu Asp Pro Glu Val Lys Phe
            180                 185                 190

Asn Trp Tyr Val Asp Gly Val Glu Val His Asn Ala Lys Thr Lys Pro
        195                 200                 205

Arg Glu Glu Gln Tyr Asn Ser Thr Tyr Arg Val Val Ser Val Leu Thr
    210                 215                 220

Val Leu His Gln Asp Trp Leu Asn Gly Lys Glu Tyr Lys Cys Lys Val
225                 230                 235                 240

Ser Asn Lys Ala Leu Pro Ala Pro Ile Glu Lys Thr Ile Ser Lys Ala
                245                 250                 255

Lys Gly Gln Pro Arg Glu Pro Gln Val Tyr Thr Leu Pro Pro Ser Arg
            260                 265                 270

Asp Glu Leu Thr Lys Asn Gln Val Ser Leu Thr Cys Leu Val Lys Gly
        275                 280                 285

Phe Tyr Pro Ser Asp Ile Ala Val Glu Trp Glu Ser Asn Gly Gln Pro
    290                 295                 300

Glu Asn Asn Tyr Lys Thr Thr Pro Pro Val Leu Asp Ser Asp Gly Ser
305                 310                 315                 320

Phe Phe Leu Tyr Ser Lys Leu Thr Val Asp Lys Ser Arg Trp Gln Gln
                325                 330                 335

Gly Asn Val Phe Ser Cys Ser Val Met His Glu Ala Leu His Asn His
            340                 345                 350

Tyr Thr Gln Lys Ser Leu Ser Leu Ser Pro Gly Lys
        355                 360

<210> SEQ ID NO 50
<211> LENGTH: 361
<212> TYPE: PRT
<213> ORGANISM: Artificial Sequence
<220> FEATURE:
<223> OTHER INFORMATION: FZD8-Fc variant 54F16, 54F17, 54F18, 54F23,
      54F25, 54F27, 54F29, 54F31, and 54F34 (without predicted signal)

<400> SEQUENCE: 50

Ala Ser Ala Lys Glu Leu Ala Cys Gln Glu Ile Thr Val Pro Leu Cys
1               5                   10                  15

Lys Gly Ile Gly Tyr Asn Tyr Thr Tyr Met Pro Asn Gln Phe Asn His
            20                  25                  30

Asp Thr Gln Asp Glu Ala Gly Leu Glu Val His Gln Phe Trp Pro Leu
        35                  40                  45

Val Glu Ile Gln Cys Ser Pro Asp Leu Lys Phe Phe Leu Cys Ser Met
    50                  55                  60

Tyr Thr Pro Ile Cys Leu Glu Asp Tyr Lys Lys Pro Leu Pro Pro Cys
65                  70                  75                  80

Arg Ser Val Cys Glu Arg Ala Lys Ala Gly Cys Ala Pro Leu Met Arg
                85                  90                  95

Gln Tyr Gly Phe Ala Trp Pro Asp Arg Met Arg Cys Asp Arg Leu Pro
            100                 105                 110

Glu Gln Gly Asn Pro Asp Thr Leu Cys Met Asp Tyr Asn Arg Thr Asp
        115                 120                 125

Leu Thr Thr Lys Ser Ser Asp Lys Thr His Thr Cys Pro Pro Cys Pro
130                 135                 140

Ala Pro Glu Leu Leu Gly Gly Pro Ser Val Phe Leu Phe Pro Pro Lys
145                 150                 155                 160

Pro Lys Asp Thr Leu Met Ile Ser Arg Thr Pro Glu Val Thr Cys Val
```

```
                165                 170                 175
Val Val Asp Val Ser His Glu Asp Pro Glu Val Lys Phe Asn Trp Tyr
                    180                 185                 190

Val Asp Gly Val Glu Val His Asn Ala Lys Thr Lys Pro Arg Glu Glu
            195                 200                 205

Gln Tyr Asn Ser Thr Tyr Arg Val Val Ser Val Leu Thr Val Leu His
        210                 215                 220

Gln Asp Trp Leu Asn Gly Lys Glu Tyr Lys Cys Lys Val Ser Asn Lys
225                 230                 235                 240

Ala Leu Pro Ala Pro Ile Glu Lys Thr Ile Ser Lys Ala Lys Gly Gln
                245                 250                 255

Pro Arg Glu Pro Gln Val Tyr Thr Leu Pro Pro Ser Arg Asp Glu Leu
            260                 265                 270

Thr Lys Asn Gln Val Ser Leu Thr Cys Leu Val Lys Gly Phe Tyr Pro
        275                 280                 285

Ser Asp Ile Ala Val Glu Trp Glu Ser Asn Gly Gln Pro Glu Asn Asn
290                 295                 300

Tyr Lys Thr Thr Pro Pro Val Leu Asp Ser Asp Gly Ser Phe Phe Leu
305                 310                 315                 320

Tyr Ser Lys Leu Thr Val Asp Lys Ser Arg Trp Gln Gln Gly Asn Val
                325                 330                 335

Phe Ser Cys Ser Val Met His Glu Ala Leu His Asn His Tyr Thr Gln
            340                 345                 350

Lys Ser Leu Ser Leu Ser Pro Gly Lys
        355                 360

<210> SEQ ID NO 51
<211> LENGTH: 363
<212> TYPE: PRT
<213> ORGANISM: Artificial Sequence
<220> FEATURE:
<223> OTHER INFORMATION: FZD8-Fc variant 54F16

<400> SEQUENCE: 51

Ala Ala Ala Ala Ser Ala Lys Glu Leu Ala Cys Gln Glu Ile Thr Val
1               5                   10                  15

Pro Leu Cys Lys Gly Ile Gly Tyr Asn Tyr Thr Tyr Met Pro Asn Gln
                20                  25                  30

Phe Asn His Asp Thr Gln Asp Glu Ala Gly Leu Glu Val His Gln Phe
            35                  40                  45

Trp Pro Leu Val Glu Ile Gln Cys Ser Pro Asp Leu Lys Phe Phe Leu
50                  55                  60

Cys Ser Met Tyr Thr Pro Ile Cys Leu Glu Asp Tyr Lys Lys Pro Leu
65                  70                  75                  80

Pro Pro Cys Arg Ser Val Cys Glu Arg Ala Lys Ala Gly Cys Ala Pro
                85                  90                  95

Leu Met Arg Gln Tyr Gly Phe Ala Trp Pro Asp Arg Met Arg Cys Asp
            100                 105                 110

Arg Leu Pro Glu Gln Gly Asn Pro Asp Thr Leu Cys Met Asp Tyr Asn
        115                 120                 125

Arg Thr Asp Leu Thr Thr Lys Ser Ser Asp Lys Thr His Thr Cys Pro
    130                 135                 140

Pro Cys Pro Ala Pro Glu Leu Leu Gly Gly Pro Ser Val Phe Leu Phe
145                 150                 155                 160

Pro Pro Lys Pro Lys Asp Thr Leu Met Ile Ser Arg Thr Pro Glu Val
```

```
                    165                 170                 175
Thr Cys Val Val Val Asp Val Ser His Glu Asp Pro Glu Val Lys Phe
                180                 185                 190

Asn Trp Tyr Val Asp Gly Val Glu Val His Asn Ala Lys Thr Lys Pro
            195                 200                 205

Arg Glu Glu Gln Tyr Asn Ser Thr Tyr Arg Val Val Ser Val Leu Thr
        210                 215                 220

Val Leu His Gln Asp Trp Leu Asn Gly Lys Glu Tyr Lys Cys Lys Val
225                 230                 235                 240

Ser Asn Lys Ala Leu Pro Ala Pro Ile Glu Lys Thr Ile Ser Lys Ala
                245                 250                 255

Lys Gly Gln Pro Arg Glu Pro Gln Val Tyr Thr Leu Pro Pro Ser Arg
            260                 265                 270

Asp Glu Leu Thr Lys Asn Gln Val Ser Leu Thr Cys Leu Val Lys Gly
        275                 280                 285

Phe Tyr Pro Ser Asp Ile Ala Val Glu Trp Glu Ser Asn Gly Gln Pro
    290                 295                 300

Glu Asn Asn Tyr Lys Thr Thr Pro Pro Val Leu Asp Ser Asp Gly Ser
305                 310                 315                 320

Phe Phe Leu Tyr Ser Lys Leu Thr Val Asp Lys Ser Arg Trp Gln Gln
                325                 330                 335

Gly Asn Val Phe Ser Cys Ser Val Met His Glu Ala Leu His Asn His
            340                 345                 350

Tyr Thr Gln Lys Ser Leu Ser Leu Ser Pro Gly
        355                 360
```

<210> SEQ ID NO 52
<211> LENGTH: 388
<212> TYPE: PRT
<213> ORGANISM: Artificial Sequence
<220> FEATURE:
<223> OTHER INFORMATION: FZD8-Fc variant 54F16 (with signal)

<400> SEQUENCE: 52

```
Met Glu Trp Gly Tyr Leu Leu Glu Val Thr Ser Leu Leu Ala Ala Leu
1               5                   10                  15

Ala Leu Leu Gln Arg Ser Ser Gly Ala Ala Ala Ser Ala Lys Glu
            20                  25                  30

Leu Ala Cys Gln Glu Ile Thr Val Pro Leu Cys Lys Gly Ile Gly Tyr
        35                  40                  45

Asn Tyr Thr Tyr Met Pro Asn Gln Phe Asn His Asp Thr Gln Asp Glu
    50                  55                  60

Ala Gly Leu Glu Val His Gln Phe Trp Pro Leu Val Glu Ile Gln Cys
65                  70                  75                  80

Ser Pro Asp Leu Lys Phe Phe Leu Cys Ser Met Tyr Thr Pro Ile Cys
                85                  90                  95

Leu Glu Asp Tyr Lys Lys Pro Leu Pro Pro Cys Arg Ser Val Cys Glu
            100                 105                 110

Arg Ala Lys Ala Gly Cys Ala Pro Leu Met Arg Gln Tyr Gly Phe Ala
        115                 120                 125

Trp Pro Asp Arg Met Arg Cys Asp Arg Leu Pro Glu Gln Gly Asn Pro
    130                 135                 140

Asp Thr Leu Cys Met Asp Tyr Asn Arg Thr Asp Leu Thr Thr Lys Ser
145                 150                 155                 160

Ser Asp Lys Thr His Thr Cys Pro Pro Cys Pro Ala Pro Glu Leu Leu
```

```
               165                 170                 175
Gly Gly Pro Ser Val Phe Leu Phe Pro Pro Lys Pro Lys Asp Thr Leu
            180                 185                 190

Met Ile Ser Arg Thr Pro Glu Val Thr Cys Val Val Val Asp Val Ser
            195                 200                 205

His Glu Asp Pro Glu Val Lys Phe Asn Trp Tyr Val Asp Gly Val Glu
            210                 215                 220

Val His Asn Ala Lys Thr Lys Pro Arg Glu Glu Gln Tyr Asn Ser Thr
225                 230                 235                 240

Tyr Arg Val Val Ser Val Leu Thr Val Leu His Gln Asp Trp Leu Asn
            245                 250                 255

Gly Lys Glu Tyr Lys Cys Lys Val Ser Asn Lys Ala Leu Pro Ala Pro
            260                 265                 270

Ile Glu Lys Thr Ile Ser Lys Ala Lys Gly Gln Pro Arg Glu Pro Gln
            275                 280                 285

Val Tyr Thr Leu Pro Pro Ser Arg Asp Glu Leu Thr Lys Asn Gln Val
            290                 295                 300

Ser Leu Thr Cys Leu Val Lys Gly Phe Tyr Pro Ser Asp Ile Ala Val
305                 310                 315                 320

Glu Trp Glu Ser Asn Gly Gln Pro Glu Asn Asn Tyr Lys Thr Thr Pro
            325                 330                 335

Pro Val Leu Asp Ser Asp Gly Ser Phe Phe Leu Tyr Ser Lys Leu Thr
            340                 345                 350

Val Asp Lys Ser Arg Trp Gln Gln Gly Asn Val Phe Ser Cys Ser Val
            355                 360                 365

Met His Glu Ala Leu His Asn His Tyr Thr Gln Lys Ser Leu Ser Leu
            370                 375                 380

Ser Pro Gly Lys
385

<210> SEQ ID NO 53
<211> LENGTH: 363
<212> TYPE: PRT
<213> ORGANISM: Artificial Sequence
<220> FEATURE:
<223> OTHER INFORMATION: FZD8-Fc variant 54F19, 54F20, 54F24, 54F26,
      54F28, 54F30, 54F32, 54F34 and 54F35

<400> SEQUENCE: 53

Ala Ser Ala Lys Glu Leu Ala Cys Gln Glu Ile Thr Val Pro Leu Cys
1               5                   10                  15

Lys Gly Ile Gly Tyr Asn Tyr Thr Tyr Met Pro Asn Gln Phe Asn His
            20                  25                  30

Asp Thr Gln Asp Glu Ala Gly Leu Glu Val His Gln Phe Trp Pro Leu
        35                  40                  45

Val Glu Ile Gln Cys Ser Pro Asp Leu Lys Phe Phe Leu Cys Ser Met
    50                  55                  60

Tyr Thr Pro Ile Cys Leu Glu Asp Tyr Lys Lys Pro Leu Pro Pro Cys
65                  70                  75                  80

Arg Ser Val Cys Glu Arg Ala Lys Ala Gly Cys Ala Pro Leu Met Arg
                85                  90                  95

Gln Tyr Gly Phe Ala Trp Pro Asp Arg Met Arg Cys Asp Arg Leu Pro
            100                 105                 110

Glu Gln Gly Asn Pro Asp Thr Leu Cys Met Asp Tyr Asn Arg Thr Asp
        115                 120                 125
```

-continued

Leu Thr Thr Glu Pro Lys Ser Ser Asp Lys Thr His Thr Cys Pro Pro
130                 135                 140

Cys Pro Ala Pro Glu Leu Leu Gly Gly Pro Ser Val Phe Leu Phe Pro
145                 150                 155                 160

Pro Lys Pro Lys Asp Thr Leu Met Ile Ser Arg Thr Pro Glu Val Thr
                165                 170                 175

Cys Val Val Val Asp Val Ser His Glu Asp Pro Glu Val Lys Phe Asn
                180                 185                 190

Trp Tyr Val Asp Gly Val Glu Val His Asn Ala Lys Thr Lys Pro Arg
            195                 200                 205

Glu Glu Gln Tyr Asn Ser Thr Tyr Arg Val Val Ser Val Leu Thr Val
    210                 215                 220

Leu His Gln Asp Trp Leu Asn Gly Lys Glu Tyr Lys Cys Lys Val Ser
225                 230                 235                 240

Asn Lys Ala Leu Pro Ala Pro Ile Glu Lys Thr Ile Ser Lys Ala Lys
                245                 250                 255

Gly Gln Pro Arg Glu Pro Gln Val Tyr Thr Leu Pro Pro Ser Arg Asp
                260                 265                 270

Glu Leu Thr Lys Asn Gln Val Ser Leu Thr Cys Leu Val Lys Gly Phe
            275                 280                 285

Tyr Pro Ser Asp Ile Ala Val Glu Trp Glu Ser Asn Gly Gln Pro Glu
    290                 295                 300

Asn Asn Tyr Lys Thr Thr Pro Pro Val Leu Asp Ser Asp Gly Ser Phe
305                 310                 315                 320

Phe Leu Tyr Ser Lys Leu Thr Val Asp Lys Ser Arg Trp Gln Gln Gly
                325                 330                 335

Asn Val Phe Ser Cys Ser Val Met His Glu Ala Leu His Asn His Tyr
                340                 345                 350

Thr Gln Lys Ser Leu Ser Leu Ser Pro Gly Lys
            355                 360

<210> SEQ ID NO 54
<211> LENGTH: 366
<212> TYPE: PRT
<213> ORGANISM: Artificial Sequence
<220> FEATURE:
<223> OTHER INFORMATION: FZD8-Fc variant 54F19 amino acid sequence
      (without predicted signal sequence; alternative cleavage)

<400> SEQUENCE: 54

Ala Leu Ala Ala Ser Ala Lys Glu Leu Ala Cys Gln Glu Ile Thr Val
1               5                   10                  15

Pro Leu Cys Lys Gly Ile Gly Tyr Asn Tyr Thr Tyr Met Pro Asn Gln
                20                  25                  30

Phe Asn His Asp Thr Gln Asp Glu Ala Gly Leu Glu Val His Gln Phe
            35                  40                  45

Trp Pro Leu Val Glu Ile Gln Cys Ser Pro Asp Leu Lys Phe Phe Leu
    50                  55                  60

Cys Ser Met Tyr Thr Pro Ile Cys Leu Glu Asp Tyr Lys Lys Pro Leu
65                  70                  75                  80

Pro Pro Cys Arg Ser Val Cys Glu Arg Ala Lys Ala Gly Cys Ala Pro
                85                  90                  95

Leu Met Arg Gln Tyr Gly Phe Ala Trp Pro Asp Arg Met Arg Cys Asp
                100                 105                 110

Arg Leu Pro Glu Gln Gly Asn Pro Asp Thr Leu Cys Met Asp Tyr Asn
            115                 120                 125

```
Arg Thr Asp Leu Thr Thr Glu Pro Lys Ser Ser Asp Lys Thr His Thr
    130                 135                 140

Cys Pro Pro Cys Pro Ala Pro Glu Leu Leu Gly Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
            180                 185                 190

Lys Phe Asn Trp Tyr Val Asp Gly Val Glu Val His Asn Ala Lys Thr
        195                 200                 205

Lys Pro Arg Glu Glu Gln Tyr Asn Ser Thr Tyr Arg Val Val Ser Val
    210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Pro Ile Glu Lys Thr Ile Ser
                245                 250                 255

Lys Ala Lys Gly Gln Pro Arg Glu Pro Gln Val Tyr Thr Leu Pro Pro
            260                 265                 270

Ser Arg Asp Glu Leu Thr Lys Asn Gln Val Ser Leu Thr Cys Leu Val
        275                 280                 285

Lys Gly Phe Tyr Pro Ser Asp Ile Ala Val Glu Trp Glu Ser Asn Gly
    290                 295                 300

Gln Pro Glu Asn Asn Tyr Lys Thr Thr Pro Pro Val Leu Asp Ser Asp
305                 310                 315                 320

Gly Ser Phe Phe Leu Tyr Ser Lys Leu Thr Val Asp Lys Ser Arg Trp
                325                 330                 335

Gln Gln Gly Asn Val Phe Ser Cys Ser Val Met His Glu Ala Leu His
            340                 345                 350

Asn His Tyr Thr Gln Lys Ser Leu Ser Leu Ser Pro Gly Lys
        355                 360                 365

<210> SEQ ID NO 55
<211> LENGTH: 366
<212> TYPE: PRT
<213> ORGANISM: Artificial Sequence
<220> FEATURE:
<223> OTHER INFORMATION: FZD8-Fc variant 54F20 (without predicted
      signal); alternative cleavage

<400> SEQUENCE: 55

Val Leu Ala Ala Ser Ala Lys Glu Leu Ala Cys Gln Glu Ile Thr Val
1               5                   10                  15

Pro Leu Cys Lys Gly Ile Gly Tyr Asn Tyr Thr Tyr Met Pro Asn Gln
                20                  25                  30

Phe Asn His Asp Thr Gln Asp Glu Ala Gly Leu Glu Val His Gln Phe
            35                  40                  45

Trp Pro Leu Val Glu Ile Gln Cys Ser Pro Asp Leu Lys Phe Phe Leu
        50                  55                  60

Cys Ser Met Tyr Thr Pro Ile Cys Leu Glu Asp Tyr Lys Lys Pro Leu
65                  70                  75                  80

Pro Pro Cys Arg Ser Val Cys Glu Arg Ala Lys Ala Gly Cys Ala Pro
                85                  90                  95

Leu Met Arg Gln Tyr Gly Phe Ala Trp Pro Asp Arg Met Arg Cys Asp
            100                 105                 110

Arg Leu Pro Glu Gln Gly Asn Pro Asp Thr Leu Cys Met Asp Tyr Asn
```

```
                115                 120                 125
Arg Thr Asp Leu Thr Thr Glu Pro Lys Ser Ser Asp Lys Thr His Thr
        130                 135                 140
Cys Pro Pro Cys Pro Ala Pro Glu Leu Leu Gly Gly Pro Ser Val Phe
145                 150                 155                 160
Leu Phe Pro Pro Lys Pro Lys Asp Thr Leu Met Ile Ser Arg Thr Pro
                165                 170                 175
Glu Val Thr Cys Val Val Val Asp Val Ser His Glu Asp Pro Glu Val
            180                 185                 190
Lys Phe Asn Trp Tyr Val Asp Gly Val Glu Val His Asn Ala Lys Thr
        195                 200                 205
Lys Pro Arg Glu Glu Gln Tyr Asn Ser Thr Tyr Arg Val Val Ser Val
210                 215                 220
Leu Thr Val Leu His Gln Asp Trp Leu Asn Gly Lys Glu Tyr Lys Cys
225                 230                 235                 240
Lys Val Ser Asn Lys Ala Leu Pro Ala Pro Ile Glu Lys Thr Ile Ser
                245                 250                 255
Lys Ala Lys Gly Gln Pro Arg Glu Pro Gln Val Tyr Thr Leu Pro Pro
            260                 265                 270
Ser Arg Asp Glu Leu Thr Lys Asn Gln Val Ser Leu Thr Cys Leu Val
        275                 280                 285
Lys Gly Phe Tyr Pro Ser Asp Ile Ala Val Glu Trp Glu Ser Asn Gly
    290                 295                 300
Gln Pro Glu Asn Asn Tyr Lys Thr Thr Pro Pro Val Leu Asp Ser Asp
305                 310                 315                 320
Gly Ser Phe Phe Leu Tyr Ser Lys Leu Thr Val Asp Lys Ser Arg Trp
                325                 330                 335
Gln Gln Gly Asn Val Phe Ser Cys Ser Val Met His Glu Ala Leu His
            340                 345                 350
Asn His Tyr Thr Gln Lys Ser Leu Ser Leu Ser Pro Gly Lys
        355                 360                 365

<210> SEQ ID NO 56
<211> LENGTH: 406
<212> TYPE: PRT
<213> ORGANISM: Artificial Sequence
<220> FEATURE:
<223> OTHER INFORMATION: Human ROR1 ECD with signal

<400> SEQUENCE: 56

Met His Arg Pro Arg Arg Arg Gly Thr Arg Pro Pro Leu Leu Ala Leu
1               5                   10                  15
Leu Ala Ala Leu Leu Leu Ala Ala Arg Gly Ala Ala Ala Gln Glu Thr
                20                  25                  30
Glu Leu Ser Val Ser Ala Glu Leu Val Pro Thr Ser Ser Trp Asn Ile
            35                  40                  45
Ser Ser Glu Leu Asn Lys Asp Ser Tyr Leu Thr Leu Asp Glu Pro Met
        50                  55                  60
Asn Asn Ile Thr Thr Ser Leu Gly Gln Thr Ala Glu Leu His Cys Lys
65                  70                  75                  80
Val Ser Gly Asn Pro Pro Pro Thr Ile Arg Trp Phe Lys Asn Asp Ala
                85                  90                  95
Pro Val Val Gln Glu Pro Arg Arg Leu Ser Phe Arg Ser Thr Ile Tyr
            100                 105                 110
Gly Ser Arg Leu Arg Ile Arg Asn Leu Asp Thr Thr Asp Thr Gly Tyr
```

```
            115                 120                 125
Phe Gln Cys Val Ala Thr Asn Gly Lys Glu Val Val Ser Ser Thr Gly
        130                 135                 140

Val Leu Phe Val Lys Phe Gly Pro Pro Thr Ala Ser Pro Gly Tyr
145                 150                 155                 160

Ser Asp Glu Tyr Glu Asp Gly Phe Cys Gln Pro Tyr Arg Gly Ile
                165                 170                 175

Ala Cys Ala Arg Phe Ile Gly Asn Arg Thr Val Tyr Met Glu Ser Leu
            180                 185                 190

His Met Gln Gly Glu Ile Glu Asn Gln Ile Thr Ala Ala Phe Thr Met
            195                 200                 205

Ile Gly Thr Ser Ser His Leu Ser Asp Lys Cys Ser Gln Phe Ala Ile
        210                 215                 220

Pro Ser Leu Cys His Tyr Ala Phe Pro Tyr Cys Asp Glu Thr Ser Ser
225                 230                 235                 240

Val Pro Lys Pro Arg Asp Leu Cys Arg Asp Glu Cys Glu Ile Leu Glu
                245                 250                 255

Asn Val Leu Cys Gln Thr Glu Tyr Ile Phe Ala Arg Ser Asn Pro Met
            260                 265                 270

Ile Leu Met Arg Leu Lys Leu Pro Asn Cys Glu Asp Leu Pro Gln Pro
        275                 280                 285

Glu Ser Pro Glu Ala Ala Asn Cys Ile Arg Ile Gly Ile Pro Met Ala
    290                 295                 300

Asp Pro Ile Asn Lys Asn His Lys Cys Tyr Asn Ser Thr Gly Val Asp
305                 310                 315                 320

Tyr Arg Gly Thr Val Ser Val Thr Lys Ser Gly Arg Gln Cys Gln Pro
                325                 330                 335

Trp Asn Ser Gln Tyr Pro His Thr His Thr Phe Thr Ala Leu Arg Phe
            340                 345                 350

Pro Glu Leu Asn Gly Gly His Ser Tyr Cys Arg Asn Pro Gly Asn Gln
        355                 360                 365

Lys Glu Ala Pro Trp Cys Phe Thr Leu Asp Glu Asn Phe Lys Ser Asp
    370                 375                 380

Leu Cys Asp Ile Pro Ala Cys Asp Ser Lys Asp Ser Lys Glu Lys Asn
385                 390                 395                 400

Lys Met Glu Ile Leu Tyr
                405

<210> SEQ ID NO 57
<211> LENGTH: 403
<212> TYPE: PRT
<213> ORGANISM: Artificial Sequence
<220> FEATURE:
<223> OTHER INFORMATION: Human ROR2 ECD with signal

<400> SEQUENCE: 57

Met Ala Arg Gly Ser Ala Leu Pro Arg Arg Pro Leu Leu Cys Ile Pro
1               5                   10                  15

Ala Val Trp Ala Ala Ala Ala Leu Leu Leu Ser Val Ser Arg Thr Ser
            20                  25                  30

Gly Glu Val Glu Val Leu Asp Pro Asn Asp Pro Leu Gly Pro Leu Asp
        35                  40                  45

Gly Gln Asp Gly Pro Ile Pro Thr Leu Lys Gly Tyr Phe Leu Asn Phe
    50                  55                  60

Leu Glu Pro Val Asn Asn Ile Thr Ile Val Gln Gly Gln Thr Ala Ile
```

Leu His Cys Lys Val Ala Gly Asn Pro Pro Asn Val Arg Trp Leu
65                  70                  75                  80

Lys Asn Asp Ala Pro Val Val Gln Glu Pro Arg Ile Ile Ile Arg
            85                  90                  95

Lys Thr Glu Tyr Gly Ser Arg Leu Arg Ile Gln Asp Leu Asp Thr Thr
        100                 105                 110

Asp Thr Gly Tyr Tyr Gln Cys Val Ala Thr Asn Gly Met Lys Thr Ile
    115                 120                 125

Thr Ala Thr Gly Val Leu Phe Val Arg Leu Gly Pro Thr His Ser Pro
130                 135                 140

Asn His Asn Phe Gln Asp Asp Tyr His Glu Asp Gly Phe Cys Gln Pro
145                 150                 155                 160

Tyr Arg Gly Ile Ala Cys Ala Arg Phe Ile Gly Asn Arg Thr Ile Tyr
            165                 170                 175

Val Asp Ser Leu Gln Met Gln Gly Glu Ile Glu Asn Arg Ile Thr Ala
        180                 185                 190

Ala Phe Thr Met Ile Gly Thr Ser Thr His Leu Ser Asp Gln Cys Ser
    195                 200                 205

Gln Phe Ala Ile Pro Ser Phe Cys His Phe Val Phe Pro Leu Cys Asp
210                 215                 220

Ala Arg Ser Arg Thr Pro Lys Pro Arg Glu Leu Cys Arg Asp Glu Cys
225                 230                 235                 240

Glu Val Leu Glu Ser Asp Leu Cys Arg Gln Glu Tyr Thr Ile Ala Arg
            245                 250                 255

Ser Asn Pro Leu Ile Leu Met Arg Leu Gln Leu Pro Lys Cys Glu Ala
        260                 265                 270

Leu Pro Met Pro Glu Ser Pro Asp Ala Ala Asn Cys Met Arg Ile Gly
    275                 280                 285

Ile Pro Ala Glu Arg Leu Gly Arg Tyr His Gln Cys Tyr Asn Gly Ser
290                 295                 300

Gly Met Asp Tyr Arg Gly Thr Ala Ser Thr Thr Lys Ser Gly His Gln
305                 310                 315                 320

Cys Gln Pro Trp Ala Leu Gln His Pro His Ser His His Leu Ser Ser
            325                 330                 335

Thr Asp Phe Pro Glu Leu Gly Gly Gly His Ala Tyr Cys Arg Asn Pro
        340                 345                 350

Gly Gly Gln Met Glu Gly Pro Trp Cys Phe Thr Gln Asn Lys Asn Val
    355                 360                 365

Arg Met Glu Leu Cys Asp Val Pro Ser Cys Ser Pro Arg Asp Ser Ser
370                 375                 380

Lys Met Gly
385                 390                 395                 400

<210> SEQ ID NO 58
<211> LENGTH: 127
<212> TYPE: PRT
<213> ORGANISM: Artificial Sequence
<220> FEATURE:
<223> OTHER INFORMATION: h-ROR1 minimal Fri domain

<400> SEQUENCE: 58

Cys Gln Pro Tyr Arg Gly Ile Ala Cys Ala Arg Phe Ile Gly Asn Arg
1               5                   10                  15

Thr Val Tyr Met Glu Ser Leu His Met Gln Gly Glu Ile Glu Asn Gln
            20                  25                  30

```
Ile Thr Ala Ala Phe Thr Met Ile Gly Thr Ser Ser His Leu Ser Asp
            35                  40                  45

Lys Cys Ser Gln Phe Ala Ile Pro Ser Leu Cys His Tyr Ala Phe Pro
 50                      55                  60

Tyr Cys Asp Glu Thr Ser Ser Val Pro Lys Pro Arg Asp Leu Cys Arg
 65                  70                  75                  80

Asp Glu Cys Glu Ile Leu Glu Asn Val Leu Cys Gln Thr Glu Tyr Ile
                 85                  90                  95

Phe Ala Arg Ser Asn Pro Met Ile Leu Met Arg Leu Lys Leu Pro Asn
                100                 105                 110

Cys Glu Asp Leu Pro Gln Pro Glu Ser Pro Glu Ala Ala Asn Cys
                115                 120                 125

<210> SEQ ID NO 59
<211> LENGTH: 127
<212> TYPE: PRT
<213> ORGANISM: Artificial Sequence
<220> FEATURE:
<223> OTHER INFORMATION: h-ROR2 minimal Fri domain

<400> SEQUENCE: 59

Cys Gln Pro Tyr Arg Gly Ile Ala Cys Ala Arg Phe Ile Gly Asn Arg
 1               5                  10                  15

Thr Ile Tyr Val Asp Ser Leu Gln Met Gln Gly Glu Ile Glu Asn Arg
             20                  25                  30

Ile Thr Ala Ala Phe Thr Met Ile Gly Thr Ser Thr His Leu Ser Asp
            35                  40                  45

Gln Cys Ser Gln Phe Ala Ile Pro Ser Phe Cys His Phe Val Phe Pro
 50                      55                  60

Leu Cys Asp Ala Arg Ser Arg Thr Pro Lys Pro Arg Glu Leu Cys Arg
 65                  70                  75                  80

Asp Glu Cys Glu Val Leu Glu Ser Asp Leu Cys Arg Gln Glu Tyr Thr
                 85                  90                  95

Ile Ala Arg Ser Asn Pro Leu Ile Leu Met Arg Leu Gln Leu Pro Lys
                100                 105                 110

Cys Glu Ala Leu Pro Met Pro Glu Ser Pro Asp Ala Ala Asn Cys
                115                 120                 125

<210> SEQ ID NO 60
<211> LENGTH: 8
<212> TYPE: PRT
<213> ORGANISM: Artificial Sequence
<220> FEATURE:
<223> OTHER INFORMATION: Linker

<400> SEQUENCE: 60

Glu Ser Gly Gly Gly Gly Val Thr
 1               5

<210> SEQ ID NO 61
<211> LENGTH: 9
<212> TYPE: PRT
<213> ORGANISM: Artificial Sequence
<220> FEATURE:
<223> OTHER INFORMATION: Linker

<400> SEQUENCE: 61

Leu Glu Ser Gly Gly Gly Gly Val Thr
 1               5
```

```
<210> SEQ ID NO 62
<211> LENGTH: 6
<212> TYPE: PRT
<213> ORGANISM: Artificial Sequence
<220> FEATURE:
<223> OTHER INFORMATION: Linker

<400> SEQUENCE: 62

Gly Arg Ala Gln Val Thr
1               5

<210> SEQ ID NO 63
<211> LENGTH: 6
<212> TYPE: PRT
<213> ORGANISM: Artificial Sequence
<220> FEATURE:
<223> OTHER INFORMATION: Linker

<400> SEQUENCE: 63

Trp Arg Ala Gln Val Thr
1               5

<210> SEQ ID NO 64
<211> LENGTH: 8
<212> TYPE: PRT
<213> ORGANISM: Artificial Sequence
<220> FEATURE:
<223> OTHER INFORMATION: Linker

<400> SEQUENCE: 64

Ala Arg Gly Arg Ala Gln Val Thr
1               5

<210> SEQ ID NO 65
<211> LENGTH: 360
<212> TYPE: PRT
<213> ORGANISM: Artificial Sequence
<220> FEATURE:
<223> OTHER INFORMATION: FZD8-Fc variant 54F34 (without signal)

<400> SEQUENCE: 65

Lys Glu Leu Ala Cys Gln Glu Ile Thr Val Pro Leu Cys Lys Gly Ile
1               5                   10                  15

Gly Tyr Asn Tyr Thr Tyr Met Pro Asn Gln Phe Asn His Asp Thr Gln
            20                  25                  30

Asp Glu Ala Gly Leu Glu Val His Gln Phe Trp Pro Leu Val Glu Ile
        35                  40                  45

Gln Cys Ser Pro Asp Leu Lys Phe Phe Leu Cys Ser Met Tyr Thr Pro
    50                  55                  60

Ile Cys Leu Glu Asp Tyr Lys Lys Pro Leu Pro Pro Cys Arg Ser Val
65                  70                  75                  80

Cys Glu Arg Ala Lys Ala Gly Cys Ala Pro Leu Met Arg Gln Tyr Gly
                85                  90                  95

Phe Ala Trp Pro Asp Arg Met Arg Cys Asp Arg Leu Pro Glu Gln Gly
            100                 105                 110

Asn Pro Asp Thr Leu Cys Met Asp Tyr Asn Arg Thr Asp Leu Thr Thr
        115                 120                 125

Glu Pro Lys Ser Ser Asp Lys Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160
```

-continued

```
Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Asp Glu Leu Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 66
<211> LENGTH: 358
<212> TYPE: PRT
<213> ORGANISM: Artificial Sequence
<220> FEATURE:
<223> OTHER INFORMATION: FZD8-Fc variant 54F33 (without signal)

<400> SEQUENCE: 66

Lys Glu Leu Ala Cys Gln Glu Ile Thr Val Pro Leu Cys Lys Gly Ile
1               5                   10                  15

Gly Tyr Asn Tyr Thr Tyr Met Pro Asn Gln Phe Asn His Asp Thr Gln
            20                  25                  30

Asp Glu Ala Gly Leu Glu Val His Gln Phe Trp Pro Leu Val Glu Ile
        35                  40                  45

Gln Cys Ser Pro Asp Leu Lys Phe Phe Leu Cys Ser Met Tyr Thr Pro
    50                  55                  60

Ile Cys Leu Glu Asp Tyr Lys Lys Pro Leu Pro Pro Cys Arg Ser Val
65                  70                  75                  80

Cys Glu Arg Ala Lys Ala Gly Cys Ala Pro Leu Met Arg Gln Tyr Gly
                85                  90                  95

Phe Ala Trp Pro Asp Arg Met Arg Cys Asp Arg Leu Pro Glu Gln Gly
            100                 105                 110

Asn Pro Asp Thr Leu Cys Met Asp Tyr Asn Arg Thr Asp Leu Thr Thr
        115                 120                 125

Lys Ser Ser Asp Lys Thr His Thr Cys Pro Pro Cys Pro Ala Pro Glu
    130                 135                 140

Leu Leu Gly Gly Pro Ser Val Phe Leu Phe Pro Pro Lys Pro Lys Asp
145                 150                 155                 160
```

Thr Leu Met Ile Ser Arg Thr Pro Glu Val Thr Cys Val Val Val Asp
                165                 170                 175

Val Ser His Glu Asp Pro Glu Val Lys Phe Asn Trp Tyr Val Asp Gly
            180                 185                 190

Val Glu Val His Asn Ala Lys Thr Lys Pro Arg Glu Glu Gln Tyr Asn
        195                 200                 205

Ser Thr Tyr Arg Val Val Ser Val Leu Thr Val Leu His Gln Asp Trp
    210                 215                 220

Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
                245                 250                 255

Pro Gln Val Tyr Thr Leu Pro Pro Ser Arg Asp Glu Leu Thr Lys Asn
            260                 265                 270

Gln Val Ser Leu Thr Cys Leu Val Lys Gly Phe Tyr Pro Ser Asp Ile
        275                 280                 285

Ala Val Glu Trp Glu Ser Asn Gly Gln Pro Glu Asn Asn Tyr Lys Thr
    290                 295                 300

Thr Pro Pro Val Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
            340                 345                 350

Ser Leu Ser Pro Gly Lys
        355

<210> SEQ ID NO 67
<211> LENGTH: 27
<212> TYPE: PRT
<213> ORGANISM: Artificial Sequence
<220> FEATURE:
<223> OTHER INFORMATION: Signal

<400> SEQUENCE: 67

Met Glu Trp Gly Tyr Leu Leu Glu Val Thr Ser Leu Leu Ala Ala Leu
1               5                   10                  15

Ala Leu Leu Gln Arg Ser Ser Gly Ala Ala Ala
            20                  25

<210> SEQ ID NO 68
<211> LENGTH: 27
<212> TYPE: PRT
<213> ORGANISM: Artificial Sequence
<220> FEATURE:
<223> OTHER INFORMATION: Signal

<400> SEQUENCE: 68

Met Glu Trp Gly Tyr Leu Leu Glu Val Thr Ser Leu Leu Ala Ala Leu
1               5                   10                  15

Ala Leu Leu Gln Arg Ser Ser Gly Ala Leu Ala
            20                  25

<210> SEQ ID NO 69
<211> LENGTH: 27
<212> TYPE: PRT
<213> ORGANISM: Artificial Sequence
<220> FEATURE:
<223> OTHER INFORMATION: Signal

<400> SEQUENCE: 69

Met Glu Trp Gly Tyr Leu Leu Glu Val Thr Ser Leu Leu Ala Ala Leu
1               5                   10                  15

Ala Leu Leu Gln Arg Ser Ser Gly Val Leu Ala
            20                  25

<210> SEQ ID NO 70
<211> LENGTH: 27
<212> TYPE: PRT
<213> ORGANISM: Artificial Sequence
<220> FEATURE:
<223> OTHER INFORMATION: Signal

<400> SEQUENCE: 70

Met Glu Trp Gly Tyr Leu Leu Glu Val Thr Ser Leu Leu Ala Ala Leu
1               5                   10                  15

Leu Leu Leu Gln Arg Ser Pro Ile Val His Ala
            20                  25

<210> SEQ ID NO 71
<211> LENGTH: 27
<212> TYPE: PRT
<213> ORGANISM: Artificial Sequence
<220> FEATURE:
<223> OTHER INFORMATION: Signal

<400> SEQUENCE: 71

Met Glu Trp Gly Tyr Leu Leu Glu Val Thr Ser Leu Leu Ala Ala Leu
1               5                   10                  15

Phe Leu Leu Gln Arg Ser Pro Ile Val His Ala
            20                  25

<210> SEQ ID NO 72
<211> LENGTH: 27
<212> TYPE: PRT
<213> ORGANISM: Artificial Sequence
<220> FEATURE:
<223> OTHER INFORMATION: Signal

<400> SEQUENCE: 72

Met Glu Trp Gly Tyr Leu Leu Glu Val Thr Ser Leu Leu Ala Ala Leu
1               5                   10                  15

Leu Leu Leu Gln Arg Ser Pro Phe Val His Ala
            20                  25

<210> SEQ ID NO 73
<211> LENGTH: 27
<212> TYPE: PRT
<213> ORGANISM: Artificial Sequence
<220> FEATURE:
<223> OTHER INFORMATION: Signal

<400> SEQUENCE: 73

Met Glu Trp Gly Tyr Leu Leu Glu Val Thr Ser Leu Leu Ala Ala Leu
1               5                   10                  15

Leu Leu Leu Gln Arg Ser Pro Ile Ile Tyr Ala
            20                  25

<210> SEQ ID NO 74
<211> LENGTH: 27
<212> TYPE: PRT
<213> ORGANISM: Artificial Sequence
<220> FEATURE:
<223> OTHER INFORMATION: Signal

<400> SEQUENCE: 74

```
Met Glu Trp Gly Tyr Leu Leu Glu Val Thr Ser Leu Leu Ala Ala Leu
1               5                   10                  15

Leu Leu Leu Gln Arg Ser Pro Ile Ala His Ala
            20                  25
```

<210> SEQ ID NO 75
<211> LENGTH: 390
<212> TYPE: PRT
<213> ORGANISM: Artificial Sequence
<220> FEATURE:
<223> OTHER INFORMATION: FZD8-Fc variant 54F26 (with signal)

<400> SEQUENCE: 75

```
Met Glu Trp Gly Tyr Leu Leu Glu Val Thr Ser Leu Leu Ala Ala Leu
1               5                   10                  15

Phe Leu Leu Gln Arg Ser Pro Ile Val His Ala Ala Ser Ala Lys Glu
            20                  25                  30

Leu Ala Cys Gln Glu Ile Thr Val Pro Leu Cys Lys Gly Ile Gly Tyr
        35                  40                  45

Asn Tyr Thr Tyr Met Pro Asn Gln Phe Asn His Asp Thr Gln Asp Glu
    50                  55                  60

Ala Gly Leu Glu Val His Gln Phe Trp Pro Leu Val Glu Ile Gln Cys
65                  70                  75                  80

Ser Pro Asp Leu Lys Phe Phe Leu Cys Ser Met Tyr Thr Pro Ile Cys
                85                  90                  95

Leu Glu Asp Tyr Lys Lys Pro Leu Pro Pro Cys Arg Ser Val Cys Glu
            100                 105                 110

Arg Ala Lys Ala Gly Cys Ala Pro Leu Met Arg Gln Tyr Gly Phe Ala
        115                 120                 125

Trp Pro Asp Arg Met Arg Cys Asp Arg Leu Pro Glu Gln Gly Asn Pro
    130                 135                 140

Asp Thr Leu Cys Met Asp Tyr Asn Arg Thr Asp Leu Thr Thr Glu Pro
145                 150                 155                 160

Lys Ser Ser Asp Lys Thr His Thr Cys Pro Pro Cys Pro Ala Pro Glu
                165                 170                 175

Leu Leu Gly Gly Pro Ser Val Phe Leu Phe Pro Pro Lys Pro Lys Asp
            180                 185                 190

Thr Leu Met Ile Ser Arg Thr Pro Glu Val Thr Cys Val Val Val Asp
        195                 200                 205

Val Ser His Glu Asp Pro Glu Val Lys Phe Asn Trp Tyr Val Asp Gly
    210                 215                 220

Val Glu Val His Asn Ala Lys Thr Lys Pro Arg Glu Glu Gln Tyr Asn
225                 230                 235                 240

Ser Thr Tyr Arg Val Val Ser Val Leu Thr Val Leu His Gln Asp Trp
                245                 250                 255

Leu Asn Gly Lys Glu Tyr Lys Cys Lys Val Ser Asn Lys Ala Leu Pro
            260                 265                 270

Ala Pro Ile Glu Lys Thr Ile Ser Lys Ala Lys Gly Gln Pro Arg Glu
        275                 280                 285

Pro Gln Val Tyr Thr Leu Pro Pro Ser Arg Asp Glu Leu Thr Lys Asn
    290                 295                 300

Gln Val Ser Leu Thr Cys Leu Val Lys Gly Phe Tyr Pro Ser Asp Ile
305                 310                 315                 320
```

-continued

```
Ala Val Glu Trp Glu Ser Asn Gly Gln Pro Glu Asn Asn Tyr Lys Thr
                325                 330                 335

Thr Pro Pro Val Leu Asp Ser Asp Gly Ser Phe Phe Leu Tyr Ser Lys
            340                 345                 350

Leu Thr Val Asp Lys Ser Arg Trp Gln Gln Gly Asn Val Phe Ser Cys
        355                 360                 365

Ser Val Met His Glu Ala Leu His Asn His Tyr Thr Gln Lys Ser Leu
    370                 375                 380

Ser Leu Ser Pro Gly Lys
385             390

<210> SEQ ID NO 76
<211> LENGTH: 6
<212> TYPE: PRT
<213> ORGANISM: Artificial Sequence
<220> FEATURE:
<223> OTHER INFORMATION: N-terminal

<400> SEQUENCE: 76

Ala Ala Ala Ala Ser Ala
1               5
```

WNT ANTAGONIST AND METHODS OF TREATMENT AND SCREENING

CROSS REFERENCE TO RELATED APPLICATIONS

This application is a divisional of U.S. application Ser. No. 13/005,214, filed Jan. 12, 2011, now U.S. Pat. No. 9,157,904, which claims the priority benefit of U.S. Provisional Application No. 61/294,270, filed Jan. 12, 2010, U.S. Provisional Application No. 61/393,675, filed Oct. 15, 2010, and U.S. Provisional Application No. 61/424,408, filed Dec. 17, 2010, each of which is hereby incorporated by reference herein in its entirety.

REFERENCE TO SEQUENCE LISTING SUBMITTED ELECTRONICALLY

The content of the electronically submitted sequence listing (Name: 2293.0640004sequencelisting_ascii.txt, Size: 129,011 bytes; and Date of Creation: Aug. 31, 2015) is herein incorporated by reference in its entirety.

FIELD OF THE INVENTION

The present invention provides novel compositions and methods for treating cancer and other Wnt-associated diseases or disorders, as well as novel screening methods for identifying additional novel therapeutic agents. In particular, the present invention provides Wnt antagonists including soluble receptor proteins useful for the treatment of solid tumors and other Wnt-associated diseases and conditions.

BACKGROUND OF THE INVENTION

Cancer is one of the leading causes of death in the developed world, with over one million people diagnosed with cancer and 500,000 deaths per year in the United States alone. Overall it is estimated that more than 1 in 3 people will develop some form of cancer during their lifetime. There are more than 200 different types of cancer, four of which—breast, lung, colorectal, and prostate—account for over half of all new cases (Jemal et al., 2009, *Cancer J. Clin.*, 58:225-249).

The Wnt signaling pathway has been identified as a potential target for cancer therapy. The Wnt signaling pathway is one of several critical regulators of embryonic pattern formation, post-embryonic tissue maintenance, and stem cell biology. More specifically, Wnt signaling plays an important role in the generation of cell polarity and cell fate specification including self-renewal by stem cell populations. Unregulated activation of the Wnt pathway is associated with numerous human cancers where it can alter the developmental fate of tumor cells to maintain them in an undifferentiated and proliferative state. Thus carcinogenesis can proceed by usurping homeostatic mechanisms controlling normal development and tissue repair by stem cells (reviewed in Reya & Clevers, 2005, *Nature*, 434:843-50; Beachy et al., 2004, *Nature*, 432:324-31).

The Wnt signaling pathway was first elucidated in the *Drosophila* developmental mutant wingless (wg) and from the murine proto-oncogene int-1, now Wnt1 (Nusse & Varmus, 1982, *Cell*, 31:99-109; Van Ooyen & Nusse, 1984, *Cell*, 39:233-40; Cabrera et al., 1987, *Cell*, 50:659-63; Rijsewijk et al., 1987, *Cell*, 50:649-57). Wnt genes encode secreted lipid-modified glycoproteins of which 19 have been identified in mammals. These secreted ligands activate a receptor complex consisting of a Frizzled (FZD) receptor family member and low-density lipoprotein (LDL) receptor-related protein 5 or 6 (LRP5/6). The FZD receptors are seven transmembrane domain proteins of the G-protein coupled receptor (GPCR) superfamily and contain a large extracellular N-terminal ligand binding domain with 10 conserved cysteines, known as a cysteine-rich domain (CRD) or Fri domain. There are ten human FZD receptors, FZD1, FZD2, FZD3, FZD4, FZD5, FZD6, FZD7, FZD8, FZD9 and FZD10. Different FZD CRDs have different binding affinities for specific Wnts (Wu & Nusse, 2002, *J. Biol. Chem.*, 277:41762-9), and FZD receptors have been grouped into those that activate the canonical β-catenin pathway and those that activate non-canonical pathways described below (Miller et al., 1999, *Oncogene*, 18:7860-72). To form the receptor complex that binds the FZD ligands, FZD receptors interact with LRP5/6, single pass transmembrane proteins with four extracellular EGF-like domains separated by six YWTD amino acid repeats (Johnson et al., 2004, *J. Bone Mineral Res.*, 19:1749).

The canonical Wnt signaling pathway activated upon receptor binding is mediated by the cytoplasmic protein Dishevelled (Dsh) interacting directly with the FZD receptor and results in the cytoplasmic stabilization and accumulation of β-catenin. In the absence of a Wnt signal, β-catenin is localized to a cytoplasmic destruction complex that includes the tumor suppressor proteins adenomatous polyposis coli (APC) and Axin. These proteins function as critical scaffolds to allow glycogen synthase kinase-3β (GSK3β) to bind and phosphorylate β-catenin, marking it for degradation via the ubiquitin/proteasome pathway. Activation of Dsh results in phophorylation of GSK3β and the dissociation of the destruction complex. Accumulated cytoplasmic β-catenin is then transported into the nucleus where it interacts with the DNA-binding proteins of the TCF/LEF family to activate transcription.

In addition to the canonical signaling pathway, Wnt ligands also activate β-catenin-independent pathways (Veeman et al., 2003, *Dev. Cell*, 5:367-77). Non-canonical Wnt signaling has been implicated in numerous processes but most convincingly in gastrulation movements via a mechanism similar to the *Drosophila* planar cell polarity (PCP) pathway. Other potential mechanisms of non-canonical Wnt signaling include calcium flux, JNK, and both small and heterotrimeric G-proteins. Antagonism is often observed between the canonical and non-canonical pathways, and some evidence indicates that non-canonical signaling can suppress cancer formation (Olson & Gibo, 1998, *Exp. Cell Res.*, 241:134; Topol et al., 2003, *J. Cell Biol.*, 162:899-908). Thus in certain contexts, FZD receptors act as negative regulators of the canonical Wnt signaling pathway. For example, FZD6 represses Wnt3a-induced canonical signaling when co-expressed with FZD1 via the TAK1-NLK pathway (Golan et al., 2004, *JBC*, 279:14879-88). Similarly, FZD2 was shown to antagonize canonical Wnt signaling in the presence of Wnt5a via the TAK1-NLK MAPK cascade (Ishitani et al., 2003, *Mol. Cell. Biol.*, 23:131-39).

The canonical Wnt signaling pathway also plays a central role in the maintenance of stem cell populations in the small intestine and colon, and the inappropriate activation of this pathway plays a prominent role in colorectal cancers (Reya & Clevers, 2005, *Nature*, 434:843). The absorptive epithelium of the intestines is arranged into villi and crypts. Stem cells reside in the crypts and slowly divide to produce rapidly proliferating cells that give rise to all the differentiated cell populations that move out of the crypts to occupy the intestinal villi. The Wnt signaling cascade plays a dominant role in controlling cell fates along the crypt-villi axis and is essential for the maintenance of the stem cell population. Disruption of Wnt signaling either by genetic loss of TCF7/2 by homologous recombination (Korinek et al., 1998, *Nat. Genet.*, 19:379) or overexpression of Dickkopf-1 (Dkk1), a potent secreted Wnt antagonist (Pinto et al., 2003, *Genes Dev.*, 17:1709-13; Kuhnert et al., 2004, *PNAS*, 101:266-71), results in depletion of intestinal stem cell populations.

A role for Wnt signaling in cancer was first uncovered with the identification of Wnt1 (originally int1) as an oncogene in mammary tumors transformed by the nearby insertion of a murine virus (Nusse & Varmus, 1982, *Cell*, 31:99-109). Additional evidence for the role of Wnt signaling in breast cancer has since accumulated. For instance, transgenic overexpression of β-catenin in the mammary glands results in hyperplasias and adenocarcinomas (Imbert et al., 2001, *J. Cell Biol.*, 153:555-68; Michaelson & Leder, 2001, *Oncogene*, 20:5093-9) whereas loss of Wnt signaling disrupts normal mammary gland development (Tepera et al., 2003, *J. Cell Sci.*, 116:1137-49; Hatsell et al., 2003, *J. Mammary Gland Biol. Neoplasia*, 8:145-58). More recently mammary stem cells have been shown to be activated by Wnt signaling (Liu et al., 2004, *PNAS*, 101:4158-4163). In human breast cancer, β-catenin accumulation implicates activated Wnt signaling in over 50% of carcinomas, and though specific mutations have not been identified, upregulation of Frizzled receptor expression has been observed (Brennan & Brown, 2004, *J. Mammary Gland Neoplasia*, 9:119-31; Malovanovic et al., 2004, *Int. J. Oncol.*, 25:1337-42).

Colorectal cancer is most commonly initiated by activating mutations in the Wnt signaling cascade. Approximately 5-10% of all colorectal cancers are hereditary with one of the main forms being familial adenomatous polyposis (FAP), an autosomal dominant disease in which about 80% of affected individuals contain a germline mutation in the adenomatous polyposis coli (APC) gene. Mutations have also been identified in other Wnt pathway components including Axin and β-catenin. Individual adenomas are clonal outgrowths of epithelial cells containing a second inactivated allele, and the large number of FAP adenomas inevitably results in the development of adenocarcinomas through additional mutations in oncogenes and/or tumor suppressor genes. Furthermore, activation of the Wnt signaling pathway, including gain-of-function mutations in APC and β-catenin, can induce hyperplastic development and tumor growth in mouse models (Oshima et al., 1997, *Cancer Res.*, 57:1644-9; Harada et al., 1999, *EMBO J.*, 18:5931-42).

BRIEF SUMMARY OF THE INVENTION

The present invention provides a variety of agents that bind to one or more human Wnt proteins, including, but not limited to, soluble FZD receptors and other agents comprising a Fri domain, and novel methods of using those agents. The invention further provides methods of using the agents in the treatment of cancer by administering the agents to a subject in need thereof. In some embodiments, the methods comprise inhibiting the growth of cancer cells. In certain embodiments, the Wnt-binding agent is a Wnt antagonist. Novel methods of screening for such Wnt-binding agents are also provided. Polynucleotides encoding the agents, methods of making the agents, and a variety of compositions comprising the agents are likewise provided.

Thus, in one aspect, the invention provides a method of inhibiting the growth of a tumor. In certain embodiments, the method comprises contacting the tumor with an effective amount of an agent that binds to one or more Wnt proteins (e.g., human Wnt proteins). The method may be in vivo or in vitro. In certain embodiments, the tumor is in a subject, and the contacting of the tumor with the agent comprises administration of a therapeutically effective amount of the Wnt-binding agent to the subject.

In another aspect, the invention provides a method of reducing the frequency of cancer stem cells in a tumor comprising cancer stem cells. Accordingly, the invention also provides methods of reducing the tumorigenicity of tumors. In some embodiments, the methods comprise contacting the tumor with an effective amount of an agent that binds to one or more Wnt proteins (e.g., human Wnt proteins). The method may be in vivo or in vitro. For example, the contacting may comprise administration of the effective amount of the Wnt-binding agent to a human having the tumor.

In another aspect, the invention provides a method of inducing cells in a tumor to differentiate or inducing expression of differentiation markers in a tumor. In certain embodiments, the method comprises contacting the tumor with an effective amount of an agent that binds to one or more Wnt proteins (e.g., human Wnt proteins). The method may be in vivo or in vitro.

In a still further aspect, the invention provides a method of treating a cancer in a subject, comprising administering a therapeutically effective amount of the Wnt-binding agent to the subject.

In an additional aspect, the invention provides a method of treating a disease in a subject wherein the disease is associated with Wnt signaling activation, comprising administering a therapeutically effective amount of the Wnt-binding agent to the subject.

In yet another aspect, the invention provides a method of treating a disorder in a subject, wherein the disorder is characterized by an increased level of stem cells and/or progenitor cells, comprising administering a therapeutically effective amount of the Wnt-binding agent to the subject.

In certain embodiments of each of the aforementioned aspects, as well as other aspects provided herein, the Wnt-binding agent is a polypeptide. In certain embodiments, the agent is a soluble receptor.

In certain embodiments of each of the aforementioned aspects, as well as other aspects provided herein, the agent comprises a Fri domain of a FZD receptor, or a fragment of a FZD Fri domain that binds one or more Wnt proteins. In certain embodiments, the FZD receptors are human FZD receptors. For example, the Fri domain may be from human FZD4 or human FZD5. In certain alternative embodiments, the agent may comprise a Fri domain of a human FZD8 receptor or a fragment of that Fri domain that binds one or more Wnt proteins. In certain embodiments, the Wnt-binding agent is a soluble FZD receptor. In alternative embodiments, the Wnt-binding agent does not comprise a Fri domain of a FZD receptor.

In certain embodiments of each of the aforementioned aspects, as well as other aspects provided herein, the agent comprises a Fri domain of a soluble Frizzled-related protein (SFRP), or a fragment of a SFRP Fri domain that binds one or more Wnt proteins. In certain embodiments the SFRP is a human SFRP.

In certain embodiments of each of the aforementioned aspects, as well as other aspects provided herein, the agent comprises a Fri domain of a Ror protein or a fragment of a Ror Fri domain that binds one or more Wnt proteins. In certain embodiments the Ror protein is a human Ror protein.

In certain embodiments of each of the aforementioned aspects, as well as other aspects provided herein, the agent further comprises a human Fc region. In certain embodiments, the Wnt-binding agent is a fusion protein. In certain embodiments, the Wnt-binding agent comprises SEQ ID NO:1. In certain embodiments, the Wnt-binding agent comprises SEQ ID NO:46. In certain embodiments, the Wnt-binding agent comprises SEQ ID NO:48. In certain embodiments, the Wnt-binding agent comprises SEQ ID NO:50. In certain embodiments, the Wnt-binding agent comprises SEQ ID NO:53. In some embodiments, the Wnt-binding agent (before signal sequence cleavage) comprises SEQ ID NO:50 and a signal sequence selected from the group consisting of SEQ ID NO:67, SEQ ID NO:68, SEQ ID NO:69, SEQ ID NO:70, SEQ ID NO:71, SEQ ID NO:72, SEQ ID NO:73, and SEQ ID NO:74. In some embodiments, the Wnt-binding agent (before signal sequence cleavage) comprises SEQ ID NO:50 and a signal sequence selected from the group consisting of SEQ ID NO:70, SEQ ID NO:71, SEQ ID NO:72, SEQ ID NO:73, and SEQ ID NO:74. In some embodiments, the Wnt-binding agent (before signal sequence cleavage) comprises SEQ ID NO:50 and SEQ ID NO:71. In some embodiments, the Wnt-binding agent (before signal sequence cleavage) comprises SEQ ID NO:53 and a signal sequence selected from the group consisting of SEQ ID NO:67, SEQ ID NO:68, SEQ ID NO:69, SEQ ID NO:70, SEQ ID NO:71, SEQ ID NO:72, SEQ ID NO:73, and SEQ ID NO:74. In some embodiments, the Wnt-binding agent (before signal sequence cleavage) comprises SEQ ID NO:53 and a signal sequence selected from the group consisting of SEQ ID NO:70, SEQ ID NO:71, SEQ ID NO:72, SEQ ID NO:73, and SEQ ID NO:74. In some embodiments, the Wnt-binding agent (before signal sequence cleavage) comprises SEQ ID NO:53 and SEQ ID NO:71.

In certain embodiments of each of the aforementioned aspects, as well as other aspects provided herein, the Wnt-binding agent binds to one or more, two or more, three or more, or four or more human Wnt proteins selected from the group consisting of Wnt1, Wnt2, Wnt2b, Wnt3, Wnt3a, Wnt7a, Wnt7b, Wnt8a, Wnt8b, Wnt10a, and Wnt10b. In certain embodiments, the agent binds to Wnt1, Wnt2, Wnt3, Wnt3a, and Wnt7b.

In certain embodiments of each of the aforementioned aspects, as well as other aspects provided herein, the agent is a Wnt antagonist. In certain embodiments, the agent inhibits Wnt signaling. In certain embodiments, the agent inhibits Wnt canonical Wnt signaling.

In certain embodiments of each of the aforementioned aspects, as well as other aspects provided herein, the tumor or cancer is a tumor/cancer selected from the group consisting of colorectal tumor/cancer, pancreatic tumor/cancer, lung tumor/cancer, ovarian tumor/cancer, liver tumor/cancer, breast tumor/cancer, kidney tumor/cancer, prostate tumor/cancer, gastrointestinal tumor/cancer, melanoma, cervical tumor/cancer, bladder tumor/cancer, glioblastoma, and head and neck tumor/cancer.

In certain embodiments of each of the aforementioned aspects, as well as other aspects provided herein, the methods further comprise contacting the tumor with a second therapeutic agent or administering a second therapeutic agent to the subject. In certain embodiments, the second therapeutic agent is a chemotherapeutic agent. In certain embodiments, the second chemotherapeutic agent is an antimetabolite (e.g., gemcitabine) or an antimitotic agent (e.g., a taxane such as paclitaxel).

In a still further aspect, the invention provides a polypeptide comprising a sequence selected from the group consisting of SEQ ID NO:1, SEQ ID NO:45, SEQ ID NO:46, SEQ ID NO:47, SEQ ID NO:48, SEQ ID NO:49, SEQ ID NO:50, SEQ ID NO:51, SEQ ID NO:53, SEQ ID NO:54, SEQ ID NO:55, SEQ ID NO:65 and SEQ ID NO:66, as well as cells producing and compositions comprising the polypeptide. Pharmaceutical compositions comprising the polypeptide and a pharmaceutically acceptable carrier are also provided. In addition, polynucleotides comprising a polynucleotide that encodes the polypeptides of SEQ ID NO:1, SEQ ID NO:45, SEQ ID NO:46, SEQ ID NO:47, SEQ ID NO:48, SEQ ID NO:49, SEQ ID NO:50, SEQ ID NO:51, SEQ ID NO:53, SEQ ID NO:54, SEQ ID NO:55, SEQ ID NO:65 and SEQ ID NO:66 or having the sequence of SEQ ID NO:2 are also provided. Vectors and cells comprising the polynucleotides are likewise provided.

In an additional aspect, the invention provides a method of screening an agent for anti-tumor activity and/or activity against cancer stem cells. In certain embodiments, the method comprises comparing the level of one or more differentiation markers and/or one or more stemness markers in a first solid tumor (e.g., a solid tumor comprising cancer stem cells) that has been exposed to an agent to the level of the one or more differentiation markers in a second solid tumor that has not been exposed to the agent. In some embodiments, the method comprises: (a) exposing a first solid tumor, but not a second solid tumor, to the agent; (b) assessing the level of one or more differentiation markers and/or one or more stemness markers in the first and second solid tumors; and (c) comparing the level of the one or more differentiation markers in the first tumor to the level of the one or more differentiation markers in the second solid tumor. In certain embodiments, the (a) increased levels of the one or more differentiation markers in the first solid tumor relative to the second solid tumor indicates anti-tumor or anti-cancer stem cell activity of the agent; and/or (b) decreased levels of the one or more stemness markers indicates anti-tumor or anti-cancer stem cell activity of the agent. In certain embodiments, the agent binds one or more Wnt proteins. In certain embodiments, the agent is a soluble FZD receptor. In certain methods, the agent is an antibody, such as an anti-FZD or anti-Wnt antibody. In certain alternative embodiments, the agent is a small molecule.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

BRIEF DESCRIPTION OF THE
DRAWINGS/FIGURES

FIG. 1. Pharmacokinetics of FZD8-Fc (54F03) in the rat. Administration of a single dose (10 mg/kg) of FZD8-Fc was followed by assessment of the pharmacokinetic properties of FZD8-Fc. Serum concentrations of FZD8-Fc were determined at 1, 24, 48, 72, 96, 168, 240 and 336 hours post-administration.

Figure 2:
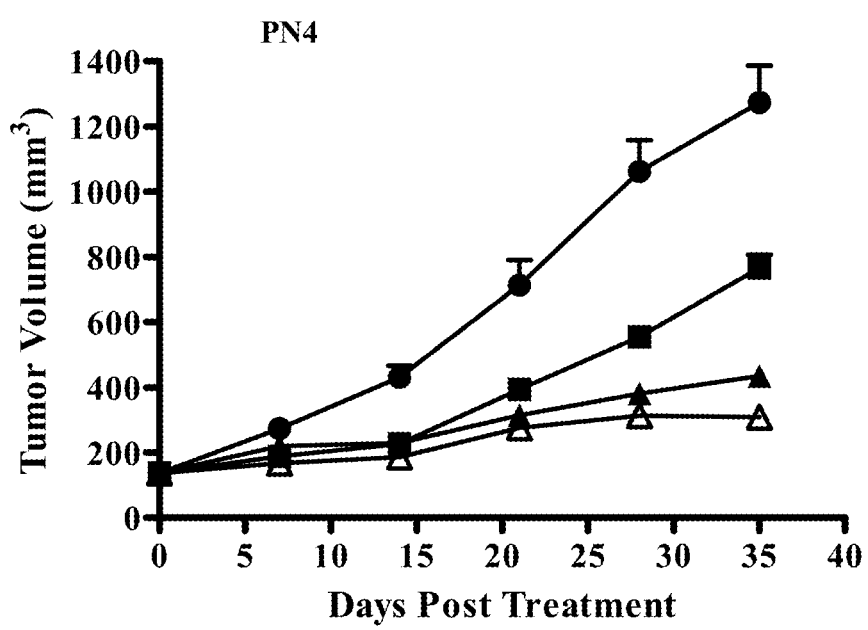

FIG. 2. Inhibition of PN4 pancreas tumor growth by FZD8-Fc (54F03) treatment. PN4 pancreas tumor cells were injected subcutaneously into NOD/SCID mice. Mice were treated with FZD8-Fc (-▲-), gemcitabine (-■-), a combination of FZD8-Fc and gemcitabine (-△-) or a control antibody (-•-). Data are shown as tumor volume (mm³), over days post treatment.

Figure 3:
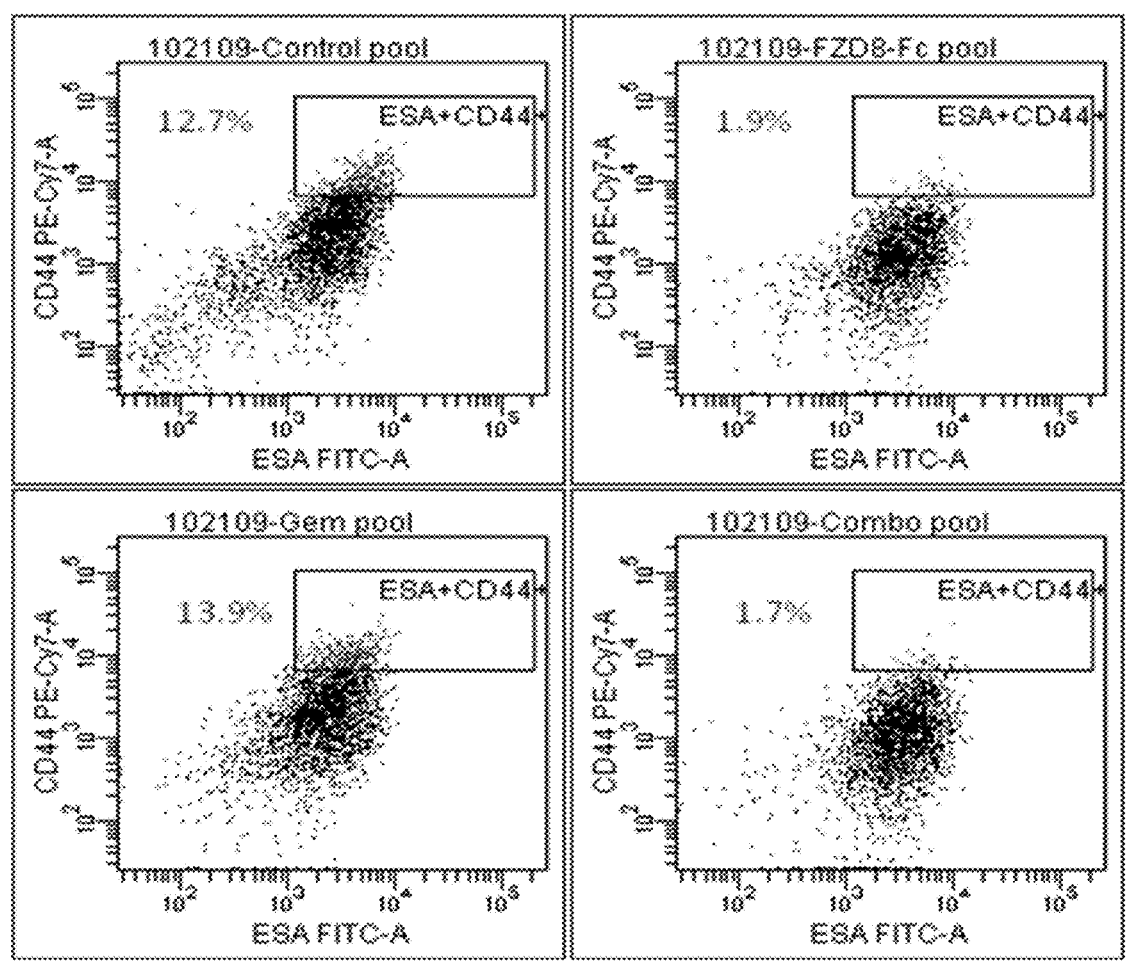

FIG. 3. Reduction of CD44$^{hi}$ cell population in PN4 tumors treated with FZD8-Fc (54F03). Cell surface staining for ESA and CD44 on tumor cells treated with control antibody, FZD8-Fc, gemcitabine, or a combination of FZD8-Fc and gemcitabine was performed. For each treatment group, single cell suspensions from five tumors were pooled prior to staining.

Figure 4:
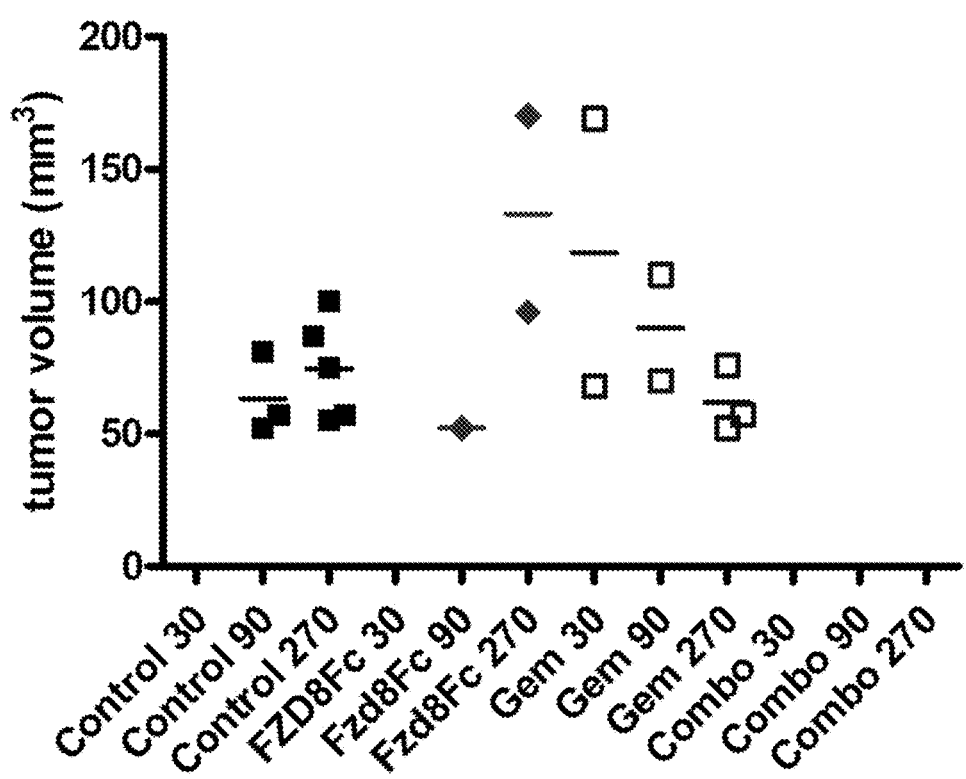

FIG. 4. In vivo limiting dilution assay of FZD8-Fc (54F03)-treated PN4 pancreatic tumors.

Figure 5:
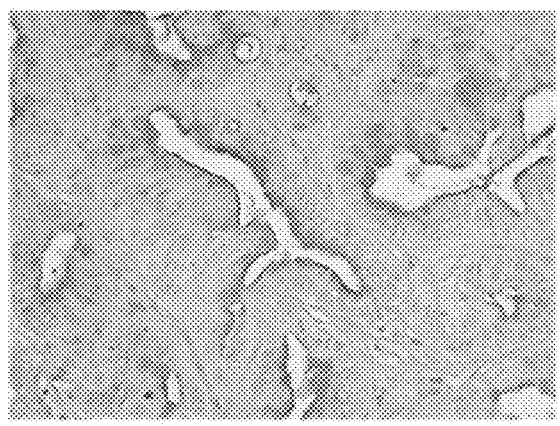
Figure 5:
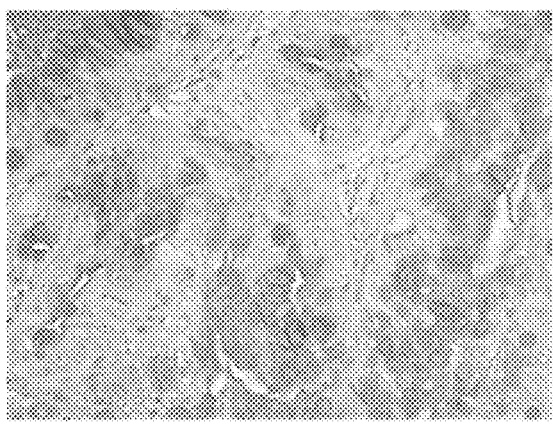
Figure 5:
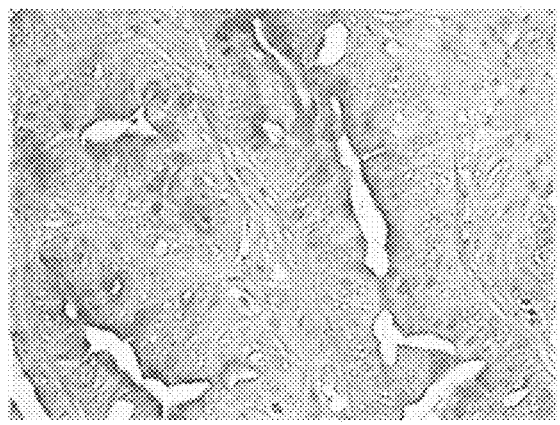
Figure 5:
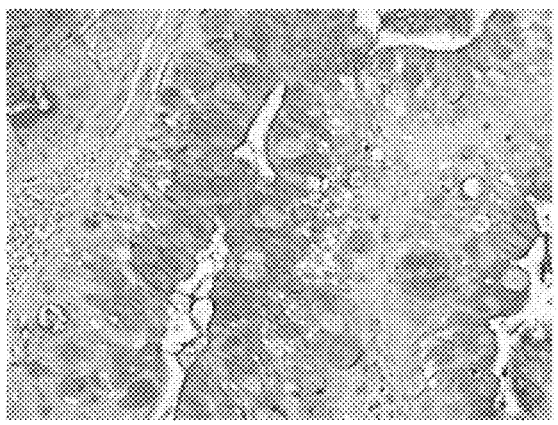

FIG. 5. Increased cell differentiation of PN4 pancreatic tumors treated with FZD8-Fc (54F03). Paraffin embedded sections of PN4 tumors treated with control antibody, FZD8-Fc, gemcitabine, or a combination of FZD8-Fc and gemcitabine were stained with alcian blue to detect mucin-expressing cells.

Figure 6:
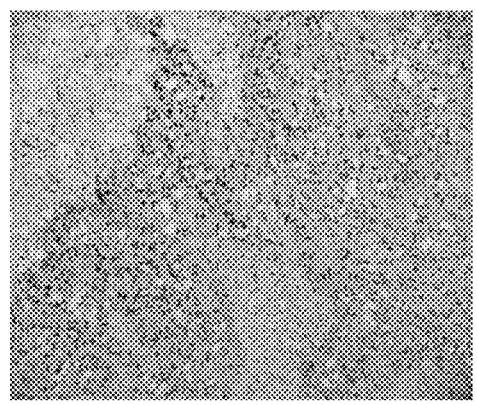
Figure 6:
Figure 6:
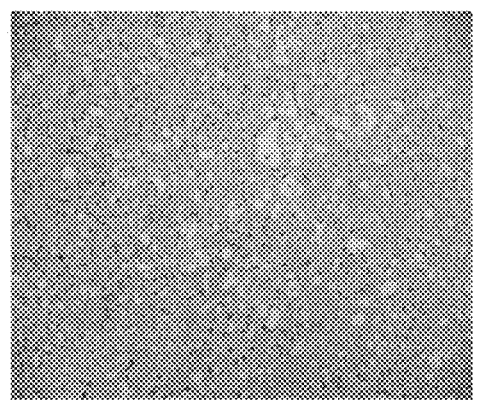
Figure 6:
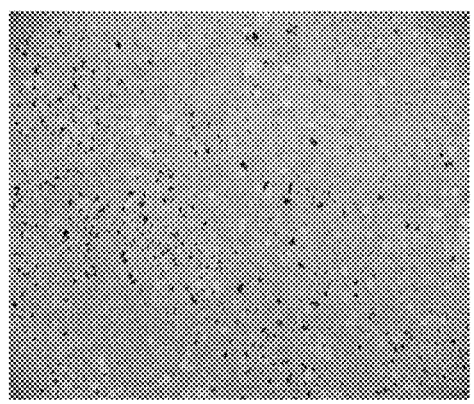

FIG. 6. Increased cell differentiation of PN8 pancreatic tumors treated with FZD8-Fc (54F03). Paraffin embedded sections of PN8 tumors treated with control antibody, FZD8-Fc, gemcitabine, or a combination of FZD8-Fc and gemcitabine were stained with alcian blue to detect mucin-expressing cells.

Figure 7:
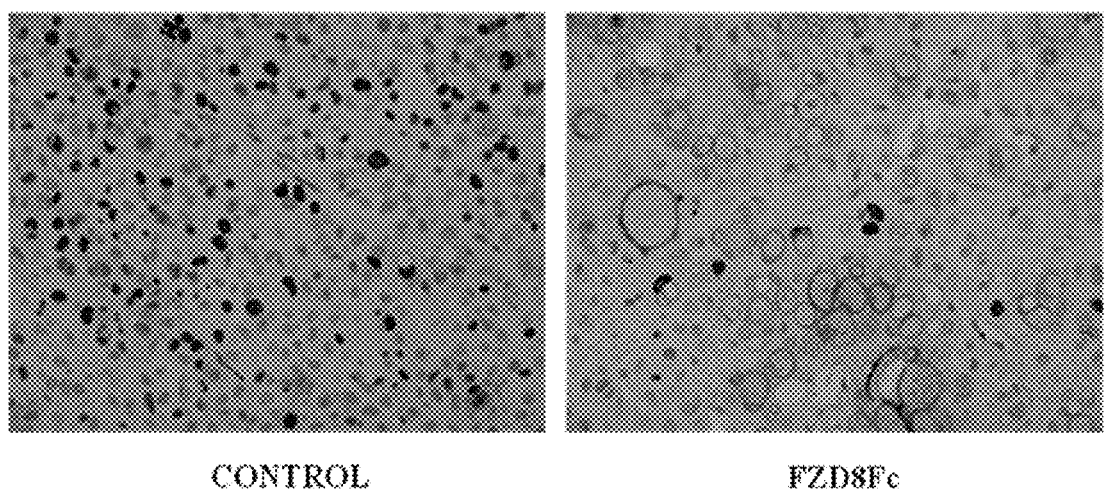

FIG. 7. Increased cell differentiation and reduced proliferation in PN13 pancreatic tumors following treatment with FZD8-Fc (54F03). Paraffin embedded sections of PN13 tumors treated with control antibody or FZD8-Fc were stained with alcian blue to detect mucin-expressing cells. In addition, the sections were stained for Ki67, a marker of actively proliferating cells.

Figure 8:
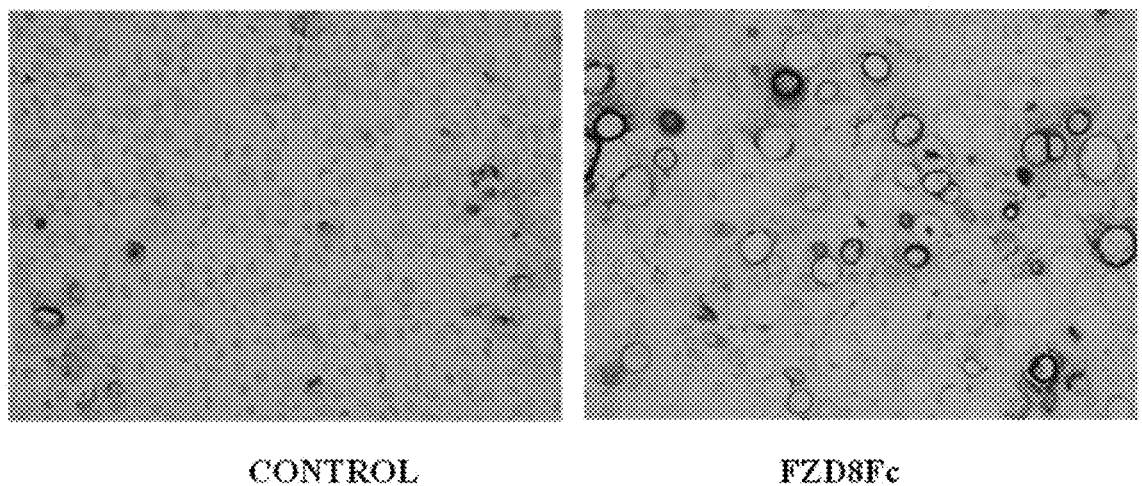

FIG. 8. Increased Muc16 staining in PN13 pancreatic tumors following treatment with FZD8-Fc (54F03). Paraffin embedded sections of PN13 tumors treated with a control antibody or FZD8-Fc were stained for Muc16 protein.

Figure 9:
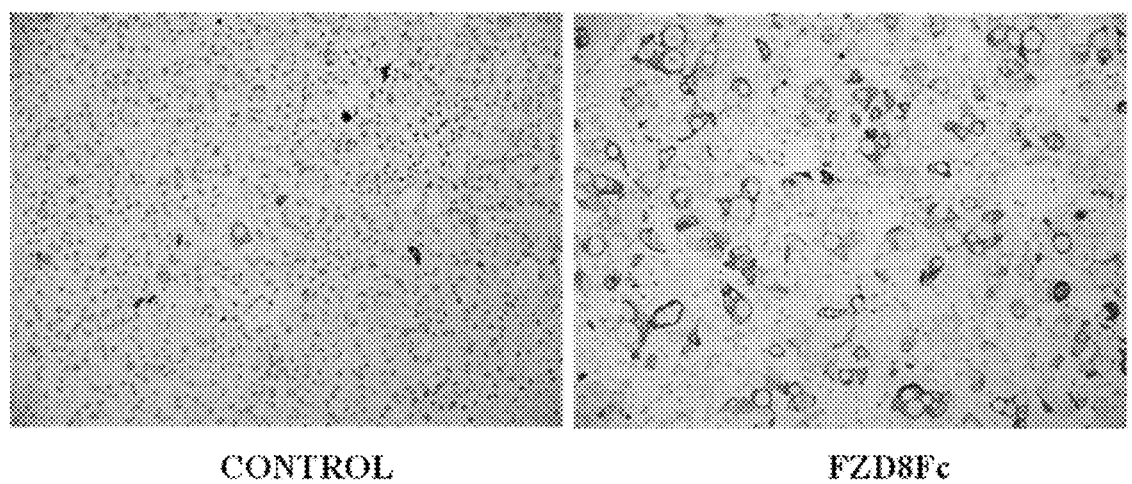

FIG. 9. Increased CK20 staining in PN13 pancreatic tumors following treatment with FZD8-Fc (54F03). Paraffin embedded sections of PN13 tumors treated with a control antibody or FZD8-Fc were stained for CK20 protein.

Figure 10:
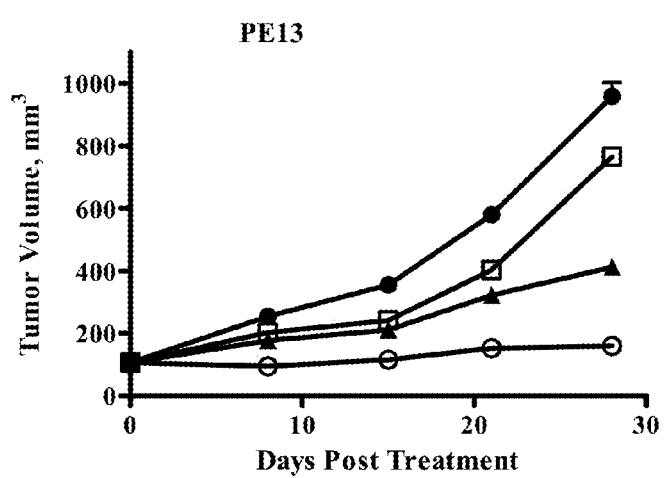

FIG. 10. Inhibition of PE13 breast tumor growth following treatment with FZD8-Fc (54F03) in combination with paclitaxel. PE13 breast tumor cells were injected subcutaneously into NOD/SCID mice. Mice were treated with a control antibody (-•-), FZD8-Fc (□), paclitaxel (-▲-), or a combination of FZD8-Fc and paclitaxel (-o-). Data is shown as tumor volume (mm³) over days post treatment.

Figure 11A:
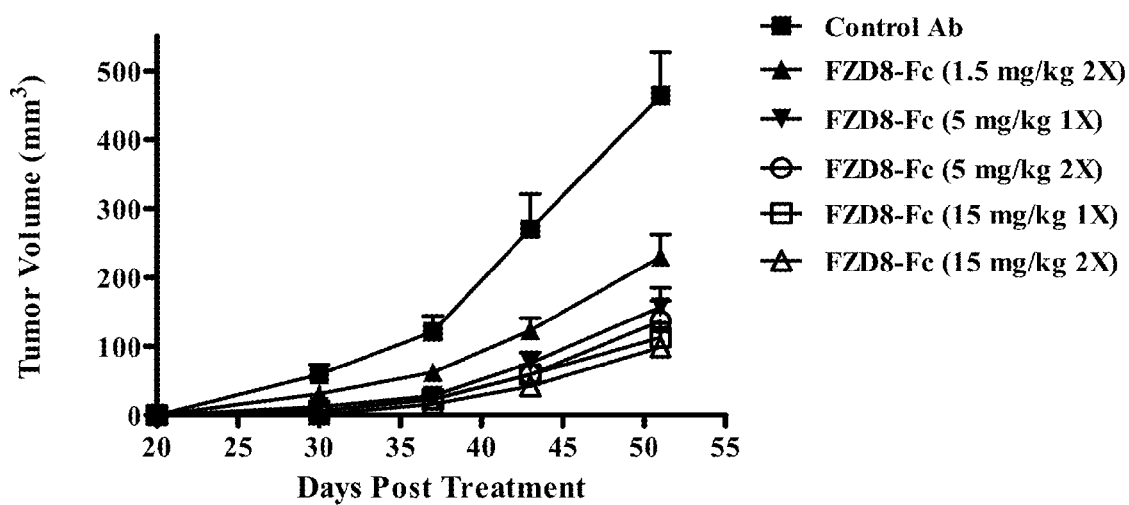
Figure 11B:
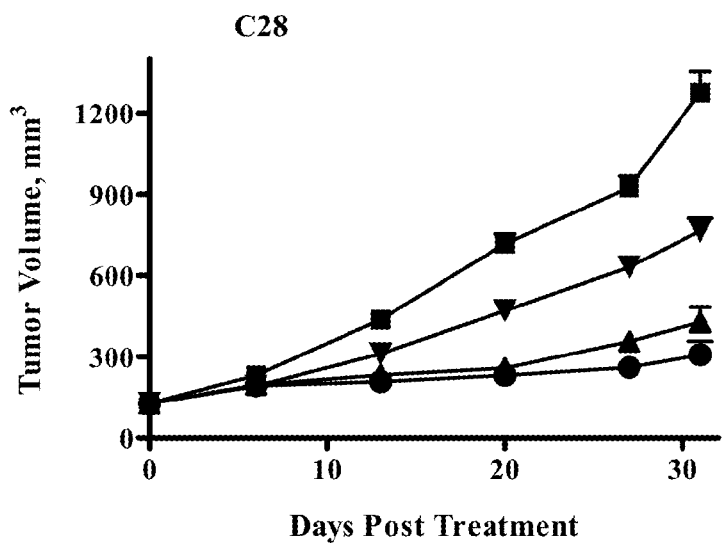

FIGS. 11A and 11B. Dose-dependent inhibition of C28 colon tumor growth with FZD8-Fc (54F03). C28 colon tumor cells were injected subcutaneously into NOD/SCID mice. Mice were treated with FZD8-Fc 1.5 mg/kg twice weekly (-▲-), 5 mg/kg once weekly (-▼-), 5 mg/kg twice weekly (-o-), 15 mg/kg once weekly (-□-) or 15 mg/kg twice weekly (-△-) or control antibody (-■-). Data is shown as tumor volume (mm³) over days post treatment (FIG. 11A) Inhibition of colon tumor growth with FZD8-Fc in combination with irinotecan. Mice were treated with FZD8-Fc (-▲-), irinotecan (-▼-), a combination of FZD8-Fc and irinotecan (-•-), or a control antibody (-■-). Data is shown as tumor volume (mm³) over days post treatment (FIG. 11B).

Figure 12:
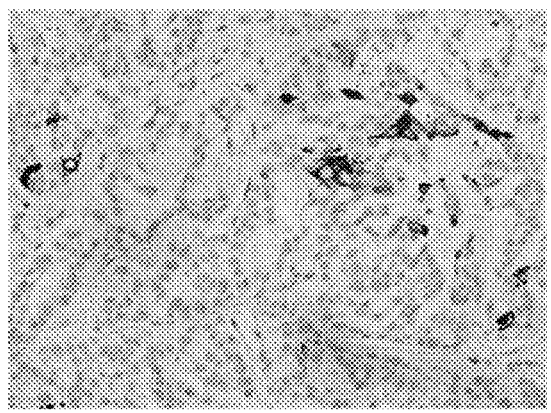
Figure 12:
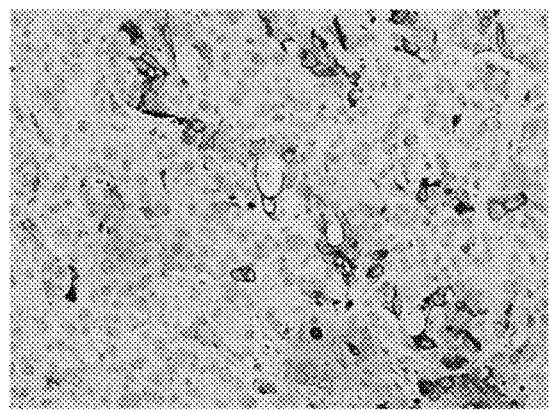

FIG. 12. Increased CK20 staining in C28 tumors following treatment with FZD8-Fc (54F03). Paraffin embedded sections of C28 tumors treated with a control antibody or FZD8-Fc were stained for CK20 protein.

Figure 13A:
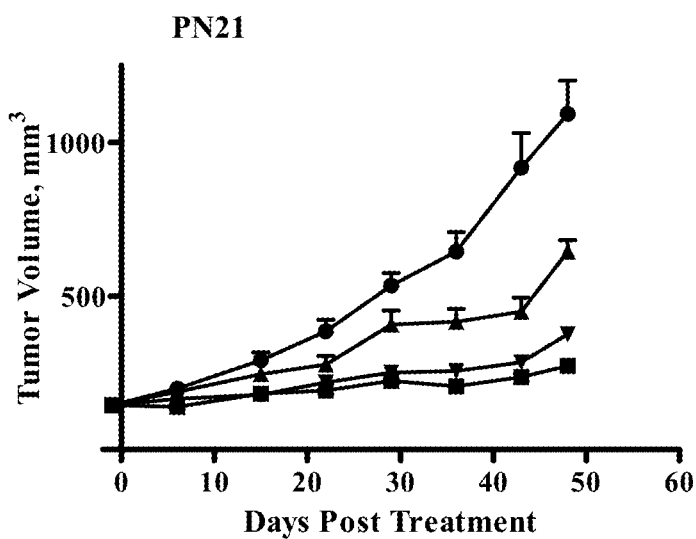
Figure 13B:
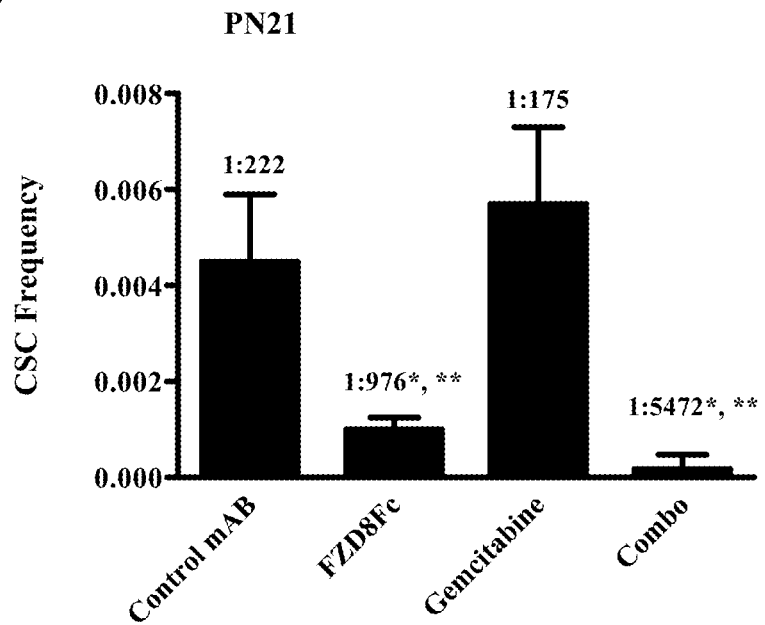

FIGS. 13A and 13B Inhibition of PN21 pancreatic tumor growth and decrease in cancer stem cell frequency by FZD8-Fc (54F03) treatment. PN21 pancreatic tumor cells were injected subcutaneously into NOD/SCID mice. Mice were treated with FZD8-Fc (-▼-), gemcitabine (-▲-), a combination of FZD8-Fc and gemcitabine (-■-), or a control antibody (-•-). Data are shown as tumor volume (mm³), over days post treatment (FIG. 13A). In vivo limiting dilution assay of FZD8-Fc treated PN21 pancreatic tumors (FIG. 13B).

Figure 14:
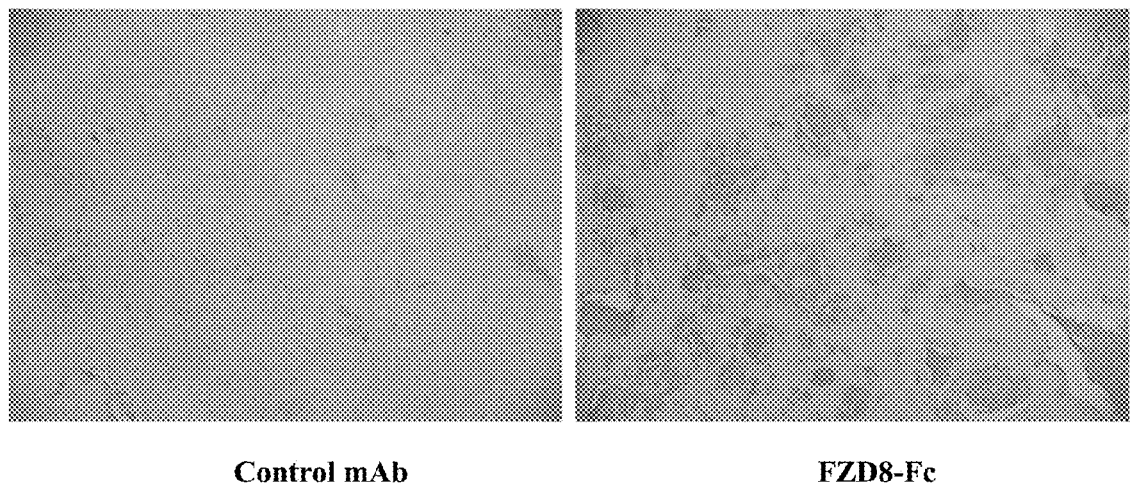

FIG. 14. Increased cell differentiation of PN21 pancreatic tumors following treatment with FZD8-Fc (54F03). Paraffin embedded sections of PN21 tumors treated with control antibody or FZD8-Fc were stained with alcian blue to detect mucins.

Figure 15:
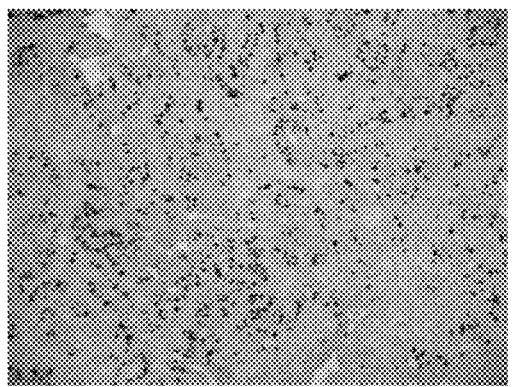
Figure 15:
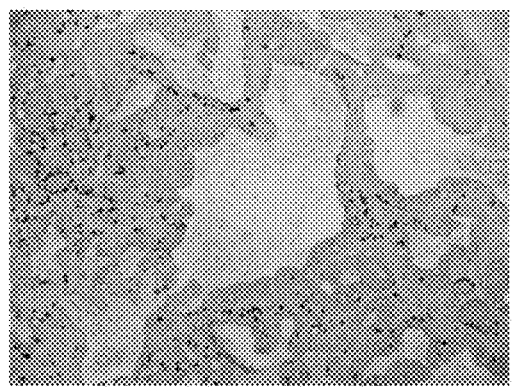
Figure 15:
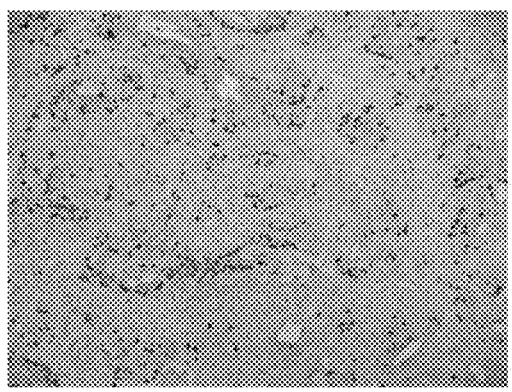
Figure 15:
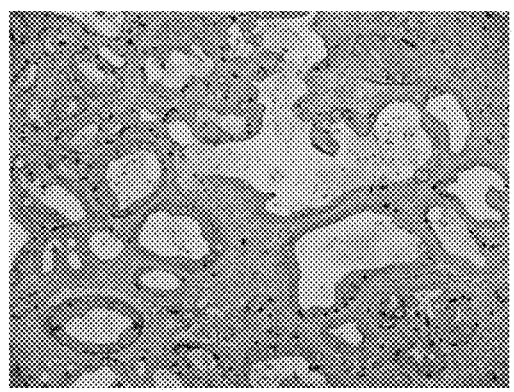

FIG. 15. Increased cell differentiation and reduced proliferation in PN21 pancreatic tumors following treatment with FZD8-Fc (54F03). Paraffin embedded sections of PN21 tumors treated with control antibody, FZD8-Fc, gemcitabine, or a combination of FZD8-Fc and gemcitabine were stained with alcian blue to detect mucins. In addition, the sections were stained for Ki67, a marker of actively proliferating cells.

Figure 16:
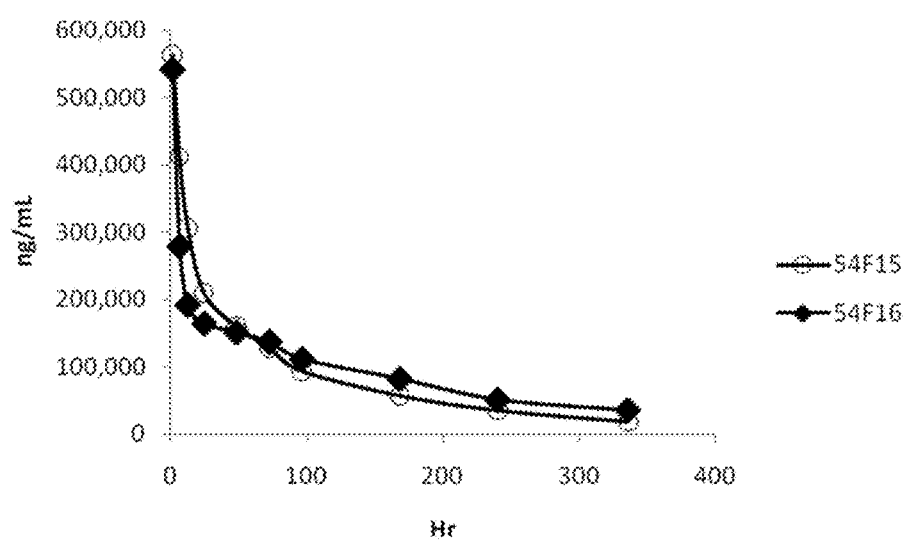

FIG. 16. Pharmacokinetics of FZD8-Fc variants in monkeys. Administration of a single dose (30 mg/kg) of FZD8-Fc variants 54F15 and 54F16 was followed by assessment of the pharmacokinetic properties of the variants. Serum concentrations of 54F15 (-o-) and 54F16 (-♦-) were determined at 1, 6, 12, 24, 48, 72, 96, 168, 240 and 336 hours post-administration.

Figure 17:
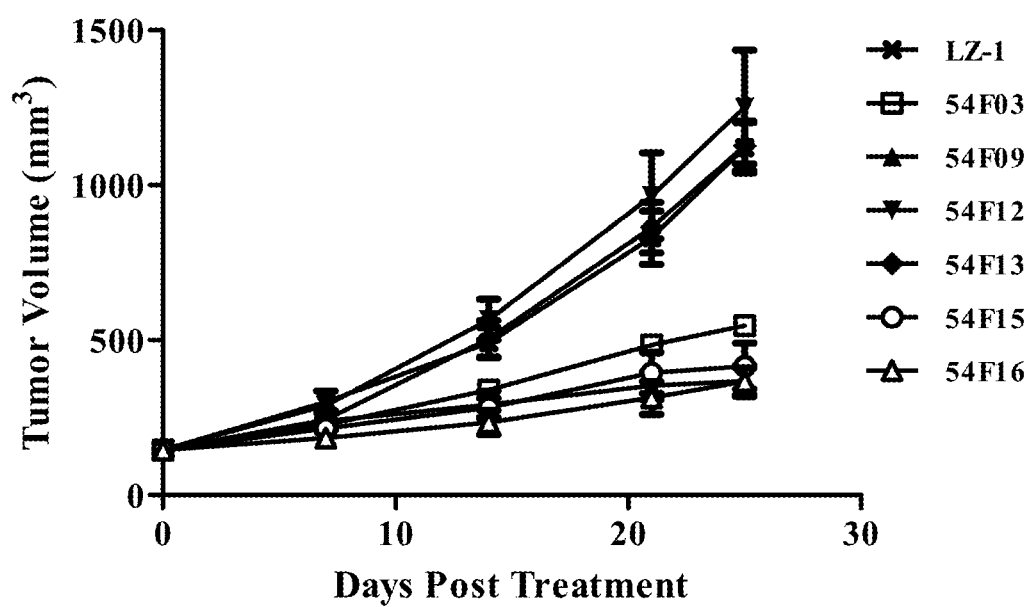

FIG. 17. Inhibition of C28 colon tumor growth following treatment with FZD8-Fc variants. C28 colon tumor cells were injected subcutaneously into NOD/SCID mice. Mice were treated with a control antibody (—X—), 54F03 (-□-), 54F09 (-▲-), 54F12 (-▼-), 54F13 (-♦-), 54F15 (-o-) or 54F16 (-△-). Data is shown as tumor volume (mm³) over days post treatment.

Figure 18:
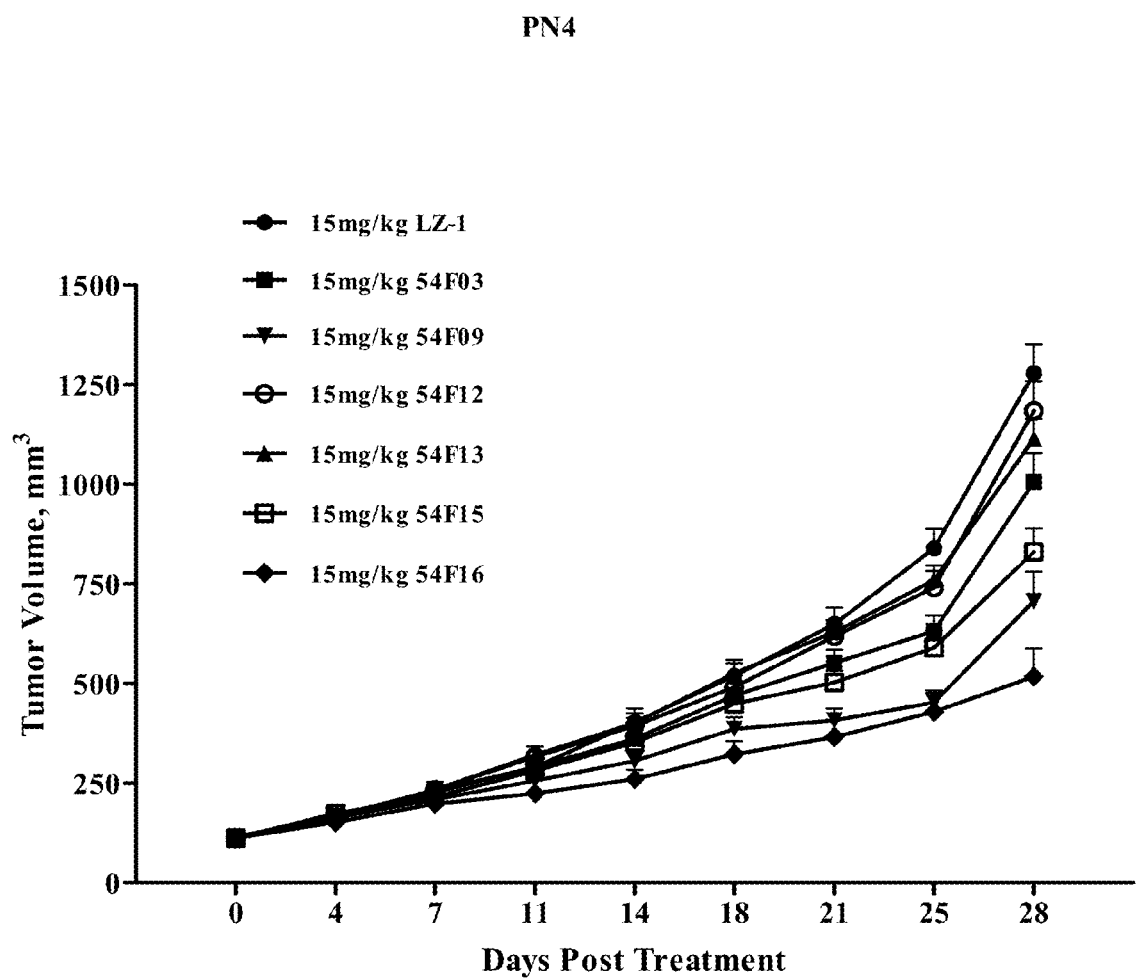

FIG. 18. Inhibition of PN4 pancreatic tumor growth following treatment with FZD8-Fc variants. PN4 colon tumor cells were injected subcutaneously into NOD/SCID mice. Mice were treated with a control antibody (-•-), 54F03 (-■-), 54F09 (-▼-), 54F12 (-o-), 54F13 (-▲-), 54F15 (-□-) or 54F16 (-♦-). Data is shown as tumor volume (mm³) over days post treatment.

Figure 19:
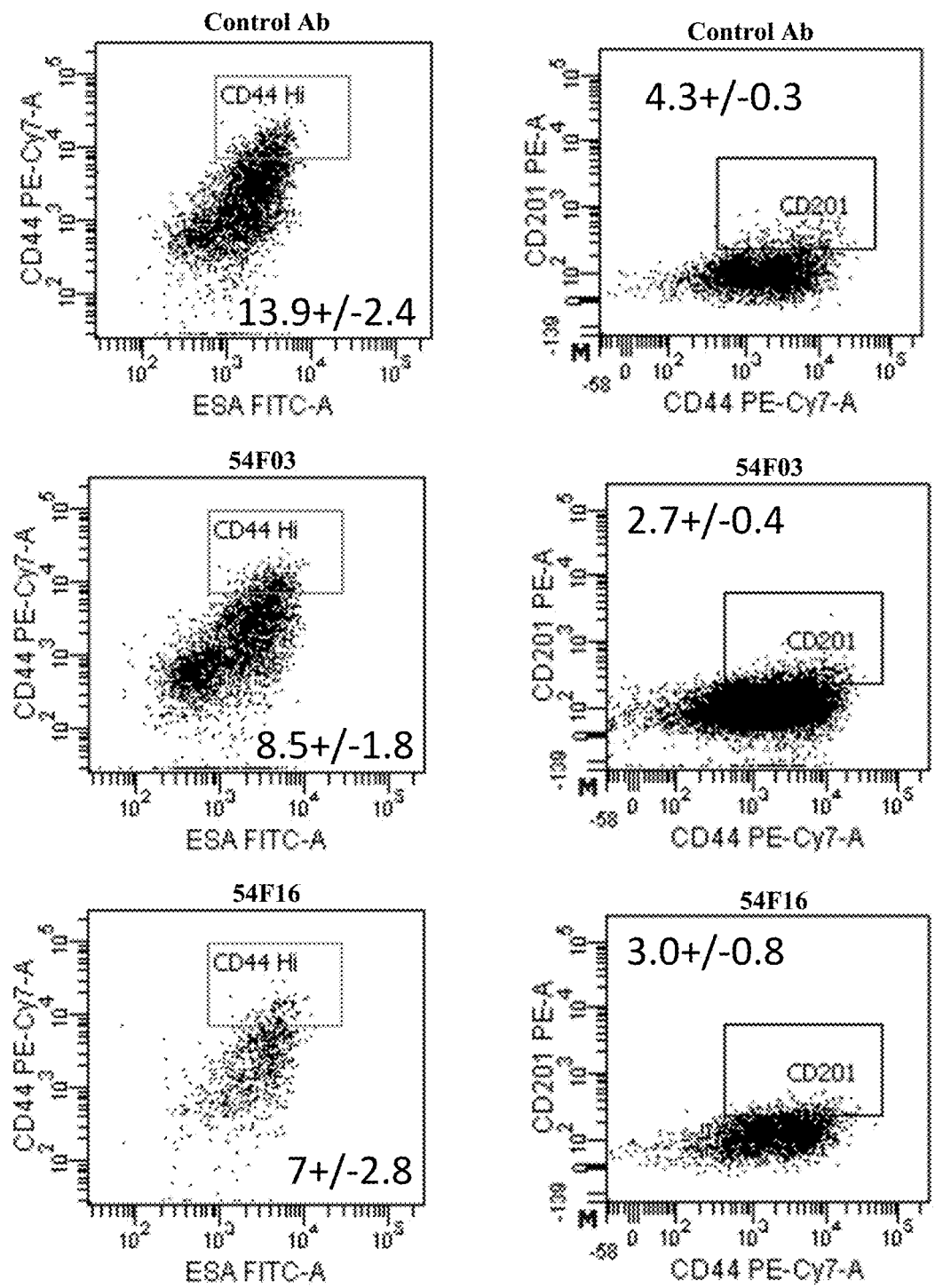

FIG. 19. Reduction of CD44$^{hi}$ and CD44$^+$CD201$^+$ cells in PN4 tumors treated with FZD8-Fc variants 54F03 and 54F16. Cell surface staining for ESA, CD44 and CD201 on tumor cells treated with control antibody, FZD8-Fc variant 54F03 or variant 54F16 was performed and analyzed by FACS.

FIGS. 20A-20E Characterization of N-termini of FZD8-Fc proteins. FZD8-Fc variants were analyzed by mass spectrometry and results for 54F16 (FIG. 20A), 54F26 (FIG. 20B), 54F28 (FIG. 20C), 54F30 (FIG. 20D), and 54F32 (FIG. 20E) are shown.

Figure 21:
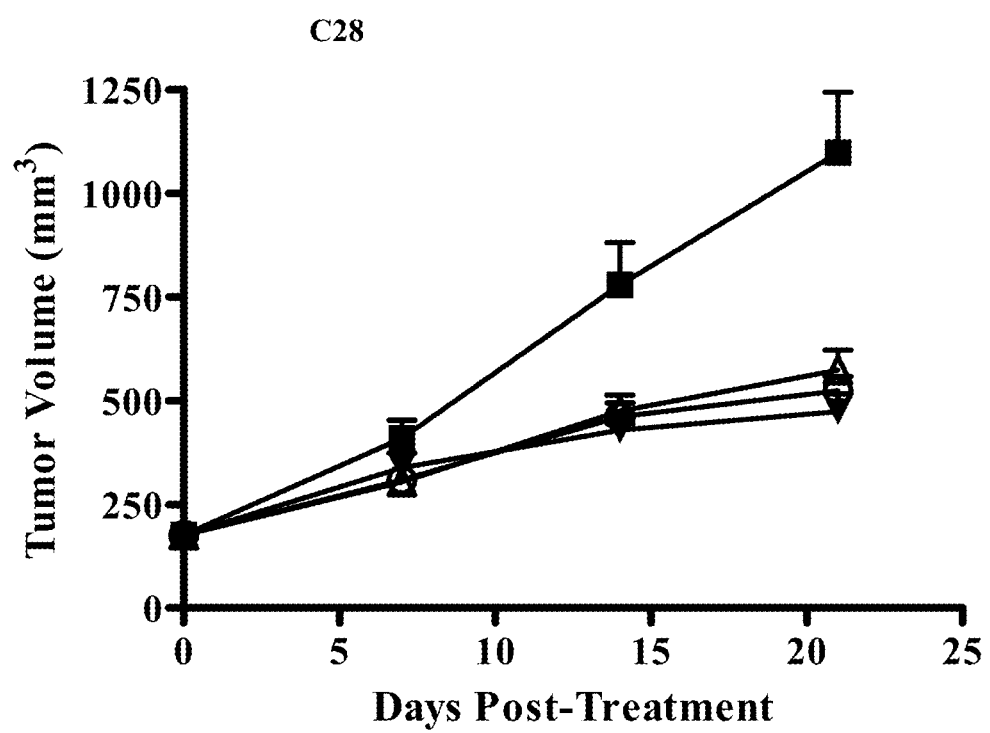

FIG. 21. Inhibition of C28 colon tumor growth following treatment with FZD8-Fc variants. C28 colon tumor cells were injected subcutaneously into NOD/SCID mice. Mice were treated with a control antibody (-■-), 54F03 (-△-), 54F23 (-▼-), or 54F26 (-o-). Data is shown as tumor volume (mm³) over days post treatment.

DETAILED DESCRIPTION OF THE INVENTION

The present invention provides novel agents, including, but not limited to, polypeptides comprising the Fri domain of human Frizzled (FZD) receptors, human secreted Frizzled-related proteins (SFRPs), or Ror proteins that bind to one or more human Wnts. Related polypeptides and polynucleotides, compositions comprising the Wnt-binding agents, and methods of making the Wnt-binding agents are also provided. Methods of using the Wnt-binding agents, such as methods of inhibiting tumor growth, treating cancer, inducing differentiation, and reducing tumorigenicity are further provided. Methods of screening agents to identify novel Wnt-binding agents with anti-tumor activity and/or anti-cancer stem cell activity are also provided.

A Wnt-binding agent comprising the Fri domain of human FZD8 and a Fc domain was produced and referred to herein as FZD8-Fc or FZD8-Fc (54F03) (Example 1). A number of variants of the FZD8-Fc protein were generated (Example 10). FZD8-Fc proteins were produced that were shown to be approximately 95% or greater homogeneous at the N-termini (Example 16). Pharmacokinetic studies using several of the FZD8-Fc variants were done in rats showing that the half-life of the FZD8-Fc variants was at least 100 hours (Examples 2 and 12; FIG. 1 and Table 4). A pharmacokinetic study was undertaken in monkeys with FZD8-Fc variants 54F15 and 54F16, which demonstrated that these proteins had a half-life of at least 100 hours (Example 13 and Table 5). Treatment with FZD8-Fc (54F03), either alone or in combination with a chemotherapeutic agent was shown to reduce the growth of pancreatic tumors, breast tumors and colon tumors (Examples 3, 5, 6 and 8 and FIGS. 2, 10, 11B, and 13A). Furthermore, the treatment was shown to decrease the percentage of $CD44^+$ cells and to reduce the frequency of cancer stem cells in the pancreatic model (Examples 3 and 8 and FIGS. 3, 4, and 13B). Treatment with FZD8-Fc (54F03), either alone or in combination with a chemotherapeutic agent was shown to increase cell differentiation of pancreatic tumor cells and colon tumor cells (Examples 4, 7 and 9 and FIGS. 5-9, 12, 14, and 15). Treatment with FZD8-Fc variants demonstrated inhibition of tumor growth in colon and pancreatic tumors, with the extent of inhibition depending upon the variant (Examples 14, 15, and 17 and FIGS. 17, 18, and 21). Treatment with FZD8-Fc variant 54F03 and variant 54F16 was shown to decrease the percentage of $CD44^{hi}$ cells, as well as $CD44^+CD202^+$ cells in pancreatic tumors (Example 15 and FIG. 19).

I. Definitions

The term "antagonist" is used herein to include any molecule that partially or fully blocks, inhibits, or neutralizes the expression of or the biological activity of a protein, (e.g., a cancer stem cell marker). The blocking, inhibiting, and/or neutralizing of biological activity includes, but is not limited to, inhibition of tumor growth. The term "antagonist" includes any molecule that partially or fully blocks, inhibits, or neutralizes a biological activity of the Wnt pathway. Suitable antagonist molecules include, but are not limited to, fragments and/or amino acid sequence variants of native FZD receptor proteins including soluble FZD receptors, as well as derivatives of SFRPs and derivatives of Ror proteins.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cells or compositions include those which have been purified to a degree that they are no longer in a form in which they are found in nature. In some embodiments, an antibody, polynucleotide, vector, cell, or composition which is isolated is substantially pure.

As used herein, "substantially pure" refers to material which is at least 50% pure (i.e., free from contaminants), more preferably at least 90% pure, more preferably at least 95% pure, more preferably at least 98% pure, more preferably at least 99% pure.

As used herein the term "soluble receptor" refers to an N-terminal extracellular fragment of a receptor protein preceding the first transmembrane domain of the receptor that can be secreted from a cell in soluble form. In some embodiments, the receptor protein is a FZD receptor. In some embodiments, the receptor protein is a Ror receptor.

As used herein the term "FZD soluble receptor" refers to an N-terminal extracellular fragment of a human FZD receptor protein preceding the first transmembrane domain of the receptor that can be secreted from a cell in soluble form. Both FZD soluble receptors comprising the entire N-terminal extracellular domain (ECD) (referred to herein as "FZD ECD") as well as smaller fragments are envisioned. FZD soluble receptors comprising the Fri domain (referred to herein as "FZD Fri") are also disclosed. FZD Fri soluble receptors can demonstrate altered biological activity, (e.g., increased protein half-life) compared to soluble receptors comprising the entire FZD ECD. Protein half-life can be further increased by covalent modification with polyethylene glycol (PEG) or polyethylene oxide (PEO). FZD soluble receptors include FZD ECD or Fri domains linked in-frame to other functional and structural proteins including, but not limited to, a human Fc region (e.g., human Fc derived from immunoglobulins IgG1, IgG2, IgG3, IgG4, IgA1, IgA2, IgD, IgE, or IgM); protein tags (e.g., myc, FLAG, GST); other endogenous proteins or protein fragments; or any other useful protein sequence including any linker region between a FZD ECD or Fri domain and a linked protein. In certain embodiments, the Fri domain of a FZD receptor is directly linked to a human Fc region. In certain embodiments, the Fri domain of a FZD receptor is linked to human IgG1 Fc (referred to herein as "FZD Fri.Fc"). In some embodiments, the Fri domain of a FZD receptor is linked to a human Fc region with a peptide linker. FZD soluble receptors also include variant proteins comprising amino acid insertions, deletions, substitutions, and/or conservative substitutions.

As used herein, the term "linker" or "linker region" refers to a linker inserted between a first polypeptide (e.g., a FZD component) and a second polypeptide (e.g., a Fc region). In some embodiments, the linker is a peptide linker. Linkers should not adversely affect the expression, secretion, or bioactivity of the polypeptides. Preferably, linkers are not antigenic and do not elicit an immune response.

As used herein, the terms "cancer" and "cancerous" refer to or describe the physiological condition in mammals in which a population of cells are characterized by unregulated cell growth. The term cancer is understood to encompass Wnt-dependent cancers. Examples of cancers include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, skin cancer, melanoma, endometrial or uterine carcinoma, salivary gland carcinoma, kidney cancer, liver cancer, prostate cancer, vulval cancer, thyroid cancer, hepatic carcinoma and various types of head and neck cancer.

The terms "proliferative disorder" and "proliferative disease" refer to disorders associated with abnormal cell proliferation such as cancer.

"Tumor" and "neoplasm" as used herein refer to any mass of tissue that results from excessive cell growth or proliferation, either benign (noncancerous) or malignant (cancerous) including pre-cancerous lesions. In certain embodiments, the tumor is an epithelial tumor. In certain embodiments, the tumor is a Wnt-dependent tumor.

As used herein, the term "subject" refers to any animal (e.g., a mammal), including, but not limited to humans, non-human primates, canines, felines, rodents, and the like, which is to be the recipient of a particular treatment. Typically, the terms "subject" and "patient" are used interchangeably herein in reference to a human subject.

The terms "cancer stem cell" and "CSC" and "tumor stem cell" and "solid tumor stem cell" are used interchangeably herein and refer to a population of cells from a solid tumor that: (1) have extensive proliferative capacity; (2) are capable of asymmetric cell division to generate one or more kinds of differentiated progeny with reduced proliferative or developmental potential; and (3) are capable of symmetric cell divisions for self-renewal or self-maintenance. These properties of "cancer stem cells," "CSCs," "tumor stem cells," or "solid tumor stem cells" confer on those cancer stem cells the ability to form palpable tumors upon serial transplantation into an immunocompromised host (e.g., a mouse) compared to the majority of tumor cells that fail to form tumors. Cancer stem cells undergo self-renewal versus differentiation in a chaotic manner to form tumors with abnormal cell types that can change over time as mutations occur.

The terms "cancer cell" and "tumor cell" and grammatical equivalents refer to the total population of cells derived from a tumor including both non-tumorigenic cells, which comprise the bulk of the tumor cell population, and tumorigenic stem cells also referred to herein as cancer stem cells.

The term "tumorigenic" refers to the functional features of a solid tumor stem cell including the properties of self-renewal (giving rise to additional tumorigenic cancer stem cells) and proliferation to generate all other tumor cells (giving rise to differentiated and thus non-tumorigenic tumor cells) that allow solid tumor stem cells to form a tumor. These properties of self-renewal and proliferation to generate all other tumor cells confer on cancer stem cells the ability to form palpable tumors upon serial transplantation into an immunocompromised host (e.g., a mouse) compared to non-tumorigenic tumor cells, which are unable to form tumors upon serial transplantation. It has been observed that non-tumorigenic tumor cells may form a tumor upon primary transplantation into an immunocompromised host (e.g., a mouse) after obtaining the tumor cells from a solid tumor, but those non-tumorigenic tumor cells do not give rise to a tumor upon serial transplantation.

As used herein an "acceptable pharmaceutical carrier" or "pharmaceutically acceptable carrier" refers to any material that, when combined with an active ingredient of a pharmaceutical composition such as a therapeutic polypeptide, allows the therapeutic polypeptide, for example, to retain its biological activity. In addition, an "acceptable pharmaceutical carrier" does not trigger an immune response in a recipient subject. In some embodiments, the term "pharmaceutical vehicle" is used interchangeably with "pharmaceutical carrier". Examples include, but are not limited to, any of the standard pharmaceutical carriers such as a phosphate buffered saline solution, water, and various oil/water emulsions. Examples of diluents for aerosol or parenteral administration are phosphate buffered saline or normal (0.9%) saline.

The term "therapeutically effective amount" refers to an amount of an agent (e.g., a soluble receptor or other drug) effective to "treat" a disease or disorder in a subject or mammal. In the case of cancer, the therapeutically effective amount of the agent (e.g., a soluble receptor) can reduce the number of cancer cells; reduce the tumor size; reduce the frequency of cancer stem cells; inhibit and/or stop cancer cell infiltration into peripheral organs; inhibit and/or stop tumor metastasis; inhibit and/or stop tumor growth; and/or relieve to some extent one or more of the symptoms associated with the cancer. To the extent the agent (e.g., a soluble receptor) prevents growth and/or kills existing cancer cells, it can be referred to as cytostatic and/or cytotoxic.

As used herein the term "inhibit tumor growth" refers to any mechanism by which tumor cell growth can be inhibited. In certain embodiments, tumor cell growth is inhibited by slowing proliferation of tumor cells. In certain embodiments, tumor cell growth is inhibited by halting proliferation of tumor cells. In certain embodiments, tumor cell growth is inhibited by killing tumor cells. In certain embodiments, tumor cell growth is inhibited by inducing apoptosis of tumor cells. In certain embodiments, tumor cell growth is inhibited by inducing differentiation of tumor cells. In certain embodiments, tumor cell growth is inhibited by depriving tumor cells of nutrients. In certain embodiments, tumor cell growth is inhibited by preventing migration of tumor cells. In certain embodiments, tumor cell growth is inhibited by preventing invasion of tumor cells.

Terms such as "treating" and "treatment" and "to treat" and "alleviating" and "to alleviate" refer to both 1) therapeutic measures that cure, slow down, lessen symptoms of, and/or halt progression of a diagnosed pathologic condition or disorder, and 2) prophylactic or preventative measures that prevent or slow the development of a targeted pathologic condition or disorder. Thus, those in need of treatment include those who already have the disorder; those prone to have the disorder; and those in whom the disorder is to be prevented. In certain embodiments, a subject is successfully "treated" for cancer according to the methods of the present invention if the patient shows one or more of the following: a reduction in the number of, or complete absence of, cancer or tumor cells; a reduction in the tumor size; inhibition of, or an absence of, cancer or tumor cell infiltration into peripheral organs including, for example, the spread of cancer into soft tissue and bone; inhibition of, or an absence of, tumor metastasis; inhibition of, or an absence of, tumor or cancer growth; relief of one or more symptoms associated with the specific cancer; reduced morbidity and mortality; improvement in quality of life; reduction in tumorigenicity, tumorgenic frequency, or tumorgenic capacity of a tumor; reduction in the number or frequency of cancer stem cells in the tumor; differentiation of tumorigenic cells to a non-tumorigenic state; or some combination of these effects.

As used herein, the terms "polynucleotide" and "nucleic acid" refer to a polymer composed of a multiplicity of nucleotide units (ribonucleotide or deoxyribonucleotide or related structural variants) linked via phosphodiester bonds, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methyl-cytosine, 5-methylcytosine, N6-methyladenine, 7-methylguanine, 5-methylaminomethyluracil, 5-methoxyamino-methyl-2-thiouracil, beta D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine. The sequence of nucleotides may be interrupted by non-nucleotide components. A polynucleotide may be further modified after polymerization, such as by conjugation with a labeling component. Other types of modifications include, for example, "caps"; substitution of one or more of the naturally occurring nucleotides with an analog; internucleotide modifications such as uncharged linkages (e.g., methyl phosphonates, phosphotriesters, phosphoamidates, carbamates, etc.) and charged linkages (e.g., phosphorothioates, phosphorodithioates, etc.); pendant moieties, such as proteins (e.g., nucleases, toxins, antibodies, signal peptides, poly-L-lysine, etc.); intercalators (e.g., acridine, psoralen, etc.); chelators (e.g., metals, radioactive metals, boron, oxidative metals, etc.); alkylators; modified linkages (e.g., alpha anomeric nucleic acids, etc.); as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, heptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR2 ("amidate"), P(O)R, P(O)OR', CO or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical.

As used herein, the term "vector" is used in reference to nucleic acid molecules that transfer DNA segment(s) from one cell to another. The term "vector" means a construct, which is capable of delivering, and preferably expressing, one or more gene(s) or sequence(s) of interest to a host cell. Examples of vectors include, but are not limited to, viral vectors, naked DNA or RNA expression vectors, plasmid, phagemid, cosmid or phage vectors, DNA or RNA expression vectors associated with cationic condensing agents, and DNA or RNA expression vectors encapsulated in liposomes.

The terms "polypeptide" and "peptide" and "protein" and "protein fragment" are used interchangeably herein to refer to a polymer of amino acid residues of any length. The terms apply to amino acid polymers in which one or more amino acid residue in the polymer is an artificial chemical mimetic of a corresponding naturally occurring amino acid, as well as to naturally occurring amino acid polymers and non-naturally occurring amino acid polymers. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based, at least in part, upon antibodies, in certain embodiments, the polypeptides can occur as single chains or associated chains.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, e.g., an alpha carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but retain the same basic chemical structure as a naturally occurring amino acid Amino acid mimetic refers to chemical compounds that have a structure that is different from the general chemical structure of an amino acid, but that function similarly to a naturally occurring amino acid.

That a polypeptide or other agent "specifically binds" to a protein means that the polypeptide or other agent reacts or associates more frequently, more rapidly, with greater duration, with greater affinity, or with some combination of the above to the protein than with alternative substances, including unrelated proteins. In certain embodiments, "specifically binds" means, for instance, that an agent binds to a protein with a $K_D$ of about 0.1 mM or less, but more usually less than about 1 µM. In certain embodiments, "specifically binds" means that an agent binds to a protein at times with a $K_D$ of at least about 0.1 µM or less, at least about 0.01 µM or less, and at other times at least about 1 nM or less. Because of the sequence identity between homologous proteins in different species, specific binding can include an agent that recognizes a particular protein such as a Wnt protein in more than one species. Likewise, because of homology between different Wnt proteins in certain regions of the sequences of the Wnts, specific binding can include an polypeptide (or other agent) that recognizes more than one Wnt protein. It is understood that an agent that specifically binds to a first target may or may not specifically bind to a second target. As such, "specific binding" does not necessarily require (although it can include) exclusive binding, i.e. binding to a single target. Thus, an agent may, in certain embodiments, specifically bind to more than one target (e.g., multiple different human Wnts). Generally, but not necessarily, reference to binding means specific binding.

The terms "identical" or "percent identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software that may be used to obtain alignments of amino acid or nucleotide sequences are known in the art. One such non-limiting example of a sequence alignment algorithm is the algorithm described in Karlin et al, 1990, *Proc. Natl. Acad. Sci.,* 87:2264-2268, as modified in Karlin et al., 1993, *PNAS,* 90:5873-5877, and incorporated into the NBLAST and XBLAST programs (Altschul et al., 1991, *Nucleic Acids Res.,* 25:3389-3402). Additional publicly available software programs that can be used to align sequences include, but are not limited to, Gapped BLAST, BLAST-2, WU-BLAST-2 (Altschul et al., 1996, *Methods in Enzymology,* 266:460-480), ALIGN, ALIGN-2 (Genentech, South San Francisco, Calif.), Megalign (DNASTAR), and the Bestfit program (Wisconsin Sequence Analysis Package, Version 8 for Unix, Genetics Computer Group, University Research Park, 575 Science Drive, Madison, Wis. 53711).

In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the sequences that is at least about 10, at least about 20, at least about 40-60, at least about 60-80 residues in length or any integral value therebetween. In some embodiments, identity exists over a longer region than 60-80 residues, such as at least about 90-100 residues. In some embodiments, the sequences are substantially identical over the full length of the sequences being compared, such as the coding region of a nucleotide sequence.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Preferably, conservative substitutions in the sequences of the polypeptides and other agents of the invention do not abrogate the binding of the polypeptide containing the amino acid sequence, to the target(s), i.e., the one or more Wnts to which the polypeptide or other agent binds. Methods of identifying nucleotide and amino acid conservative substitutions which do not eliminate target binding are well-known in the art (see, e.g., Brummell et al., 1993, *Biochem.,* 32: 1180-87; Kobayashi et al., 1999, *Protein Eng.* 12:879-84; and Burks et al., 1997, *PNAS,* 94:412-17).

As used herein, "about" refers to plus or minus 10% of the indicated number. For example, "about 10%" indicates a range of 9% to 11%.

As used in the present disclosure and claims, the singular forms "a" "an" and "the" include plural forms unless the context clearly dictates otherwise.

It is understood that wherever embodiments are described herein with the language "comprising," otherwise analogous embodiments described in terms of "consisting of" and/or "consisting essentially of" are also provided.

The term "and/or" as used in a phrase such as "A and/or B" herein is intended to include both A and B; A or B; A (alone), and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. Wnt-Binding Agents

The present invention provides agents that bind (e.g., specifically bind) one or more human Wnt proteins (Wnts). These agents are referred to herein as "Wnt-binding agent(s)." In certain embodiments, the agents specifically bind one, two, three, four, five, six, seven, eight, nine, ten, or more Wnt proteins. By way of non-limiting example, the Wnt-binding agent may bind Wnt1, Wnt2, Wnt2b, Wnt3, Wnt3a, Wnt7a, Wnt7b, Wnt8a, Wnt8b, Wnt10a, and/or Wnt10b. In certain embodiments, the Wnt-binding agent binds Wnt1, Wnt2, Wnt3, Wnt3a, and Wnt7b.

In certain embodiments, the Wnt-binding agent is a Wnt antagonist. In certain embodiments, the agent inhibits Wnt-signaling. In some embodiments, the agent inhibits canonical Wnt signaling.

In certain embodiments, the Wnt-binding agent is a polypeptide. In certain embodiments, the Wnt-binding agent is a soluble receptor.

In certain embodiments, the Wnt-binding agent comprises the extracellular domain of a FZD receptor. In some embodiments, the Wnt-binding agent comprises a Fri domain of a FZD receptor. In certain embodiments, the FZD receptor is a human FZD receptor. In certain embodiments, the human FZD receptor is FZD1, FZD2, FZD3, FZD4, FZD5, FZD6, FZD7, FZD8, FZD9, or FZD10. In some alternative embodiments, the Wnt-binding agent comprises a portion of a SFRP. In some embodiments, the Wnt-binding agent comprises a Fri domain of a SFRP. In certain embodiments, the SFRP is a human SFRP. In some embodiments, the human SFRP is SFRP1, SFRP2, SFRP3, SFRP4, or SFRP5. In other alternative embodiments, the Wnt-binding agent comprises the extracellular domain of a Ror protein. In some embodiments, the Wnt-binding agent comprises a Fri domain of a Ror protein. In certain embodiments, the Ror is a human Ror. In some embodiments, the human Ror is Ror1 or Ror2.

In certain embodiments, the Wnt-binding agent is a soluble receptor. In some embodiments, the Wnt-binding agent is a soluble protein. In certain embodiments, the Wnt-binding agent is a soluble FZD receptor. Nonlimiting examples of soluble FZD receptors can be found in U.S. Pat. No. 7,723,477, which is incorporated by reference herein in its entirety. In certain embodiments, the Wnt-binding agent is a soluble SFRP or a soluble Ror receptor.

The Fri domain of FZD1 includes approximately amino acids 87-237 of SEQ ID NO:27. The Fri domain of FZD2 includes approximately amino acids 24-159 of SEQ ID NO:28. The Fri domain of FZD3 includes approximately amino acids 23-143 of SEQ ID NO:29. The Fri domain of FZD4 includes approximately amino acids 40-170 of SEQ ID NO:22. The Fri domain of FZD5 includes approximately amino acids 27-157 of SEQ ID NO:23. The Fri domain of FZD6 includes approximately amino acids 19-146 of SEQ ID NO:24. The Fri domain of FZD7 includes approximately amino acids 33-170 of SEQ ID NO:25. The Fri domain of FZD8 includes approximately amino acids 28-158 of SEQ ID NO:30. The Fri domain of FZD9 includes approximately amino acids 23-159 of SEQ ID NO:31. The Fri domain of FZD10 includes approximately amino acids 21-154 of SEQ ID NO:26. The corresponding, predicted Fri domains for each of the human FZD receptors are provided as SEQ ID NOs:32-41. The minimal, core Fri domain sequences for each of the human FZD receptors (FZD1-10) are provided as SEQ ID NOs:3-12. The minimal, core Fri domain sequences for each of the human SFRPs (SFRP1-5) are provided as SEQ ID NOs:13-17. The minimal, core Fri domain sequences of human Ror1 and Ror2 are provided as SEQ ID NO:58 and SEQ ID NO:59. Those of skill in the art may differ in their understanding of the exact amino acids corresponding to the various Fri domains. Thus the N-terminus or C-terminus of the domains outlined above and herein may extend or be shortened by 1, 2, 3, 4, 5, 6, 7, 8, 9, or even 10 amino acids.

In certain embodiments, the Wnt-binding agent comprises a Fri domain of a human FZD receptor, or a fragment or variant of the Fri domain that binds one or more human Wnt proteins. In certain embodiments, the human FZD receptor is FZD1, FZD2, FZD3, FZD4, FZD5, FZD6, FZD7, FZD8, FZD9, or FZD10. In certain embodiments, the human FZD receptor is FZD4. In certain alternative embodiments, the human FZD receptor is FZD5. In certain additional alternative embodiments, the human FZD receptor is FZD8. In certain embodiments, the FZD is FZD4 and the Wnt-binding agent comprises SEQ ID NO:6 or comprises approximately amino acids 40 to 170 of SEQ ID NO:19. In certain embodiments, the FZD is FZD5 and the Wnt-binding agent comprises SEQ ID NO:7 or comprises approximately amino acids 27-157 of SEQ ID NO:20. In certain embodiments, the FZD is FZD7 and the Wnt-binding agent comprises SEQ ID NO:9 or comprises approximately amino acids 33 to 170 of SEQ ID NO:25. In certain embodiments, the FZD is FZD8 and the Wnt-binding agent comprises SEQ ID NO:10 or comprises approximately amino acids 28-158 of SEQ ID NO:21. In certain embodiments, the FZD is FZD10 and the Wnt-binding agent comprises SEQ ID NO:12 or comprises approximately amino acids 21-154 of SEQ ID NO:26.

In certain embodiments, the Wnt-binding agent comprises a minimal Fri domain sequence selected from the group consisting of SEQ ID NOs:3-12. In certain embodiments, the Wnt-binding agent comprises a minimal Fri domain sequence selected from the group consisting of SEQ ID NOs:13-17. In certain embodiments, the Wnt-binding agent comprises a minimal Fri domain sequence selected from the group consisting of SEQ ID NO:58 and SEQ ID NO:59.

In certain embodiments, the Wnt-binding agent comprises a variant of any one of the aforementioned FZD Fri domain sequences that comprises one or more (e.g., one, two, three, four, five, six, seven, eight, nine, ten, etc.) conservative substitutions and is capable of binding Wnt(s).

In certain alternative embodiments, the Wnt-binding agent comprises a Fri domain of a human SFRP, or a fragment or variant of such a Fri domain that binds to one or more human Wnt proteins. For example, in certain embodiments, the agent comprises a minimal SFRP Fri domain sequence selected from the group consisting of SEQ ID NOs:13-17. In certain embodiments, the Wnt-binding agent comprises a variant of any one of the aforementioned SFRP Fri domain sequences that comprises one or more (e.g., one, two, three, four, five, six, seven, eight, nine, ten, etc.) conservative substitutions and maintains the ability to bind Wnt(s).

In certain alternative embodiments, the Wnt-binding agent comprises a Fri domain of a human Ror protein, or a fragment or variant of such a Fri domain that binds to one or more human Wnt proteins. For example, in certain embodiments, the agent comprises a minimal Ror Fri domain sequence selected from the group consisting of SEQ ID NO:58 and SEQ ID NO:59. In certain embodiments, the Wnt-binding agent comprises a variant of any one of the aforementioned Ror Fri domain sequences that comprises one or more (e.g., one, two, three, four, five, six, seven, eight, nine, ten, etc.) conservative substitutions and maintains the ability to bind Wnt(s).

In certain embodiments, the Wnt-binding agent, such as an agent comprising a minimum Fri domain of a human FZD receptor or other soluble FZD receptor, further comprises a human Fc region (e.g., a human IgG1 Fc region). The Fc region can be obtained from any of the classes of immunoglobulin, IgG, IgA, IgM, IgD and IgE. In some embodiments, the Fc region is a wild-type Fc region. In some embodiments, the Fc region is a mutated Fc region. In some embodiments, the Fc region is truncated at the N-terminal end by 1, 2, 3, 4, 5, 6, 7, 8, 9, or 10 amino acids, (e.g., in the hinge domain). In some embodiments, an amino acid in the hinge domain is changed to hinder undesirable disulfide bond formation. In some embodiments, a cysteine is replaced with a serine to hinder undesirable disulfide bond formation. In certain embodiments, the Fc region comprises or consists of SEQ ID NO:18, SEQ ID NO:42, or SEQ ID NO:43.

In certain embodiments, a Wnt-binding agent is a fusion protein comprising at least a minimum Fri domain of a FZD receptor, a SFRP or Ror protein and a Fc region. As used herein, a "fusion protein" is a hybrid protein expressed by a nucleic acid molecule comprising nucleotide sequences of at least two genes. In some embodiments, the C-terminus of the first polypeptide is linked to the N-terminus of the immunoglobulin Fc region. In some embodiments, the first polypeptide (e.g., a FZD Fri domain) is directly linked to the Fc region (i.e. without an intervening peptide linker). In some embodiments, the first polypeptide is linked to the Fc region via a peptide linker.

As used herein, the term "linker" refers to a linker inserted between a first polypeptide (e.g., a FZD component) and a second polypeptide (e.g., a Fc region). In some embodiments, the linker is a peptide linker. Linkers should not adversely affect the expression, secretion, or bioactivity of the polypeptide. Linkers should not be antigenic and should not elicit an immune response. Suitable linkers are known to those of skill in the art and often include mixtures of glycine and serine residues and often include amino acids that are sterically unhindered. Other amino acids that can be incorporated into useful linkers include threonine and alanine residues. Linkers can range in length, for example from 1-50 amino acids in length, 1-22 amino acids in length, 1-10 amino acids in length, 1-5 amino acids in length, or 1-3 amino acids in length. Linkers may include, but are not limited to, SerGly, GGSG, GSGS, GGGS, S(GGS)$_n$ where n is 1-7, GRA, poly(Gly), poly(Ala), ESGGGGVT (SEQ ID NO:60), LESGGGGVT (SEQ ID NO:61), GRAQVT (SEQ ID NO:62), WRAQVT (SEQ ID NO:63), and ARGRAQVT (SEQ ID NO:64). As used herein, a linker is an intervening peptide sequence that does not include amino acid residues from either the C-terminus of the first polypeptide (e.g., a FZD Fri domain) or the N-terminus of the second polypeptide (e.g., the Fc region).

FZD receptors, SFRPs and Ror proteins contain a signal sequence that directs the transport of the proteins. Signal sequences (also referred to as signal peptides or leader sequences) are located at the N-terminus of nascent polypeptides. They target the polypeptide to the endoplasmic reticulum and the proteins are sorted to their destinations, for example, to the inner space of an organelle, to an interior membrane, to the cell's outer membrane, or to the cell exterior via secretion. Most signal sequences are cleaved from the protein by a signal peptidase after the proteins are transported to the endoplasmic reticulum. The cleavage of the signal sequence from the polypeptide usually occurs at a specific site in the amino acid sequence and is dependent upon amino acid residues within the signal sequence. Although there is usually one specific cleavage site, more than one cleavage site may be recognized and/or used by a signal peptidase resulting in a non-homogenous N-terminus of the polypeptide. For example, the use of different cleavage sites within a signal sequence can result in a polypeptide expressed with different N-terminal amino acids. Accordingly, in some embodiments, the polypeptides as described herein may comprise a mixture of polypeptides with different N-termini. In some embodiments, the N-termini differ in length by 1, 2, 3, 4, or 5 amino acids. In some embodiments, the polypeptide is substantially homogeneous, i.e., the polypeptides have the same N-terminus. In some embodiments, the signal sequence of the polypeptide comprises one or more (e.g., one, two, three, four, five, six, seven, eight, nine, ten, etc.) amino acid substitutions and/or deletions. In some embodiments, the signal sequence of the polypeptide comprises amino acid substitutions and/or deletions that allow one cleavage site to be dominant, thereby resulting in a substantially homogeneous polypeptide with one N-terminus. In some embodiments, the signal sequence is SEQ ID NO:67 (amino acids 1-27 of SEQ ID NO:30). In some embodiments, amino acids 25 and/or 26 of SEQ ID NO:67 are substituted with different amino acids. In some embodiments, amino acids 17, 18, 19, 23, 24, 25, and/or 26 of SEQ ID NO:67 are substituted with different amino acids. In some embodiments, amino acids 17, 23, 24, 25, and 26 of SEQ ID NO:67 are substituted with different amino acids. In some embodiments, amino acid 17 of SEQ ID NO:67 is substituted with a phenylalanine or a leucine. In some embodiments, amino acid 23 of SEQ ID NO:67 is substituted with a proline. In some embodiments, amino acid 24 of SEQ ID NO:67 is substituted with an isoleucine or a phenylalanine. In some embodiments, amino acid 25 of SEQ ID NO:67 is substituted with a valine, an isoleucine, or an alanine. In some embodiments, amino acid 26 of SEQ ID NO:67 is substituted with a histidine, a tyrosine, or a histidine. In some embodiments, amino acid 25 of SEQ ID NO:67 is substituted with a valine. In some embodiments, amino acid 26 of SEQ ID NO:67 is substituted with a leucine. In some embodiments, the signal sequence of the polypeptide comprises or consists of a sequence selected from the group listed in Table 1.

TABLE 1

| | |
|---|---|
| MEWGYLLEVTSLLAALALLQRSSGAAA | SEQ ID NO: 67 |
| MEWGYLLEVTSLLAALALLQRSSGALA | SEQ ID NO: 68 |
| MEWGYLLEVTSLLAALALLQRSSGVLA | SEQ ID NO: 69 |

TABLE 1-continued

| | |
|---|---|
| MEWGYLLEVTSLLAALLLLQRSPIVHA | SEQ ID NO: 70 |
| MEWGYLLEVTSLLAALFLLQRSPIVHA | SEQ ID NO: 71 |
| MEWGYLLEVTSLLAALLLLQRSPFVHA | SEQ ID NO: 72 |
| MEWGYLLEVTSLLAALLLLQRSPIIYA | SEQ ID NO: 73 |
| MEWGYLLEVTSLLAALLLLQRSPIAHA | SEQ ID NO: 74 |

In certain embodiments, the Wnt-binding agent comprises a first polypeptide comprising a FZD domain component and a Fc region. In some embodiments, the FZD domain component is from FZD1, FZD2, FZD3, FZD4, FZD5, FZD6, FZD7, FZD8, FZD9, or FZD10. In some embodiments, the Fc region is from an IgG1 immunoglobulin. In some embodiments, the Wnt-binding agent comprises: (a) a first polypeptide consisting essentially of amino acids selected from the group consisting of: X1 to Y1 of SEQ ID NO:27, X2 to Y2 of SEQ ID NO:28, X3 to Y3 of SEQ ID NO:29, X4 to Y4 of SEQ ID NO:22, X5 to Y5 of SEQ ID NO:23, X6 to Y6 of SEQ ID NO:24, X7 to Y7 of SEQ ID NO:25, X8 to Y8 of SEQ ID NO:30, X9 to Y9 of SEQ ID NO:31, and X10 to Y10 of SEQ ID NO:26; and
(b) a second polypeptide consisting essentially of amino acids A to B of SEQ ID NO:43;
wherein X1=amino acid 69, 70, 71, 72, 73, 74, 75, or 76
Y1=amino acid 236, 237, 238, 239, 240, 241, 242, or 243
X2=amino acid 22, 23, 24, 25, 26, 27 or 28
Y2=amino acid 158, 159, 160, 161, 162, 163, 164, 165, 166, 167, 168, 169, 170, 171 or 172
X3=amino acid 18, 19, 20, 21, 22, 23, 24, or 25
Y3=amino acid 141, 142, 143, 144, 145, 146, 147, 148, or 149
X4=amino acid 38, 39, 40, 41, or 42
Y4=amino acid 168, 169, 170, 171, 172, 173, 174, 175 or 176
X5=amino acid 25, 26, 27, 28 or 29
Y5=amino acid 155, 156, 157, 158, 159, 160, 161, 162, 163, or 164
X6=amino acid 19, 20, 21, 22, 23, or 24
Y6=amino acid 144, 145, 146, 147, 148, 149, 150, 151 or 152
X7=amino acid 22, 23, 24, 25, 26, 27, 28, 29, 30, 31, 32, 33, or 34
Y7=amino acid 178, 179, 180, 181, 182, 183, 184, 185, or 186
X8=amino acid 25, 26, 27, 28, 29, 30, or 31
Y8=amino acid 156, 157, 158, 159, 160, 161, 162, 163, or 164
X9=amino acid 21, 22, 23, or 24
Y9=amino acid 137, 138, 139, 140, 141, 142, 143, 144, 145, or 146
X10=amino acid 20, 21, 22, 23, 24, or 25
Y10=amino acid 152, 153, 154, 155, 156, 157, 158, 159, or 160
A=amino acid 1, 2, 3, 4, 5, or 6
B=amino acid 231 or 232.

In some embodiments, the first polypeptide is directly linked to the second polypeptide. In some embodiments, the first polypeptide is linked to the second polypeptide via a peptide linker. In some embodiments, the first polypeptide is linked to the second polypeptide via the peptide linker GRA. A polypeptide (e.g., a first or second polypeptide) that "consists essentially of" certain amino acids or is "consisting essentially of" certain amino acids may, in some embodiments, include one or more (e.g., one, two, three, four or more) additional amino acids at one or both ends, so long as the additional amino acids do not materially affect the function of the Wnt-binding agent.

In certain embodiments, the Wnt-binding agent comprises: (a) a first polypeptide consisting essentially of amino acids X to Y of SEQ ID NO:30; and (b) a second polypeptide consisting essentially of amino acids A to B of SEQ ID NO:43; wherein the first polypeptide is directly linked to the second polypeptide; and wherein X=amino acid 25, 26, 27, 28, 29, 30, or 31
Y=amino acid 156, 157, 158, 159, 160, 161, 162, 163, or 164
A=amino acid 1, 2, 3, 4, 5, or 6
B=amino acid 231 or 232.

In some embodiments, the first polypeptide consists essentially of amino acids 25-158 of SEQ ID NO:30. In other embodiments, the first polypeptide consists of amino acids 25-158 of SEQ ID NO:30. In some embodiments, the first polypeptide consists essentially of amino acids 28-158 of SEQ ID NO:30. In other embodiments, the first polypeptide consists of amino acids 28-158 of SEQ ID NO:30. In some embodiments, the first polypeptide consists of amino acids 31-158 of SEQ ID NO:30. In some embodiments, the second polypeptide consists of amino acids 1-232 of SEQ ID NO:43. In some embodiments, the second polypeptide consists of amino acids 3-232 of SEQ ID NO:43. In some embodiments, the second polypeptide consists of amino acids 6-232 of SEQ ID NO:43. In some embodiments, the first polypeptide is SEQ ID NO:39 and the second polypeptide is SEQ ID NO:43. In some embodiments, the first polypeptide is SEQ ID NO:39 and the second polypeptide is SEQ ID NO:42. In some embodiments, the first polypeptide is SEQ ID NO:39 and the second polypeptide is SEQ ID NO:18.

In some embodiments, the Wnt-binding agent is a polypeptide comprising a first polypeptide and a second polypeptide, wherein the polypeptides are selected from Table 2.

TABLE 2

| First Polypeptide | Second Polypeptide |
| --- | --- |
| Amino acids 25-158 of SEQ ID NO: 30 | Amino acids 1-232 of SEQ ID NO: 43 |
| Amino acids 25-158 of SEQ ID NO: 30 | Amino acids 1-231 of SEQ ID NO: 43 |
| Amino acids 25-158 of SEQ ID NO: 30 | Amino acids 2-232 of SEQ ID NO: 43 |
| Amino acids 25-158 of SEQ ID NO: 30 | Amino acids 2-231 of SEQ ID NO: 43 |
| Amino acids 25-158 of SEQ ID NO: 30 | Amino acids 3-232 of SEQ ID NO: 43 |
| Amino acids 25-158 of SEQ ID NO: 30 | Amino acids 3-231 of SEQ ID NO: 43 |
| Amino acids 25-158 of SEQ ID NO: 30 | Amino acids 4-232 of SEQ ID NO: 43 |
| Amino acids 25-158 of SEQ ID NO: 30 | Amino acids 4-231 of SEQ ID NO: 43 |
| Amino acids 25-158 of SEQ ID NO: 30 | Amino acids 5-232 of SEQ ID NO: 43 |
| Amino acids 25-158 of SEQ ID NO: 30 | Amino acids 5-231 of SEQ ID NO: 43 |
| Amino acids 25-158 of SEQ ID NO: 30 | Amino acids 6-232 of SEQ ID NO: 43 |
| Amino acids 25-158 of SEQ ID NO: 30 | Amino acids 6-231 of SEQ ID NO: 43 |
| Amino acids 26-158 of SEQ ID NO: 30 | Amino acids 1-232 of SEQ ID NO: 43 |
| Amino acids 26-158 of SEQ ID NO: 30 | Amino acids 1-231 of SEQ ID NO: 43 |
| Amino acids 26-158 of SEQ ID NO: 30 | Amino acids 2-232 of SEQ ID NO: 43 |
| Amino acids 26-158 of SEQ ID NO: 30 | Amino acids 2-231 of SEQ ID NO: 43 |
| Amino acids 26-158 of SEQ ID NO: 30 | Amino acids 3-232 of SEQ ID NO: 43 |
| Amino acids 26-158 of SEQ ID NO: 30 | Amino acids 3-231 of SEQ ID NO: 43 |
| Amino acids 26-158 of SEQ ID NO: 30 | Amino acids 4-232 of SEQ ID NO: 43 |
| Amino acids 26-158 of SEQ ID NO: 30 | Amino acids 4-231 of SEQ ID NO: 43 |
| Amino acids 26-158 of SEQ ID NO: 30 | Amino acids 5-232 of SEQ ID NO: 43 |
| Amino acids 26-158 of SEQ ID NO: 30 | Amino acids 5-231 of SEQ ID NO: 43 |
| Amino acids 26-158 of SEQ ID NO: 30 | Amino acids 6-232 of SEQ ID NO: 43 |
| Amino acids 26-158 of SEQ ID NO: 30 | Amino acids 6-231 of SEQ ID NO: 43 |
| Amino acids 27-158 of SEQ ID NO: 30 | Amino acids 1-232 of SEQ ID NO: 43 |
| Amino acids 27-158 of SEQ ID NO: 30 | Amino acids 1-231 of SEQ ID NO: 43 |
| Amino acids 27-158 of SEQ ID NO: 30 | Amino acids 2-232 of SEQ ID NO: 43 |
| Amino acids 27-158 of SEQ ID NO: 30 | Amino acids 2-231 of SEQ ID NO: 43 |
| Amino acids 27-158 of SEQ ID NO: 30 | Amino acids 3-232 of SEQ ID NO: 43 |
| Amino acids 27-158 of SEQ ID NO: 30 | Amino acids 3-231 of SEQ ID NO: 43 |
| Amino acids 27-158 of SEQ ID NO: 30 | Amino acids 4-232 of SEQ ID NO: 43 |
| Amino acids 27-158 of SEQ ID NO: 30 | Amino acids 4-231 of SEQ ID NO: 43 |
| Amino acids 27-158 of SEQ ID NO: 30 | Amino acids 5-232 of SEQ ID NO: 43 |
| Amino acids 27-158 of SEQ ID NO: 30 | Amino acids 5-231 of SEQ ID NO: 43 |
| Amino acids 27-158 of SEQ ID NO: 30 | Amino acids 6-232 of SEQ ID NO: 43 |
| Amino acids 27-158 of SEQ ID NO: 30 | Amino acids 6-231 of SEQ ID NO: 43 |
| Amino acids 28-158 of SEQ ID NO: 30 | Amino acids 1-232 of SEQ ID NO: 43 |
| Amino acids 28-158 of SEQ ID NO: 30 | Amino acids 1-231 of SEQ ID NO: 43 |
| Amino acids 28-158 of SEQ ID NO: 30 | Amino acids 2-232 of SEQ ID NO: 43 |
| Amino acids 28-158 of SEQ ID NO: 30 | Amino acids 2-231 of SEQ ID NO: 43 |
| Amino acids 28-158 of SEQ ID NO: 30 | Amino acids 3-232 of SEQ ID NO: 43 |
| Amino acids 28-158 of SEQ ID NO: 30 | Amino acids 3-231 of SEQ ID NO: 43 |
| Amino acids 28-158 of SEQ ID NO: 30 | Amino acids 4-232 of SEQ ID NO: 43 |
| Amino acids 28-158 of SEQ ID NO: 30 | Amino acids 4-231 of SEQ ID NO: 43 |
| Amino acids 28-158 of SEQ ID NO: 30 | Amino acids 5-232 of SEQ ID NO: 43 |
| Amino acids 28-158 of SEQ ID NO: 30 | Amino acids 5-231 of SEQ ID NO: 43 |
| Amino acids 28-158 of SEQ ID NO: 30 | Amino acids 6-232 of SEQ ID NO: 43 |
| Amino acids 28-158 of SEQ ID NO: 30 | Amino acids 6-231 of SEQ ID NO: 43 |
| Amino acids 25-161 of SEQ ID NO: 30 | Amino acids 1-232 of SEQ ID NO: 43 |
| Amino acids 25-161 of SEQ ID NO: 30 | Amino acids 1-231 of SEQ ID NO: 43 |
| Amino acids 25-161 of SEQ ID NO: 30 | Amino acids 2-232 of SEQ ID NO: 43 |
| Amino acids 25-161 of SEQ ID NO: 30 | Amino acids 2-231 of SEQ ID NO: 43 |

TABLE 2-continued

| First Polypeptide | Second Polypeptide |
|---|---|
| Amino acids 25-161 of SEQ ID NO: 30 | Amino acids 3-232 of SEQ ID NO: 43 |
| Amino acids 25-161 of SEQ ID NO: 30 | Amino acids 3-231 of SEQ ID NO: 43 |
| Amino acids 25-161 of SEQ ID NO: 30 | Amino acids 4-232 of SEQ ID NO: 43 |
| Amino acids 25-161 of SEQ ID NO: 30 | Amino acids 4-231 of SEQ ID NO: 43 |
| Amino acids 25-161 of SEQ ID NO: 30 | Amino acids 5-232 of SEQ ID NO: 43 |
| Amino acids 25-161 of SEQ ID NO: 30 | Amino acids 5-231 of SEQ ID NO: 43 |
| Amino acids 25-161 of SEQ ID NO: 30 | Amino acids 6-232 of SEQ ID NO: 43 |
| Amino acids 25-161 of SEQ ID NO: 30 | Amino acids 6-231 of SEQ ID NO: 43 |
| Amino acids 26-161 of SEQ ID NO: 30 | Amino acids 1-232 of SEQ ID NO: 43 |
| Amino acids 26-161 of SEQ ID NO: 30 | Amino acids 1-231 of SEQ ID NO: 43 |
| Amino acids 26-161 of SEQ ID NO: 30 | Amino acids 2-232 of SEQ ID NO: 43 |
| Amino acids 26-161 of SEQ ID NO: 30 | Amino acids 2-231 of SEQ ID NO: 43 |
| Amino acids 26-161 of SEQ ID NO: 30 | Amino acids 3-232 of SEQ ID NO: 43 |
| Amino acids 26-161 of SEQ ID NO: 30 | Amino acids 3-231 of SEQ ID NO: 43 |
| Amino acids 26-161 of SEQ ID NO: 30 | Amino acids 4-232 of SEQ ID NO: 43 |
| Amino acids 26-161 of SEQ ID NO: 30 | Amino acids 4-231 of SEQ ID NO: 43 |
| Amino acids 26-161 of SEQ ID NO: 30 | Amino acids 5-232 of SEQ ID NO: 43 |
| Amino acids 26-161 of SEQ ID NO: 30 | Amino acids 5-231 of SEQ ID NO: 43 |
| Amino acids 26-161 of SEQ ID NO: 30 | Amino acids 6-232 of SEQ ID NO: 43 |
| Amino acids 26-161 of SEQ ID NO: 30 | Amino acids 6-231 of SEQ ID NO: 43 |
| Amino acids 27-161 of SEQ ID NO: 30 | Amino acids 1-232 of SEQ ID NO: 43 |
| Amino acids 27-161 of SEQ ID NO: 30 | Amino acids 1-231 of SEQ ID NO: 43 |
| Amino acids 27-161 of SEQ ID NO: 30 | Amino acids 2-232 of SEQ ID NO: 43 |
| Amino acids 27-161 of SEQ ID NO: 30 | Amino acids 2-231 of SEQ ID NO: 43 |
| Amino acids 27-161 of SEQ ID NO: 30 | Amino acids 3-232 of SEQ ID NO: 43 |
| Amino acids 27-161 of SEQ ID NO: 30 | Amino acids 3-231 of SEQ ID NO: 43 |
| Amino acids 27-161 of SEQ ID NO: 30 | Amino acids 4-232 of SEQ ID NO: 43 |
| Amino acids 27-161 of SEQ ID NO: 30 | Amino acids 4-231 of SEQ ID NO: 43 |
| Amino acids 27-161 of SEQ ID NO: 30 | Amino acids 5-232 of SEQ ID NO: 43 |
| Amino acids 27-161 of SEQ ID NO: 30 | Amino acids 5-231 of SEQ ID NO: 43 |
| Amino acids 27-161 of SEQ ID NO: 30 | Amino acids 6-232 of SEQ ID NO: 43 |
| Amino acids 27-161 of SEQ ID NO: 30 | Amino acids 6-231 of SEQ ID NO: 43 |
| Amino acids 28-161 of SEQ ID NO: 30 | Amino acids 1-232 of SEQ ID NO: 43 |
| Amino acids 28-161 of SEQ ID NO: 30 | Amino acids 1-231 of SEQ ID NO: 43 |
| Amino acids 28-161 of SEQ ID NO: 30 | Amino acids 2-232 of SEQ ID NO: 43 |
| Amino acids 28-161 of SEQ ID NO: 30 | Amino acids 2-231 of SEQ ID NO: 43 |
| Amino acids 28-161 of SEQ ID NO: 30 | Amino acids 3-232 of SEQ ID NO: 43 |
| Amino acids 28-161 of SEQ ID NO: 30 | Amino acids 3-231 of SEQ ID NO: 43 |
| Amino acids 28-161 of SEQ ID NO: 30 | Amino acids 4-232 of SEQ ID NO: 43 |
| Amino acids 28-161 of SEQ ID NO: 30 | Amino acids 4-231 of SEQ ID NO: 43 |
| Amino acids 28-161 of SEQ ID NO: 30 | Amino acids 5-232 of SEQ ID NO: 43 |
| Amino acids 28-161 of SEQ ID NO: 30 | Amino acids 5-231 of SEQ ID NO: 43 |
| Amino acids 28-161 of SEQ ID NO: 30 | Amino acids 6-232 of SEQ ID NO: 43 |
| Amino acids 28-161 of SEQ ID NO: 30 | Amino acids 6-231 of SEQ ID NO: 43 |
| Amino acids 25-164 of SEQ ID NO: 30 | Amino acids 1-232 of SEQ ID NO: 43 |
| Amino acids 25-164 of SEQ ID NO: 30 | Amino acids 1-231 of SEQ ID NO: 43 |
| Amino acids 25-164 of SEQ ID NO: 30 | Amino acids 2-232 of SEQ ID NO: 43 |
| Amino acids 25-164 of SEQ ID NO: 30 | Amino acids 2-231 of SEQ ID NO: 43 |
| Amino acids 25-164 of SEQ ID NO: 30 | Amino acids 3-232 of SEQ ID NO: 43 |
| Amino acids 25-164 of SEQ ID NO: 30 | Amino acids 3-231 of SEQ ID NO: 43 |
| Amino acids 25-164 of SEQ ID NO: 30 | Amino acids 4-232 of SEQ ID NO: 43 |
| Amino acids 25-164 of SEQ ID NO: 30 | Amino acids 4-231 of SEQ ID NO: 43 |
| Amino acids 25-164 of SEQ ID NO: 30 | Amino acids 5-232 of SEQ ID NO: 43 |
| Amino acids 25-164 of SEQ ID NO: 30 | Amino acids 5-231 of SEQ ID NO: 43 |
| Amino acids 25-164 of SEQ ID NO: 30 | Amino acids 6-232 of SEQ ID NO: 43 |
| Amino acids 25-164 of SEQ ID NO: 30 | Amino acids 6-231 of SEQ ID NO: 43 |
| Amino acids 26-164 of SEQ ID NO: 30 | Amino acids 1-232 of SEQ ID NO: 43 |
| Amino acids 26-164 of SEQ ID NO: 30 | Amino acids 1-231 of SEQ ID NO: 43 |
| Amino acids 26-164 of SEQ ID NO: 30 | Amino acids 2-232 of SEQ ID NO: 43 |
| Amino acids 26-164 of SEQ ID NO: 30 | Amino acids 2-231 of SEQ ID NO: 43 |
| Amino acids 26-164 of SEQ ID NO: 30 | Amino acids 3-232 of SEQ ID NO: 43 |
| Amino acids 26-164 of SEQ ID NO: 30 | Amino acids 3-231 of SEQ ID NO: 43 |
| Amino acids 26-164 of SEQ ID NO: 30 | Amino acids 4-232 of SEQ ID NO: 43 |
| Amino acids 26-164 of SEQ ID NO: 30 | Amino acids 4-231 of SEQ ID NO: 43 |
| Amino acids 26-164 of SEQ ID NO: 30 | Amino acids 5-232 of SEQ ID NO: 43 |
| Amino acids 26-164 of SEQ ID NO: 30 | Amino acids 5-231 of SEQ ID NO: 43 |
| Amino acids 26-164 of SEQ ID NO: 30 | Amino acids 6-232 of SEQ ID NO: 43 |
| Amino acids 26-164 of SEQ ID NO: 30 | Amino acids 6-231 of SEQ ID NO: 43 |
| Amino acids 27-164 of SEQ ID NO: 30 | Amino acids 1-232 of SEQ ID NO: 43 |
| Amino acids 27-164 of SEQ ID NO: 30 | Amino acids 1-231 of SEQ ID NO: 43 |
| Amino acids 27-164 of SEQ ID NO: 30 | Amino acids 2-232 of SEQ ID NO: 43 |
| Amino acids 27-164 of SEQ ID NO: 30 | Amino acids 2-231 of SEQ ID NO: 43 |
| Amino acids 27-164 of SEQ ID NO: 30 | Amino acids 3-232 of SEQ ID NO: 43 |
| Amino acids 27-164 of SEQ ID NO: 30 | Amino acids 3-231 of SEQ ID NO: 43 |
| Amino acids 27-164 of SEQ ID NO: 30 | Amino acids 4-232 of SEQ ID NO: 43 |
| Amino acids 27-164 of SEQ ID NO: 30 | Amino acids 4-231 of SEQ ID NO: 43 |
| Amino acids 27-164 of SEQ ID NO: 30 | Amino acids 5-232 of SEQ ID NO: 43 |
| Amino acids 27-164 of SEQ ID NO: 30 | Amino acids 5-231 of SEQ ID NO: 43 |

TABLE 2-continued

| First Polypeptide | Second Polypeptide |
|---|---|
| Amino acids 27-164 of SEQ ID NO: 30 | Amino acids 6-232 of SEQ ID NO: 43 |
| Amino acids 27-164 of SEQ ID NO: 30 | Amino acids 6-231 of SEQ ID NO: 43 |
| Amino acids 28-164 of SEQ ID NO: 30 | Amino acids 1-232 of SEQ ID NO: 43 |
| Amino acids 28-164 of SEQ ID NO: 30 | Amino acids 1-231 of SEQ ID NO: 43 |
| Amino acids 28-164 of SEQ ID NO: 30 | Amino acids 2-232 of SEQ ID NO: 43 |
| Amino acids 28-164 of SEQ ID NO: 30 | Amino acids 2-231 of SEQ ID NO: 43 |
| Amino acids 28-164 of SEQ ID NO: 30 | Amino acids 3-232 of SEQ ID NO: 43 |
| Amino acids 28-164 of SEQ ID NO: 30 | Amino acids 3-231 of SEQ ID NO: 43 |
| Amino acids 28-164 of SEQ ID NO: 30 | Amino acids 4-232 of SEQ ID NO: 43 |
| Amino acids 28-164 of SEQ ID NO: 30 | Amino acids 4-231 of SEQ ID NO: 43 |
| Amino acids 28-164 of SEQ ID NO: 30 | Amino acids 5-232 of SEQ ID NO: 43 |
| Amino acids 28-164 of SEQ ID NO: 30 | Amino acids 5-231 of SEQ ID NO: 43 |
| Amino acids 28-164 of SEQ ID NO: 30 | Amino acids 6-232 of SEQ ID NO: 43 |
| Amino acids 28-164 of SEQ ID NO: 30 | Amino acids 6-231 of SEQ ID NO: 43 |

In some embodiments, the Wnt-binding agent comprises an amino acid sequence selected from the group consisting of: SEQ ID NO:1, SEQ ID NO:45, SEQ ID NO:46, SEQ ID NO:47, SEQ ID NO:48, SEQ ID NO:49, SEQ ID NO:50, SEQ ID NO:51, SEQ ID NO:53, SEQ ID NO:54, SEQ ID NO:55, SEQ ID NO:65, and SEQ ID NO:66.

In certain embodiments, the Wnt-binding agent comprises the sequence of SEQ ID NO:1. In certain alternative embodiments, the agent comprises the sequence of SEQ ID NO:1, comprising one or more (e.g., one, two, three, four, five, six, seven, eight, nine, ten, etc.) conservative substitutions. In certain embodiments, the agent comprises a sequence having at least about 90%, about 95%, or about 98% sequence identity with SEQ ID NO:1. In certain embodiments, the variants of SEQ ID NO:1 maintain the ability to bind one or more human Wnts.

In certain embodiments, the Wnt-binding agent comprises the sequence of SEQ ID NO:46. In some embodiments, the Wnt-binding agent is SEQ ID NO:46. In certain alternative embodiments, the agent comprises the sequence of SEQ ID NO:46, comprising one or more (e.g., one, two, three, four, five, six, seven, eight, nine, ten, etc.) conservative substitutions. In certain embodiments, the agent comprises a sequence having at least about 90%, about 95%, or about 98% sequence identity with SEQ ID NO:46. In certain embodiments, the variants of SEQ ID NO:46 maintain the ability to bind one or more human Wnts.

In certain embodiments, the Wnt-binding agent comprises the sequence of SEQ ID NO:48. In some embodiments, the Wnt-binding agent is SEQ ID NO:48. In certain alternative embodiments, the agent comprises the sequence of SEQ ID NO:48, comprising one or more (e.g., one, two, three, four, five, six, seven, eight, nine, ten, etc.) conservative substitutions. In certain embodiments, the agent comprises a sequence having at least about 90%, about 95%, or about 98% sequence identity with SEQ ID NO:48. In certain embodiments, the variants of SEQ ID NO:48 maintain the ability to bind one or more human Wnts.

In certain embodiments, the Wnt-binding agent comprises the sequence of SEQ ID NO:50. In some embodiments, the Wnt-binding agent is SEQ ID NO:50. In certain alternative embodiments, the agent comprises the sequence of SEQ ID NO:50, comprising one or more (e.g., one, two, three, four, five, six, seven, eight, nine, ten, etc.) conservative substitutions. In certain embodiments, the agent comprises a sequence having at least about 90%, about 95%, or about 98% sequence identity with SEQ ID NO:50. In certain embodiments, the variants of SEQ ID NO:50 maintain the ability to bind one or more human Wnts.

In certain embodiments, the Wnt-binding agent comprises the sequence of SEQ ID NO:53. In some embodiments, the Wnt-binding agent is SEQ ID NO:53. In certain alternative embodiments, the agent comprises the sequence of SEQ ID NO:53, comprising one or more (e.g., one, two, three, four, five, six, seven, eight, nine, ten, etc.) conservative substitutions. In certain embodiments, the agent comprises a sequence having at least about 90%, about 95%, or about 98% sequence identity with SEQ ID NO:53. In certain embodiments, the variants of SEQ ID NO:53 maintain the ability to bind one or more human Wnts.

In some embodiments, the Wnt-binding agents as described herein inhibit the growth of a tumor or tumor cells. In some embodiments, the Wnt-binding agents induce cells in a tumor to differentiate. In some embodiments, the Wnt-binding agents induce the expression of differentiation markers on a tumor or tumor cell. In certain embodiments, the Wnt-binding agents reduce the frequency of cancer stem cells in a tumor. In some embodiments, a Wnt-binding agent comprising SEQ ID NO:46 inhibits tumor growth to a greater extent than a Wnt-binding agent comprising SEQ ID NO:1. In some embodiments, a Wnt-binding agent comprising SEQ ID NO:48 inhibits tumor growth to a greater extent than a Wnt-binding agent comprising SEQ ID NO:1. In some embodiments, a Wnt-binding agent comprising SEQ ID NO:50 inhibits tumor growth to a greater extent than a Wnt-binding agent comprising SEQ ID NO:1. In some embodiments, a Wnt-binding agent comprising SEQ ID NO:53 inhibits tumor growth to a greater extent than a Wnt-binding agent comprising SEQ ID NO:1. In some embodiments, a Wnt-binding agent as described herein inhibits tumor growth to a greater extent than a Wnt-binding agent comprising a FZD domain component, a Fc domain and a linker component connecting the FZD domain component and the Fc domain. In some embodiments, the linker component is an intervening peptide linker.

In certain embodiments, the Wnt-binding agents as described herein inhibit the growth of a Wnt-dependent tumor. In some embodiments, the tumor is a tumor selected from selected from the group consisting of colorectal tumor, colon tumor, pancreatic tumor, lung tumor, ovarian tumor, liver tumor, breast tumor, kidney tumor, prostate tumor, gastrointestinal tumor, melanoma, cervical tumor, bladder tumor, glioblastoma, and head and neck tumor. In certain embodiments, the tumor is a colorectal tumor. In certain embodiments, the tumor is a pancreatic tumor. In certain embodiments, the tumor is a breast tumor.

In certain embodiments, a polypeptide comprising an amino acid sequence selected from the group consisting of SEQ ID NO:1, SEQ ID NO:45, SEQ ID NO:46, SEQ ID NO:47, SEQ ID NO:48, SEQ ID NO:49, SEQ ID NO:50, SEQ ID NO:51, SEQ ID NO:53, SEQ ID NO:54, SEQ ID NO:55, SEQ ID NO:65 and SEQ ID NO:66 is provided. In certain embodiments, the polypeptide comprises an amino acid sequence selected from the group consisting of SEQ ID NO:1, SEQ ID NO:46, SEQ ID NO:48, SEQ ID NO:50, and SEQ ID NO:53. In some embodiments, a polypeptide consists of an amino acid sequence selected from the group consisting of SEQ ID NO:1, SEQ ID NO:46, SEQ ID NO:48, SEQ ID NO:50, and SEQ ID NO:53. In certain embodiments, the polypeptide comprises the amino acid sequence of SEQ ID NO:50. In some embodiments, the polypeptide is SEQ ID NO:50. In certain embodiments, the polypeptide comprises the amino acid sequence of SEQ ID NO:53. In some embodiments, the polypeptide is SEQ ID NO:53.

In certain embodiments, the polypeptide (before signal sequence cleavage) comprises SEQ ID NO:50 and a signal sequence selected from the group consisting of SEQ ID NO:67, SEQ ID NO:68, SEQ ID NO:69, SEQ ID NO:70, SEQ ID NO:71, SEQ ID NO:72, SEQ ID NO:73, and SEQ ID NO:74. In certain embodiments, the polypeptide (before signal sequence cleavage) comprises SEQ ID NO:50 and a signal sequence selected from the group consisting of SEQ ID NO:70, SEQ ID NO:71, SEQ ID NO:72, SEQ ID NO:73, and SEQ ID NO:74. In some embodiments, the polypeptide (before signal sequence cleavage) comprises SEQ ID NO:53 and a signal sequence selected from the group consisting of SEQ ID NO:67, SEQ ID NO:68, SEQ ID NO:69, SEQ ID NO:70, SEQ ID NO:71, SEQ ID NO:72, SEQ ID NO:73, and SEQ ID NO:74. In some embodiments, the polypeptide (before signal sequence cleavage) comprises SEQ ID NO:53 and a signal sequence selected from the group consisting of SEQ ID NO:70, SEQ ID NO:71, SEQ ID NO:72, SEQ ID NO:73, and SEQ ID NO:74. In some embodiments, the polypeptide comprises SEQ ID NO:71 and SEQ ID NO:50. In some embodiments, the polypeptide comprises SEQ ID NO:71 and SEQ ID NO:53. In some embodiments, the polypeptide comprises SEQ ID NO:75. In some embodiments, the polypeptide consists essentially of SEQ ID NO:75.

In some embodiments, the polypeptide is a substantially purified polypeptide comprising an amino acid sequence selected from the group consisting of SEQ ID NO:1, SEQ ID NO:46, SEQ ID NO:48, SEQ ID NO:50, and SEQ ID NO:53. In certain embodiments, the substantially purified polypeptide consists of at least 90% of a polypeptide that has an N-terminal sequence of ASA. In some embodiments, the nascent polypeptide comprises a signal sequence selected from the group consisting of SEQ ID NOs:67-74. In some embodiments, the nascent polypeptide comprises a signal sequence of SEQ ID NOs:71. In some embodiments, the nascent polypeptide comprises a signal sequence that results in a substantially homogeneous polypeptide product with one N-terminal sequence.

In certain alternative embodiments, the agent does not comprise a Fri domain of a FZD receptor.

In certain embodiments, the Wnt-binding agent is an antibody (e.g., an antibody that specifically binds to one or more Wnt proteins).

In certain embodiments, the Wnt-binding agent comprises a Fc region of an immunoglobulin. Those skilled in the art will appreciate that the binding agents of this invention will comprise fusion proteins in which at least a portion of the Fc region has been deleted or otherwise altered so as to provide desired biochemical characteristics, such as increased cancer cell localization, increased tumor penetration, reduced serum half-life, or increased serum half-life, when compared with a fusion protein of approximately the same immunogenicity comprising a native or unaltered constant region. Modifications to the Fc region may include additions, deletions, or substitutions of one or more amino acids in one or more domains. The modified fusion proteins disclosed herein may comprise alterations or modifications to one or more of the two heavy chain constant domains (CH2 or CH3) or to the hinge region. In other embodiments, the entire CH2 domain is removed (ΔCH2 constructs). In some embodiments, the omitted constant region domain is replaced by a short amino acid spacer (e.g., 10 aa residues) that provides some of the molecular flexibility typically imparted by the absent constant region domain.

In some embodiments, the modified fusion proteins are engineered to link the CH3 domain directly to the hinge region of the antibody. In other embodiments, a peptide spacer is inserted between the hinge region and the modified CH2 and/or CH3 domains. For example, constructs may be expressed wherein the CH2 domain has been deleted and the remaining CH3 domain (modified or unmodified) is joined to the hinge region with a 5-20 amino acid spacer. Such a spacer may be added to ensure that the regulatory elements of the constant domain remain free and accessible or that the hinge region remains flexible. However, it should be noted that amino acid spacers may, in some cases, prove to be immunogenic and elicit an unwanted immune response against the construct. Accordingly, in certain embodiments, any spacer added to the construct will be relatively non-immunogenic so as to maintain the desired biological qualities of the modified antibodies.

In some embodiments, the modified fusion proteins may have only a partial deletion of a constant domain or substitution of a few or even a single amino acid. For example, the mutation of a single amino acid in selected areas of the CH2 domain may be enough to substantially reduce Fc binding and thereby increase cancer cell localization and/or tumor penetration. Similarly, it may be desirable to simply delete that part of one or more constant region domains that control a specific effector function (e.g., complement C1q binding) to be modulated. Such partial deletions of the constant regions may improve selected characteristics of the antibody (e.g., serum half-life) while leaving other desirable functions associated with the subject constant region domain intact. Moreover, as alluded to above, the constant regions of the disclosed fusion proteins may be modified through the mutation or substitution of one or more amino acids that enhances the profile of the resulting construct. In this respect it may be possible to disrupt the activity provided by a conserved binding site (e.g., Fc binding) while substantially maintaining the configuration and immunogenic profile of the modified antibody. In certain embodiments, the modified fusion proteins comprise the addition of one or more amino acids to the constant region to enhance desirable characteristics such as decreasing or increasing effector function, or provide for more cytotoxin or carbohydrate attachment.

It is known in the art that the constant region mediates several effector functions. For example, binding of the C1 component of complement to the Fc region of IgG or IgM antibodies (bound to antigen) activates the complement system. Activation of complement is important in the opsonization and lysis of cell pathogens. The activation of complement also stimulates the inflammatory response and can also be involved in autoimmune hypersensitivity. In addition, the Fc region of an antibody can bind to a cell expressing a Fc receptor (FcR). There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (antibody-dependent cell-mediated cytotoxicity or ADCC), release of inflammatory mediators, placental transfer, and control of immunoglobulin production.

In some embodiments, the Wnt-binding agents provide for altered effector functions that, in turn, affect the biological profile of the administered agent. For example, in some embodiments, the deletion or inactivation (through point mutations or other means) of a constant region domain may reduce Fc receptor binding of the circulating modified agent (e.g., Wnt-binding agent) thereby increasing cancer cell localization and/or tumor penetration. In other embodiments, the constant region modifications increase or reduce the serum half-life of the agent. In some embodiments, the constant region is modified to eliminate disulfide linkages or oligosaccharide moieties.

In certain embodiments, a Wnt-binding agent does not have one or more effector functions normally associated with an Fc region. In some embodiments, the agent has no ADCC activity, and/or no complement-dependent cytotoxicity (CDC) activity. In certain embodiments, the agent does not bind to the Fc receptor and/or complement factors. In certain embodiments, the agent has no effector function.

In some embodiments, the Wnt-binding agents described herein are modified to reduce immunogenicity. In general, immune responses against completely normal human proteins are rare when these proteins are used as therapeutics. However, although many fusion proteins comprise polypeptides sequences that are the same as the sequences found in nature, several therapeutic fusion proteins have been shown to be immunogenic in mammals. In some studies, a fusion protein comprising a linker has been found to be more immunogenic than a fusion protein that does not contain a linker. Accordingly, in some embodiments, the polypeptides of the invention are analyzed by computation methods to predict immunogenicity. In some embodiments, the polypeptides are analyzed for the presence of T-cell and/or B-cell epitopes. If any T-cell or B-cell epitopes are identified and/or predicted, modifications to these regions (e.g., amino acid substitutions) may be made to disrupt or destroy the epitopes. Various algorithms and software that can be used to predict T-cell and/or B-cell epitopes are known in the art. For example, the software programs SYFPEITHI, HLA Bind, PEPVAC, RANKPEP, DiscoTope, ElliPro and Antibody Epitope Prediction are all publicly available.

In some embodiments, a cell producing any of the Wnt-binding agents or polypeptides described herein is provided. In some embodiments, a composition comprising any of the Wnt-binding agents or polypeptides described herein is provided. In some embodiments, the composition comprises a polypeptide wherein at least 80%, 90%, 95%, 97%, 98%, or 99% of the polypeptide has an N-terminal sequence of ASA. In some embodiments, the composition comprises a polypeptide wherein 100% of the polypeptide has an N-terminal sequence of ASA. In some embodiments, the composition comprises a polypeptide wherein at least 80% of the polypeptide has an N-terminal sequence of ASA. In some embodiments, the composition comprises a polypeptide wherein at least 90% of the polypeptide has an N-terminal sequence of ASA. In some embodiments, the composition comprises a polypeptide wherein at least 95% of the polypeptide has an N-terminal sequence of ASA.

The polypeptides of the present invention can be recombinant polypeptides, natural polypeptides, or synthetic polypeptides. It will be recognized in the art that some amino acid sequences of the invention can be varied without significant effect on the structure or function of the protein. If such differences in sequence are contemplated, it should be remembered that there will be critical areas on the protein which determine activity. Thus, the invention further includes variations of the polypeptides which show substantial activity or which include regions of FZD proteins, SFRP proteins or Ror proteins such as the protein portions discussed herein. Such mutants include deletions, insertions, inversions, repeats, and type substitutions. As indicated below, guidance concerning which amino acid changes are likely to be phenotypically silent can be found in Bowie, et al., 1990, Science, 247:1306-10.

Of course, the number of amino acid substitutions a skilled artisan would make depends on many factors, including those described above. In certain embodiments, the number of substitutions for any given soluble receptor polypeptide will not be more than 50, 40, 30, 25, 20, 15, 10, 5 or 3.

Fragments or portions of the polypeptides of the present invention can be employed for producing the corresponding full-length polypeptide by peptide synthesis; therefore, the fragments can be employed as intermediates for producing the full-length polypeptides. These fragments or portion of the polypeptides can also be referred to as "protein fragments" or "polypeptide fragments".

A protein fragment of this invention is a portion, or all, of a protein which is capable of binding to one or more human Wnt proteins (e.g., a human FZD receptor, a human SFRP or a Ror protein). In some embodiments, the fragment has a high affinity for one or more human Wnt proteins. Some fragments of fusion proteins described herein are protein fragments comprising at least part of the extracellular portion of a FZD receptor, a SFRP or the extracellular portion of a Ror protein which contains a binding domain linked to at least part of a constant region of an immunoglobulin (e g, a Fc region). The binding affinity of the protein fragment can be in the range of about $10^{-11}$ to $10^{-12}$ M, although the affinity can vary considerably with fragments of different sizes, ranging from $10^{-7}$ to $10^{-13}$ M. In some embodiments, the fragment is about 100 to about 200 amino acids in length and comprises a binding domain linked to at least part of a constant region of an immunoglobulin.

The Wnt-binding agents of the present invention can be assayed for specific binding by any method known in the art. The immunoassays which can be used include, but are not limited to, competitive and non-competitive assay systems using techniques such as BIAcore analysis, FACS analysis, immunofluorescence, immunocytochemistry, Western blots, radioimmunoassays, ELISA, "sandwich" immunoassays, immunoprecipitation assays, precipitation reactions, gel diffusion precipitin reactions, immunodiffusion assays, agglutination assays, complement-fixation assays, immunoradiometric assays, fluorescent immunoassays, and protein A immunoassays. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety).

For example, the specific binding of a polypeptide to a human Wnt may be determined using ELISA. An ELISA assay comprises preparing antigen, coating wells of a 96 well microtiter plate with antigen, adding the polypeptide (e.g., a Wnt-binding agent) conjugated to a detectable compound such as an enzymatic substrate (e.g. horseradish peroxidase or alkaline phosphatase) to the well, incubating for a period of time and detecting the presence of the agent. In some embodiments, the polypeptide (e.g., Wnt-binding agent) is not conjugated to a detectable compound, but instead a second conjugated antibody that recognizes the polypeptide is added to the well. In some embodiments, instead of coating the well with the antigen, the polypeptide (e.g., Wnt-binding agent) can be coated to the well and a second antibody conjugated to a detectable compound can be added following the addition of the antigen to the coated well. One of skill in the art would be knowledgeable as to the parameters that can be modified to increase the signal detected as well as other variations of ELISAs known in the art (see e.g. Ausubel et al, eds, 1994, Current Protocols in Molecular Biology, Vol. 1, John Wiley & Sons, Inc., New York at 11.2.1).

The binding affinity of an agent to a Wnt and the off-rate of a binding agent-antigen interaction can be determined by competitive binding assays. One example of a competitive binding assay is a radioimmunoassay comprising the incubation of labeled antigen (e.g., $^{3}$H or $^{125}$I), or fragment or variant thereof, with the binding agent of interest in the presence of increasing amounts of unlabeled antigen followed by the detection of the antibody bound to the labeled antigen. The affinity of the binding agent against a Wnt and the binding off-rates can be determined from the data by Scatchard plot analysis. In some embodiments, BIAcore kinetic analysis is used to determine the binding on and off rates of agents that bind one or more human Wnts. BIAcore kinetic analysis comprises analyzing the binding and dissociation of antibodies from chips with immobilized Wnt antigens on their surface.

In certain embodiments, the Wnt-binding agent binds to at least one Wnt with a dissociation constant ($K_D$) of about 1 µM or less, about 100 nM or less, about 40 nM or less, about 20 nM or less, or about 10 nM or less.

In certain embodiments, the Wnt-binding agent (e.g., a FZD8-Fc) is an antagonist of at least one Wnt (i.e., 1, 2, 3, 4, 5, 6, 7, 8, 9, or 10 Wnts) bound by the agent. In certain embodiments, the agent inhibits at least about 10%, at least about 20%, at least about 30%, at least about 50%, at least about 75%, at least about 90%, or about 100% of one or more activity of the bound human Wnt(s).

In vivo and in vitro assays for determining whether a Wnt-binding agent (or candidate Wnt-binding agent) inhibits Wnt signaling are known in the art. For example, cell-based, luciferase reporter assays utilizing a TCF/Luc reporter vector containing multiple copies of the TCF-binding domain upstream of a firefly luciferase reporter gene may be used to measure canonical Wnt signaling levels in vitro (Gazit et al., 1999, *Oncogene* 18; 5959-66). The level of Wnt signaling in the presence of one or more Wnts (e.g., Wnt(s) expressed by transfected cells or provided by Wnt-conditioned media) with the Wnt-binding agent present is compared to the level of signaling without the Wnt-binding agent present. In addition to the TCF/Luc reporter assay, the effect of a Wnt-binding agent (or candidate agent) on canonical Wnt signaling may be measured in vitro or in vivo by measuring the effect of the agent on the level of expression of β-catenin regulated genes, such as c-myc (He et al., *Science,* 281:1509-12 (1998)), cyclin D1 (Tetsu et al., *Nature,* 398:422-6 (1999)) and/or fibronectin (Gradl et al. *Mol. Cell Biol.,* 19:5576-87 (1999)). In certain embodiments, the effect of an agent on Wnt signaling may also be assessed by measuring the effect of the agent on the phosphorylation state of Dishevelled-1, Dishevelled-2, Dishevelled-3, LRP5, LRP6, and/or β-catenin.

The polypeptides described herein can be produced by any suitable method known in the art. Such methods range from direct protein synthesis methods to constructing DNA sequences that encode polypeptide sequences and expressing those sequences in a suitable host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g., Zoeller et al., 1984, *PNAS,* 81:5662-66 and U.S. Pat. No. 4,588,585. In some embodiments, a DNA sequence is constructed using recombinant technology by isolating more than one DNA sequence encoding two polypeptides of interest and ligating these DNA sequences together to generate a fusion protein. In some embodiments, the fusion of the two polypeptides adds additional amino acids to the junction between the two polypeptides (i.e., the ligation site for the DNA sequences). These additional amino acids are considered a linker. In some embodiments, a peptide linker is inserted between the two polypeptides of the fusion protein.

In some embodiments, a DNA sequence that encodes a polypeptide of interest may be constructed by chemical synthesis using an oligonucleotide synthesizer. Such oligonucleotides can be designed based on the amino acid sequence of the desired polypeptide. In some embodiments, the oligonucleotides are designed to select codons that are favored in the host cell in which the recombinant polypeptide of interest will be produced. Standard methods can be applied to synthesize a polynucleotide sequence that encodes a polypeptide of interest. For example, a complete amino acid sequence can be used to construct a back-translated gene. Further, a DNA oligomer containing a nucleotide sequence coding for the particular polypeptide can be synthesized. For example, several small oligonucleotides coding for portions of the desired polypeptide can be synthesized and then ligated. The individual oligonucleotides typically contain 5' or 3' overhangs for complementary assembly. In some embodiments, a nucleotide sequence coding for the desired fusion protein is synthesized so that the two polypeptides are directly linked without an intervening peptide linker.

Once assembled (by synthesis, site-directed mutagenesis, recombinant technology, or another method), the polynucleotide sequences encoding a particular polypeptide of interest can be inserted into an expression vector and operatively linked to an expression control sequence appropriate for expression of the polypeptide in a desired host. Proper assembly can be confirmed by nucleotide sequencing, restriction mapping, and/or expression of a biologically active polypeptide in a suitable host. As is well-known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA that encode Wnt-binding agents and polypeptides described herein. For example, recombinant expression vectors can be replicable DNA constructs which have synthetic or cDNA-derived DNA fragments encoding a fusion protein comprising a FZD Fri domain and a Fc region, operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters and/or enhancers, (2) a structural or coding sequence which is transcribed into mRNA and translated into protein, and (3) appropriate transcription and translation initiation and termination sequences. Regulatory elements can include an operator sequence to control transcription. The ability to replicate in a host, usually conferred by an origin of replication, and a selection gene to facilitate recognition of transformants can additionally be incorporated. DNA regions are "operatively linked" when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Generally, operatively linked means contiguous and, in the case of secretory leaders, means contiguous and in reading frame. In some embodiments, structural elements intended for use in yeast expression systems can include a leader sequence enabling extracellular secretion of translated protein by a host cell. In some embodiments, where recombinant protein is expressed without a leader or transport sequence, it can include an N-terminal methionine residue. This residue can optionally be subsequently cleaved from the expressed recombinant protein to provide a final product.

The choice of an expression control sequence and expression vector depends upon the choice of host. A wide variety of expression host/vector combinations can be employed. Useful expression vectors for eukaryotic hosts include, for example, vectors comprising expression control sequences from SV40, bovine papilloma virus, adenovirus and cytomegalovirus. Useful expression vectors for bacterial hosts include known bacterial plasmids, such as plasmids from *E. coli*, including pCR1, pBR322, pMB9 and their derivatives, and wider host range vectors, such as M13 and other filamentous single-stranded DNA phages.

Suitable host cells for expression of a Wnt-binding agent include prokaryotes, yeast, insect, or higher eukaryotic cells under the control of appropriate promoters. Prokaryotes include gram-negative or gram-positive organisms, for example *E. coli* or Bacilli. Higher eukaryotic cells include established cell lines of mammalian origin as described below. Cell-free translation systems can also be employed. Appropriate cloning and expression vectors for use with bacterial, fungal, yeast, and mammalian cellular hosts are described by Pouwels et al., 1985, *Cloning Vectors: A Laboratory Manual*, Elsevier, N.Y., the relevant disclosure of which is hereby incorporated by reference.

Various mammalian or insect cell culture systems are used to express recombinant polypeptides. In some embodiments, expression of recombinant proteins in mammalian cells is preferred because such proteins are generally correctly folded, appropriately modified and completely functional. Examples of suitable mammalian host cell lines include the COS-7 (monkey kidney-derived), L-929 (murine fibroblast-derived), C127 (murine mammary tumor-derived), 3T3 (murine fibroblast-derived), CHO (Chinese hamster ovary-derived), HeLa (human cervical cancer-derived) and BHK (hamster kidney fibroblast-derived) cell lines. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences. Baculovirus systems for production of heterologous proteins in insect cells are known to those of skill in the art and are reviewed by Luckow and Summers, 1988, *Bio/Technology*, 6:47.

The proteins produced by a transformed host can be purified according to any suitable method. Such standard methods include chromatography (e.g., ion exchange, affinity, and sizing column chromatography), centrifugation, differential solubility, or by any other standard technique for protein purification. Affinity tags such as hexahistidine, maltose binding domain, influenza coat sequence, and glutathione-S-transferase can be attached to the protein to allow easy purification by passage over an appropriate affinity column. Isolated proteins can also be physically characterized using such techniques as proteolysis, mass spectrometry (MS), high performance liquid chromatography (HPLC), nuclear magnetic resonance (NMR), and x-ray crystallography.

In some embodiments, supernatants from expression systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. In some embodiments, an anion exchange resin can be employed, for example, a matrix or substrate having pendant diethylaminoethyl (DEAE) groups. The matrices can be acrylamide, agarose, dextran, cellulose, or other types commonly employed in protein purification. In some embodiments, a cation exchange step can be employed. Suitable cation exchangers include various insoluble matrices comprising sulfopropyl or carboxymethyl groups. In some embodiments, a hydroxyapatite (CHT) media can be employed, including but not limited to, ceramic hydroxyapatite. In some embodiments, one or more reversed-phase HPLC steps employing hydrophobic RP-HPLC media, e.g., silica gel having pendant methyl or other aliphatic groups, can be employed to further purify a fusion protein. Some or all of the foregoing purification steps, in various combinations, can also be employed to provide a homogeneous recombinant protein.

In some embodiments, recombinant protein produced in bacterial culture can be isolated, for example, by initial extraction from cell pellets, followed by one or more concentration, salting-out, aqueous ion exchange, and/or size exclusion chromatography steps. HPLC can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Appl. Nos. 2008/0312425; 2008/0177048; and 2009/0187005.

The polypeptides described herein can be further modified to contain additional chemical moieties not normally part of the protein. Those derivatized moieties can improve the solubility, the biological half life, or absorption of the protein. The moieties can also reduce or eliminate any undesirable side effects of the proteins and the like. An overview for those moieties can be found in *Remington: The Science and Practice of Pharmacy*, 21$^{st}$ Edition, University of the Sciences, Philadelphia, 2005.

The chemical moieties most suitable for derivatization include water soluble polymers. A water soluble polymer is desirable because the protein to which it is attached does not precipitate in an aqueous environment, such as a physiological environment. In some embodiments, the polymer will be pharmaceutically acceptable for the preparation of a therapeutic product or composition. One skilled in the art will be able to select the desired polymer based on such considerations as whether the polymer/protein conjugate will be used therapeutically, and if so, the desired dosage, circulation time, resistance to proteolysis, and other considerations. The effectiveness of the derivatization can be ascertained by administering the derivative, in the desired form (i.e., by osmotic pump, or by injection or infusion, or, further formulated for oral, pulmonary or other delivery routes), and determining its effectiveness. Suitable water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), dextran, poly (n-vinyl pyrrolidone)-polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde can have advantages in manufacturing due to its stability in water.

The number of polymer molecules so attached can vary, and one skilled in the art will be able to ascertain the effect on function. One can mono-derivatize, or can provide for a di-, tri-, tetra- or some combination of derivatization, with the same or different chemical moieties (e.g., polymers, such as different weights of polyethylene glycols). The proportion of polymer molecules to protein (or peptide) molecules will vary, as will their concentrations in the reaction mixture. In general, the optimum ratio (in terms of efficiency of reaction in that there is no excess unreacted protein or polymer) will be determined by factors such as the desired degree of derivatization (e.g., mono-, di-, tri-, etc.), the molecular weight of the polymer selected, whether the polymer is branched or unbranched, and the reaction conditions.

The polyethylene glycol molecules (or other chemical moieties) should be attached to the protein with consideration of effects on functional or antigenic domains of the protein. There are a number of attachment methods available to those skilled in the art. See for example, EP 0401384, the disclosure of which is hereby incorporated by reference (coupling PEG to G-CSF), see also Malik et al., 1992, *Exp. Hematol.*, 20:1028-35 (reporting pegylation of GM-CSF using tresyl chloride). For example, polyethylene glycol can be covalently bound through amino acid residues via a reactive group, such as, a free amino or carboxyl group. Reactive groups are those to which an activated polyethylene glycol molecule can be bound. The amino acid residues having a free amino group can include lysine residues and the N-terminal amino acid residue. Those having a free carboxyl group can include aspartic acid residues, glutamic acid residues, and the C-terminal amino acid residue. Sulfhydryl groups can also be used as a reactive group for attaching the polyethylene glycol molecule(s). For therapeutic purposes, attachment at an amino group, such as attachment at the N-terminus or lysine group can be performed. Attachment at residues important for receptor binding should be avoided if receptor binding is desired.

One can specifically design an amino-terminal chemically modified protein. Using polyethylene glycol as an illustration of the present compositions, one can select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) can be by purification of the N-terminally pegylated material from a population of pegylated protein molecules. Selective N-terminal chemical modification can be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved. For example, one can selectively N-terminally pegylate the protein by performing the reaction at a pH which allows one to take advantage of the pKa differences between the epsilon amino group of the lysine residues and that of the alpha amino group of the N-terminal residue of the protein. By such selective derivatization, attachment of a water soluble polymer to a protein is controlled, e.g., the conjugation with the polymer takes place predominantly at the N-terminus of the protein and no significant modification of other reactive groups, such as the lysine side chain amino groups, occurs. Using reductive alkylation, the water soluble polymer can be of the type described above, and should have a single reactive aldehyde for coupling to the protein. Polyethylene glycol propionaldehyde, containing a single reactive aldehyde, can be used.

Pegylation can be carried out by any of the pegylation reactions known in the art. See, e.g., *Focus on Growth Factors*, 1992, 3: 4-10; EP 0154316, the disclosure of which is hereby incorporated by reference; EP 0401384; and the other publications cited herein that relate to pegylation. The pegylation can be carried out via an acylation reaction or an alkylation reaction with a reactive polyethylene glycol molecule (or an analogous reactive water soluble polymer).

Thus, it is contemplated that soluble receptor polypeptides to be used in accordance with the present invention can include pegylated soluble receptor proteins or variants, wherein the PEG group(s) is (are) attached via acyl or alkyl groups. Such products can be mono-pegylated or polypegylated. The PEG groups are generally attached to the protein at the α or ε amino groups of amino acids, but it is also contemplated that the PEG groups could be attached to any amino group attached to the protein, which is sufficiently reactive to become attached to a PEG group under suitable reaction conditions.

The polymer molecules used in both the acylation and alkylation approaches can be selected from among water soluble polymers as described above. The polymer selected should be modified to have a single reactive group, such as an active ester for acylation or an aldehyde for alkylation, so that the degree of polymerization can be controlled as provided for in the present methods. An exemplary reactive PEG aldehyde is polyethylene glycol propionaldehyde, which is water stable, or mono C1-C10 alkoxy or aryloxy derivatives thereof (see U.S. Pat. No. 5,252,714). The polymer can be branched or unbranched. For the acylation reactions, the polymer(s) selected should have a single reactive ester group. For the present reductive alkylation, the polymer(s) selected should have a single reactive aldehyde group. Generally, the water soluble polymer will not be selected from naturally occurring glycosyl residues since these are usually made more conveniently by mammalian recombinant expression systems. The polymer can be of any molecular weight, and can be branched or unbranched. One water soluble polymer for use herein is polyethylene glycol. As used herein, polyethylene glycol is meant to encompass any of the forms of PEG that have been used to derivatize other proteins, such as mono (C1-C10) alkoxy- or aryloxy-polyethylene glycol.

Other reaction parameters, such as solvent, reaction times, temperatures, etc., and means of purification of products, can be determined case by case based on the published information relating to derivatization of proteins with water soluble polymers (see the publications cited herein). In certain embodiments, the Wnt-binding agent is a polypeptide that is not derived from a human FZD or SFRP. A variety of methods for identifying and producing polypeptides that bind with high affinity to a protein target are known in the art. See, e.g., Skerra, 2007, *Curr. Opin. Biotechnol.*, 18:295-304; Hosse et al., 2006, *Protein Science*, 15:14-27; Gill et al., 2006, *Curr. Opin. Biotechnol.*, 17:653-58; Nygren, 2008, *FEBS J.*, 275:2668-76; and Skerra, 2008, *FEBS J.*, 275:2677-83, each of which is incorporated by reference herein in its entirety. In certain embodiments, phage display technology has been used to identify/produce the Wnt-binding polypeptide. In certain embodiments, the polypeptide comprises a protein scaffold of a type selected from the group consisting of protein A, a lipocalin, a fibronectin domain, an ankyrin consensus repeat domain, and thioredoxin.

In some embodiments, the Wnt-binding agent is a non-protein molecule. In certain embodiments, the agent is a small molecule. Combinatorial chemistry libraries and techniques useful in the identification of non-protein Wnt-binding agents are known to those skilled in the art. See, e.g., Kennedy et al., 2008, *J. Comb. Chem.*, 10:345-54; Dolle et al, 2007, *J. Comb. Chem.*, 9:855-902; and Bhattacharyya, 2001, *Curr. Med. Chem.*, 8:1383-404, each of which is incorporated by reference herein in its entirety. In certain further embodiments, the agent is a carbohydrate, a glycosaminoglycan, a glycoprotein, or a proteoglycan.

In certain embodiments, the agent is a nucleic acid aptamer. Aptamers are polynucleotide molecules that are selected (e.g., from random or mutagenized pools) on the basis of their ability to bind to another molecule. In some embodiments, the aptamer comprises a DNA polynucleotide. In certain alternative embodiments, the aptamer comprises an RNA polynucleotide. In certain embodiments, the aptamer comprises one or more modified nucleic acid residues. Methods of generating and screening nucleic acid aptamers for binding to proteins are well known in the art. See, e.g., U.S. Pat. Nos. 5,270,163; 5,683,867; 5,763,595; 6,344,321; 7,368,236; 5,582,981; 5,756,291; 5,840,867; 7,312,325; and 7,329,742, International Patent Publication Nos. WO 02/077262 and WO 03/070984, U.S. Patent Application Publication Nos. 2005/0239134; 2005/0124565; and 2008/0227735, each of which is incorporated by reference herein in its entirety.

In certain embodiments, the Wnt-binding agent has a circulating half-life in mice, cynomolgus monkeys, or humans of at least about 5 hours, at least about 10 hours, at least about 24 hours, at least about 3 days, at least about 1 week, or at least about 2 weeks. In certain embodiments, the Wnt-binding agent is an IgG (e.g., IgG1 or IgG2) antibody that has a circulating half-life in mice, cynomolgus monkeys, or humans of at least about 10 hours, at least about 24 hours, at least about 3 days, at least about 1 week, or at least about 2 weeks. Methods of increasing the half-life of agents such as polypeptides and antibodies are known in the art. For example, known methods of increasing the circulating half-life of IgG antibodies include the introduction of mutations in the Fc region which increase the pH-dependent binding of the antibody to the neonatal Fc receptor (FcRn) at pH 6.0 (see, e.g., U.S. Pat. Pub. Nos. 2005/0276799, 2007/0148164, and 2007/0122403). Known methods of increasing the circulating half-life of antibody fragments lacking the Fc region include such techniques as pegylation.

In certain embodiments, the Wnt-binding agents and polypeptides as described herein have a half-life of at least about 50 hours in a rat when administered via the tail vein at a dose ranging from about 2 mg/kg to about 10 mg/kg. In certain embodiments, the Wnt-binding agent or polypeptide has a half-life of at least about 50 hours in a rat when administered via the tail vein at a dose of about 10 mg/kg. In certain embodiments, the Wnt-binding agent or polypeptide has a half-life of at least about 100 hours in a rat when administered via the tail vein at a dose ranging from about 2 mg/kg to about 10 mg/kg. In certain embodiments, the Wnt-binding agent or polypeptide has a half-life of at least about 100 hours in a rat when administered via the tail vein at a dose of about 10 mg/kg. In certain embodiments, the Wnt-binding agent has a half-life of at least about 120 hours in a rat when administered via the tail vein at a dose ranging from about 2 mg/kg to about 10 mg/kg. In certain embodiments, the Wnt-binding agent has a half-life of at least about 150 hours in a rat when administered via the tail vein at a dose ranging from about 2 mg/kg to about 10 mg/kg.

In certain embodiments, the agent is a soluble FZD receptor that comprises a Fri domain of a human FZD receptor (or a fragment or variant of the Fri domain that binds one or more Wnts) and a human Fc region and has a half-life in vivo (e.g., in a mouse or rat) that is longer than a soluble FZD receptor comprising the extracellular domain of the FZD receptor and a human Fc region.

Cells producing the Wnt-binding agents or polypeptides described herein are provided. In some embodiments, the cell produces a soluble Wnt-binding agent which comprises a Fri domain of human FZD8, wherein at least about 80% of the Wnt-binding agent has an N-terminal sequence of ASA. In some embodiments, the cell produces a soluble Wnt-binding agent which comprises a Fri domain of human FZD8, wherein at least about 85%, at least about 90%, at least about 95%, or at least about 98% of the Wnt-binding agent has an N-terminal sequence of ASA. In some embodiments, the cell is a mammalian cell. In some embodiments, the cell produces a Wnt-binding agent which comprises a human Fc region. In some embodiments, the cell produces a Wnt-binding agent which comprises an amino acid sequence selected from the group consisting of SEQ ID NO:53, SEQ ID NO:50, SEQ ID NO:46, SEQ ID NO:48, and SEQ ID NO:1. In some embodiments, the cell produces a Wnt-binding agent which comprises an amino acid sequence of SEQ ID NO:53. In some embodiments, the cell produces a Wnt-binding agent which comprises an amino acid sequence of SEQ ID NO:50.

Wnt-binding agents produced by the cells described herein are provided.

Compositions comprising the Wnt-binding agents or polypeptides described herein are also provided. In some embodiments, the composition comprises a soluble Wnt-binding agent which comprises a Fri domain of human FZD8, wherein at least about 80% of the Wnt-binding agent has an N-terminal sequence of ASA. In some embodiments, the composition comprises a soluble Wnt-binding agent which comprises a Fri domain of human FZD8, wherein at least about 85%, at least about 90%, at least about 95%, or at least about 98% of the Wnt-binding agent has an N-terminal sequence of ASA. In some embodiments, the composition comprises a Wnt-binding agent which comprises a human Fc region. In some embodiments, the composition comprises a Wnt-binding agent which comprises an amino acid sequence selected from the group consisting of SEQ ID NO:53, SEQ ID NO:50, SEQ ID NO:46, SEQ ID NO:48, and SEQ ID NO:1. In some embodiments, the composition comprises a Wnt-binding agent which comprises an amino acid sequence of SEQ ID NO:53. In some embodiments, the composition comprises a Wnt-binding agent which comprises an amino acid sequence of SEQ ID NO:50. In some embodiments, the compositions as described herein further comprise a pharmaceutically acceptable carrier.

Methods of using the compositions comprising the Wnt-binding agents or polypeptides described herein are also provided.

III. Polynucleotides

In certain embodiments, the invention encompasses polynucleotides comprising polynucleotides that encode a polypeptide that specifically binds a human Wnt protein or a fragment of such a polypeptide. For example, the invention provides a polynucleotide comprising a nucleic acid sequence that encodes a soluble FZD receptor or encodes a fragment of such a soluble receptor. In some embodiments, the invention provides a polynucleotide comprising a nucleic acid sequence that encodes a soluble SFRP, a soluble Ror protein or encodes a fragment of such a soluble protein. In some embodiments, the polynucleotides comprise polynucleotides that encode any of the Wnt-binding agents as described herein. The polynucleotides of the invention can be in the form of RNA or in the form of DNA. DNA includes cDNA, genomic DNA, and synthetic DNA; and can be double-stranded or single-stranded, and if single-stranded can be the coding strand or non-coding (anti-sense) strand.

In certain embodiments, the polynucleotides are isolated. In certain embodiments, the polynucleotides are substantially pure.

The invention provides a polynucleotide comprising a polynucleotide that encodes a polypeptide comprising the sequence of SEQ ID NO:1, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:65, SEQ ID NO:66 and SEQ ID NO:75. In some embodiments, the polynucleotide further comprises a polynucleotide that encodes a polypeptide signal sequence selected from the group consisting of SEQ ID NO:67, SEQ ID NO:68, SEQ ID NO:69, SEQ ID NO:70, SEQ ID NO:71, SEQ ID NO:72, SEQ ID NO:73, and SEQ ID NO:74. In some embodiments, the polynucleotide further comprises a polynucleotide that encodes a polypeptide signal sequence selected from the group consisting of SEQ ID NO:70, SEQ ID NO:71, SEQ ID NO:72, SEQ ID NO:73, and SEQ ID NO:74. In some embodiments, the polynucleotide comprises a polynucleotide that encodes a polypeptide having the sequence of SEQ ID NO:71 and SEQ ID NO:50. In some embodiments, the polynucleotide comprises a polynucleotide that encodes a polypeptide having the sequence of SEQ ID NO:71 and SEQ ID NO:53. In some embodiments, the polynucleotide comprises a polynucleotide that encodes a polypeptide having the sequence of SEQ ID NO:75. The invention further provides a polynucleotide comprising the sequence of SEQ ID NO:2.

The invention provides a polynucleotide comprising a polynucleotide that encodes a polypeptide comprising: a signal sequence selected from the group consisting of SEQ ID NO:71, SEQ ID NO:70, SEQ ID NO:72, SEQ ID NO:73, and SEQ ID NO:74; a Fri domain of human FZD8; and a human Fc region. In some embodiments, the polynucleotide comprises a polynucleotide that encodes a polypeptide comprising a signal sequence of SEQ ID NO:71; a Fri domain of human FZD8; and a human Fc region.

Also provided is a polynucleotide that comprises a polynucleotide that hybridizes to a polynucleotide having the sequence of SEQ ID NO:2 and/or to a polynucleotide that encodes a polypeptide having the sequence of SEQ ID NO:1, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:65, SEQ ID NO:66 and SEQ ID NO:75. In certain embodiments, the hybridization is under conditions of high stringency.

In certain embodiments, the polynucleotides comprise the coding sequence for the mature polypeptide joined in the same reading frame to a polynucleotide which aids, for example, in expression and secretion of a polypeptide from a host cell (e.g. a leader sequence or signal sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

In certain embodiments, the polynucleotides comprise the coding sequence for the mature polypeptide joined in the same reading frame to a marker sequence that allows, for example, for purification of the encoded polypeptide. For example, the marker sequence can be a hexahistidine tag supplied by a pQE-9 vector to provide for purification of the mature polypeptide joined to the marker in the case of a bacterial host, or the marker sequence can be a hemagglutinin (HA) tag derived from the influenza hemagglutinin protein when a mammalian host (e.g., COS-7 cells) is used.

The present invention further relates to variants of the hereinabove described polynucleotides encoding, for example, fragments, analogs, and derivatives. Fragments or portions of the polynucleotides of the present invention can be used to synthesize full-length polynucleotides of the present invention.

In certain embodiments, the present invention provides isolated polynucleotides comprising polynucleotides having a nucleotide sequence at least 80% identical, at least 85% identical, at least 90% identical, at least 95% identical, and in some embodiments, at least 96%, 97%, 98% or 99% identical to a polynucleotide encoding a polypeptide comprising a soluble FZD receptor or other Wnt-binding agent described herein.

By a polynucleotide having a nucleotide sequence at least, for example, 95% "identical" to a reference nucleotide sequence is intended that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the amino- or carboxy-terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments the polynucleotide variants contain alterations which produce silent amino acid substitutions, additions, or deletions, but do not alter the properties or activities of the encoded polypeptide. In some embodiments, nucleotide variants are produced by silent substitutions due to the degeneracy of the genetic code. In some embodiments, nucleotide variants comprise nucleotide sequences which result in expression differences (e.g., increased or decreased expression), even though the amino acid sequence is not changed. Polynucleotide variants can be produced for a variety of reasons, e.g., to optimize codon expression for a particular host (change codons in the human mRNA to those preferred by a bacterial host such as E. coli).

The polynucleotides described herein can be produced by any suitable method known in the art. As described herein in some embodiments, a DNA sequence is constructed using recombinant technology by isolating or synthesizing a DNA sequence encoding a wild-type protein of interest. In some embodiments, a DNA sequence is constructed using recombinant technology by isolating more than one DNA sequence encoding two polypeptides of interest and ligating these DNA sequences together to generate a fusion protein.

In some embodiments, a DNA sequence may be constructed by chemical synthesis using an oligonucleotide synthesizer. Such oligonucleotides can be designed based on the amino acid sequence of the desired polypeptide. Standard methods can be applied to synthesize a polynucleotide sequence encoding a polypeptide of interest. For example, a complete amino acid sequence can be used to construct a back-translated gene. Further, a DNA oligomer containing a nucleotide sequence coding for the particular polypeptide can be synthesized. For example, several small oligonucleotides coding for portions of the desired polypeptide can be synthesized and then ligated. The individual oligonucleotides typically contain 5' or 3' overhangs for complementary assembly. In some embodiments, a nucleotide sequence coding for the desired fusion protein is synthesized so that the two polypeptides are directly linked without an intervening peptide linker.

Once assembled (by synthesis, site-directed mutagenesis, recombinant technology, or another method), the polynucleotide sequences encoding a particular polypeptide of interest can be inserted into an expression vector and operatively linked to an expression control sequence appropriate for expression of the polypeptide in a desired host. Proper assembly can be confirmed by nucleotide sequencing, restriction mapping, and/or expression of a biologically active polypeptide in a suitable host. As is well-known in the art, in order to obtain high expression levels of a transfected gene in a host, the gene must be operatively linked to transcriptional and translational expression control sequences that are functional in the chosen expression host.

Vectors comprising the polynucleotides described herein are provided. Cells comprising the vectors or polynucleotides described herein are also provided.

IV. Pharmaceutical Compositions

The present invention further provides pharmaceutical compositions comprising agents (e.g., soluble FZD receptors) that bind to one or more Wnt proteins and/or are Wnt antagonists. In some embodiments, the pharmaceutical compositions comprise the Wnt-binding agents and polypeptides as described herein. These pharmaceutical compositions find use in inhibiting tumor cell growth and treating cancer in human patients. In some embodiments, the Wnt-binding agents as described herein find use in the manufacture of a medicament for the treatment of cancer.

Formulations are prepared for storage and use by combining a purified agent or antagonist of the present invention with a pharmaceutically acceptable carrier, excipient, and/or stabilizer as a sterile lyophilized powder, aqueous solution, etc. (Remington: The Science and Practice of Pharmacy, 21' Edition, University of the Sciences, Philadelphia, 2005). Suitable carriers, excipients, or stabilizers comprise non-toxic buffers such as phosphate, citrate, and other organic acids; salts such as sodium chloride; antioxidants including ascorbic acid and methionine; preservatives (e.g. octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol); low molecular weight polypeptides (such as less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosacchandes, disaccharides, glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN or polyethylene glycol (PEG).

The pharmaceutical compositions of the present invention can be administered in any number of ways for either local or systemic treatment. Administration can be topical (such as to mucous membranes including vaginal and rectal delivery) such as transdermal patches, ointments, lotions, creams, gels, drops, suppositories, sprays, liquids and powders; pulmonary (e.g., by inhalation or insufflation of powders or aerosols, including by nebulizer; intratracheal, intranasal, epidermal and transdermal); oral; or parenteral including intravenous, intraarterial, subcutaneous, intraperitoneal or intramuscular injection or infusion; or intracranial (e.g., intrathecal or intraventricular) administration.

The therapeutic formulation can be in unit dosage form. Such formulations include tablets, pills, capsules, powders, granules, solutions or suspensions in water or non-aqueous media, or suppositories for oral, parenteral, or rectal administration or for administration by inhalation. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and other diluents (e.g. water) to form a solid preformulation composition containing a homogeneous mixture of a compound of the present invention, or a non-toxic pharmaceutically acceptable salt thereof. The solid preformulation composition is then subdivided into unit dosage forms of the type described above. The tablets, pills, etc., of the novel composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, including a number of polymeric acids and mixtures of polymeric acids with such materials as shellac, cetyl alcohol and cellulose acetate.

Pharmaceutical formulations include antagonists (e.g., Wnt-binding agents) of the present invention complexed with liposomes (Epstein et al., 1985, *PNAS*, 82:3688; Hwang et al., 1980, *PNAS*, 77:4030; and U.S. Pat. Nos. 4,485,045 and 4,544,545). Liposomes with enhanced circulation time are disclosed in U.S. Pat. No. 5,013,556. Liposomes can be generated by the reverse phase evaporation with a lipid composition comprising phosphatidylcholine, cholesterol, and PEG-derivatized phosphatidylethanolamine (PEG-PE). Liposomes are extruded through filters of defined pore size to yield liposomes with the desired diameter.

The antagonist (e.g. Wnt-binding agent) can also be entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions as described in *Remington: The Science and Practice of Pharmacy*, 21$^{st}$ Edition, University of the Sciences, Philadelphia, 2005.

In addition, sustained-release preparations can be prepared. Suitable examples of sustained-release preparations include semipermeable matrices of solid hydrophobic polymers containing the agent, which matrices are in the form of shaped articles (e.g., films or microcapsules). Examples of sustained-release matrices include polyesters, hydrogels such as poly(2-hydroxyethyl-methacrylate) or poly(vinylalcohol), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

V. Methods of Use

The Wnt-binding agents (including soluble receptors) of the invention are useful in a variety of applications including, but not limited to, therapeutic treatment methods, such as the treatment of cancer. In certain embodiments, the agents are useful for inhibiting Wnt signaling (e.g., canonical Wnt signaling), inhibiting tumor growth, inducing differentiation, reducing tumor volume, reducing cancer stem cell frequency, and/or reducing the tumorigenicity of a tumor. The methods of use may be in vitro, ex vivo, or in vivo methods. In certain embodiments, the Wnt-binding agent or polypeptide is an antagonist of the one or more human Wnt proteins to which it binds.

In certain embodiments, the Wnt-binding agents or antagonists are used in the treatment of a disease associated with Wnt signaling activation. In particular embodiments, the disease is a disease dependent upon Wnt signaling. In particular embodiments, the Wnt signaling is canonical Wnt signaling. In certain embodiments, the Wnt-binding agents or antagonists are used in the treatment of disorders characterized by increased levels of stem cells and/or progenitor cells.

In certain embodiments, the disease treated with the Wnt-binding agent or antagonist (e.g., a soluble FZD receptor, SFRP-derived protein, or soluble Ror receptor) is a cancer. In certain embodiments, the cancer is characterized by Wnt-dependent tumors. In certain embodiments, the cancer is characterized by tumors expressing the one or more Wnts to which the Wnt-binding agent (e.g., soluble receptor) binds.

In certain embodiments, the disease treated with the Wnt-binding agent or antagonist is not a cancer. For example, the disease may be a metabolic disorder such as obesity or diabetes (e.g., type II diabetes) (Jin T., 2008, *Diabetologia*, 51:1771-80). Alternatively, the disease may be a bone disorder such as osteoporosis, osteoarthritis, or rheumatoid arthritis (Corr M., 2008, *Nat. Clin. Pract. Rheumatol.*, 4:550-6; Day et al., 2008, *Bone Joint Surg. Am.*, 90 Suppl 1:19-24). The disease may also be a kidney disorder, such as a polycystic kidney disease (Harris et al., 2009, *Ann. Rev. Med.*, 60:321-37; Schmidt-Ott et al., 2008, *Kidney Int.*, 74:1004-8; Benzing et al., 2007, *J. Am. Soc. Nephrol.*, 18:1389-98). Alternatively, eye disorders including, but not limited to, macular degeneration and familial exudative vitreoretinopathy may be treated (Lad et al., 2009, *Stem Cells Dev.*, 18:7-16). Cardiovascular disorders, including myocardial infarction, atherosclerosis, and valve disorders, may also be treated (Al-Aly Z., 2008, *Transl. Res.*, 151:233-9; Kobayashi et al., 2009, *Nat. Cell Biol.*, 11:46-55; van Gijn et al., 2002, *Cardiovasc. Res.*, 55:16-24; Christman et al., 2008, *Am. J. Physiol. Heart Circ. Physiol.*, 294:H2864-70). In some embodiments, the disease is a pulmonary disorder such as idiopathic pulmonary arterial hypertension or pulmonary fibrosis (Laumanns et al., 2008, *Am. J. Respir. Cell Mol. Biol.*, 2009, 40:683-91; Königshoff et al., 2008 *PLoS ONE*, 3:e2142). In some embodiments, the disease treated with the Wnt-binding agent is a liver disease, such as cirrhosis or liver fibrosis (Cheng et al., 2008, *Am. J. Physiol. Gastrointest. Liver Physiol.*, 294:G39-49).

The present invention provides methods of treating cancer comprising administering a therapeutically effective amount of a Wnt-binding agent to a subject (e.g., a subject in need of treatment). In certain embodiments, the cancer is a cancer selected from the group consisting of colorectal cancer, pancreatic cancer, lung cancer, ovarian cancer, liver cancer, breast cancer, kidney cancer, prostate cancer, gastrointestinal cancer, melanoma, cervical cancer, bladder cancer, glioblastoma, and head and neck cancer. In certain embodiments, the cancer is pancreatic cancer. In certain embodiments, the cancer is colorectal cancer. In certain embodiments, the cancer is breast cancer. In certain embodiments, the subject is a human.

The present invention further provides methods for inhibiting tumor growth using the Wnt-binding agents described herein. In certain embodiments, the method of inhibiting tumor growth comprises contacting the tumor or tumor cell with a Wnt-binding agent in vitro. For example, an immortalized cell line or a cancer cell line that expresses the targeted Wnt(s) is cultured in medium to which is added the Wnt-binding agent to inhibit tumor cell growth. In some embodiments, tumor cells are isolated from a patient sample such as, for example, a tissue biopsy, pleural effusion, or blood sample and cultured in medium to which is added a Wnt-binding agent to inhibit tumor cell growth.

In some embodiments, the method of inhibiting tumor growth comprises contacting the tumor or tumor cells with the Wnt-binding agent (e.g., a FZD soluble receptor) in vivo. In certain embodiments, contacting a tumor or tumor cell with a Wnt-binding agent is undertaken in an animal model. For example, Wnt-binding agents may be administered to xenografts expressing one or more Wnts that have been grown in immunocompromised mice (e.g. NOD/SCID mice) to inhibit tumor growth. In certain embodiments, cancer stem cells are isolated from a patient sample such as, for example, a tissue biopsy, pleural effusion, or blood sample and injected into immunocompromised mice that are then administered a Wnt-binding agent to inhibit tumor cell growth. In some embodiments, the Wnt-binding agent is administered at the same time or shortly after introduction of tumorigenic cells into the animal to prevent tumor growth. In some embodiments, the Wnt-binding agent is administered as a therapeutic after the tumorigenic cells have grown to a tumor of a specified size.

In certain embodiments, the method of inhibiting the growth of a tumor comprises administering to a subject a therapeutically effective amount of a Wnt-binding agent. In certain embodiments, the subject is a human. In certain embodiments, the subject has a tumor or has had a tumor removed.

The invention also provides methods of reducing cancer stem cell frequency in a tumor comprising cancer stem cells, the method comprising administering a therapeutically effective amount of a Wnt-binding agent to a subject. In addition are provided methods of inducing differentiation of tumor cells in a subject, wherein the method comprises administering a therapeutically effective amount of a Wnt-binding agent to the subject. In some embodiments, methods for inducing expression of differentiation markers in a tumor comprise administering a therapeutically effective amount of a Wnt-binding agent to a subject. In certain embodiments, the subject is a human.

In certain embodiments, the tumor is a tumor in which Wnt signaling is active. In certain embodiments, the Wnt signaling that is active is canonical Wnt signaling. In certain embodiments, the tumor is a Wnt-dependent tumor. For example, in some embodiments, the tumor is sensitive to axin overexpression. In certain embodiments, the tumor does not comprise an inactivating mutation (e.g., a truncating mutation) in the adenomatous polyposis coli (APC) tumor suppressor gene or an activating mutation in the beta-catenin gene. In certain embodiments, the tumor expresses one or more genes in a Wnt gene signature. In certain embodiments, the cancer for which a subject is being treated involves such a tumor.

In certain embodiments, the tumor expresses the one or more human Wnt proteins to which the Wnt-binding agent binds. In certain embodiments, the tumor over-expresses the human Wnt(s).

In certain embodiments, the tumor is a tumor selected from the group consisting of colorectal tumor, pancreatic tumor, lung tumor, ovarian tumor, liver tumor, breast tumor, kidney tumor, prostate tumor, gastrointestinal tumor, melanoma, cervical tumor, bladder tumor, glioblastoma, and head and neck tumor. In certain embodiments, the tumor is a colorectal tumor. In certain embodiments, the tumor is a pancreatic tumor. In certain embodiments, the tumor is a breast tumor.

The invention also provides a method of inhibiting Wnt signaling in a cell comprising contacting the cell with an effective amount of a Wnt-binding agent. In certain embodiments, the cell is a tumor cell. In certain embodiments, the method is an in vivo method wherein the step of contacting the cell with the agent comprises administering a therapeutically effective amount of the agent to the subject. In some alternative embodiments, the method is an in vitro or ex vivo method. In certain embodiments, the Wnt signaling that is inhibited is canonical Wnt signaling. In certain embodiments, the Wnt signaling is signaling by Wnt1, Wnt2, Wnt3, Wnt3a, Wnt7a, Wnt7b, and/or Wnt10b. In certain embodiments, the Wnt signaling is signaling by Wnt1, Wnt3a, Wnt7b, and/or Wnt10b.

In addition, the invention provides a method of reducing the tumorigenicity of a tumor in a subject, comprising administering a therapeutically effective amount of a Wnt-binding agent to the subject. In certain embodiments, the tumor comprises cancer stem cells. In some embodiments, the tumorigenicity of a tumor is reduced by reducing the frequency of cancer stem cells in the tumor. In certain embodiments, the frequency of cancer stem cells in the tumor is reduced by administration of the Wnt-binding agent. In certain embodiments, the agent or antibody is capable of reducing the tumorigenicity of a tumor comprising cancer stem cells in an animal model, such as a mouse xenograft model. In certain embodiments, the number or frequency of cancer stem cells in a tumor is reduced by at least about two-fold, about three-fold, about five-fold, about ten-fold, about 50-fold, about 100-fold, or about 1000-fold. In certain embodiments, the reduction in the number or frequency of cancer stem cells is determined by limiting dilution assay using an animal model. Additional examples and guidance regarding the use of limiting dilution assays to determine a reduction in the number or frequency of cancer stem cells in a tumor can be found, e.g., in International Publication Number WO 2008/042236, U.S. Patent Application Publication No. 2008/0064049, and U.S. Patent Application Publication No. 2008/0178305, each of which is incorporated by reference herein in its entirety.

Thus, the invention also provides a method of reducing the frequency of cancer stem cells in a tumor comprising cancer stem cells, the method comprising contacting the tumor with an effective amount of a Wnt-binding agent (e.g., a soluble FZD receptor, a soluble Ror receptor or a SFRP-Fc fusion).

The invention further provides methods of differentiating tumorigenic cells into non-tumorigenic cells comprising contacting the tumorigenic cells with a Wnt-binding agent (for example, by administering the Wnt-binding agent to a subject that has a tumor comprising the tumorigenic cells or that has had such a tumor removed). In certain embodiments, the tumorigenic cells are pancreatic tumor cells. In certain alternative embodiments, the tumorigenic cells are colon tumor cells.

The use of the Wnt-binding agents described herein to induce the differentiation of cells, including, but not limited to tumor cells, is also provided. For example, methods of inducing cells to differentiate comprising contacting the cells with an effective amount of a Wnt-binding agent (e.g., a soluble FZD receptor, a soluble Ror receptor, or a SFRP-Fc fusion) described herein are envisioned. Methods of inducing cells in a tumor in a subject to differentiate comprising administering a therapeutically effective amount of a Wnt-binding agent to the subject are also provided. In certain embodiments, the tumor is a pancreatic tumor. In certain other embodiments, the tumor is a colon tumor.

Methods of treating a disease or disorder in a subject, wherein the disease or disorder is associated with Wnt signaling activation and/or is characterized by an increased level of stem cells and/or progenitor cells are further provided. In some embodiments, the treatment methods comprise administering a therapeutically effective amount of the Wnt-binding agent to the subject. In certain embodiments, the Wnt signaling is canonical Wnt signaling.

The Wnt-binding agents or antagonists are administered as an appropriate pharmaceutical composition to a human patient according to known methods. Suitable methods of administration include, but are not limited to, intravenous (administration as a bolus or by continuous infusion over a period of time), intramuscular, intraperitoneal, intracerobrospinal, subcutaneous, intra-articular, intrasynovial, intrathecal, oral, topical, or inhalation routes.

In certain embodiments, in addition to administering the Wnt-binding agent, the method or treatment further comprises administering a second therapeutic agent (e.g. an anti-cancer agent) prior to, concurrently with, and/or subsequently to administration of the Wnt-binding agent. Pharmaceutical compositions comprising the Wnt-binding agent and the second therapeutic agent are also provided.

It will be appreciated that the combination of a Wnt-binding agent and a second therapeutic agent may be administered in any order or concurrently. In selected embodiments, the Wnt-binding agents will be administered to patients that have previously undergone treatment with the second therapeutic agent. In certain other embodiments, the Wnt-binding agent and the second therapeutic agent will be administered substantially simultaneously or concurrently. For example, a subject may be given the Wnt-binding agent while undergoing a course of treatment with the second therapeutic agent (e.g., chemotherapy). In certain embodiments, the Wnt-binding agent will be administered within 1 year of the treatment with the second therapeutic agent. In certain alternative embodiments, the Wnt-binding agent will be administered within 10, 8, 6, 4, or 2 months of any treatment with the second therapeutic agent. In certain other embodiments, the Wnt-binding agent will be administered within 4, 3, 2, or 1 week of any treatment with the second therapeutic agent. In some embodiments, the Wnt-binding agent will be administered within 5, 4, 3, 2, or 1 days of any treatment with the second therapeutic agent. It will further be appreciated that the two agents or treatment may be administered to the subject within a matter of hours or minutes (i.e., substantially simultaneously).

Combination therapy with at least two therapeutic agents often uses agents that work by different mechanisms of action, although this is not required. Combination therapy using agents with different mechanisms of action may result in additive or synergetic effects. Combination therapy may allow for a lower dose of each agent than is used in monotherapy, thereby reducing toxic side effects. Combination therapy may decrease the likelihood that resistant cancer cells will develop. In some embodiments, combination therapy comprises a therapeutic agent that affects (e.g., inhibits or kills) non-tumorigenic cells and a therapeutic agent that affects (e.g., inhibits or kills) tumorigenic CSCs.

Useful classes of therapeutic (e.g., anti-cancer) agents include, for example, antitubulin agents, auristatins, DNA minor groove binders, DNA replication inhibitors, alkylating agents (e.g., platinum complexes such as cis-platin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosureas, platinols, performing compounds, purine antimetabolites, puromycins, radiation sensitizers, steroids, taxanes, topoisomerase inhibitors, vinca alkaloids, or the like. In certain embodiments, the second therapeutic agent is an antimetabolite, an antimitotic, a topoisomerase inhibitor, or an angiogenesis inhibitor.

Therapeutic agents that may be administered in combination with the Wnt-binding agents include chemotherapeutic agents. Thus, in some embodiments, the method or treatment involves the combined administration of a Wnt-binding agent of the present invention and a chemotherapeutic agent or cocktail of multiple different chemotherapeutic agents. Treatment with a Wnt-binding agent can occur prior to, concurrently with, or subsequent to administration of chemotherapies. Chemotherapies contemplated by the invention include chemical substances or drugs which are known in the art and are commercially available, such as gemcitabine, irinotecan, doxorubicin, 5-fluorouracil, cytosine arabinoside ("Ara-C"), cyclophosphamide, thiotepa, busulfan, cytoxin, paclitaxel, methotrexate, cisplatin, melphalan, vinblastine, and carboplatin. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

Chemotherapeutic agents useful in the instant invention also include, but are not limited to, alkylating agents such as thiotepa and cyclosphosphamide; alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone;

mitoxantrone; mopidamol; nitracrine; pentostatin; phenamet; pirarubicin; podophyllinic acid; 2-ethylhydrazide; procarbazine; PSK.; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL) and docetaxel (TAXOTERE), chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitor RFS 2000; difluoromethylornithine (DMFO); retinoic acid; esperamicins; capecitabine; and pharmaceutically acceptable salts, acids or derivatives of any of the above. Chemotherapeutic agents also include anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and antiandrogens such as flutamide, nilutamide, bicalutamide, leuprolide, and goserelin; and pharmaceutically acceptable salts, acids or derivatives of any of the above.

In certain embodiments, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide (VM-26), and irinotecan. In certain embodiments, the second therapeutic agent is irinotecan. In certain embodiments, the tumor to be treated is a colorectal tumor and the second therapeutic agent is a topoisomerase inhibitor, such as irinotecan. In some embodiments, the Wnt-binding agent comprises SEQ ID NO:53 and the second therapeutic agent is irinotecan. In some embodiments, the Wnt-binding agent comprises SEQ ID NO:75 and the second therapeutic agent is irinotecan.

In certain embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, ralitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these. In certain embodiments, the second therapeutic agent is gemcitabine. In certain embodiments, the tumor to be treated is a pancreatic tumor and the second therapeutic agent is an anti-metabolite (e.g., gemcitabine). In some embodiments, the Wnt-binding agent comprises SEQ ID NO:53 and the second therapeutic agent is gemcitabine. In some embodiments, the Wnt-binding agent comprises SEQ ID NO:75 and the second therapeutic agent is gemcitabine.

In certain embodiments, the chemotherapeutic agent is an antimitotic agent, including, but not limited to, agents that bind tubulin. By way of non-limiting example, the agent comprises a taxane. In certain embodiments, the agent comprises paclitaxel or docetaxel, or a pharmaceutically acceptable salt, acid, or derivative of paclitaxel or docetaxel. In certain embodiments, the agent is paclitaxel (TAXOL), docetaxel (TAXOTERE), albumin-bound paclitaxel (ABRAXANE), DHA-paclitaxel, or PG-paclitaxel. In certain alternative embodiments, the antimitotic agent comprises a vinka alkaloid, such as vincristine, binblastine, vinorelbine, or vindesine, or pharmaceutically acceptable salts, acids, or derivatives thereof. In some embodiments, the antimitotic agent is an inhibitor of Eg5 kinesin or an inhibitor of a mitotic kinase such as Aurora A or Plk1. In certain embodiments where the chemotherapeutic agent administered in combination with the Wnt-binding agent or polypeptide comprises an antimitotic agent, the cancer or tumor being treated is breast cancer or a breast tumor. In certain embodiments, the tumor to be treated is a breast tumor and the second therapeutic agent is paclitaxel. In some embodiments, the Wnt-binding agent comprises SEQ ID NO:53 and the second therapeutic agent is paclitaxel. In some embodiments, the Wnt-binding agent comprises SEQ ID NO:75 and the second therapeutic agent is paclitaxel.

In certain embodiments, the treatment involves the combined administration of a Wnt-binding agent of the present invention and radiation therapy. Treatment with the Wnt-binding agent can occur prior to, concurrently with, or subsequent to administration of radiation therapy. Any dosing schedules for such radiation therapy can be used as determined by the skilled practitioner.

In some embodiments, the second therapeutic agent comprises an antibody. Thus, treatment can involve the combined administration of Wnt-binding agents of the present invention with antibodies against tumor-associated antigens including, but not limited to, antibodies that bind to EGFR, ErbB2, HER2, DLL4, Notch, and/or VEGF. Exemplary, anti-DLL4 antibodies are described, for example, in U.S. Pat. No. 7,750,124, incorporated by reference herein in its entirety. Additional anti-DLL4 antibodies are described in, e.g., International Patent Publication Nos. WO 2008/091222 and WO 2008/0793326, and U.S. Patent Application Publication Nos. US 2008/0014196, US 2008/0175847, US 2008/0181899, and US 2008/0107648, each of which is incorporated by reference herein in its entirety. In certain embodiments, the second therapeutic agent is an antibody that is an angiogenesis inhibitor (e.g., an anti-VEGF antibody). In some embodiments, the Wnt-binding agent comprises SEQ ID NO:53 and the second therapeutic agent is an anti-VEGF antibody. In some embodiments, the Wnt-binding agent comprises SEQ ID NO:75 and the second therapeutic agent is an anti-VEGF antibody. In certain embodiments, the second therapeutic agent is an inhibitor of Notch signaling. In some embodiments, the second therapeutic agent is an anti-Notch antibody. Exemplary anti-Notch antibodies are described, for example, in U.S. Patent Application Publication No. US 2008/0131434, incorporated by reference herein in its entirety. In certain embodiments, the second therapeutic agent is bevacizumab (AVASTIN), trastuzumab (HERCEPTIN), panitumumab (VECTIBIX), or cetuximab (ERBITUX). Combined administration can include co-administration, either in a single pharmaceutical formulation or using separate formulations, or consecutive administration in either order but generally within a time period such that all active agents can exert their biological activities simultaneously.

Furthermore, treatment can include administration of one or more cytokines (e.g., lymphokines, interleukins, tumor necrosis factors, and/or growth factors) or can be accompanied by surgical removal of tumor or cancer cells or any other therapy deemed necessary by a treating physician.

For the treatment of the disease, the appropriate dosage of an agent of the present invention depends on the type of disease to be treated, the severity and course of the disease, the responsiveness of the disease, whether the agent is administered for therapeutic or preventative purposes, previous therapy, patient's clinical history, and so on all at the discretion of the treating physician. The agent can be administered one time or over a series of treatments lasting from several days to several months, or until a cure is effected or a diminution of the disease state is achieved (e.g. reduction in tumor size). Optimal dosing schedules can be calculated from measurements of drug accumulation in the body of the patient and will vary depending on the relative potency of an individual agent. The administering physician can easily determine optimum dosages, dosing methodologies and repetition rates. In certain embodiments, dosage is from 0.01 µg to 100 mg per kg of body weight, and can be given once or more daily, weekly, monthly or yearly. In certain embodiments, the dosage of the soluble receptor or other Wnt-binding agent is from about 0.1 mg to about 20 mg per kg of body weight. In certain embodiments, the Wnt-binding agent is given once every week. In certain embodiments, the Wnt-binding agent is given once every two weeks or once every three weeks. The treating physician can estimate repetition rates for dosing based on measured residence times and concentrations of the drug in bodily fluids or tissues.

The present invention further provides methods of screening agents for efficacy in inhibiting Wnt signaling, for anti-tumor activity, and/or activity against cancer stem cells. In certain embodiments, the method comprises comparing the level of one or more differentiation markers and/or one or more stemness markers in a first solid tumor (e.g., a solid tumor comprising cancer stem cells) that has been exposed to the agent to the level of the one or more differentiation markers in a second solid tumor that has not been exposed to the agent. In some embodiments, the method comprises: (a) exposing a first solid tumor, but not a second solid tumor, to the agent; (b) assessing the level of one or more differentiation markers and/or one or more stemness markers in the first and second solid tumors; and (c) comparing the level of the one or more differentiation markers in the first tumor and the level of the one or more differentiation markers in the second solid tumor. In certain embodiments, the (a) increased levels of the one or more differentiation markers in the first solid tumor relative to the levels of the one or more differentiation markers in the second solid tumor indicates anti-tumor (or anti-cancer stem cell) activity; and (b) decreased levels of the one or more stemness markers indicate anti-tumor (or anti-cancer stem cell) activity. In certain embodiments, the agent binds one or more Wnt proteins. In certain embodiments, the agent is a FZD soluble receptor. In certain methods, the agent is an antibody, such as an anti-Wnt antibody.

Additional methods for screening agents include, but are not limited to, methods comprising comparing the levels of one or more differentiation markers in a first solid tumor that has been exposed to an agent to the levels of the one or more differentiation markers in a second solid tumor that has not been exposed to the agent. In certain embodiments, the methods include comprising (a) exposing a first solid tumor, but not a second solid tumor, to the agent; (b) assessing the levels of one or more differentiation markers in the first and second solid tumors; and (c) comparing the levels of the one or more differentiation markers in the first tumor to the levels of the one or more differentiation markers in the second solid tumor. In certain embodiments, the agent is a Wnt-binding agent. In certain embodiments, the agent is an inhibitor of the canonical Wnt signaling pathway. In certain embodiments, the agent inhibits binding of one or more human Wnt proteins to one or more human FZD receptors. In certain embodiments, increased levels of one or more differentiation markers in the first solid tumor relative to levels of one or more differentiation markers in the second solid tumor indicates efficacy against solid tumor stem cells (CSCs). In certain alternative embodiments, decreased levels of one or more differentiation markers (i.e., negative markers for differentiation) in the first solid tumor relative to the levels of one or more differentiation markers in the second solid tumor indicates efficacy against solid tumor stem cells.

In certain embodiments, the solid tumor in the screening method is a pancreatic tumor. In certain embodiments, the solid tumor is a pancreatic tumor and the one or more differentiation markers may comprise one or more mucins (e.g., Muc16), one or more cytokeratins (e.g., CK20) and/or chromogranin A (CHGA).

In certain alternative embodiments, the solid tumor in the screening method is a colon tumor. In some embodiments, the solid tumor is a colon tumor and the one or more differentiation markers may comprise one or more cytokeratins (e.g., cytokeratin 7 or CK20).

In certain embodiments, the one or more stemness markers used in the screening methods described herein comprise ALDH1A1, APC, AXIN2, BMI1, CD44, FGF1, GJB1, GJB2, HES1, JAG1, LGR5, LHX8, MYC, NANOG, NEUROD1, NEUROG2, NOTCH1, NOTCH2, NOTCH3, NOTCH4, PROCR, RARRES1, RARRES3, RBP2, SOX1, SOX2, ASCL2, TDGF1, OLFM4, MSI1, DASH1, EPHB3 and/or EPHB4. In certain embodiments, two or more stemness markers, three or more stemness markers, four or more stemness markers, five or more stemness markers, six or more, or ten or more stemness markers are selected from the group consisting of ALDH1A1, APC, AXIN2, BMI1, CD44, FGF1, GJB1, GJB2, HES1, JAG1, LGR5, LHX8, MYC, NANOG, NEUROD1, NEUROG2, NOTCH1, NOTCH2, NOTCH3, NOTCH4, PROCR, RARRES1, RARRES3, RBP2, SOX1, SOX2, ASCL2, TDGF1, OLFM4, MSI1, DASH1, EPHB3 and EPHB4.

In certain embodiments, the one or more differentiation markers used in the screening methods comprise ALDOB, BMP2, BMP7, BMPR1B, CEACAM5, CEACAM6, CDX1, CDX2, CLCA2, COL1A2, COL6A1, CHGA, CSTA, CST4, CK20, DAB2, FABP4, GST1, KRT4, KRT7, KRT15, KRT17, KRT20, LAMA1, MUC3A, MUC4, MUC5AC, MUC5B, MUC13, MUC15, MUC16, MUC17, NDRG2, PIP, PLUNC, SPRR1A, REG4, VSIG1, and/or XAF1. In certain embodiments two or more, three or more, four or more, five or more, six or more, or ten or more differentiation markers used in the screening methods are selected from the group consisting of ALDOB, BMP2, BMP7, BMPR1B, CEACAM5, CEACAM6, CDX1, CDX2, CLCA2, COL1A2, COL6A1, CHGA, CSTA, CST4, CK20, DAB2, FABP4, GST1, KRT4, KRT7, KRT15, KRT17, KRT20, LAMA1, MUC3A, MUC4, MUC5AC, MUC5B, MUC13, MUC15, MUC16, MUC17, NDRG2, PIP, PLUNC, SPRR1A, REG4, VSIG1, and XAF1.

Other potential differentiation markers for pancreas and colon as well as other tumor types are known to those skilled in the art. In addition, the usefulness of potential differentiation markers in a screening method can be readily assessed by one skilled in the art by treating the desired tumor type with one or more of the soluble FZD receptors describe herein such as FZD8-Fc and then assessing for changes in expression of the marker by the treated tumor relative to control. Non-limiting examples of such methods, can for instance, be found in the specific Examples below.

The present invention further provides methods for producing soluble Wnt-binding agents. In certain embodiments, the method comprises producing a soluble Wnt-binding agent which comprises a Fri domain of human FZD8 in a cell, wherein at least 80% of the Wnt-binding agent has an N-terminal sequence of ASA, the method comprising using a signal sequence selected from the group consisting of: SEQ ID NO:71, SEQ ID NO:70, SEQ ID NO:72, SEQ ID NO:73, and SEQ ID NO:74 for production of the Wnt-binding agent. In some embodiments of the method, the signal sequence is SEQ ID NO:71. In some embodiments, at least about 90%, at least about 95%, or at least about 98% of the Wnt-binding agent has an N-terminal sequence of ASA. In some embodiments, the cell is a mammalian cell. In some embodiments, the Wnt-binding agent comprises a human Fc region. In some embodiments, the Wnt-binding agent comprises an amino acid sequence selected from the group consisting of: SEQ ID NO:53, SEQ ID NO:50, SEQ ID NO:46, SEQ ID NO:48, and SEQ ID NO:1. In some embodiments, the Wnt-binding agent comprises SEQ ID NO:53. In some embodiments, the Wnt-binding agent comprises SEQ ID NO:50. In some embodiments, the cell comprises a polynucleotide comprising a polynucleotide that encodes a polypeptide having the sequence of SEQ ID NO:75.

EXAMPLES

It is understood that the examples and embodiments described herein are for illustrative purposes only and that various modifications or changes in light thereof will be suggested to persons skilled in the art and are to be included within the spirit and purview of this application.

Example 1

Production of FZD8-Fc cDNA encoding FZD8-Fc (54F03) was subcloned into a pEE14.4 expression vector (Lonza) digested with HindIII and EcoRI. After cloning, the pEE14.4-FZD8-Fc DNA was linearized by digestion with PvuI and subsequently introduced into GS-CHOK1 cells by electroporation using standard procedures. Stable clones expressing FZD8-Fc were obtained, and expanded in serum free medium. FZD8-Fc was purified by affinity capture using a protein A-conjugated resin. SDS-PAGE analysis revealed greater than 98% purity and endotoxin level was lower than 1 EU/mg protein.

The amino acid sequence of FZD8-Fc is SEQ ID NO:1 and the polynucleotide sequence encoding FZD8-Fc is SEQ ID NO:2.

Example 2

Pharmacokinetics of FZD8-Fc in Rat

The pharmacokinetics of FZD8-Fc (54F03) were assessed in rats in a two week pharmacokinetics (PK) study using doses of 2 mg/kg and 10 mg/kg. Sprague Dawley rats, five males in each group, were dosed with FZD8-Fc via the tail vein at 2 mg/kg or 10 mg/kg and followed for two weeks with samples collected at the time points 1, 24, 48, 72, 96, 168, 240, and 336 hours. At each time point, 1 ml of blood was collected into potassium-EDTA tubes and centrifuged. The plasma supernatants were collected and frozen until the samples were analyzed.

The level of FZD8-Fc fusion protein present in the plasma at each time point was quantified and the half-life of FZD8-Fc was calculated for the two doses. As shown in FIG. 1, the half-life of FZD8-Fc was estimated to be 163 hours at 2 mg/kg and to be 157 hours at 10 mg/kg.

Example 3

Anti-Tumor Activity of FZD8-Fc in Pancreatic Tumor Model

Inhibition of Tumor Growth by FZD8-Fc in Pancreatic Tumor Model.

The anti-tumor activity of FZD8-Fc (54F03) was evaluated in the PN4 pancreas tumor xenograft model. Dissociated OMP-PN4 cells (50,000 per animal) were injected subcutaneously into 6-8 week old male NOD/SCID mice. Tumor growth was monitored weekly and tumor measurements were initiated once tumors were palpable. On day 50, mice with average tumor volumes of 137 $mm^3$ were randomized into 4 groups of 10 animals each. Animals were injected with either control antibody, FZD8-Fc (15 mg/kg), gemcitabine (2 mg/kg) or a combination of FZD8-Fc and gemcitabine. Administration of the FZD8-Fc and gemcitabine was performed via injection into the intra-peritoneal cavity, once weekly (gemcitabine) or twice weekly (FZD8-Fc). Tumors were measured twice a week and tumor volume was determined using the formula $\frac{1}{2}(a \times b^2)$; where a=length, and b=breadth. Data are expressed as mean and mean±S.E.M. Group means were compared using Student's two-tailed, unpaired t test. Probability (p) values of <0.05 were interpreted as significantly different.

Treatment with FZD8-Fc resulted in a 66% reduction in tumor growth, as shown in FIG. 2 (p<0.001). Furthermore, treatment with FZD8-Fc and gemcitabine resulted in a 29% reduction of tumor growth relative to treatment with FZD8-Fc alone (p=0.04 vs. FZD8-Fc alone) (FIG. 2). Thus, FZD8-Fc demonstrated anti-tumor growth activity in the PN4 pancreas tumor model as a single agent as well as in combination with gemcitabine.

Reduction of CD44hi Population in PN4 Tumors Treated with FZD8-Fc.

Control and treated tumors from the OMP-PN4 xenograft study described above were harvested at the end of the study (day 85). The tumors were processed and dissociated into single cells. Single cell suspensions derived from 5 tumors of each treatment group were pooled, and the pooled samples were then incubated on ice for 30 min with antibodies that bind mouse cells selectively (α-mouse CD45-biotin 1:200 dilution and rat α-mouse H2Kd-biotin 1:100 dilution, BioLegend, San Diego, Calif.), followed by addition of streptavidin-labeled magnetic beads (Invitrogen, Carlsbad, Calif.). Mouse cells were removed with the aid of a magnet. For analysis of human cell surface markers, the single tumor cell suspension was stained with anti-ESA (Biomeda, Hayward, Calif.) and anti-CD44 (BD Biosciences, San Jose, Calif.) antibodies which were directly conjugated to fluorochromes. Dead cells were excluded by using the viability dye DAPI. Flow cytometry was performed using a FACS Aria instrument (Becton Dickinson, Franklin Lakes, N.J.). Side scatter and forward scatter profiles were used to eliminate cell clumps.

Analysis of the tumors treated with control antibody revealed that 12.7% of the bulk tumor population expressed both ESA and CD44 at high levels. The double positive population was not significantly affected by treatment with gemcitabine alone (13.9%) as shown in FIG. 3, but treatment with either FZD8-Fc or the combination of FZD8-Fc with gemcitabine reduced the double positive population (1.9% and 1.7% respectively).

Analysis of FZD8-Fc-Treated PN4 Tumors by Limiting Dilution Assay.

Limiting dilution assays (LDA) can be used to assess the effect of therapeutic agents on solid tumor cancer stem cells and on the tumorigenicity of a tumor comprising the cancer stem cells. Such assays can be used to determine the frequency of cancer stem cells in tumors from animals treated with the FZD8-Fc fusion protein or other agent and to compare that frequency to the frequency of cancer stem cells in tumors from control animals.

Control and treated tumors from the PN4 xenograft study described above were harvested at the end of the study (day 85). The tumors were processed and dissociated into single cells. Single cell suspensions derived from 5 tumors of each treatment group were pooled, and the pooled samples were then incubated on ice for 30 min with antibodies that bind mouse cells selectively ($\alpha$-mouse CD45-biotin 1:200 dilution and rat $\alpha$-mouse H2Kd-biotin 1:100 dilution, BioLegend, San Diego, Calif.), followed by addition of streptavidin-labeled magnetic beads (Invitrogen, Carlsbad, Calif.). The mouse cells were removed with the aid of a magnet. The human cells in the suspension were harvested, counted, and stained for cell surface markers and appropriate cell doses (30, 90, and 270 cells) in FACS buffer were mixed in a 1:1 mixture with Matrigel and injected subcutaneously in NOD/SCID mice (10 mice per cell dose per treatment group). Tumors are allowed to grow for up to 4 months.

At the desired time point, the percentage of mice with detectable tumors was determined in all groups injected with FZD8-Fc-treated tumor cells and compared to the percentage of mice with detectable tumors in the controls. For example, the number of mice injected with 125 control antibody-treated tumor cells that have detectable tumors is determined and compared to the number of mice injected with 125 FZD8-Fc treated tumor cells that have detectable tumors.

On day 75 after injection of the cells, tumor take rates in the various groups were as follows: control—7 mice out of 30 mice; FZD8-Fc—3 mice out of 30 mice; gemcitabine—7 mice out of 30 mice; FZD8-Fc and gemcitabine—0 mice out of 30 mice (FIG. 4). The reduced tumor take rate in the FZD8-Fc and in the combination treated groups indicated that the cancer stem cell frequency was reduced in PN4 pancreatic tumors by FZD8-Fc. The evidence from the assessment of both, CD44 expression and limiting dose dilution analysis revealed that FZD8-Fc treatment reduces cancer stem cell frequency in PN4 pancreatic tumors.

The cancer stem cell (CSC) frequency can be calculated using L-Calc™ software (StemCell Technologies Inc.; www.stemcell.com). Briefly, based on Poisson statistics, exactly one cancer stem cell exists among the known number of injected cells if 37% of the animals fail to develop tumors. The CSC frequency for the control antibody treated group was 1:280, the CSC frequency for the gemcitabine treated group was 1:476, the CSC frequency for the FZD8-Fc treated group was 1:881, and the CSC frequency for the group treated with a combination of FZD8-Fc and gemcitabine was calculated to be lower than 1:3763. This number could not be accurately determined because the tumor take rate in this group was zero, even at the highest cell dose.

Example 4

Increased Cell Differentiation of Pancreatic Tumors by FZD8-Fc

Increased Cell Differentiation of PN4 and PN8 Tumors with FZD8-Fc Treatment.

Control and treated tumors from the OMP-PN4 xenograft study described above (Example 3) were harvested at the end of the study (day 85). Tumors were fixed in formalin, embedded in paraffin, and tumor sections of 4 μm thickness were cut. After deparaffinization and hydration, the sections were treated with aqueous acetic acid for 5 minutes at room temperature. The sections were then treated with 1% alcian blue in 3% aqueous acetic acid for 30 minutes and washed with water. Sections were counter-stained in neutral fast red, dehydrated and mounted. Using this method, sialomucins in the tissue samples stain blue and the background appears as pink or red.

The treatment of PN4 tumors with FZD8-Fc caused an increase in cells expressing sialomucins as compared to tumors treated with control antibody or gemcitabine (FIG. 5, where the sialomucins appear as a dark gray). The combination treatment of FZD8-Fc and gemcitabine also increased the expression of sialomucins in PN4 pancreatic tumors. Therefore, FZD8-Fc treatment of PN4 tumors increased the frequency of mucin-expressing differentiated cells. Similar results were seen in the PN8 pancreatic tumor xenograft model (FIG. 6).

Increased Cell Differentiation of PN13 Tumors with FZD8-Fc Treatment.

The cell differentiation capability of FZD8-Fc was also evaluated in the OMP-PN13 pancreas tumor xenograft model. Dissociated OMP-PN13 cells (50,000 per animal) were injected subcutaneously into 6-8 week old male NOD/SCID mice. Tumor growth was monitored weekly and tumor measurements were initiated once tumors were palpable. On day 40 mice with average tumor volume of 114 mm$^3$ were randomized into 4 groups of 10 animals each. Animals were injected with either control antibody or FZD8-Fc (15 mg/kg). Administration of the FZD8-Fc and control antibody was performed via injection into the intraperitoneal cavity, twice weekly. After 19 days of treatment, the tumors were excised and immunohistochemistry analysis was performed using standard techniques. Briefly, tumors were fixed in formalin, embedded in paraffin, and tumor sections of 4 μm thickness were cut. After deparaffinization and hydration, the tumor sections were subjected to an antigen retrieval process in Tris buffer (pH 9.5). Sections were incubated with hydrogen peroxide (Sigma-Aldrich, St Louis, Mo.) for 10 minutes to block endogenous peroxidases. Anti-Ki67 antibody (Dako, clone MIB-1) at 1:200 dilution in blocking buffer (3% NHS, 1% BSA, 0.1% Tween-20, in PBS) was added to each section and incubated for 1 hour. Slides were rinsed 3 times in PBST for 5 minutes each. Anti-mouse secondary antibody conjugated with HRP (ImmPRESS™ anti-mouse, Vector Laboratories Inc., Burlingame, Calif.) was added to the slides and incubated for 30 minutes. After multiple washes with PBST, Vector Nova Red substrate (Vector Laboratories Inc., Burlingame, Calif.) was added for localization of Ki67 antigen. The sections were treated with aqueous acetic acid for 5 minutes at room temperature. The sections were then treated with 1% alcian blue in 3% aqueous acetic acid for 30 min and washed with water. Sections were counter-stained in neutral fast red, dehydrated and mounted. Using this method, sialomucins in the tissue samples stain blue and proliferating cells are marked dark red.

The treatment of PN13 tumors with FZD8-Fc resulted in an increase in cells expressing sialomucins as compared to tumors treated with control antibody. Treatment of PN13 tumors with FZD8-Fc also resulted in a decrease in proliferating cells as denoted by expression of Ki67. FIG. 7 shows a clear decrease in the number of proliferating cells (identified by black spots) in the tissue from FZD8-Fc treated tumors. Therefore treatment of PN13 tumors with FZD8-Fc decreased cell proliferation, and increased frequency of mucin expressing differentiated cells.

Increased Muc16 Staining in Pn13 Tumors with FZD8-Fc.

Tumor sections from PN13 tumors treated with control antibody or FZD8-Fc were obtained and treated as described above. In this example, anti-Muc16 (Abcam, Cambridge, Mass.) antibody in blocking buffer at 1:200 dilution (3% NHS, 1% BSA, 0.1% Tween-20 in PBS) was added to each section and incubated for 1 hour. The bound antibody was detected using the immunohistochemistry protocol described above.

The treatment of PN13 tumors with FZD8-Fc resulted in an increase in cells expressing Muc16 as compared to tumors treated with control antibody (FIG. 8, dark staining).

Increased CK20 Staining in Pn13 Tumors with FZD8-Fc.

Tumor sections were obtained and treated as described above. In this example, anti-CK20 (clone Ks20.8, Dako, Carpinteria, Calif.) antibody in blocking buffer at 1:200 dilution (3% NHS, 1% BSA, 0.1% Tween-20, in PBS) was added to each section and incubated for 1 hour. The bound antibody was detected using the immunohistochemistry protocol described above.

The treatment of PN13 tumors with FZD8-Fc resulted in an increase in cells expressing CK20 as compared to tumors treated with control antibody (FIG. 9, dark staining).

Example 5

Inhibition of Breast Tumor Growth In Vivo by FZD8-Fc

Dissociated PE13 breast tumor cells (50,000 per animal) were injected subcutaneously into the mammary fat pads of NOD/SCID mice. Mice were monitored weekly and tumors were allowed to grow until they were approximately 106 mm$^3$. On day 27 post cell injection the mice were randomized into four treatment groups (n=10 mice/group) and treated with control antibody, FZD8-Fc (54F03), taxol or a combination of FZD8-Fc and taxol. Taxol was administered intraperitoneally at a dose of 7.5 mg/kg once a week and FZD8-Fc was administered intraperitoneally at a dose of 5 mg/kg twice a week. Tumors were measured on the days indicated in FIG. 10.

Treatment with FZD8-Fc was observed to reduce tumor growth by 20% (p=0.002) as a single agent relative to the control antibody group. In addition, treatment with the combination of FZD8-Fc and taxol reduced tumor growth by 55% (p=0.003) as compared to taxol treatment alone (FIG. 10).

Example 6

Inhibition of Colon Tumor Growth In Vivo by FZD8-Fc

The effect of multiple doses and dosing regimen of FZD8-Fc (54F03) on the growth of C28 colon tumor xenografts was analyzed. Dissociated C28 cells (10,000 per animal) were injected subcutaneously into 6-8 week old male NOD/SCID mice. On day 2, mice were randomized into 6 groups of 10 animals each. Animals were injected with either control antibody or FZD8-Fc at doses of 1.5 mg/kg (twice a week), 5 mg/kg (once and twice a week) and 15 mg/kg (once and twice a week). Administration of the antibody and FZD8-Fc was performed via injection into the intraperitoneal cavity. Tumor growth was monitored weekly and tumor measurements were initiated once tumors were palpable. Tumors were measured twice a week and tumor volume was determined as described herein.

Treatment with 15 mg/kg of FZD8-Fc (twice weekly) resulted in 83% reduction in tumor growth over treatment with the control antibody, as shown in FIG. 11A (p<0.001). Furthermore, treatment with FZD8-Fc at the lowest dose evaluated (1.5 mg/kg administered twice a week) also resulted in a 52% reduction of growth over control antibody treatment group (FIG. 11A). Thus, FZD8-Fc demonstrated anti-tumor growth activity in the OMP-C28 colon tumor model as a single agent in a dose dependent manner.

The effect of FZD8-Fc in combination with a chemotherapeutic agent on the growth of C28 colon tumor xenografts was analyzed. Dissociated C28 colon tumor cells (10,000 cells) were injected subcutaneously into 6-8 week old male NOD/SCID mice. Tumors were allowed to grow for 21 days until they reached an average volume of 128 mm$^3$. The mice were randomized (n=10 per group) and treated with FZD8-Fc (54F03) (15 mg/kg once a week), irinotecan (15 mg/kg once a week), a combination of FZD8-Fc and irinotecan or a control antibody. Administration of the FZD8-Fc, irinotecan and control antibody was performed via injection into the intraperitoneal cavity. Tumor growth was monitored and tumor volumes were measured with electronic calipers at the indicated time points. Data are expressed as mean±S.E.M.

As shown in FIG. 11B, treatment with FZD8-Fc as a single agent (-▲-) resulted in 66% reduction in tumor growth over treatment with the control antibody (-■-) (p<0.001). Furthermore, treatment with FZD8-Fc in combination with irinotecan (-•-) resulted in a 76% reduction of growth over control antibody treatment group (p<0.001), which was greater than either agent alone. Thus, FZD8-Fc demonstrated anti-tumor growth activity in the OMP-C28 colon tumor model as a single agent, as well as in combination with a chemotherapeutic agent.

Example 7

Increased Cell Differentiation of Colon Tumors by FZD8-Fc

Increased CK20 Staining in C28 Tumors with FZD8-Fc.

Control and treated tumors from the C28 xenograft study described above (Example 6) were harvested at the end of the study. The tumors were excised and immunohistochemistry analysis was performed using standard techniques. Briefly, tumors were fixed in formalin, embedded in paraffin, and tumor sections of 4 um thickness were cut. After deparaffinization and hydration, the tumor sections were subjected to an antigen retrieval process in Tris buffer (pH 9.5). Sections were incubated with hydrogen peroxide (Sigma-Aldrich, St Louis, Mo.) for 10 minutes to block endogenous peroxidases. Anti-CK20 (clone Ks20.8, Dako, Carpinteria, Calif.) antibody in blocking buffer at 1:200 dilution (3% NHS, 1% BSA, 0.1% Tween-20, in PBS) was added to each section and incubated for 1 hour. Slides were rinsed 3 times in PBST for 5 minutes each. Anti-mouse secondary antibody conjugated with HRP (ImmPRESS™ anti-mouse Ig, Vector Laboratories Inc., Burlingame, Calif.) was added to the slides and incubated for 30 minutes. After multiple washes with PBST, Vector Nova Red substrate (Vector Laboratories Inc., Burlingame, Calif.) was added for localization of CK20 antigen.

The treatment of C28 tumors with FZD8-Fc resulted in an increase in cells expressing CK20 as compared to tumors treated with control antibody (FIG. 12, dark staining).

Example 8

Anti-Tumor Activity of FZD8-Fc in Pancreatic Tumor Model

Inhibition of Tumor Growth by FZD8-Fc in PN21 Pancreatic Tumor Model.

The anti-tumor activity of FZD8-Fc (54F03) was evaluated in the PN21 pancreas tumor xenograft model. Dissociated OMP-PN21 cells (50,000 per animal) were injected subcutaneously into 6-8 week old male NOD/SCID mice. Tumor growth was monitored weekly and tumor measurements were initiated once tumors were palpable. On day 36, mice with average tumor volumes of 144 mm$^3$ were randomized into 4 groups of 9 animals each Animals were injected with control antibody, FZD8-Fc (15 mg/kg), gemcitabine (2 mg/kg) or a combination of FZD8-Fc and gemcitabine. Administration of the FZD8-Fc and gemcitabine was performed via injection into the intraperitoneal cavity, once weekly. Tumors were measured twice a week and tumor volume was determined as described herein.

Treatment with FZD8-Fc resulted in a 66% reduction in tumor growth as compared to control, as shown in FIG. 13A ($p<0.001$). Furthermore, treatment with a combination of FZD8-Fc and gemcitabine resulted in a greater reduction of tumor growth compared to either agent alone ($p=0.001$ vs. gemcitabine). Thus, FZD8-Fc demonstrated anti-tumor growth activity in the PN21 pancreas tumor model as a single agent as well as in combination with gemcitabine.

Analysis of FZD8-Fc-Treated PN21 Tumors by Limiting Dilution Assay.

As described above in Example 3, a limiting dilution assays was used to assess the effect of treatment with FZD8-Fc alone or in combination with gemcitabine on solid tumor cancer stem cells in the PN21 pancreatic tumor model.

Control and treated tumors from the PN21 xenograft study described above were harvested at the end of the study. The tumors were processed and dissociated into single cells. Single cell suspensions derived from 5 tumors of each treatment group were pooled, and the pooled samples were then incubated on ice for 30 min with antibodies that bind mouse cells selectively (α-mouse CD45-biotin 1:200 dilution and rat α-mouse H2Kd-biotin 1:100 dilution, BioLegend, San Diego, Calif.), followed by addition of streptavidin-labeled magnetic beads (Invitrogen, Carlsbad, Calif.). The mouse cells were removed with the aid of a magnet. The human cells in the suspension were harvested, counted, and stained for cell surface markers and appropriate cell doses (30, 90, and 270 cells) in FACS buffer were mixed in a 1:1 mixture with Matrigel and injected subcutaneously in NOD/SCID mice (10 mice per cell dose per treatment group). Tumors are allowed to grow for up to 4 months.

At the desired time point, the percentage of mice with detectable tumors was determined in all groups injected with treated tumor cells and compared to the percentage of mice with detectable tumors in control treated cells. For example, the number of mice injected with 125 control antibody-treated tumor cells that have detectable tumors is determined and compared to the number of mice injected with 125 FZD8-Fc treated tumor cells that have detectable tumors.

On day 72 after injection of the cells, tumor take rates in the various groups were determined and the cancer stem cell frequency was calculated using L-Calc™ software (StemCell Technologies Inc.; www.stemcell.com). As shown in FIG. 13B, treatment with FZD8-Fc reduced cancer stem cell frequency to 1:976, approximately a four-fold reduction as compared to treatment with the control antibody. In contrast, treatment with gemcitabine slightly increased cancer stem cell frequency. Significantly, treatment with a combination of FZD8-Fc and gemcitabine reduced the cancer stem cell frequency to 1:5472, almost a 25-fold reduction as compared to treatment with control. Surprisingly, treatment with the combination of FZD8-Fc and gemcitabine reduced the cancer stem cell frequency approximately 5.5-fold greater than FZD8-Fc treatment alone and despite the fact that gemcitabine appeared to actually increase the cancer stem cell frequency.

Example 9

Increased Cell Differentiation of PN21 Tumors with FZD8-Fc

The cell differentiation capability of FZD8-Fc was also evaluated in the OMP-PN21 pancreas tumor xenograft model. PN21 tumors from studies described in Example 8 were harvested and fixed in formalin, embedded in paraffin, and tumor sections of 4 μm thickness were cut. After deparaffinization and hydration, the tumor sections were subjected to an antigen retrieval process in Tris buffer (pH 9.5). Sections were incubated with hydrogen peroxide (Sigma-Aldrich, St Louis, Mo.) for 10 minutes to block endogenous peroxidases. Anti-Ki67 antibody (clone MIB-1, Dako, Carpinteria, Calif.) in blocking buffer (3% NHS, 1% BSA, 0.1% Tween-20 in PBS) at 1:200 dilution was added to each section and incubated for 1 hour. Slides were rinsed 3 times in PBST for 5 minutes each. Anti-mouse secondary antibody conjugated with HRP (ImmPRESS™ anti-mouse, Vector Laboratories Inc., Burlingame, Calif.) was added to the slides and incubated for 30 minutes. After multiple washes with PBST, Vector Nova Red substrate (Vector Laboratories Inc., Burlingame, Calif.) was added for localization of Ki67 antigen. The sections were treated with aqueous acetic acid for 5 minutes at room temperature. The sections were then treated with 1% alcian blue in 3% aqueous acetic acid for 30 minutes and washed with water. Sections were counter-stained in neutral fast red, dehydrated and mounted. Using this method, sialomucins in the tissue samples stain blue and the background appears as pink or red.

The treatment of PN21 tumors with FZD8-Fc resulted in an increase in cells expressing sialomucins as compared to tumors treated with control antibody (FIG. 14, dark gray staining) The treatment of PN21 tumors with FZD8-Fc or FZD-Fc in combination with gemcitabine resulted in an increase in cells expressing sialomucins as compared to tumors treated with control antibody or gemcitabine alone (FIG. 15). Treatment of PN21 tumors with FZD8-Fc or the combination of FZD8-Fc and gemcitabine also resulted in a decrease in proliferating cells denoted by expression of Ki67. Therefore treatment of PN21 tumors with FZD8-Fc, either alone or in combination with gemcitabine, decreased cell proliferation, and increased frequency of mucin-expressing differentiated cells.

Example 10

Production of FZD8-Fc Variants

Production of FZD8-Fc Variants.

FZD8-Fc variants were produced at DNA2.0 (Menlo Park, Calif.). DNA2.0 synthesized and assembled short single-stranded oligonucleotides to produce the different FZD8-Fc variant proteins, 54F05, 54F08, 54F09, 54F12, 54F13, 54F14, 54F15, 54F16, 54F17, 54F18, 54F19, 54F20, 54F21 and 54F22. The assembled oligonucleotides were subsequently cloned and sequence verified.

Example 11

Inhibition of Wnt Signaling by FZD8-Fc Variants

The ability of the FZD8-Fc variants to block or inhibit activation of the Wnt signaling pathway was determined in vitro using a luciferase reporter assay. STF293 cells were cultured in DMEM supplemented with antibiotics and 10% FCS. The STF293 cells are stably transfected with a reporter vector containing seven copies of the TCF transcriptional response element linked to a promoter upstream of a firefly luciferase reporter gene. This construct measures the activity of the canonical Wnt signaling pathway. The cells were added to cultures plates at 10,000 cells per well. After an overnight incubation the FZD8-Fc variants or control mouse JAG1-Fc were added in combination with Wnt3a-conditioned medium. The FZD8-Fc variants and JAG1-Fc were used at concentrations of 20, 4, 0.8, 0.16, 0.03, 0.006, 0.0012, and 0.0003 ug/ml. The cells were incubated in 25% Wnt3A-conditioned medium that had been prepared from L cells that stably express Wnt3a. After overnight incubation (approximately 18 hrs), luciferase levels were measured using a Steady-Glo® luciferase assay kit (Promega, Madison, Wis.).

The blocking activity of the FZD8-Fc variants was determined and is presented in Table 3 as relative activity as compared to the same reference standard run in each assay which was set at 100%.

TABLE 3

| FZD8-Fc Variant | % Relative Activity |
|---|---|
| 54F03 | 107, 143 |
| 54F05 | 167 |
| 54F08 | 137 |
| 54F09 | 156, 157 |
| 54F12 | 52 |
| 54F13 | 103 |
| 54F14 | 125 |
| 54F15 | 128 |
| 54F16 | 125 |

Example 12

Pharmacokinetics of FZD8-Fc Variants in Rats

The pharmacokinetics of several FZD8-Fc variants were assessed in rats in a two week pharmacokinetics (PK) study. The FZD8-Fc variants evaluated were 54F03, 54F09, 54F12, 54F13, 54F15 and 54F16. Sprague Dawley rats, five males in each group, were dosed with FZD8-Fc variants via the tail vein at 10 mg/kg and followed for two weeks with samples collected at time points 1, 24, 48, 72, 96, 168, 240, and 336 hours. At each time point, 1 ml of blood was collected into potassium-EDTA tubes and centrifuged. The plasma supernatants were collected and frozen until the samples were analyzed.

The level of FZD8-Fc variant protein present in the plasma at each time point was quantified and the half-life of each FZD8-Fc variant was calculated. The half-life of the FZD8-Fc variants is shown in Table 4.

TABLE 4

| FZD8-Fc Variant | $t_{1/2}$ in hours | Fc Region |
|---|---|---|
| 54F03 | 162 | IgG1 |
| 54F09 | 136 | IgG1 |
| 54F12 | 152 | IgG2 |
| 54F13 | 268 | IgG2 |
| 54F15 | 109 | IgG1 |
| 54F16 | 154 | IgG1 |

Example 13

Pharmacokinetics of FZD8-Fc Variants in Cynomolgus Monkeys

Four young adult/adult male naïve cynomolgus monkeys were randomly divided into two groups of two, and administered an intravenous (IV) bolus of FZD-Fc variant 54F15 or variant 54F16 at a dose of 30 mg/kg. Twice daily (a.m. and p.m.) animals were observed for mortality and signs of pain and distress. Cageside observations for general health and appearance were done once daily. On the day of dosing, each animal was observed at approximately 1 and 4 hours post-dose for mortality and signs of pain and distress. Any unusual observations noted throughout the duration of the study were recorded. Body weights were taken on the day of dose administration and at the end of blood collection. Blood (approximately 0.5 ml) was collected from a femoral vein via syringe and needle and transferred into tubes containing EDTA K3 anticoagulant pre-dose and at 1, 6, 12, 24, 48, 72, 96, 168, 240, and 336 hours post-dose for PK analysis. In addition, blood (approximately 0.5 ml) was collected from a femoral vein via syringe and needle and transferred into tubes containing no anticoagulant pre-dose and at 336 hours post-dose for anti-drug antibody (ADA) analysis. Plasma supernatants were collected and frozen until the samples were analyzed. HTRF (homogeneous time resolved fluorescence) immunoassays were performed to determine the FZD-Fc concentration in animal plasma samples for PK analysis and the concentration of anti-drug antibody in serum. FZD-Fc concentration in plasma versus time was analyzed by non-compartmental analysis (NCA) with Phoenix™ WinNonlin® Version 6.0, using a bolus IV administration model.

The level of FZD8-Fc variants present in the plasma at each time point was quantified (FIG. 16) and the half-life of FZD8-Fc variants 54F15 and 54F16 was calculated. As shown in Table 5, the half-life of FZD8-Fc variant 54F15 was estimated to be 102 hours at 30 mg/kg and the half-life of FZD-Fc8 variant 54F16 was estimated to be 137 hours at 30 mg/kg.

TABLE 5

| Animal ID | $T_{1/2\lambda z}$ (far) | $AUC_{0-last}$ (ng * hr/ml) | $AUC_{0-\infty}$ (ng * hr/ml) | AUC % Extrap | Vz (ml) | Cl (ml/hr) |
|---|---|---|---|---|---|---|
| FZD8-Fc 54F15 | | | | | | |
| C43064 | 102.3 | 28642771.4 | 31231858.7 | 8.3 | 141.7 | 0.960 |
| C43061 | 102.5 | 31904918.2 | 34846234.1 | 8.4 | 127.3 | 0.861 |
| Mean | 102.4 | 30273845 | 33039046 | 8.35 | 134.5 | 0.9105 |
| FZD8-Fc 54F16 | | | | | | |
| C43066 | 139.0 | 29088083.0 | 35470395.6 | 18.0 | 169.6 | 0.846 |
| C43076 | 134.1 | 35934159.0 | 43449944.6 | 17.3 | 133.6 | 0.690 |
| Mean | 136.6 | 32511121 | 39460170 | 17.65 | 151.6 | 0.768 |

Example 14

Inhibition of Colon Tumor Growth In Vivo by FZD8-Fc Variants

Dissociated C28 colon tumor cells (10,000 cells) were injected subcutaneously into 6-8 week old male NOD/SCID mice. Tumors were allowed to grow for 28 days until they reached an average volume of 145 mm³. The mice were randomized (n=9 per group) and treated with FZD8-Fc variants or a control antibody at a dose of 15 mg/kg twice a week. Administration of the FZD8-Fc variants and control antibody was performed via injection into the intraperitoneal cavity. Tumor growth was monitored and tumor volumes were measured with electronic calipers at the indicated time points. Data are expressed as mean±S.E.M.

Variants 54F12 and 54F13 had no apparent effect upon tumor growth, with tumor volumes substantially the same as the tumors in mice treated with control antibody. In contrast, treatment with variants 54F03, 54F09, 54F15 and 54F16 resulted in approximately 56%, 70%, 64% and 70% reduction (respectively) in tumor growth as compared to treatment with the control antibody, as shown in FIG. 17. Thus, the anti-tumor growth activity of the FZD8-Fc variants appeared to be affected by the amino acid sequence at the junction between the FZD8 portion and the Fc portion. In addition, anti-tumor growth activity appeared to be affected by the source of the Fc region, as both variants that are IgG2 fusion proteins (54F12 and 54F13), did not inhibit tumor growth in this model.

Example 15

Inhibition of Pancreatic Tumor Growth In Vivo by FZD8-Fc Variants

Dissociated PN4 pancreatic tumor cells (10,000 cells) were injected subcutaneously into 6-8 week old male NOD/SCID mice. Tumors were allowed to grow for 36 days until they reached an average volume of 112 mm³. The mice were randomized (n=10 per group) and treated with FZD8-Fc variants or a control antibody at a dose of 15 mg/kg twice a week. Administration of the FZD8-Fc variants and control antibody was performed via injection into the intraperitoneal cavity. Tumor growth was monitored and tumor volumes were measured with electronic calipers at the indicated time points. Data are expressed as mean±S.E.M.

Variants 54F12 and 54F13 reduced tumor growth less than 20% as compared with tumors in mice treated with control antibody. Treatment with FZD8-Fc variants 54F03, 54F09, 54F15 and 54F16 reduced tumor growth approximately 20% to 60% as compared to treatment with the control antibody. As shown in FIG. 18, variants 54F09 and 54F16 reduced tumor growth by the greatest amount, 45% (p<0.001) and 60% (p<0.001), respectively. Thus, the anti-tumor growth activity of the FZD8-Fc variants appeared to be affected by the amino acid sequence at the junction between the FZD8 portion and the Fc portion. As seen in the Example 14, anti-tumor growth activity also appeared to be affected by the source of the Fc region, as both variants that are IgG2 fusion proteins (54F12 and 54F13) had weaker anti-tumor activity than the FZD8-Fc variants that are IgG1 fusion proteins.

Pancreatic tumor cells from the tumor-bearing mice described above were harvested and minced into approximately 1 mm³ fragments, followed by enzymatic digestion at 1 gram per 10 ml of 300 µg/ml collagenase and 200 U/ml DNase I for 2 hours at 37° C./5% $CO_2$ with intermittent mixing with a 10 ml pipet to disperse cells. Digestion was stopped by adding an equal volume of FACS buffer (1x Hanks Buffered Saline Solution (HBSS), 2% heat-inactivated Fetal Calf Serum (FCS) and 2 mM HEPES pH 7.4). Cells were filtered through 40 µm nylon filters and collected by centrifugation at 150×g for 5 minutes. Red blood cells were lysed in a hypotonic buffer containing ammonium chloride for 2 minutes on ice, and the cells were washed again with excess FACS buffer, and resuspended with FACS buffer at $1 \times 10^7$ cells/ml.

The freshly prepared single cell suspensions were stained for 20 minutes on ice with biotinylated anti-mouse H-2Kd (clone SF1-1.1, Biolegend, San Diego, Calif.) at 5 µg/ml, biotinylated anti-mouse CD45 (30-F11, Biolegend) at 2.5 µg/ml, and streptavidin-PerCP-Cy5.5 (eBioscience, San Diego, Calif.) at 1:200 dilution. Unbound antibody was removed by washing twice with 10 volume of FACS buffer. For analysis of human cell surface markers, the single tumor cell suspension was stained with anti-ESA-FITC (Miltenyi Biotec, Auburn, Calif.) at 1:50 dilution, anti-human CD44-PE-Cy7 (eBioscience, San Diego, Calif.) at 1:100 dilution, and anti-human CD201-PE (BD Biosciences) at 1:5 dilution. The cells are washed, and resuspended in FACS buffer containing 2.5 ug/ml of 4'-6-Diamidino-2-phenylindole (DAPI). Cells stained with a single fluorescent color were used for instrument calibration. Any remaining mouse cells (positive for H-2Kd and CD45) and dead cells (DAPI-positive) were excluded during cell sorting. Cell doublets and clumps were excluded using doublet discrimination gating.

As shown in FIG. 19, treatment of tumor-bearing mice with FZD8-Fc variants 54F03 and 54F16 decreased the percentage of $CD44^{hi}$ cells as compared to mice treated with the control antibody. Although the percentage of $CD201^+$ $CD44^+$ cells was small, treatment of tumor-bearing mice with FZD8-Fc variants 54F03 and 54F16 decreased the percentage of $CD201^+CD44^+$ cells as compared to mice treated with the control antibody. CD44 has been shown to be to marker of tumorigenic cells (e.g. cancer stem cells). In addition, in some embodiments, cells that are $CD44^{hi}CD201^+$ have been found to be more tumorigenic than $CD44^{hi}CD201^-$ cells. Thus, it is important that FZD8-Fc variants were capable of decreasing the percentage of both $CD44^{hi}$ and $CD44^{hi}CD201^+$ cell populations, thereby decreasing the percentage or number of tumorigenic cells in the treated mice.

Example 16

Characterization of N-Termini

The correct signal sequence cleavage site in the FZD8 protein is predicted to be between amino acid 25 (an alanine)

and amino acid 26 (an alanine); cleavage at this site leaves an N-termini of ASA. Analysis by mass spectrometry was used to determine the mass of FZD8-Fc proteins as compared to the theoretical mass of the FZD8-Fc protein cleaved at the predicted site.

Additional FZD8-Fc variants with modified signal sequences were produced at DNA2.0 (Menlo Park, Calif.) as described above. DNA2.0 synthesized and assembled short single-stranded oligonucleotides to produce the FZD8-Fc variant proteins, 54F23 to 54F35. The assembled oligonucleotides were subsequently cloned and sequence verified.

Plasmid DNA of each FZD8-Fc variant was prepared using QIAGEN maxi-prep kits following the manufacturer's protocol. Expression of each variant was done using FreeStyle™ MAX reagent (Life Technologies) and 293FS cells. Cells were grown to log phase and diluted to $1 \times 10^6$ cell/ml. For each reaction, 315 ug of plasmid DNA was diluted into 5 ml of OptiMEM Pro. In a different tube, 315 ul of FreeStyle™ MAX reagent was diluted into 5 ml of OptiMem Pro. Plasmid DNA was complexed with the FreeStyle™ MAX reagent by adding the diluted reagent dropwise to the DNA, followed by an incubation of 15 minutes at room temperature. The DNA-reagent complex was then added to 250 ml of 293FS cells. Expression reactions were allowed to grow for 7-10 days, at which time, they were harvested by centrifugation and filtration. Each Fzd8-Fc variant was purified by affinity purification using a 5 ml HiTrap MAbSelect SURE column. Briefly, harvested media were passed through columns that had been equilibrated with binding buffer. The columns were washed with binding buffer to remove unbound material, and then FZD8-Fc protein was eluted with elution buffer. Eluted samples were then dialyzed into a buffer suitable for mass spectrometry.

Approximately 250 μg of each FZD8-Fc sample was reduced with Tris (2-carboxyethyl) phosphine (TCEP) for 30 minutes at 37° C. to separate heavy and light chains of the antibody. Reduced samples were then alkylated by treatment with iodoacetamide for 30 minutes at 37° C. Samples were passed over NAP-5 columns (GE Health Care) to change the buffer to 10 mM Tris-HCL (pH 7.4). Buffer exchange was followed deglycosylation with endoglycosidase PNGase F. Samples were incubated overnight at 37° C. at a ratio of 1:200 (enzyme:sample). The reactions were stopped by addition of acid. The reduced, alkylated, and deglycosylated FZD8-Fc samples were loaded into vials for liquid chromatography-mass spectrometry (LC/MS) analysis using a Waters UPLC™ and electrospray-QToF mass spectrometer. Mass calibration of each sample analysis using cesium trifluoroacetic acid ion clusters was conducted with a Waters LockSpray™ dual electrospray ion source.

Figure 20A:
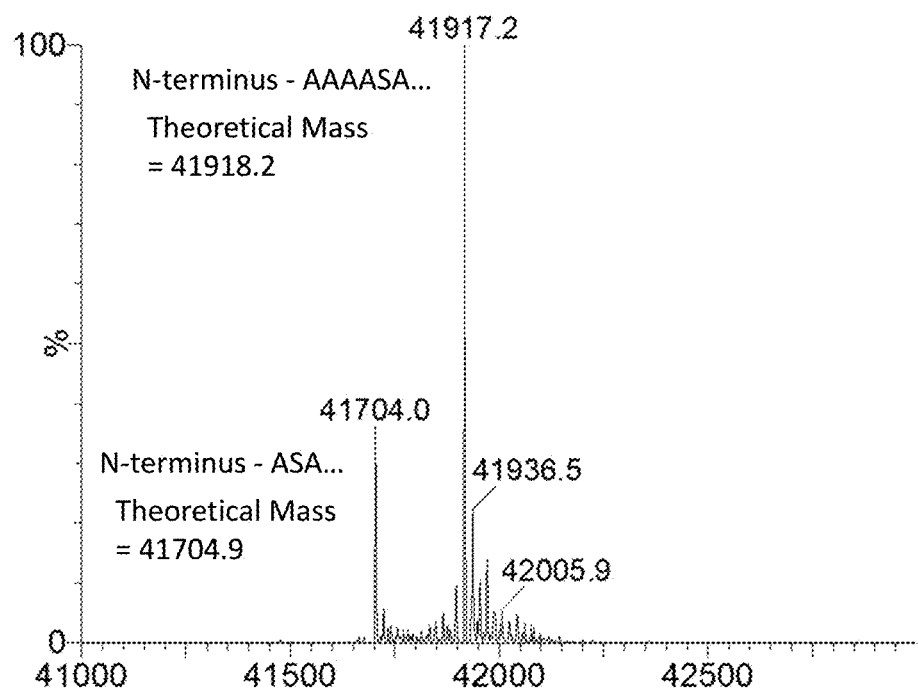

As shown in FIG. 20A, a FZD8-Fc protein (54F16) with a signal sequence that was the same sequence as the native sequence was produced as a heterogeneous mixture in regard to the N-terminal sequence. A proportional of the protein present in sample was equivalent in mass to a protein cleaved at amino acids 25 and 26 (peak at 41704.0) with an N-terminal sequence of ASA. However, greater than 50% of the protein was present in a form with a different mass (peak at 41918.2). This peak most likely represents a protein cleaved at amino acids 22 and 23; cleavage at this site leaves an N-terminal sequence of AAAASA (SEQ ID NO:76).

Figure 20B:
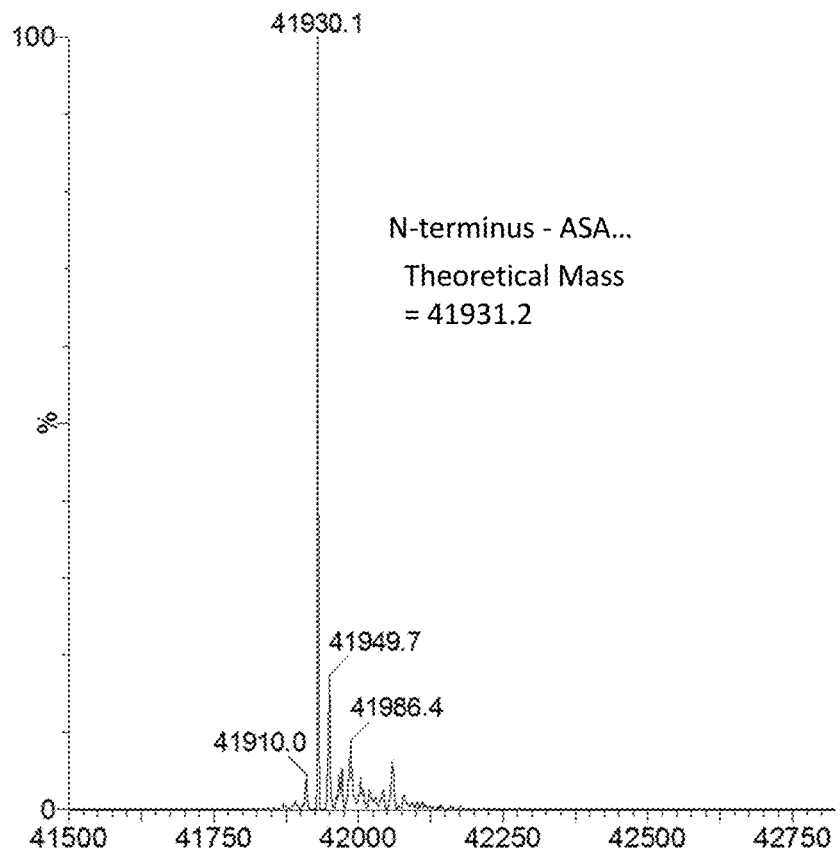
Figure 20C:
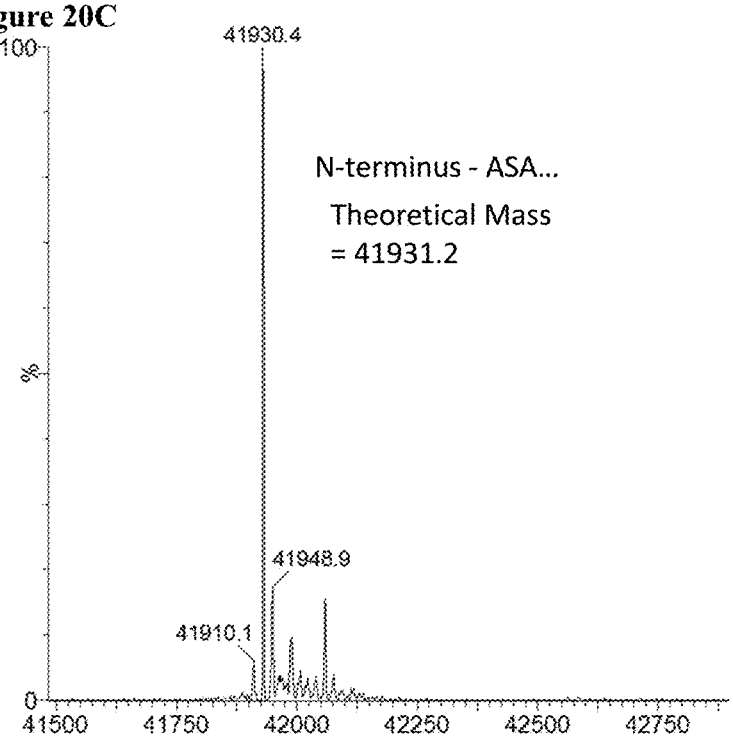
Figure 20D:
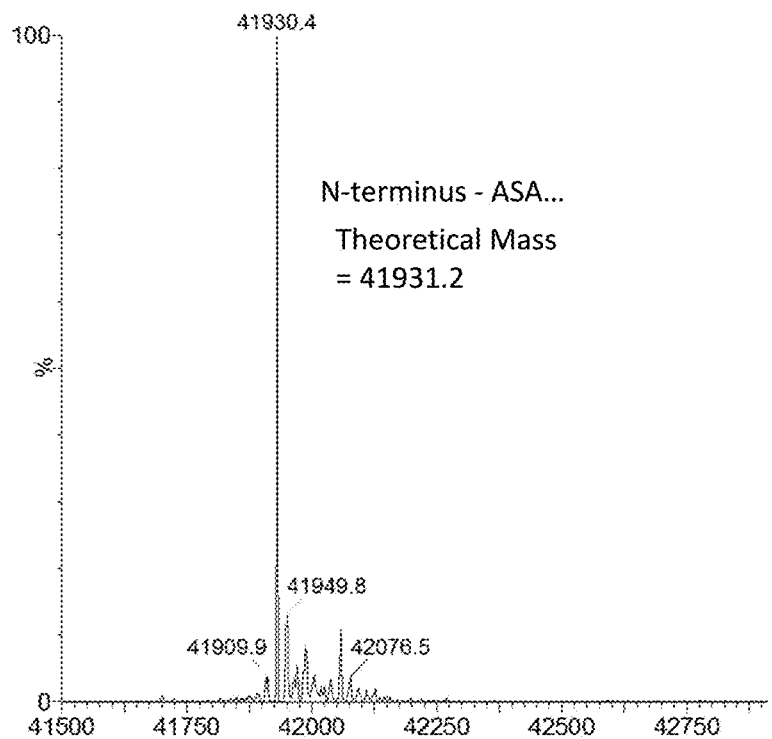
Figure 20E:
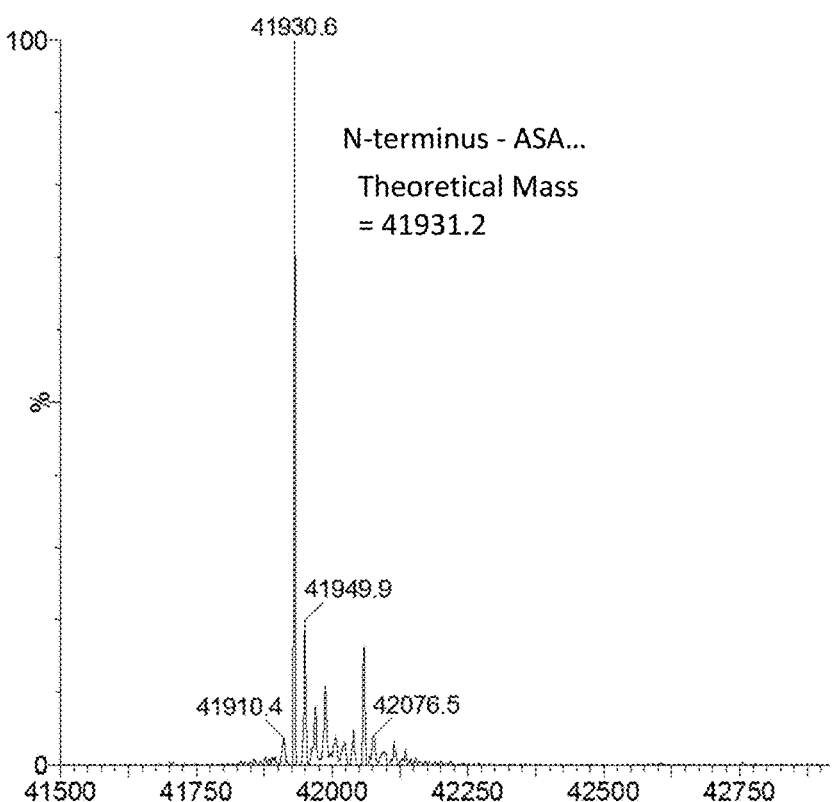

FZD8-Fc variants with signal sequences SEQ ID NO:68 to SEQ ID NO:74 were generated, purified from cell culture, and analyzed by mass spectrometry as described above. It was observed that variants with signal sequences SEQ ID NO:70 to SEQ ID NO:74 produced an almost completely homogeneous protein sample (several representative results are shown in FIGS. 20B-20E). FZD8-Fc variant 54F26 which comprises SEQ ID NO:53 with signal sequence SEQ ID NO:71 was present predominantly (greater than 95%) as a protein cleaved at amino acids 25 and 26 (peak 41930.1) with an N-terminal sequence of ASA (FIG. 20B). Similar results were also seen with a variant comprising SEQ ID NO:53 and signal sequence SEQ ID NO:72 (54F28, FIG. 20C), a variant comprising SEQ ID NO:53 and signal sequence SEQ ID NO:73 (54F30, FIG. 20D) and a variant comprising SEQ ID NO:53 and signal sequence SEQ ID NO:74 (54F32, FIG. 20E). Similar results were observed with proteins produced from transient and stable transfections.

Example 17

Inhibition of Colon Tumor Growth In Vivo by FZD8-Fc Variants

Dissociated C28 colon tumor cells (10,000 cells) were injected subcutaneously into 6-8 week old male NOD/SCID mice. Tumors were allowed to grow for 56 days until they reached an average volume of 175 mm$^3$. The mice were randomized (n=10 per group) and treated with FZD8-Fc constructs 54F03, 54F23, 54F26, or a control antibody at a dose of 15 mg/kg twice a week. Administration of the FZD8-Fc variants and control antibody was performed via injection into the intraperitoneal cavity. Tumor growth was monitored and tumor volumes were measured with electronic calipers at the indicated time points. Data are expressed as mean±S.E.M.

FZD8-Fc variants 54F23 and 54F26 are produced as predominantly a homogenous protein with an N-terminus of amino acids ASA, while 54F03 is produced as a heterogeneous protein mixture with N-termini of amino acids ASA and AAAASA. As shown in FIG. 21 treatment with FZD8-Fc variants 54F03, 54F23, and 54F26 reduced tumor growth 48%, 57% and 52%, respectively, as compared to treatment with the control antibody after three weeks of treatment.

All publications, patents, patent applications, internet sites, and accession numbers/database sequences (including both polynucleotide and polypeptide sequences) cited herein are hereby incorporated by reference in their entirety for all purposes to the same extent as if each individual publication, patent, patent application, internet site, or accession number/database sequence were specifically and individually indicated to be so incorporated by reference.

```
SEQUENCES
FZD8-Fc amino acid sequence-variant 54F03
(without predicted signal sequence; the "GRA" linker
sequence between the FZD8 sequence and the Fc
sequence of the fusion protein is underlined)
                                                    (SEQ ID NO: 1)
ASAKELACQEITVPLCKGIGYNYTYMPNQFNHDTQDEAGLEVHQFWPLVEIQCSPDLKFF

LCSMYTPICLEDYKKPLPPCRSVCERAKAGCAPLMRQYGFAWPDRMRCDRLPEQGNPDTL
```

CMDYNRTDLTT<u>GRA</u>DKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKEYKCKVSNK

ALPAPIEKTISKAKGQPREPQVYTLPPSRDELTKNQVSLTCLVKGFYPSDIAVEWESNGQ

PENNYKTTPPVLDSDGSFFLYSKLTVDKSRWQQGNVFSCSVMHEALHNHYTQKSLSLSPG

K

FZD8-Fc coding sequence (nucleotides encoding FZD8-derived
sequences are underlined)
(SEQ ID NO: 2)
<u>ATGGAGTGGGGTTACCTGTTGGAAGTGACCTCGCTGCTGGCCGCCTTGGCGCTGCTGCAG</u>

<u>CGCTCTAGCGGCGCTGCGGCCGCCTCGGCCAAGGAGCTGGCATGCCAAGAGATCACCGTG</u>

<u>CCGCTGTGTAAGGGCATCGGCTACAACTACACCTACATGCCCAATCAGTTCAACCACGAC</u>

<u>ACGCAAGACGAGGCGGGCCTGGAGGTGCACCAGTTCTGGCCGCTGGTGGAGATCCAGTGC</u>

<u>TCGCCCGATCTCAAGTTCTTCCTGTGCAGCATGTACACGCCCATCTGCCTAGAGGACTAC</u>

<u>AAGAAGCCGCTGCCGCCCTGCCGCTCGGTGTGCGAGCGCGCCAAGGCCGGCTGCGCGCCG</u>

<u>CTCATGCGCCAGTACGGCTTCGCCTGGCCCGACCGCATGCGCTGCGACCGGCTGCCCGAG</u>

<u>CAAGGCAACCCTGACACGCTGTGCATGGACTACAACCGCACCGACCTAACCACCGGGCGC</u>

GCCGACAAAACTCACACATGCCCACCGTGCCCAGCACCTGAACTCCTGGGGGGACCGTCA

GTCTTCCTCTTCCCCCCAAAACCCAAGGACACCCTCATGATCTCCCGGACCCCTGAGGTC

ACATGCGTGGTGGTGGACGTGAGCCACGAAGACCCTGAGGTCAAGTTCAACTGGTACGTG

GACGGCGTGGAGGTGCATAATGCCAAGACAAAGCCGCGGGAGGAGCAGTACAACAGCACG

TACCGTGTGGTCAGCGTCCTCACCGTCCTGCACCAGGACTGGCTGAATGGCAAGGAGTAC

AAGTGCAAGGTCTCCAACAAAGCCCTCCCAGCCCCCATCGAGAAAACCATCTCCAAAGCC

AAAGGGCAGCCCCGAGAACCACAGGTGTACACCCTGCCCCCATCCCGGGATGAGCTGACC

AAGAACCAGGTCAGCCTGACCTGCCTGGTCAAAGGCTTCTATCCCAGCGACATCGCCGTG

GAGTGGGAGAGCAATGGGCAGCCGGAGAACAACTACAAGACCACGCCTCCCGTGCTGGAC

TCCGACGGCTCCTTCTTCCTCTACAGCAAGCTCACCGTGGACAAGAGCAGGTGGCAGCAG

GGGAACGTCTTCTCATGCTCCGTGATGCATGAGGCTCTGCACAACCACTACACACAGAAG

AGCCTCTCCCTGTCTCCGGGTAAATGA

Minimum FZD and SFRP Fri domain sequences
h-FZD1 amino acids 116-227
(SEQ ID NO: 3)
CQPISIPLCTDIAYNQTIMPNLLGHTNQEDAGLEVHQFYPLVKVQCSAELKFFLCSMYAP

VCTVLEQALPPCRSLCERARQGCEALMNKFGFQWPDTLKCEKFPVHGAGELC h-FZD2 amino acids 39-150
(SEQ ID NO: 4)
CQPISIPLCTDIAYNQTIMPNLLGHTNQEDAGLEVHQFYPLVKVQCSPELRFFLCSMYAP

VCTVLEQAIPPCRSICERARQGCEALMNKFGFQWPERLRCEHFPRHGAEQIC h-FZD3 amino acids 28-133
(SEQ ID NO: 5)
CEPITLRMCQDLPYNTTFMPNLLNHYDQQTAALAMEPFHPMVNLDCSRDFRPFLCALYAP

ICMEYGRVTLPCRRLCQRAYSECSKLMEMFGVPWPEDMECSRFPDC h-FZD4 amino acids 48-161

```
                                                          (SEQ ID NO: 6)
CDPIRISMCQNLGYNVTKMPNLVGHELQTDAELQLTTFTPLIQYGCSSQLQFFLCSVYVP

MCTEKINIPIGPCGGMCLSVKRRCEPVLKEFGFAWPESLNCSKFPPQNDHNHMC h-FZD5 amino acids 33-147
                                                          (SEQ ID NO: 7)
CQEITVPMCRGIGYNLTHMPNQFNHDTQDEAGLEVHQFWPLVEIQCSPDLRFFLCSMYTP

ICLPDYHKPLPPCRSVCERAKAGCSPLMRQYGFAWPERMSCDRLPVLGRDAEVLC h-FZD6 amino acids 24-129
                                                          (SEQ ID NO: 8)
CEPITVPRCMKMAYNMTFFPNLMGHYDQSIAAVEMEHFLPLANLECSPNIETFLCKAFVP

TCIEQIHVVPPCRKLCEKVYSDCKKLIDTFGIRWPEELECDRLQYC h-FZD7 amino acids 49-160
                                                          (SEQ ID NO: 9)
CQPISIPLCTDIAYNQTILPNLLGHTNQEDAGLEVHQFYPLVKVQCSPELRFFLCSMYAP

VCTVLDQAIPPCRSLCERARQGCEALMNKFGFQWPERLRCENFPVHGAGEIC h-FZD8 amino acids 35-148
                                                         (SEQ ID NO: 10)
CQEITVPLCKGIGYNYTYMPNQFNHDTQDEAGLEVHQFWPLVEIQCSPDLKFFLCSMYTP

ICLEDYKKPLPPCRSVCERAKAGCAPLMRQYGFAWPDRMRCDRLPEQGNPDTLC h-FZD9 amino acids 39-152
                                                         (SEQ ID NO: 11)
CQAVEIPMCRGIGYNLTRMPNLLGHTSQGEAAAELAEFAPLVQYGCHSHLRFFLCSLYAP

MCTDQVSTPIPACRPMCEQARLRCAPIMEQFNFGWPDSLDCARLPTRNDPHALC h-FZD10 amino acids 34-147
                                                         (SEQ ID NO: 12)
CQPIEIPMCKDIGYNMTRMPNLMGHENQREAAIQLHEFAPLVEYGCHGHLRFFLCSLYAP

MCTEQVSTPIPACRVMCEQARLKCSPIMEQFNFKWPDSLDCRKLPNKNDPNYLC h-SFRP1 amino acids 57-165
                                                         (SEQ ID NO: 13)
CVDIPADLRLCHNVGYKKMVLPNLLEHETMAEVKQQASSWVPLLNKNCHAGTQVFLCSLF

APVCLDRPIYPCRWLCEAVRDSCEPVMQFFGFYWPEMLKCDKFPEGDVC h-SFRP2 amino acids 40-152
                                                         (SEQ ID NO: 14)
CKPIPANLQLCHGIEYQNMRLPNLLGHETMKEVLEQAGAWIPLVMKQCHPDTKKFLCSLF

APVCLDDLDETIQPCHSLCVQVKDRCAPVMSAFGFPWPDMLECDRFPQDNDLC h-SFRP3 amino acids 35-147
                                                         (SEQ ID NO: 15)
CEPVRIPLCKSLPWNMTKMPNHLHHSTQANAILAIEQFEGLLGTHCSPDLLFFLCAMYAP

ICTIDFQHEPIKPCKSVCERARQGCEPILIKYRHSWPENLACEELPVYDRGVC h-SFRP4 amino acids 24-136
                                                         (SEQ ID NO: 16)
CEAVRIPMCRHMPWNITRMPNHLHHSTQENAILAIEQYEELVDVNCSAVLRFFFCAMYAP

ICTLEFLHDPIKPCKSVCQRARDDCEPLMKMYNHSWPESLACDELPVYDRGVC h-SFRP5 amino acids 53-162
                                                         (SEQ ID NO: 17)
CLDIPADLPLCHTVGYKRMRLPNLLEHESLAEVKQQASSWLPLLAKRCHSDTQVFLCSLF

APVCLDRPIYPCRSLCEAVRAGCAPLMEAYGFPWPEMLHCHKFPLDNDLC

Fc sequences
Human IgG$_1$ Fc region
                                                         (SEQ ID NO: 18)
DKTHTCPPCPAPELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPAPIEKTISKAK
```

-continued

GQPREPQVYTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK

Human IgG₁ Fc region
(SEQ ID NO: 42)
KSSDKTHTCPPCPAPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKALPAPIEKTIS

KAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPGK

Human IgG₁ Fc region
(SEQ ID NO: 43)
EPKSSDKTHTCPPCPAPELLGGPSVFLFPPKPKDTLMISRTPEVTCVVVDVSHEDPEVKF

NWYVDGVEVHNAKTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWESNGQPENNYKTTP

PVLDSDGSFFLYSKLTVDKSRWQQGNVFSCSVMHEALHNHYTQKSLSLSPGK

Human IgG₂ Fc region
(SEQ ID NO: 44)
CVECPPCPAPPVAGPSVFLFPPKPKDTLMISRTPEVTCVVVDVSHEDPEVQFNWYVDGVE

VHNAKTKPREEQFNSTFRVVSVLTVVHQDWLNGKEYKCKVSNKGLPAPIEKTISKTKGQP

REPQVYTLPPSREEMTKNQVSLTCLVKGFYPSDIAVEWESNGQPENNYKTTPPMLDSDGS

FFLYSKLTVDKSRWQQGNVFSCSVMHEALHNHYTQKSLSLSPGK

FZD Fri domain sequences
Human FZD4 Fri domain (predicted signal sequence underlined)
(SEQ ID NO: 19)
MLAMAWRGAGPSVPGAPGGVGLSLGLLLQLLLLLGPARGFGDEEERRCDPIRISMCQNLG

YNVTKMPNLVGHELQTDAELQLTTFTPLIQYGCSSQLQFFLCSVYVPMCTEKINIPIGPC

GGMCLSVKRRCEPVLKEFGFAWPESLNCSKFPPQNDHNHMCMEGPGDEEV

Human FZD5 Fri domain (predicted signal sequence underlined)
(SEQ ID NO: 20)
MARPDPSAPPSLLLLLLAQLVGRAAAASKAPVCQEITVPMCRGIGYNLTHMPNQFNHDTQ

DEAGLEVHQFWPLVEIQCSPDLRFFLCSMYTPICLPDYHKPLPPCRSVCERAKAGCSPLM

RQYGFAWPERMSCDRLPVLGRDAEVLCMDYNRSEATT

Human FZD8 Fri domain (predicted signal sequence underlined)
(SEQ ID NO: 21)
MEWGYLLEVTSLLAALALLQRSSGAAAASAKELACQEITVPLCKGIGYNYTYMPNQFNHD

TQDEAGLEVHQFWPLVEIQCSPDLKFFLCSMYTPICLEDYKKPLPPCRSVCERAKAGCAP

LMRQYGFAWPDRMRCDRLPEQGNPDTLCMDYNRTDLTT

Human FZD1 Fri domain amino acid sequence without
predicted signal sequence
(SEQ ID NO: 32; amino acids 87-237 of SEQ ID NO: 27)
QQPPPPPQQQQSGQQYNGERGISVPDHGYCQPISIPLCTDIAYNQTIMPNLLGHTNQEDA

GLEVHQFYPLVKVQCSAELKFFLCSMYAPVCTVLEQALPPCRSLCERARQGCEALMNKFG

FQWPDTLKCEKFPVHGAGELCVGQNTSDKGT

Human FZD2 Fri domain amino acid sequence without
predicted signal sequence
        SEQ ID NO: 33; amino acids 24-159 of SEQ ID NO: 28)
QFHGEKGISIPDHGFCQPISIPLCTDIAYNQTIMPNLLGHTNQEDAGLEVHQFYPLVKVQ

CSPELRFFLCSMYAPVCTVLEQAIPPCRSICERARQGCEALMNKFGFQWPERLRCEHFPR

HGAEQICVGQNHSEDG

Human FZD3 Fri domain amino acid sequence without
predicted signal sequence
        (SEQ ID NO: 34; amino acids 23-143 of SEQ ID NO: 29)
HSLFSCEPITLRMCQDLPYNTTFMPNLLNHYDQQTAALAMEPFHPMVNLDCSRDF

RPFLCALYAPICMEYGRVTLPCRRLCQRAYSECSKLMEMFGVPWPEDMECSRFPDCDEPY

PRLVDL

Human FZD4 Fri domain amino acid sequence without
predicted signal sequence e
        (SEQ ID NO: 35; amino acids 40-170 of SEQ ID NO: 22)
FGDEEERRCDPIRISMCQNLGYNVTKMPNLVGHELQTDAELQLTTFTPLIQYGCSSQLQF

FLCSVYVPMCTEKINIPIGPCGGMCLSVKRRCEPVLKEFGFAWPESLNCSKFPPQNDHNH

MCMEGPGDEEV

Human FZD5 Fri domain amino acid sequence without
predicted signal sequence
        (SEQ ID NO: 36; amino acids 27-157 of SEQ ID NO: 23)
ASKAPVCQEITVPMCRGIGYNLTHMPNQFNHDTQDEAGLEVHQFWPLVEIQCSPDLRFFL

CSMYTPICLPDYHKPLPPCRSVCERAKAGCSPLMRQYGFAWPERMSCDRLPVLGRDAEVL

CMDYNRSEATT

Human FZD6 Fri domain amino acid sequence without
predicted signal sequence
        (SEQ ID NO: 37; amino acids 19-146 of SEQ ID NO: 24)
HSLFTCEPITVPRCMKMAYNMTFFPNLMGHYDQSIAAVEMEHFLPLANLECSPNIETFLC

KAFVPTCIEQIHVVPPCRKLCEKVYSDCKKLIDTFGIRWPEELECDRLQYCDETVPVTFD

PHTEFLG

Human FZD7 Fri domain amino acid sequence without
predicted signal sequence
        (SEQ ID NO: 38; amino acids 33-170 of SEQ ID NO: 25)
QPYHGEKGISVPDHGFCQPISIPLCTDIAYNQTILPNLLGHTNQEDAGLEVHQFYPLVKV

QCSPELRFFLCSMYAPVCTVLDQAIPPCRSLCERARQGCEALMNKFGFQWPERLRCENFP

VHGAGEICVGQNTSDGSG

Human FZD8 Fri domain amino acid sequence without
predicted signal sequence
        (SEQ ID NO: 39; amino acids 28-158 of SEQ ID NO: 30)
ASAKELACQEITVPLCKGIGYNYTYMPNQFNHDTQDEAGLEVHQFWPLVEIQCSPDLKFF

LCSMYTPICLEDYKKPLPPCRSVCERAKAGCAPLMRQYGFAWPDRMRCDRLPEQGNPDTL

CMDYNRTDLTT

Human FZD9 Fri domain amino acid sequence without
predicted signal sequence
        (SEQ ID NO: 40; amino acids 23-159 of SEQ ID NO: 31)
LEIGRFDPERGRGAAPCQAVEIPMCRGIGYNLTRMPNLLGHTSQGEAAAELAEFAPLVQY

GCHSHLRFFLCSLYAPMCTDQVSTPIPACRPMCEQARLRCAPIMEQFNFGWPDSLDCARL

PTRNDPHALCMEAPENA

Human FZD10 Fri domain amino acid sequence without
predicted signal sequence
            (SEQ ID NO: 41; amino acids 21-154 of SEQ ID NO: 26)
ISSMDMERPGDGKCQPIEIPMCKDIGYNMTRMPNLMGHENQREAAIQLHEFAPLVEYGCH

GHLRFFLCSLYAPMCTEQVSTPIPACRVMCEQARLKCSPIMEQFNFKWPDSLDCRKLPNK

NDPNYLCMEAPNNG

FZD extracellular domain (ECD) sequences
Human FZD1 ECD with signal sequence
                                                    (SEQ ID NO: 27)
MAEEEAPKKSRAAGGGASWELCAGALSARLAEEGSGDAGGRRRPPVDPRRLARQLLLLLW

LLEAPLLLGVRAQAAGQGPGQGPGPGQQPPPPPQQQQSGQQYNGERGISVPDHGYCQPIS

IPLCTDIAYNQTIMPNLLGHTNQEDAGLEVHQFYPLVKVQCSAELKFFLCSMYAPVCTVL

EQALPPCRSLCERARQGCEALMNKFGFQWPDTLKCEKFPVHGAGELCVGQNTSDKGTPTP

SLLPEFWTSNPQHGGGHRGGFPGGAGASERGKFSCPRALKVPSYLNYHFLGEKDCGAPC

EPTKVYGLMYFGPEELRFSRT

Human FZD2 ECD with signal sequence
                                                    (SEQ ID NO: 28)
MRPRSALPRLLLPLLLLPAAGPAQFHGEKGISIPDHGFCQPISIPLCTDIAYNQTIMPNL

LGHTNQEDAGLEVHQFYPLVKVQCSPELRFFLCSMYAPVCTVLEQAIPPCRSICERARQG

CEALMNKFGFQWPERLRCEHFPRHGAEQICVGQNHSEDGAPALLTTAPPPGLQPGAGGTP

GGPGGGGAPPRYATLEHPFHCPRVLKVPSYLSYKFLGERDCAAPCEPARPDGSMFFSQEE

TRFARLWILT

Human FZD3 ECD with signal sequence
                                                    (SEQ ID NO: 29)
MAMTWIVFSLWPLTVFMGHIGGHSLFSCEPITLRMCQDLPYNTTFMPNLLNHYDQQTAAL

AMEPFHPMVNLDCSRDFRPFLCALYAPICMEYGRVTLPCRRLCQRAYSECSKLMEMFGVP

WPEDMECSRFPDCDEPYPRLVDLNLAGEPTEGAPVAVQRDYGFWCPRELKIDPDLGYSFL

HVRDCSPPCPNMYFRREELSFARY

Human FZD4 ECD with signal sequence
                                                    (SEQ ID NO: 22)
MLAMAWRGAGPSVPGAPGGVGLSLGLLLQLLLLLGPARGFGDEEERRCDPIRISMCQNLG

YNVTKMPNLVGHELQTDAELQLTTFTPLIQYGCSSQLQFFLCSVYVPMCTEKINIPIGPC

GGMCLSVKRRCEPVLKEFGFAWPESLNCSKFPPQNDHNHMCMEGPGDEEVPLPHKTPIQP

GEECHSVGTNSDQYIWVKRSLNCVLKCGYDAGLYSRSAKEFTDI

Human FZD5 ECD with signal sequence
                                                    (SEQ ID NO: 23)
MARPDPSAPPSLLLLLLAQLVGRAAAASKAPVCQEITVPMCRGIGYNLTHMPNQFNHDTQ

DEAGLEVHQFWPLVEIQCSPDLRFFLCSMYTPICLPDYHKPLPPCRSVCERAKAGCSPLM

RQYGFAWPERMSCDRLPVLGRDAEVLCMDYNRSEATTAPPRPFPAKPTLPGPPGAPASGG

ECPAGGPFVCKCREPFVPILKESHPLYNKVRTGQVPNCAVPCYQPSFSADERT

Human FZD6 ECD with signal sequence
                                                    (SEQ ID NO: 24)
MEMFTFLLTCIFLPLLRGHSLFTCEPITVPRCMKMAYNMTFFPNLMGHYDQSIAAVEMEH

FLPLANLECSPNIETFLCKAFVPTCIEQIHVVPPCRKLCEKVYSDCKKLIDTFGIRWPEE

```
LECDRLQYCDETVPVTFDPHTEFLGPQKKTEQVQRDIGFWCPRHLKTSGGQGYKFLGIDQ

CAPPCPNMYFKSDELEFAKSFIGTVSI

Human FZD7 ECD with signal sequence
                                                     (SEQ ID NO: 25)
MRDPGAAAPLSSLGLCALVLALLGALSAGAGAQPYHGEKGISVPDHGFCQPISIPLCTDI

AYNQTILPNLLGHTNQEDAGLEVHQFYPLVKVQCSPELRFFLCSMYAPVCTVLDQAIPPC

RSLCERARQGCEALMNKFGFQWPERLRCENFPVHGAGEICVGQNTSDGSGGPGGGPTAYP

TAPYLPDLPFTALPPGASDGRGRPAFPFSCPRQLKVPPYLGYRFLGERDCGAPCEPGRAN

GLMYFKEEERRFARL

Human FZD8 ECD with signal sequence
                                                     (SEQ ID NO: 30)
MEWGYLLEVTSLLAALALLQRSSGAAAASAKELACQEITVPLCKGIGYNYTYMPNQFNHD

TQDEAGLEVHQFWPLVEIQCSPDLKFFLCSMYTPICLEDYKKPLPPCRSVCERAKAGCAP

LMRQYGFAWPDRMRCDRLPEQGNPDTLCMDYNRTDLTTAAPSPPRRLPPPPPGEQPPSGS

GHGRPPGARPPHRGGGRGGGGGDAAAPPARGGGGGGKARPPGGGAAPCEPGCQCRAPMVS

VSSERHPLYNRVKTGQIANCALPCHNPFFSQDERAFT

Human FZD9 ECD with signal sequence
                                                     (SEQ ID NO: 31)
MAVAPLRGALLLWQLLAAGGAALEIGRFDPERGRGAAPCQAVEIPMCRGIGYNLTRMPNL

LGHTSQGEAAAELAEFAPLVQYGCHSHLRFFLCSLYAPMCTDQVSTPIPACRPMCEQARL

RCAPIMEQFNFGWPDSLDCARLPTRNDPHALCMEAPENATAGPAEPHKGLGMLPVAPRPA

RPPGDLGPGAGGSGTCENPEKFQYVEKSRSCAPRCGPGVEVFWSRRDKDF

Human FZD10 ECD with signal sequence
                                                     (SEQ ID NO: 26)
MQRPGPRLWLVLQVMGSCAAISSMDMERPGDGKCQPIEIPMCKDIGYNMTRMPNLMGHEN

QREAAIQLHEFAPLVEYGCHGHLRFFLCSLYAPMCTEQVSTPIPACRVMCEQARLKCSPI

MEQFNFKWPDSLDCRKLPNKNDPNYLCMEAPNNGSDEPTRGSGLFPPLFRPQRPHSAQEH

PLKDGGPGRGGCDNPGKFHHVEKSASCAPLCTPGVDVYWSREDKRFA

FZD8-Fc variants
FZD8-Fc variant 54F03 amino acid sequence
(without predicted signal sequence; alternative cleavage)
                                                     (SEQ ID NO: 45)
AAAASAKELACQEITVPLCKGIGYNYTYMPNQFNHDTQDEAGLEVHQFWPLVEIQCSPDL

KFFLCSMYTPICLEDYKKPLPPCRSVCERAKAGCAPLMRQYGFAWPDRMRCDRLPEQGNP

DTLCMDYNRTDLTTGRADKTHTCPPCPAPELLGGPSVFLFPPKPKDTLMISRTPEVTCVV

VDVSHEDPEVKFNWYVDGVEVHNAKTKPREEQYNSTYRVVSVLTVLHQDWLNGKEYKCKV

SNKALPAPIEKTISKAKGQPREPQVYTLPPSRDELTKNQVSLTCLVKGFYPSDIAVEWES

NGQPENNYKTTPPVLDSDGSFFLYSKLTVDKSRWQQGNVFSCSVMHEALHNHYTQKSLSL

SPGK

FZD8-Fc variant 54F09 amino acid sequence
(without predicted signal sequence)
                                                     (SEQ ID NO: 46)
ASAKELACQEITVPLCKGIGYNYTYMPNQFNHDTQDEAGLEVHQFWPLVEIQCSPDLKFF

LCSMYTPICLEDYKKPLPPCRSVCERAKAGCAPLMRQYGFAWPDRMRCDRLPEQGNPDTL

CMDYNRTDLTTAAPSPPDKTHTCPPCPAPELLGGPSVFLFPPKPKDTLMISRTPEVTCVV

VDVSHEDPEVKFNWYVDGVEVHNAKTKPREEQYNSTYRVVSVLTVLHQDWLNGKEYKCKV

SNKALPAPIEKTISKAKGQPREPQVYTLPPSRDELTKNQVSLTCLVKGFYPSDIAVEWES
```

```
NGQPENNYKTTPPVLDSDGSFFLYSKLTVDKSRWQQGNVFSCSVMHEALHNHYTQKSLSL

SPGK

FZD8-Fc variant 54F09 amino acid sequence
(without predicted signal sequence; alternative cleavage)
                                               (SEQ ID NO: 47)
AAAASAKELACQEITVPLCKGIGYNYTYMPNQFNHDTQDEAGLEVHQFWPLVEIQCSPDL

KFFLCSMYTPICLEDYKKPLPPCRSVCERAKAGCAPLMRQYGFAWPDRMRCDRLPEQGNP

DTLCMDYNRTDLTTAAPSPPDKTHTCPPCPAPELLGGPSVFLFPPKPKDTLMISRTPEVT

CVVVDVSHEDPEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVKGFYPSDIAVE

WESNGQPENNYKTTPPVLDSDGSFFLYSKLTVDKSRWQQGNVFSCSVMHEALHNHYTQKS

LSLSPGK

FZD8-Fc variant 54F15 amino acid sequence
(without predicted signal sequence)
                                               (SEQ ID NO: 48)
ASAKELACQEITVPLCKGIGYNYTYMPNQFNHDTQDEAGLEVHQFWPLVEIQCSPDLKFF

LCSMYTPICLEDYKKPLPPCRSVCERAKAGCAPLMRQYGFAWPDRMRCDRLPEQGNPDTL

CMDYNRTDLTTAAPDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKEYKCKVSNK

ALPAPIEKTISKAKGQPREPQVYTLPPSRDELTKNQVSLTCLVKGFYPSDIAVEWESNGQ

PENNYKTTPPVLDSDGSFFLYSKLTVDKSRWQQGNVFSCSVMHEALHNHYTQKSLSLSPG

K

FZD8-Fc variant 54F15 amino acid sequence
(without predicted signal sequence; alternative cleavage)
                                               (SEQ ID NO: 49)
AAAASAKELACQEITVPLCKGIGYNYTYMPNQFNHDTQDEAGLEVHQFWPLVEIQCSPDL

KFFLCSMYTPICLEDYKKPLPPCRSVCERAKAGCAPLMRQYGFAWPDRMRCDRLPEQGNP

DTLCMDYNRTDLTTAAPDKTHTCPPCPAPELLGGPSVFLFPPKPKDTLMISRTPEVTCVV

VDVSHEDPEVKFNWYVDGVEVHNAKTKPREEQYNSTYRVVSVLTVLHQDWLNGKEYKCKV

SNKALPAPIEKTISKAKGQPREPQVYTLPPSRDELTKNQVSLTCLVKGFYPSDIAVEWES

NGQPENNYKTTPPVLDSDGSFFLYSKLTVDKSRWQQGNVFSCSVMHEALHNHYTQKSLSL

SPGK

FZD8-Fc variant 54F16, 54F17, 54F18, 54F23, 54F25, 54F27,
54F29, 54F31, and 54F34 amino acid sequence
(without predicted signal sequence)
                                               (SEQ ID NO: 50)
ASAKELACQEITVPLCKGIGYNYTYMPNQFNHDTQDEAGLEVHQFWPLVEIQCSPDLKFF

LCSMYTPICLEDYKKPLPPCRSVCERAKAGCAPLMRQYGFAWPDRMRCDRLPEQGNPDTL

CMDYNRTDLTTKSSDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKEYKCKVSNK

ALPAPIEKTISKAKGQPREPQVYTLPPSRDELTKNQVSLTCLVKGFYPSDIAVEWESNGQ

PENNYKTTPPVLDSDGSFFLYSKLTVDKSRWQQGNVFSCSVMHEALHNHYTQKSLSLSPG

K
```

FZD8-Fc variant 54F16 amino acid sequence
(without predicted signal sequence; alternative cleavage)
(SEQ ID NO: 51)
AAAASAKELACQEITVPLCKGIGYNYTYMPNQFNHDTQDEAGLEVHQFWPLVEIQCSPDL

KFFLCSMYTPICLEDYKKPLPPCRSVCERAKAGCAPLMRQYGFAWPDRMRCDRLPEQGNP

DTLCMDYNRTDLTTKSSDKTHTCPPCPAPELLGGPSVFLFPPKPKDTLMISRTPEVTCVV

VDVSHEDPEVKFNWYVDGVEVHNAKTKPREEQYNSTYRVVSVLTVLHQDWLNGKEYKCKV

SNKALPAPIEKTISKAKGQPREPQVYTLPPSRDELTKNQVSLTCLVKGFYPSDIAVEWES

NGQPENNYKTTPPVLDSDGSFFLYSKLTVDKSRWQQGNVFSCSVMHEALHNHYTQKSLSL

SPG

FZD8-Fc variant 54F16 amino acid sequence
(with signal sequence)
(SEQ ID NO: 52)
MEWGYLLEVTSLLAALALLQRSSGAAAASAKELACQEITVPLCKGIGYNYTYMPNQFNHD

TQDEAGLEVHQFWPLVEIQCSPDLKFFLCSMYTPICLEDYKKPLPPCRSVCERAKAGCAP

LMRQYGFAWPDRMRCDRLPEQGNPDTLCMDYNRTDLTTKSSDKTHTCPPCPAPELLGGPS

VFLFPPKPKDTLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYSKLTVDKSRWQQ

GNVFSCSVMHEALHNHYTQKSLSLSPGK

FZD8-Fc variant 54F19, 54F20, 54F24, 54F26, 54F28,
54F30, 54F32, 54F34 and 54F35 amino acid sequence
(without predicted signal sequence)
(SEQ ID NO: 53)
ASAKELACQEITVPLCKGIGYNYTYMPNQFNHDTQDEAGLEVHQFWPLVEIQCSPDLKFF

LCSMYTPICLEDYKKPLPPCRSVCERAKAGCAPLMRQYGFAWPDRMRCDRLPEQGNPDTL

CMDYNRTDLTTEPKSSDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDWLNGKEYKCKVS

NKALPAPIEKTISKAKGQPREPQVYTLPPSRDELTKNQVSLTCLVKGFYPSDIAVEWESN

GQPENNYKTTPPVLDSDGSFFLYSKLTVDKSRWQQGNVFSCSVMHEALHNHYTQKSLSLS

PGK

FZD8-Fc variant 54F19 amino acid sequence
(without predicted signal sequence; alternative cleavage)
(SEQ ID NO: 54)
ALAASAKELACQEITVPLCKGIGYNYTYMPNQFNHDTQDEAGLEVHQFWPLVEIQCSPDL

KFFLCSMYTPICLEDYKKPLPPCRSVCERAKAGCAPLMRQYGFAWPDRMRCDRLPEQGNP

DTLCMDYNRTDLTTEPKSSDKTHTCPPCPAPELLGGPSVFLFPPKPKDTLMISRTPEVTC

VVVDVSHEDPEVKFNWYVDGVEVHNAKTKPREEQYNSTYRVVSVLTVLHQDWLNGKEYKC

KVSNKALPAPIEKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHEALHNHYTQKSL

SLSPGK

FZD8-Fc variant 54F20 amino acid sequence
(without predicted signal sequence; alternative cleavage)
(SEQ ID NO: 55)
VLAASAKELACQEITVPLCKGIGYNYTYMPNQFNHDTQDEAGLEVHQFWPLVEIQCSPDL

KFFLCSMYTPICLEDYKKPLPPCRSVCERAKAGCAPLMRQYGFAWPDRMRCDRLPEQGNP

DTLCMDYNRTDLTTEPKSSDKTHTCPPCPAPELLGGPSVFLFPPKPKDTLMISRTPEVTC

```
VVVDVSHEDPEVKFNWYVDGVEVHNAKTKPREEQYNSTYRVVSVLTVLHQDWLNGKEYKC

KVSNKALPAPIEKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHEALHNHYTQKSL

SLSPGK

FZD8-Fc variant 54F34 amino acid sequence
(without predicted signal sequence)
                                                        (SEQ ID NO: 65)
KELACQEITVPLCKGIGYNYTYMPNQFNHDTQDEAGLEVHQFWPLVEIQCSPDLKFFLCS

MYTPICLEDYKKPLPPCRSVCERAKAGCAPLMRQYGFAWPDRMRCDRLPEQGNPDTLCMD

YNRTDLTTEPKSSDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGKEYKCKVSNKA

LPAPIEKTISKAKGQPREPQVYTLPPSRDELTKNQVSLTCLVKGFYPSDIAVEWESNGQP

ENNYKTTPPVLDSDGSFFLYSKLTVDKSRWQQGNVFSCSVMHEALHNHYTQKSLSLSPGK

FZD8-Fc variant 54F33 amino acid sequence
(without predicted signal sequence)
                                                        (SEQ ID NO: 66)
KELACQEITVPLCKGIGYNYTYMPNQFNHDTQDEAGLEVHQFWPLVEIQCSPDLKFFLCS

MYTPICLEDYKKPLPPCRSVCERAKAGCAPLMRQYGFAWPDRMRCDRLPEQGNPDTLCMD

YNRTDLTTKSSDKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKEYKCKVSNKALP

APIEKTISKAKGQPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYTQKSLSLSPGK

Human ROR1 ECD with signal sequence
                                                        (SEQ ID NO: 56)
MHRPRRRGTRPPLLALLAALLLAARGAAAQETELSVSAELVPTSSWNISSELNKDSYLTL

DEPMNNITTSLGQTAELHCKVSGNPPPTIRWFKNDAPVVQEPRRLSFRSTIYGSRLRIRN

LDTTDTGYFQCVATNGKEVVSSTGVLFVKFGPPPTASPGYSDEYEEDGFCQPYRGIACAR

FIGNRTVYMESLHMQGEIENQITAAFTMIGTSSHLSDKCSQFAIPSLCHYAFPYCDETSS

VPKPRDLCRDECEILENVLCQTEYIFARSNPMILMRLKLPNCEDLPQPESPEAANCIRIG

IPMADPINKNHKCYNSTGVDYRGTVSVTKSGRQCQPWNSQYPHTHTFTALRFPELNGGHS

YCRNPGNQKEAPWCFTLDENFKSDLCDIPACDSKDSKEKNKMEILY

Human ROR2 ECD with signal sequence
                                                        (SEQ ID NO: 57)
MARGSALPRRPLLCIPAVWAAAALLLSVSRTSGEVEVLDPNDPLGPLDGQDGPIPTLKGY

FLNFLEPVNNITIVQGQTAILHCKVAGNPPPNVRWLKNDAPVVQEPRRIIIRKTEYGSRL

RIQDLDTTDTGYYQCVATNGMKTITATGVLFVRLGPTHSPNHNFQDDYHEDGFCQPYRGI

ACARFIGNRTIYVDSLQMQGEIENRITAAFTMIGTSTHLSDQCSQFAIPSFCHFVFPLCD

ARSRTPKPRELCRDECEVLESDLCRQEYTIARSNPLILMRLQLPKCEALPMPESPDAANC

MRIGIPAERLGRYHQCYNGSGMDYRGTASTTKSGHQCQPWALQHPHSHHLSSTDFPELGG

GHAYCRNPGGQMEGPWCFTQNKNVRMELCDVPSCSPRDSSKMG h-ROR1 minimal Fri domain
                                                        (SEQ ID NO: 58)
CQPYRGIACARFIGNRTVYMESLHMQGEIENQITAAFTMIGTSSHLSDKCSQFAIPSLCH

YAFPYCDETSSVPKPRDLCRDECEILENVLCQTEYIFARSNPMILMRLKLPNCEDLPQPE

SPEAANC
```

```
h-ROR2 minimal Fri domain
                                                      (SEQ ID NO: 59)
CQPYRGIACARFIGNRTIYVDSLQMQGEIENRITAAFTMIGTSTHLSDQCSQFAIPSFCH

FVFPLCDARSRTPKPRELCRDECEVLESDLCRQEYTIARSNPLILMRLQLPKCEALPMPE

SPDAANC

Linker
                                                      (SEQ ID NO: 60)
ESGGGGVT Linker
                                                      (SEQ ID NO: 61)
LESGGGGVT Linker
                                                      (SEQ ID NO: 62)
GRAQVT Linker
                                                      (SEQ ID NO: 63)
WRAQVT Linker
                                                      (SEQ ID NO: 64)
ARGRAQVT Signal Sequence
                                                      (SEQ ID NO: 67)
MEWGYLLEVTSLLAALALLQRSSGAAA Signal Sequence
                                                      (SEQ ID NO: 68)
MEWGYLLEVTSLLAALALLQRSSGALA Signal Sequence
                                                      (SEQ ID NO: 69)
MEWGYLLEVTSLLAALALLQRSSGVLA Signal Sequence
                                                      (SEQ ID NO: 70)
MEWGYLLEVTSLLAALLLLQRSPIVHA Signal Sequence
                                                      (SEQ ID NO: 71)
MEWGYLLEVTSLLAALFLLQRSPIVHA Signal Sequence
                                                      (SEQ ID NO: 72)
MEWGYLLEVTSLLAALLLLQRSPFVHA Signal Sequence
                                                      (SEQ ID NO: 73)
MEWGYLLEVTSLLAALLLLQRSPIIYA Signal Sequence
                                                      (SEQ ID NO: 74)
MEWGYLLEVTSLLAALLLLQRSPIAHA FZD8-Fc variant 54F26 with signal sequence
                                                      (SEQ ID NO: 75)
MEWGYLLEVTSLLAALFLLQRSPIVHAASAKELACQEITVPLCKGIGYNYTYMPNQFNHD

TQDEAGLEVHQFWPLVEIQCSPDLKFFLCSMYTPICLEDYKKPLPPCRSVCERAKAGCAP

LMRQYGFAWPDRMRCDRLPEQGNPDTLCMDYNRTDLTTEPKSSDKTHTCPPCPAPELLGG

PSVFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQVYTLPPSRDE
```

LTKNQVSLTCLVKGFYPSDIAVEWESNGQPENNYKTTPPVLDSDGSFFLYSKLTVDKSRW

QQGNVFSCSVMHEALHNHYTQKSLSLSPGK

N-terminal sequence
(SEQ ID NO: 76)
AAAASA

What is claimed is:

1. A method of treating cancer in a subject comprising administering to the subject a therapeutically effective amount of a Wnt-binding agent that comprises a polypeptide comprising the amino acid sequence of SEQ ID NO:53.

2. The method of claim 1, wherein the Wnt-binding agent is present in a pharmaceutical composition comprising a pharmaceutically acceptable carrier.

3. The method of claim 1, wherein the cancer is selected from the group consisting of colorectal cancer, pancreatic cancer, breast cancer, lung cancer, ovarian cancer, liver cancer, kidney cancer, prostate cancer, gastrointestinal cancer, melanoma, cervical cancer, bladder cancer, glioblastoma, and head and neck cancer.

4. The method of claim 1, wherein the method further comprises administering to the subject a second therapeutic agent.

5. The method of claim 4, wherein the second therapeutic agent is a chemotherapeutic agent.

6. The method of claim 1, wherein the polypeptide consists of the amino acid sequence of SEQ ID NO:53.

7. The method of claim 1, wherein the cancer is pancreatic cancer.

8. The method of claim 7, wherein the polypeptide consists of the amino acid sequence of SEQ ID NO:53.

9. The method of claim 7, wherein the method further comprises administering to the subject a chemotherapeutic agent.

10. The method of claim 9, wherein the chemotherapeutic agent is an anti-metabolite.

11. The method of claim 10, wherein the anti-metabolite is selected from the group consisting of gemcitabine, fluorouracil, capecitabine, methotrexate sodium, ralitrexed, pemetrexed, tegafur, cytosine arabinoside, thioguanine, 5-azacytidine, 6-mercaptopurine, azathioprine, 6-thioguanine, pentostatin, fludarabine phosphate, and cladribine.

12. The method of claim 11, wherein the anti-metabolite is gemcitabine.

13. The method of claim 12, wherein the polypeptide consists of the amino acid sequence of SEQ ID NO:53.

14. The method of claim 9, wherein the chemotherapeutic agent is a taxane.

15. The method of claim 14, wherein the taxane is selected from the group consisting of paclitaxel, nab-paclitaxel, docetaxel, DHA-paclitaxel, and PG-paclitaxel.

16. The method of claim 15, wherein the taxane is nab-paclitaxel.

17. The method of claim 16, wherein the method further comprises administering to the subject gemcitabine.

18. The method of claim 17, wherein the polypeptide consists of the amino acid sequence of SEQ ID NO:53.

19. The method of claim 1, wherein the cancer is ovarian cancer.

20. The method of claim 19, wherein the polypeptide consists of the amino acid sequence of SEQ ID NO:53.

21. The method of claim 19, wherein the method further comprises administering to the subject a chemotherapeutic agent.

22. The method of claim 21, wherein the chemotherapeutic agent is a taxane.

23. The method of claim 22, wherein the taxane is paclitaxel, nab-paclitaxel, docetaxel, DHA-paclitaxel, or PG-paclitaxel.

24. The method of claim 23, wherein the taxane is paclitaxel.

25. The method of claim 21, wherein the chemotherapeutic agent is a platinum complex.

26. The method of claim 25, wherein the platinum complex is cisplatin or carboplatin.

27. The method of claim 26, wherein the platinum complex is carboplatin.

28. The method of claim 27, wherein the polypeptide consists of the amino acid sequence of SEQ ID NO:53.

29. The method of claim 27, wherein the method further comprising administering to the subject paclitaxel.

30. The method of claim 29, wherein the polypeptide consists of the amino acid sequence of SEQ ID NO:53.

31. The method of claim 1, wherein the cancer is liver cancer.

32. The method of claim 31, wherein the cancer is hepatocellular cancer.

33. The method of claim 32, wherein the polypeptide consists of the amino acid sequence of SEQ ID NO:53.

34. The method of claim 32, wherein the method further comprises administering to the subject a chemotherapeutic agent.

35. The method of claim 34, wherein the polypeptide consists of the amino acid sequence of SEQ ID NO:53.

* * * * *